United States Patent
Connor

(10) Patent No.: US 10,234,942 B2
(45) Date of Patent: Mar. 19, 2019

(54) WEARABLE AND MOBILE BRAIN COMPUTER INTERFACE (BCI) DEVICE AND METHOD

(71) Applicant: Robert A. Connor, Forest Lake, MN (US)

(72) Inventor: Robert A. Connor, Forest Lake, MN (US)

(73) Assignee: Medibotics LLC, St. Paul, MN (US)

( * ) Notice: Subject to any disclaimer, the term of this patent is extended or adjusted under 35 U.S.C. 154(b) by 435 days.

(21) Appl. No.: 15/136,948

(22) Filed: Apr. 24, 2016

(65) Prior Publication Data

US 2016/0239084 A1    Aug. 18, 2016

Related U.S. Application Data

(63) Continuation-in-part of application No. 14/599,522, filed on Jan. 18, 2015, now Pat. No. 9,814,426, which is a continuation-in-part of application No. 14/562,719, filed on Dec. 7, 2014.

(60) Provisional application No. 61/932,517, filed on Jan. 28, 2014, provisional application No. 61/939,244, filed on Feb. 12, 2014, provisional application No. 62/017,615, filed on Jun. 26, 2014, provisional application No. 62/089,696, filed on Dec. 9, 2014, provisional application No. 62/160,172, filed on May 12, 2015, provisional application No. 62/169,661, filed on Jun. 2, 2015, provisional application No. 62/303,126, filed on Mar. 3, 2016, provisional application No. 62/322,594, filed on Apr. 14, 2016.

(51) Int. Cl.
*A61B 5/00* (2006.01)
*G06F 3/01* (2006.01)
*A61B 5/0478* (2006.01)
*A61B 5/11* (2006.01)

(52) U.S. Cl.
CPC ............ *G06F 3/015* (2013.01); *A61B 5/0478* (2013.01); *A61B 5/6803* (2013.01); *A61B 5/6814* (2013.01); *A61B 5/1118* (2013.01); *A61B 5/4866* (2013.01); *A61B 2560/0468* (2013.01); *A61B 2562/0209* (2013.01)

(58) Field of Classification Search
CPC ... A61B 5/6814; A61B 5/0478; A61B 5/0476; A61B 5/02055; A61B 5/6803; A61B 2562/0209; A61B 5/1118; A61B 5/4866; A61B 2560/0468; A61B 5/1112; A61B 5/4205; A61B 5/021; A61B 5/02438; A61B 5/0404; A61B 5/0533; A61B 5/14551

See application file for complete search history.

(56) References Cited

U.S. PATENT DOCUMENTS

| | | |
|---|---|---|
| 3,998,213 A | 12/1976 | Price |
| 4,697,598 A | 10/1987 | Bernard et al. |
| 4,709,702 A | 12/1987 | Sherwin |

(Continued)

*Primary Examiner* — Tiffany Weston
*Assistant Examiner* — Tho Q Tran

(57) ABSTRACT

This invention is a wearable and mobile Brain Computer Interface (BCI) device which can be embodied in a head-worn undulating band. This band can have an ear-engaging segment, a side segment which spans the side part of a person's forehead and/or face, and a top segment which spans the top of the person's head. This band can encircle a person's head and include an ear prong. This band can include a movable loop which can be moved to span across a person's forehead.

8 Claims, 47 Drawing Sheets

(56) References Cited

U.S. PATENT DOCUMENTS

| | | |
|---|---|---|
| 4,770,180 A | 9/1988 | Schmidt et al. |
| 4,836,219 A | 6/1989 | Hobson et al. |
| 4,967,038 A | 10/1990 | Gevins et al. |
| 5,038,782 A | 8/1991 | Gevins et al. |
| 5,293,867 A | 3/1994 | Oommen |
| 5,479,934 A * | 1/1996 | Imran ............. A61B 5/0017 600/390 |
| 5,740,812 A | 4/1998 | Cowan |
| 5,769,878 A * | 6/1998 | Kamei ............. A61M 21/00 600/545 |
| 5,800,351 A | 9/1998 | Mann |
| 5,954,667 A | 9/1999 | Finkenzeller et al. |
| 6,001,065 A | 12/1999 | Devito |
| 6,067,464 A | 5/2000 | Musha |
| 6,154,669 A | 11/2000 | Hunter et al. |
| 6,161,030 A | 12/2000 | Levendowski et al. |
| 6,167,298 A | 12/2000 | Levin |
| 6,171,258 B1 | 1/2001 | Karakasoglu et al. |
| 6,254,536 B1 | 7/2001 | Devito |
| 6,381,481 B1 | 4/2002 | Levendowski et al. |
| 6,488,617 B1 | 12/2002 | Katz |
| 6,574,513 B1 | 6/2003 | Collura et al. |
| 6,811,538 B2 | 11/2004 | Westbrook et al. |
| 7,158,822 B2 | 1/2007 | Payne, Jr. |
| 7,297,119 B2 | 11/2007 | Westbrook et al. |
| 7,344,244 B2 | 3/2008 | Goodall et al. |
| D565,735 S | 4/2008 | Washbon |
| 7,390,088 B2 | 6/2008 | Goodall et al. |
| 7,551,952 B2 | 6/2009 | Gevins et al. |
| 7,689,274 B2 | 3/2010 | Mullen et al. |
| 7,885,706 B2 | 2/2011 | Ludvig et al. |
| 8,103,328 B2 | 1/2012 | Turner et al. |
| 8,244,342 B2 | 8/2012 | Goodall et al. |
| 8,271,075 B2 | 9/2012 | Chuang et al. |
| 8,301,218 B2 | 10/2012 | Nguyen et al. |
| 8,326,396 B2 * | 12/2012 | Picht ............. A61B 5/0478 600/383 |
| 8,346,354 B2 | 1/2013 | Hyde et al. |
| 8,355,769 B2 | 1/2013 | Levendowski et al. |
| 8,392,250 B2 | 3/2013 | Pradeep et al. |
| 8,392,251 B2 | 3/2013 | Pradeep et al. |
| 8,396,744 B2 | 3/2013 | Pradeep et al. |
| 8,463,354 B2 | 6/2013 | Fadem |
| 8,467,133 B2 | 6/2013 | Miller |
| 8,472,120 B2 | 6/2013 | Border et al. |
| 8,477,425 B2 | 7/2013 | Border et al. |
| 8,482,859 B2 | 7/2013 | Border et al. |
| 8,488,246 B2 | 7/2013 | Border et al. |
| 8,548,852 B2 | 10/2013 | Pradeep et al. |
| 8,562,540 B2 | 10/2013 | Goodall et al. |
| 8,639,313 B2 | 1/2014 | Westbrook et al. |
| 8,655,428 B2 | 2/2014 | Pradeep et al. |
| 8,812,075 B2 | 8/2014 | Nguyen et al. |
| D759,803 S * | 6/2016 | Wagner ............. D24/107 |
| 2001/0056225 A1 | 12/2001 | DeVito |
| 2002/0029005 A1 | 3/2002 | Levendowski et al. |
| 2002/0165462 A1 | 11/2002 | Westbrook et al. |
| 2002/0188216 A1 | 12/2002 | Kayyali et al. |
| 2003/0018278 A1 | 1/2003 | Jordan |
| 2004/0267152 A1 | 12/2004 | Pineda |
| 2005/0027207 A1 | 2/2005 | Westbrook et al. |
| 2005/0277821 A1 | 12/2005 | Payne |
| 2006/0252978 A1 | 11/2006 | Vesely et al. |
| 2006/0252979 A1 | 11/2006 | Vesely et al. |
| 2007/0010757 A1 | 1/2007 | Goodall et al. |
| 2007/0019279 A1 | 1/2007 | Goodall et al. |
| 2007/0093706 A1 | 4/2007 | Gevins et al. |
| 2007/0106145 A1 | 5/2007 | Kim et al. |
| 2007/0106169 A1 | 5/2007 | Fadem |
| 2007/0112262 A1 | 5/2007 | Payne |
| 2007/0191727 A1 | 8/2007 | Fadem |
| 2007/0225585 A1 | 9/2007 | Washbon |
| 2007/0238945 A1 | 10/2007 | Delic et al. |
| 2007/0249952 A1 | 10/2007 | Rubin et al. |
| 2008/0082019 A1 | 4/2008 | Ludving et al. |
| 2008/0161673 A1 | 7/2008 | Goodall et al. |
| 2008/0177197 A1 | 7/2008 | Lee et al. |
| 2008/0208072 A1 | 8/2008 | Fadem et al. |
| 2009/0088619 A1 | 4/2009 | Turner et al. |
| 2009/0105576 A1 | 4/2009 | Do et al. |
| 2009/0281446 A2 | 11/2009 | Ludvig et al. |
| 2010/0099954 A1 | 4/2010 | Dickinson et al. |
| 2010/0125190 A1 | 5/2010 | Fadem |
| 2010/0240982 A1 | 9/2010 | Westbrook et al. |
| 2011/0015503 A1 | 1/2011 | Joffe et al. |
| 2011/0028798 A1 | 2/2011 | Hyde et al. |
| 2011/0029038 A1 | 2/2011 | Hyde et al. |
| 2011/0029044 A1 | 2/2011 | Hyde et al. |
| 2011/0098593 A1 | 4/2011 | Low et al. |
| 2011/0221656 A1 | 9/2011 | Haddick et al. |
| 2011/0221669 A1 | 9/2011 | Shams et al. |
| 2011/0221672 A1 | 9/2011 | Osterhout et al. |
| 2011/0222745 A1 | 9/2011 | Osterhout et al. |
| 2011/0227820 A1 | 9/2011 | Haddick et al. |
| 2011/0237971 A1 | 9/2011 | Pradeep et al. |
| 2011/0270117 A1 | 11/2011 | Warwick et al. |
| 2011/0282231 A1 | 11/2011 | Pradeep et al. |
| 2011/0282232 A1 | 11/2011 | Pradeep et al. |
| 2012/0029379 A1 | 2/2012 | Sivadas |
| 2012/0062445 A1 | 3/2012 | Haddick et al. |
| 2012/0072289 A1 | 3/2012 | Pradeep et al. |
| 2012/0075168 A1 | 3/2012 | Osterhout et al. |
| 2012/0150545 A1 | 6/2012 | Simon |
| 2012/0212398 A1 | 8/2012 | Border et al. |
| 2012/0212400 A1 | 8/2012 | Border et al. |
| 2012/0218172 A1 | 8/2012 | Border et al. |
| 2012/0218301 A1 | 8/2012 | Miller |
| 2012/0226127 A1 | 9/2012 | Asjes et al. |
| 2012/0235883 A1 | 9/2012 | Border et al. |
| 2012/0235886 A1 | 9/2012 | Border et al. |
| 2012/0235887 A1 | 9/2012 | Border et al. |
| 2012/0235900 A1 | 9/2012 | Border et al. |
| 2012/0236030 A1 | 9/2012 | Border et al. |
| 2012/0242678 A1 | 9/2012 | Border et al. |
| 2012/0242698 A1 | 9/2012 | Haddick et al. |
| 2013/0046206 A1 | 2/2013 | Preminger |
| 2013/0056010 A1 | 3/2013 | Walker et al. |
| 2013/0060097 A1 | 3/2013 | Rubin |
| 2013/0127708 A1 * | 5/2013 | Jung ............. A61B 5/0006 345/156 |
| 2013/0127980 A1 | 5/2013 | Haddick et al. |
| 2013/0131464 A1 | 5/2013 | Westbrook et al. |
| 2013/0131537 A1 | 5/2013 | Tam |
| 2013/0177883 A1 | 7/2013 | Barnehama et al. |
| 2013/0185144 A1 | 7/2013 | Pradeep et al. |
| 2013/0242262 A1 | 9/2013 | Lewis |
| 2013/0303837 A1 | 11/2013 | Berka et al. |
| 2013/0310676 A1 | 11/2013 | Jung |
| 2013/0314243 A1 | 11/2013 | Le |
| 2013/0314303 A1 | 11/2013 | Osterhout et al. |
| 2013/0317382 A1 | 11/2013 | Le |
| 2013/0317384 A1 | 11/2013 | Le |
| 2013/0338446 A1 | 12/2013 | Van Vugt et al. |
| 2014/0023999 A1 | 1/2014 | Greder |
| 2014/0024914 A1 * | 1/2014 | Fadem ............. A61B 5/04845 600/383 |
| 2014/0267005 A1 | 9/2014 | Urbach |
| 2014/0267401 A1 | 9/2014 | Urbach |
| 2014/0316230 A1 | 10/2014 | Denison et al. |
| 2014/0347265 A1 | 11/2014 | Aimone et al. |
| 2014/0375545 A1 | 12/2014 | Ackerman et al. |

* cited by examiner

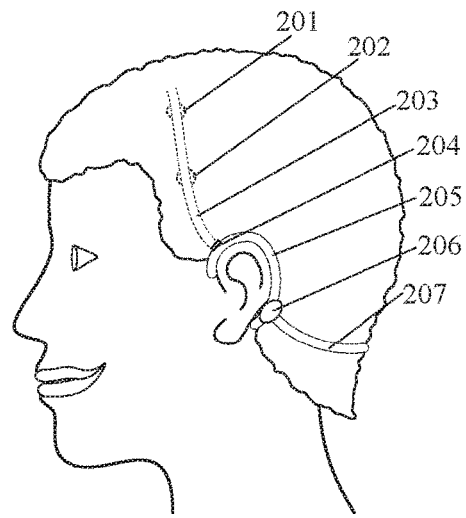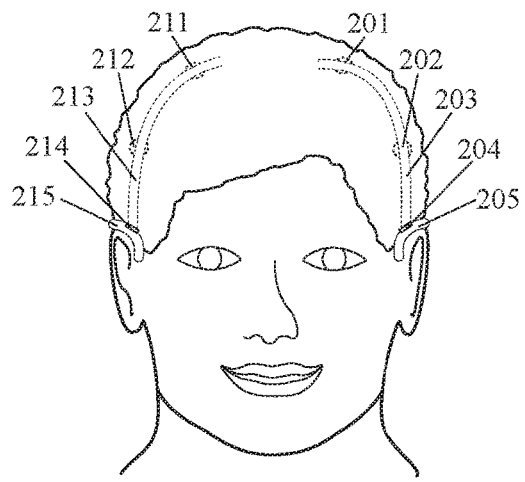
Fig. 2
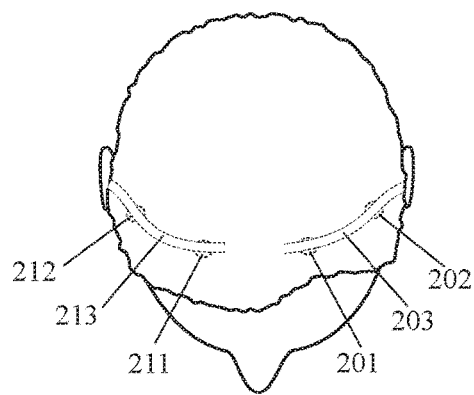

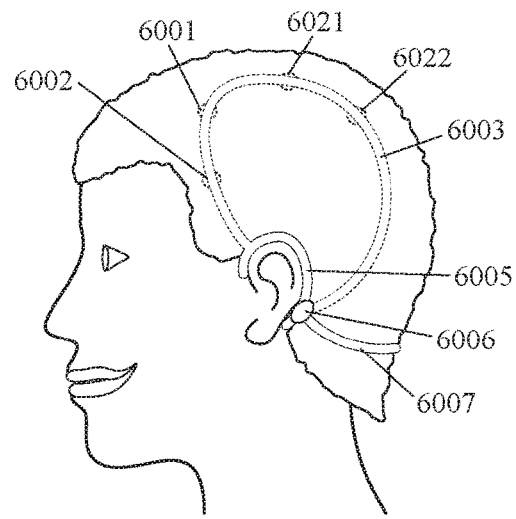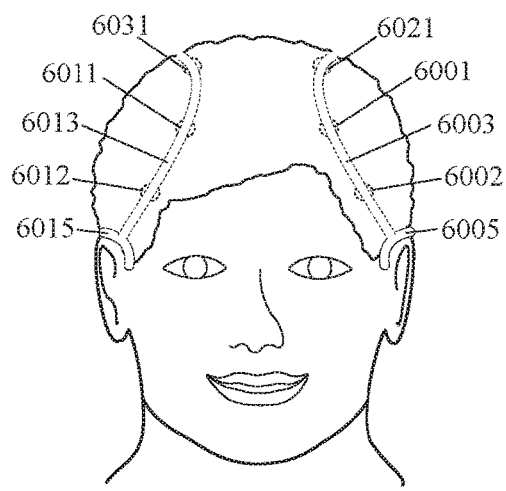
Fig. 6
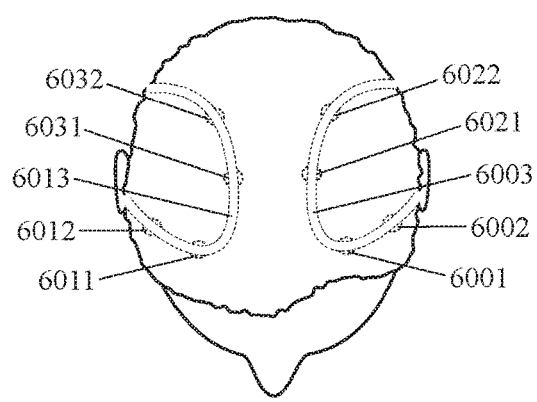

WEARABLE AND MOBILE BRAIN COMPUTER INTERFACE (BCI) DEVICE AND METHOD

CROSS-REFERENCE TO RELATED APPLICATIONS

This patent application: • is a continuation-in-part of U.S. patent application Ser. No. 14/599,522 entitled "Mobile Wearable Electromagnetic Brain Activity Monitor" by Robert A. Connor with a filing date of Jan. 18, 2015 which: (1) was a continuation in part of U.S. patent application Ser. No. 14/562,719 entitled "Willpower Glasses™—A Wearable Food Consumption Monitor" by Robert A. Connor with a filing date of Dec. 7, 2014 which claimed the priority benefit of U.S. Provisional Patent Application No. 61/932,517 entitled "Nutrode™: Wearable EEG Monitor for Modifying Food Consumption" by Robert A. Connor with a filing date of Jan. 28, 2014; (2) claimed the priority benefit of U.S. Provisional Patent Application No. 61/932,517 entitled "Nutrode™: Wearable EEG Monitor for Modifying Food Consumption" by Robert A. Connor with a filing date of Jan. 28, 2014; (3) claimed the priority benefit of U.S. Provisional Patent Application No. 61/939,244 entitled "Brainwave-Controlled Eyewear" by Robert A. Connor with a filing date of Feb. 12, 2014; (4) claimed the priority benefit of U.S. Provisional Patent Application No. 62/017,615 entitled "Nervision™ Integrated Eyewear and EEG Monitor" by Robert A. Connor with a filing date of Jun. 26, 2014; and (5) claimed the priority benefit of U.S. Provisional Patent Application No. 62/089,696 entitled "Electroencephalographic Eyewear" by Robert A. Connor with a filing date of Dec. 9, 2014; • claims the priority benefit of U.S. Provisional Patent Application No. 62/160,172 entitled "Hair-Engaging Mobile Brain Activity Monitor" by Robert A. Connor with a filing date of May 12, 2015; • claims the priority benefit of U.S. Provisional Patent Application No. 62/169,661 entitled "Internet of Thinks (IoT): A Brain Computer Interface (BCI) Using EEG Patterns Associated with the Same Command Across Different Action Modes" by Robert A. Connor with a filing date of Jun. 2, 2015; • claims the priority benefit of U.S. Provisional Patent Application No. 62/303,126 entitled "Undulating Mobile EEG Monitor Spanning a Portion of the Forehead" by Robert A. Connor with a filing date of Mar. 3, 2016; and • claims the priority benefit of U.S. Provisional Patent Application No. 62/322,594 entitled "Halo-Style Mobile Electroencephalographic (EEG) Monitor" by Robert A. Connor with a filing date of Apr. 14, 2016. The entire contents of these related applications are incorporated herein by reference.

FEDERALLY SPONSORED RESEARCH

Not Applicable

SEQUENCE LISTING OR PROGRAM

Not Applicable

BACKGROUND

Field of Invention

This invention relates to devices and methods for monitoring electromagnetic brain activity.

Introduction

This invention relates to mobile and wearable Brain Computer Interface (BCI) devices and methods for measuring electromagnetic energy from a person's brain. The ability to measure electromagnetic brain activity (such as electroencephalographic EEG activity) with a mobile wearable device allows such measurement while a person is ambulatory. With a mobile and wearable device, a person is free to do their normal activities. This provides useful information which is not possible with EEG monitoring devices which require that the person stay in fixed location (such as a hospital or medical office) with wires sprouting from their head like a modern-day Medusa. This present invention does offer some innovative device designs and methods which do not appear to be anticipated by the prior art.

Review and Categorization of the Relevant Art

It can be challenging trying to classify relevant art in this field into discrete categories. However, classification of relevant art into categories, even if imperfect, can be an invaluable tool for reviewing the relevant art. Towards this end, I herein identify 12 categories of relevant art and provide examples of relevant art in each category (including patent or patent application number, inventor, publication date, and title). Some examples of relevant art disclose multiple concepts and thus appear in more than one category.

The 12 categories of relevant art which are used for this review are as follows: (1) device with [multiple] front-to-back arcuate members and EEG/brainwave sensors; (2) device with [multiple] side-to-side arcuate members and EEG/brainwave sensors; (3) device with multiple cross-crossing arcuate members and EEG/brainwave sensors; (4) device with multiple arms radially-extending from side and EEG/brainwave sensors; (5) device with multiple arms radially-downward from top and EEG/brainwave sensors; (6) device with multiple arms radially-forward from rear and EEG/brainwave sensors; (7) device with multiple arms radially-backward from front and EEG/brainwave sensors; (8) device with circular horizontal loop (e.g. headband style) and EEG/brainwave sensors; (9) device with top semicircular loop (e.g. headphone style) and EEG/brainwave sensors; (10) device with rear semicircular loop and EEG/brainwave sensors; (11) device with frontal semicircular loop and EEG/brainwave sensors; and (12) device like eyeglasses or other eyewear with EEG/brainwave sensors.

I have labeled this section as a review of the relevant art, instead of a review of the prior art, for two reasons. First, some of the art included in this review has a priority date after the priority date of this disclosure, so I do not wish to call all of this art "prior." Second, some of the examples in this present disclosure can be classified into one or more of these categories but are nonetheless novel, so I do not wish to imply that all of the art in these categories is "prior". These caveats notwithstanding, I hope that the reader finds this review and categorization of the relevant art to be useful.

1. Device with [Multiple] Front-to-Back Arcuate Member(s) and EEG/Brainwave Sensor(s)

Devices in this category hold electromagnetic brain activity sensors in contact with (or proximity to) a person's head using (multiple) arcing member(s) which span a person's head from front-to-back (or vice versa). Devices in this category can look similar to some types of bicycle helmets with front-to-back arcuate members. In an example, the front-to-back arcing members can converge at the forehead and at the rear of the head. In an example, a device in this category can comprise: a first arcuate member which encircles a person's head: a second arcuate member which loops front-to-back over the top of the head; and third and fourth arcuate members which loop front-to-back over the sides of the head between the first and second members. Devices in this category can hold a relatively large number of electromagnetic brain activity sensors along arcuate front-to-rear lines on a person's head. However, such devices tend to be too obtrusive to wear during the activities of daily life.

Prior art which appears to be within this category includes U.S. Pat. No. 3,998,213 (Price, Dec. 21, 1976, "Self-Adjustable Holder for Automatically Positioning Electroencephalographic Electrodes"), U.S. Pat. No. 8,355,769 (Levendowski et al., Jan. 15, 2013, "System for the Assessment of Sleep Quality in Adults and Children"), U.S. Pat. No. 8,463,354 (Fadem, Jun. 11, 2013, "Electrode System with Rigid-Flex Circuit"), U.S. Pat. No. 8,639,313 (Westbrook et al, Jan. 28, 2014, "System for the Assessment of Sleep Quality in Adults and Children"); and U.S. patent applications 20100125190 (Fadem, May 20, 2010, "Electrode System"), 20100240982 (Westbrook et al., Sep. 23, 2010, "System for the Assessment of Sleep Quality in Adults and Children"), and 20130131464 (Westbrook et al., May 23, 2013, "System for the Assessment of Sleep Quality in Adults and Children").

2. Device with [Multiple] Side-to-Side Arcuate Member(s) and EEG/Brainwave Sensor(s)

Devices in this category hold electromagnetic brain activity sensors in contact with (or proximity to) a person's head using (multiple) arcing member(s) which span a person's head from side to side. In an example, side-to-side arcing members can converge near, or over, the person's ears. In an example, devices in this category can be similar to those in the previous category, except having been rotated 90 degrees so that the arcuate members converge on the sides of the person's head rather than the front and rear of the person's head. Devices in this category can hold a relatively large number of electromagnetic brain activity sensors along arcuate side-to-side lines on a person's head. However, such devices tend to be too obtrusive to wear during the activities of daily life.

Prior art which appears to be within this category includes U.S. Pat. No. 4,836,219 (Hobson et al., Jun. 6, 1989, "Electronic Sleep Monitor Headgear"), U.S. Pat. No. 5,800,351 (Mann, Sep. 1, 1998, "Electrode Supporting Head Set"), U.S. Pat. No. 6,574,513 (Collura et al., Jun. 3, 2003, "EEG Electrode Assemblies"), U.S. Pat. No. 7,158,822 (Payne Jr., Jan. 2, 2007, "Electrode Holder, Headwear, and Wire Jacket Adapted for Use in Sleep Apnea Testing"), and U.S. Pat. No. 7,885,706 (Ludvig et al., Feb. 8, 2011, "System and Device for Seizure Detection").

Prior art which appears to be within this category also includes U.S. patent applications: 20030018278 (Jordan, Jan. 23, 2003, "Electroencephalogram Acquisition Unit and System"), 20050277821 (Payne, Dec. 15, 2005, "Electrode Holder, Headwear, and Wire Jacket Adapted for Use in Sleep Apnea Testing"), 20070112262 (Payne, May 17, 2007, "Electrode Holder, Headwear, and Wire Jacket Adapted for Use in Sleep Apnea Testing"), 20080082019 (Ludving et al., Apr. 3, 2008, "System and Device for Seizure Detection"), 20090281446 (Ludvig et al., Nov. 12, 2009, "System and Device for Seizure Detection"), 20110015503 (Joffe et al., Jan. 20, 2011, "Medical Apparatus for Collecting Patient Electroencephalogram (EEG) Data"), and 20110270117 (Warwick et al., Nov. 3, 2011, "Remote Continuous Seizure Monitor and Alarm").

3. Device with Multiple Cross-Crossing Arcuate Members and EEG/Brainwave Sensor(s)

Devices in this category hold electromagnetic brain activity sensors in contact with (or proximity to) a person's head using multiple arcing members which span a person's head from front-to-rear and also multiple arcing members which span a person's head from side-to-side. In an example, the front-to-rear arcuate members and the side-to-side arcuate members can form a criss-cross pattern on the person's head. Devices in this category can hold a relatively large number of electromagnetic brain activity sensors on a person's head. However, such devices tend to be too obtrusive to wear during the activities of daily life.

Prior art which appears to be within this category includes U.S. Pat. No. 3,998,213 (Price, Dec. 21, 1976, "Self-Adjustable Holder for Automatically Positioning Electroencephalographic Electrodes"), U.S. Pat. No. 5,293,867 (Oommen, Mar. 15, 1994, "Method and Apparatus for Marking Electrode Locations for Electroencephalographic Procedure"), U.S. Pat. No. 5,479,934 (Imran, Jan. 2, 1996, "EEG Headpiece with Disposable Electrodes and Apparatus and System and Method for Use Therewith"), U.S. Pat. No. 6,488,617 (Katz, Dec. 3, 2002, "Method and Device for Producing a Desired Brain State"), U.S. Pat. No. 8,463,354 (Fadem, Jun. 11, 2013, "Electrode System with Rigid-Flex Circuit"); and U.S. patent applications 20030018278 (Jordan, Jan. 23, 2003, "Electroencephalogram Acquisition Unit and System"), and 20100125190 (Fadem, May 20, 2010, "Electrode System").

4. Device with Multiple Arms Radially-Extending from Side and EEG/Brainwave Sensor(s)

Devices in this category hold electromagnetic brain activity sensors in contact with (or proximity to) a person's head using multiple sensor-holding protrusions, fingers, or arms which extend radially outward from a central position on one side (or from central positions on both sides) of a person's head. In an example, such devices can include bilateral clusters (one on each side of the head) of radially-extending protrusions, fingers, or arms. In an example, radially-extending protrusions, fingers, or arms can curve around the head toward the front, top, and/or rear portions of the head. To use colorful language, some such devices can look like a wearer has one or two starfish (or even octopi) clinging to the sides of their head. Such devices can be less obtrusive than those in the preceding categories (especially when they do not span the forehead or the top of the head), but can still attract attention if worn during the activities of daily life.

Prior art which appears to be within this category includes U.S. Pat. No. 5,954,667 (Finkenzeller et al., Sep. 21, 1999, "Device for Deriving Acoustically Evoked Brain Potentials"), U.S. Pat. No. 8,271,075 (Chuang et al., Sep. 18, 2012, "Audio Headset with Bio-Signal Sensors"), U.S. Pat. No. 8,392,250 (Pradeep et al., Mar. 5, 2013, "Neuro-Response Evaluated Stimulus in Virtual Reality Environments"), U.S. Pat. No. 8,392,251 (Pradeep et al., Mar. 5, 2013, "Location Aware Presentation of Stimulus Material"), U.S. Pat. No. 8,396,744 (Pradeep et al., Mar. 12, 2013, "Effective Virtual Reality Environments for Presentation of Marketing Materials"), U.S. Pat. No. 8,548,852 (Pradeep et al., Oct. 1, 2013, "Effective Virtual Reality Environments for Presentation of Marketing Materials"), and U.S. Pat. No. 8,655,428 (Pradeep et al., Feb. 18, 2014, "Neuro-Response Data Synchronization").

Prior art which appears to be within this category also includes U.S. patent applications: 20070106169 (Fadem, May 10, 2007, "Method and System for an Automated E.E.G. System for Auditory Evoked Responses"), 20070191727 (Fadem, Aug. 16, 2007, "Evoked Response Testing System for Neurological Disorders"), 20070225585 (Washbon and Delic, Sep. 27, 2007, "Headset for Electrodes"), 20070238945 (Delic et al., Oct. 11, 2007, "Electrode Headset"), 20080208072 (Fadem et al., Aug. 28, 2008, "Biopotential Waveform Data Fusion Analysis and Classification Method"), 20110237971 (Pradeep et al., Sep. 29, 2011, "Discrete Choice Modeling Using Neuro-Response Data"), and 20110282231 (Pradeep et al., Nov. 17, 2011, "Mechanisms for Collecting Electroencephalography Data").

Prior art which appears to be within this category also includes U.S. patent applications: 20110282232 (Pradeep et al., Nov. 17, 2011, "Neuro-Response Data Synchronization"), 20120072289 (Pradeep et al., Mar. 22, 2012, "Biometric Aware Content Presentation"), 20130131537 (Tam, May 23, 2013, "Tong Ren Brainwave Entrainment"), 20130185144 (Pradeep et al., Jul. 18, 2013, "Systems and Methods for Analyzing Neuro-Reponse Data and Virtual Reality Environments"), 20130314243 (Le, Nov. 28, 2013, "System and Method for Enabling Collaborative Analysis of a Biosignal"), 20130317382 (Le, Nov. 28, 2013, "System and Method for Providing and Aggregating Biosignals and Action Data"), and 20130317384 (Le, Nov. 28, 2013, "System and Method for Instructing a Behavior Change in a User").

5. Device with Multiple Arms Radially-Downward from Top and EEG/Brainwave Sensor(s)

Devices in this category hold electromagnetic brain activity sensors in contact with (or proximity to) a person's head using multiple sensor-holding protrusions, fingers, or arms which extend radially downward from a position on the top of a person's head. In an example, radially-extending protrusions, fingers, or arms can curve around the head toward the front, sides, and/or rear portions of the head. To use the colorful language from the previous category, now a figurative starfish (or octopus) is clinging to the top of the person's head. Such devices can be less obtrusive than some of those in the preceding categories, but can still attract attention if worn during the activities of daily life.

Prior art which appears to be within this category includes U.S. Pat. No. 6,067,464 (Musha, May 23, 200, "Electrode"), U.S. Pat. No. 6,154,669 (Hunter et al., Nov. 28, 2000, "Headset for EEG Measurements"), U.S. Pat. No. 6,161,030 (Levendowski et al., Dec. 12, 2000, "Portable EEG Electrode Locator Headgear"), U.S. Pat. No. 6,381,481 (Levendowski et al., Apr. 30, 2002, "Portable EEG Electrode Locator Headgear"), U.S. Pat. No. 7,551,952 (Gevins et al., Jun. 23, 2009, "EEG Electrode Headset"), U.S. Pat. No. 8,103,328 (Turner et al., Jan. 24, 2012, "Self-Locating Sensor Mounting Apparatus"), U.S. Pat. No. 8,392,250 (Pradeep et al., Mar. 5, 2013, "Neuro-Response Evaluated Stimulus in Virtual Reality Environments"), U.S. Pat. No. 8,392,251 (Pradeep et al., Mar. 5, 2013, "Location Aware Presentation of Stimulus Material"), U.S. Pat. No. 8,396,744 (Pradeep et al., Mar. 12, 2013, "Effective Virtual Reality Environments for Presentation of Marketing Materials"), U.S. Pat. No. 8,548,852 (Pradeep et al., Oct. 1, 2013, "Effective Virtual Reality Environments for Presentation of Marketing Materials"), and U.S. Pat. No. 8,655,428 (Pradeep et al., Feb. 18, 2014, "Neuro-Response Data Synchronization").

Prior art which appears to be within this category also includes U.S. patent applications: 20020029005 (Levendowski et al., Mar. 7, 2002, "Portable EEG Electrode Locator Headgear"), 20070093706 (Gevins et al., Apr. 26, 2007, "EEG Electrode Headset"), 20090088619 (Turner et al., Apr. 2, 2009, "Self-Locating Sensor Mounting Apparatus"), 20110098593 (Low et al., Apr. 28, 2011, "Head Harness & Wireless EEG Monitoring System"), 20110237971 (Pradeep et al., Sep. 29, 2011, "Discrete Choice Modeling Using Neuro-Response Data"), 20110282231 (Pradeep et al., Nov. 17, 2011, "Mechanisms for Collecting Electroencephalography Data"), 20110282232 (Pradeep et al., Nov. 17, 2011, "Neuro-Response Data Synchronization"), 20120072289 (Pradeep et al., Mar. 22, 2012, "Biometric Aware Content Presentation"), and 20130185144 (Pradeep et al., Jul. 18, 2013, "Systems and Methods for Analyzing Neuro-Reponse Data and Virtual Reality Environments").

6. Device with Multiple Arms Radially-Forward from Rear and EEG/Brainwave Sensor(s)

Devices in this category hold electromagnetic brain activity sensors in contact with (or proximity to) a person's head using multiple sensor-holding protrusions, fingers, or arms which extend radially forward from a central position at the rear of a person's head. In an example, radially-extending protrusions, fingers, or arms can curve around the head toward the top and sides of the head. To use the colorful language from the previous category, now a figurative starfish (or octopus) is clinging to the back of the person's head. Such devices can be less obtrusive than some of those in the preceding categories, but can still attract attention if worn during the activities of daily life.

Prior art which appears to be within this category includes U.S. Pat. No. 4,770,180 (Schmidt et al., Sep. 13, 1988, "Electroencephalographic Head Set with a Disposable Monitor"), U.S. Pat. No. 4,967,038 (Gevins et al., Oct. 30, 1990, "Dry Electrode Brain Wave Recording System"), U.S. Pat. No. 5,038,782 (Gevins et al., Aug. 13, 1991, "Electrode System for Brain Wave Detection"), and D565735 (Washbon, Apr. 1, 2008, "Electrode Headset"); and U.S. patent applications 20070225585 (Washbon and Delic, Sep. 27, 2007, "Headset for Electrodes"), 20070238945 (Delic et al., Oct. 11, 2007, "Electrode Headset"), 20090105576 (Do et al., Apr. 23, 2009, "Electrode Conductive Element"), 20120029379 (Sivadas, Feb. 2, 2012, "Mind Strength Trainer"), and 20130046206 (Preminger, Feb. 21, 2013, "System and Method for Neurocognitive Training and/or Neuropsychological Assessment").

7. Device with Multiple Arms Radially-Backward from Front and EEG/Brainwave Sensor(s)

Devices in this category hold electromagnetic brain activity sensors in contact with (or proximity to) a person's head using multiple sensor-holding protrusions, fingers, or arms which extend radially backward from a position on the front of a person's head (such as the forehead). In an example, radially-extending protrusions, fingers, or arms can curve around the head toward the top and sides of the head. Such devices can be obtrusive and attract attention, especially if worn to a showing of the movie "Aliens". Prior art which appears to be within this category includes U.S. patent application 20020188216 (Kayyali et al., Dec. 12, 2002, "Head Mounted Medical Device").

8. Device with Circular Horizontal Loop (e.g. Headband Style) and EEG/Brainwave Sensor(s)

Devices in this category hold electromagnetic brain activity sensors in contact with (or proximity to) a person's head using a sensor-holding member which is configured like a headband, ring, or other generally-circular member which encircles a person's head in (or close to) a horizontal plane when the person is upright. In an example, such a device can span a portion of a person's forehead as it encircles the person's head. Since devices in this category can span a portion of the forehead, such devices can be used with sensors which require contact with (or proximity to) portions of the head which do not have hair. Such devices can be appropriate for wearing while running or doing other types of exercise, but there are still many settings wherein wearing a headband or head-encircling ring is generally not appropriate.

Prior art which appears to be within this category includes U.S. Pat. No. 6,001,065 (Devito, Dec. 14, 1999, "Method and Apparatus for Measuring and Analyzing Physiological Signals for Active or Passive Control of Physical and Virtual Spaces and the Contents Therein"), U.S. Pat. No. 6,171,258 (Karakasoglu et al., Jan. 9, 2001, "Multi-Channel Self-Contained Apparatus and Method for Diagnosis of Sleep Disorders"), U.S. Pat. No. 6,254,536 (Devito, Jul. 3, 2001, "Method and Apparatus for Measuring and Analyzing Physiological Signals for Active or Passive Control of Physical and Virtual Spaces and the Contents Therein"), U.S. Pat. No. 6,811,538 (Westbrook et al., Nov. 2, 2004, "Sleep Apnea Risk Evaluation"), U.S. Pat. No. 7,297,119 (Westbrook et al., Nov. 20, 2007, "Sleep Apnea Risk Evaluation"), and U.S. Pat. No. 7,885,706 (Ludvig et al., Feb. 8, 2011, "System and Device for Seizure Detection").

Prior art which appears to be within this category also includes U.S. patent applications: 20010056225 (DeVito, Dec. 27, 2001, "Method and Apparatus for Measuring and Analyzing Physiological Signals for Active or Passive Control of Physical and Virtual Spaces and the Contents Therein"), 20020165462 (Westbrook et al., Nov. 7, 2002, "Sleep Apnea Risk Evaluation"), 20020188216 (Kayyali et al., Dec. 12, 2002, "Head Mounted Medical Device"), 20040267152 (Pineda, Dec. 20, 2004, "Method and System for Predicting and Preventing Seizures"), 20050027207 (Westbrook et al., Feb. 3, 2005, "Sleep Apnea Risk Evaluation"), and 20070249952 (Rubin et al., Oct. 25, 2007, "Systems and Methods for Sleep Monitoring").

Prior art which appears to be within this category also includes U.S. patent applications: 20080082019 (Ludving et al., Apr. 3, 2008, "System and Device for Seizure Detection"), 20090281446 (Ludvig et al., Nov. 12, 2009, "System and Device for Seizure Detection"), 20100099954 (Dickinson et al., Apr. 22, 2010, "Data-Driven Sleep Coaching System"), 20120150545 (Simon, Jun. 14, 2012, "Brain-Computer Interface Test Battery for the Physiological Assessment of Nervous System Health"), 20130060097 (Rubin, Mar. 7, 2013, "Multi-Modal Sleep System"), 20130127708 (Jung et al., May 23, 2013, "Cell-Phone Based Wireless and Mobile Brain-Machine Interface"), and 20130338446 (Van Vugt et al., Dec. 19, 2013, "Sleep Disturbance Monitoring Apparatus").

9. Device with Top Semicircular Loop (e.g. Headphone Style) and EEG/Brainwave Sensor(s)

Devices in this category hold electromagnetic brain activity sensors in contact with (or proximity to) a person's head using a (semicircular) arcuate member which looks like a set of headphones, hair band, or tiara. In an example, such a device can loop over the top of a person's head, from one side to the other side. In an example, such a device can loop over the top of a person's head from one ear to the other ear. In example, such a device can not only look like a set of headphones, but can actually be a set of headphones, wherein these headphones also include one or more electromagnetic brain activity sensors. Wearing a set of headphones or a hair band is more common (and thus may attract less attention) than wearing most of the devices discussed in preceding categories, but there are still many settings wherein wearing such a device would attract attention and be inappropriate.

Prior art which appears to be within this category includes U.S. Pat. No. 4,697,598 (Bernard et al., Oct. 6, 1987, "Evoked Potential Autorefractometry System"), U.S. Pat. No. 4,709,702 (Sherwin, Dec. 1, 1987, "Electroencephalographic Cap"), U.S. Pat. No. 5,740,812 (Cowan, Apr. 21, 1998, "Apparatus for and Method of Providing Brainwave Biofeedback"), U.S. Pat. No. 6,154,669 (Hunter et al., Nov. 28, 2000, "Headset for EEG Measurements"), U.S. Pat. No. 6,167,298 (Levin, Dec. 26, 2000, "Devices and Methods for Maintaining an Alert State of Consciousness Through Brain Wave Monitoring"), U.S. Pat. No. 7,689,274 (Mullen et al., Mar. 30, 2010, "Brain-Wave Aware Sleep Management"), U.S. Pat. No. 8,271,075 (Chuang et al., Sep. 18, 2012, "Audio Headset with Bio-Signal Sensors"), and U.S. Pat. No. 8,301,218 (Nguyen et al., Oct. 30, 2012, "Contoured Electrode"), U.S. Pat. No. 8,812,075 (Nguyen et al., Aug. 19, 2014, "Contoured Electrode").

Prior art which appears to be within this category also includes U.S. patent applications: 20120029379 (Sivadas, Feb. 2, 2012, "Mind Strength Trainer"), 20120226127 (Asjes et al., Sep. 6, 2012, "Device for Positioning Electrodes on a User's Scalp"), 20130177883 (Barnehama et al., Jul. 11, 2013, "Systems and Methods for Directing Brain Activity"), and 20130310676 (Jung, Nov. 21, 2013, "EEG Hair Band").

10. Device with Rear Semicircular Loop and EEG/Brainwave Sensor(s)

Devices in this category hold electromagnetic brain activity sensors in contact with (or proximity to) a person's head using a (semicircular) arcuate member which loops around the rear portion of a person's head, from one side to the other side. In an example, such a device can loop around the rear portion of a person's head from one ear to the other ear. Such a device can be less obtrusive than many of the devices in preceding categories because it does not span the top of the head or face, but it is not well-suited for use with sensors which require contact with skin without hair. Prior art which appears to be within this category includes U.S. patent application 20140316230 (Denison et al., Oct. 23, 2014, "Methods and Devices for Brain Activity Monitoring Supporting Mental State Development and Training").

11. Device with Frontal Semicircular Loop and EEG/Brainwave Sensor(s)

Devices in this category hold electromagnetic brain activity sensors in contact with (or proximity to) a person's head using a (semicircular) arcuate member which loops around the front of a person's head, from one side to the other side. In an example, such a device can loop around the front of a person's head from one ear to the other ear. In an example, such a device can span a person's forehead. Such a device can be well-suited for use with sensors which require contact with skin without hair, but can be somewhat obtrusive since it spans a portion of a person's face. Prior art which appears to be within this category includes U.S. patent application 20080177197 (Lee et al., Jul. 24, 2008, "Method and Apparatus for Quantitatively Evaluating Mental States Based on Brain Wave Signal Processing System").

12. Device Like Eyeglasses or Other Eyewear with EEG/Brainwave Sensor(s)

Devices in this category hold electromagnetic brain activity sensors in contact with (or proximity to) a person's head using a sensor-holding member which looks like a pair of eyeglasses, goggles, or other eyewear. In an example, such a device can span from one ear, to the face, across the face (over the bridge of the nose), and then to the other ear. In example, such a device can not only look like a pair of eyeglasses, but can actually be a pair of eyeglasses, wherein these eyeglasses include one or more electromagnetic brain activity sensors. Some of the art in this category predominantly focuses on the optical aspects of a pair of eyeglasses, with only tangential mention of a possible EEG sensor, but such art is included in this category for the sake of completeness. Wearing a pair of eyeglasses is very common and thus attracts less attention than virtually all of the devices discussed in preceding categories. However, conventional eyeglass frames (especially those with straight side pieces) do not contact a person's temple or forehead. Accordingly, conventional eyeglass frame configurations are not ideally-suited for holding one or more electromagnetic brain activity sensors in contact with a person's temple and/or forehead.

Prior art which appears to be within this category includes U.S. Pat. No. 7,344,244 (Goodall et al., Mar. 18, 2008, "Adjustable Lens System with Neural-Based Control"), U.S. Pat. No. 7,390,088 (Goodall et al., Jun. 24, 2008, "Adjustable Lens System with Neural-Based Control"), U.S. Pat. No. 7,486,988 (Goodall et al., Feb. 3, 2009, "Method and System for Adaptive Vision Modification"), U.S. Pat. No. 8,244,342 (Goodall et al., Aug. 14, 2012, "Method and System for Adaptive Vision Modification"), U.S. Pat. No. 8,346,354 (Hyde et al., Jan. 1, 2013, "Determining a Neuromodulation Treatment Regimen in Response to Contactlessly Acquired Information"), U.S. Pat. No. 8,467,133 (Miller, Jun. 18, 2013, "See-Through Display with an Optical Assembly Including a Wedge-Shaped Illumination System"), U.S. Pat. No. 8,472,120 (Border et al., Jun. 25, 2013, "See-Through Near-Eye Display Glasses with a Small Scale Image Source"), U.S. Pat. No. 8,477,425 (Border et al., Jul. 2, 2013, "See-Through Near-Eye Display Glasses Including a Partially Reflective, Partially Transmitting Optical Element"), U.S. Pat. No. 8,482,859 (Border et al., Jul. 9, 2013, "See-Through Near-Eye Display Glasses Wherein Image Light Is Transmitted to and Reflected From an Optically Flat Film"), U.S. Pat. No. 8,488,246 (Border et al., Jul. 16, 2013, "See-Through Near-Eye Display Glasses Including a Curved Polarizing Film in the Image Source, a Partially Reflective, Partially Transmitting Optical Element and an Optically Flat Film"), and U.S. Pat. No. 8,562,540 (Goodall et al., Oct. 22, 2013, "Method and System for Adaptive Vision Modification").

Prior art which appears to be within this category also includes U.S. patent applications: 20060252978 (Vesely et al., Nov. 9, 2006, "Biofeedback Eyewear System"), 20060252979 (Vesely et al., Nov. 9, 2006, "Biofeedback Eyewear System"), 20070010757 (Goodall et al., Jan. 11, 2007, "Method and System for Adaptive Vision Modification"), 20070019279 (Goodall et al., Jan. 25, 2007, "Adjustable Lens System with Neural-Based Control"), 20070106145 (Kim et al., May 10, 2007, "Accessories for Remote Monitoring"), 20080161673 (Goodall et al., Jul. 3, 2008, "Method and System for Adaptive Vision Modification"), 20110028798 (Hyde et al., Feb. 3, 2011, "Electronically Initiating an Administration of a Neuromodulation Treatment Regimen Chosen in Response to Contactlessly Acquired Information"), 20110029038 (Hyde et al., Feb. 3, 2011, "Determining a Neuromodulation Treatment Regimen in Response to Contactlessly Acquired Information"), 20110029044 (Hyde et al., Feb. 3, 2011, "Stimulating a Nervous System Component of a Mammal in Response to Contactlessly Acquired Information"), 20110221656 (Haddick et al., Sep. 15, 2011, "Displayed Content Vision Correction with Electrically Adjustable Lens"), and 20110221669 (Shams et al., Sep. 15, 2011, "Gesture Control in an Augmented Reality Eyepiece").

Prior art which appears to be within this category also includes U.S. patent applications: 20110221672 (Osterhout et al., Sep. 15, 2011, "Hand-Worn Control Device in an Augmented Reality Eyepiece"), 20110222745 (Osterhout et al., Sep. 15, 2011, "Method and Apparatus for Biometric Data Capture"), 20110227820 (Haddick et al., Sep. 22, 2011, "Lock Virtual Keyboard Position in an Augmented Reality Eyepiece"), 20120062445 (Haddick et al., Mar. 15, 2012, "Adjustable Wrap Around Extendable Arm for a Head-Mounted Display"), 20120075168 (Osterhout et al., Mar. 29, 2012, "Eyepiece with Uniformly Illuminated Reflective Display"), 20120150545 (Simon, Jun. 14, 2012, "Brain-Computer Interface Test Battery for the Physiological Assessment of Nervous System Health"), 20120212398 (Border et al., Aug. 23, 2012, "See-Through Near-Eye Display Glasses Including a Partially Reflective, Partially Transmitting Optical Element"), and 20120212400 (Border et al., Aug. 23, 2012, "See-Through Near-Eye Display Glasses Including a Curved Polarizing Film in the Image Source, a Partially Reflective, Partially Transmitting Optical Element and an Optically Flat Film").

Prior art which appears to be within this category also includes U.S. patent applications: 20120218172 (Border et al., Aug. 30, 2012, "See-Through Near-Eye Display Glasses with a Small Scale Image Source"), 20120218301 (Miller, Aug. 30, 2012, "See-Through Display with an Optical Assembly Including a Wedge-Shaped Illumination System"), 20120235883 (Border et al., Sep. 20, 2012, "See-Through Near-Eye Display Glasses with a Light Transmissive Wedge Shaped Illumination System"), 20120235886 (Border et al., Sep. 20, 2012, "See-Through Near-Eye Display Glasses with a Small Scale Image Source"), 20120235887 (Border et al., Sep. 20, 2012, "See-Through Near-Eye Display Glasses Including a Partially Reflective, Partially Transmitting Optical Element and an Optically Flat Film"), and 20120235900 (Border et al., Sep. 20, 2012, "See-Through Near-Eye Display Glasses with a Fast Response Photochromic Film System for Quick Transition From Dark to Clear").

Prior art which appears to be within this category also includes U.S. patent applications: 20120236030 (Border et al., Sep. 20, 2012, "See-Through Near-Eye Display Glasses Including a Modular Image Source"), 20120242678 (Border et al., Sep. 27, 2012, "See-Through Near-Eye Display Glasses Including an Auto-Brightness Control for the Display Brightness Based on the Brightness in the Environment"), 20120242698 (Haddick et al., Sep. 27, 2012, "See-Through Near-Eye Display Glasses with a Multi-Segment Processor-Controlled Optical Layer"), 20130056010 (Walker et al., Mar. 7, 2013, "Autonomous Positive Airway Pressure System"), 20130127980 (Haddick et al., May 23, 2013, "Video Display Modification Based on Sensor Input for a See-Through Near-to-Eye Display"), and 20130242262 (Lewis, Sep. 19, 2013, "Enhanced Optical and Perceptual Digital Eyewear").

Prior art which appears to be within this category also includes U.S. patent applications: 20130303837 (Berka et al., Nov. 14, 2013, "Systems and Methods for Optimization of Sleep and Post-Sleep Performance"), 20130314303 (Osterhout et al., Nov. 28, 2013, "AR Glasses with User Action Control of and Between Internal and External Applications with Feedback"), 20140023999 (Greder, Jan. 23, 2014, "Detection and Feedback of Information Associated with Executive Function"), 20140267005 (Urbach, Sep. 18, 2014, "Eye Piece for Augmented and Virtual Reality"), 20140267401 (Urbach, Sep. 18, 2014, "Visual Cortex Thought Detector Interface"), 20140347265 (Aimone et al., Nov. 27, 2014, "Wearable Computing Apparatus and Method"), and 20140375545 (Ackerman et al., Dec. 25, 2014, "Adaptive Event Recognition").

SUMMARY OF THE INVENTION

This invention is a wearable and mobile Brain Computer Interface (BCI) device. In an example, it can comprise: a rear ear-engaging segment; a side segment which spans from the rear ear-engaging segment to a person's temple, to a side portion of the person's face, and/or to a side portion of the person's forehead; a top segment which spans from the side segment to the top of the person's head; at least one electromagnetic energy sensor which collects data concerning electromagnetic brain activity; a data processor; a data transmitter; and a power source. In an example, it can comprise: a forward-upward sloped headband which encircles a person's head; an ear prong which engages a portion of the perimeter of an outer ear; at least one electromagnetic energy sensor which collects data concerning electromagnetic brain activity; a data processor; a data transmitter; and a power source.

In an example, this invention can be embodied in a BCI device comprising: a rear loop which loops around the rear portion or upper-rear portion of a person's head; a rear ear-engaging member; a movable loop, wherein this movable loop has a first configuration in which it loops around the rear or upper-rear portion of a person's head, wherein this movable loop has a second configuration in which it loops across the person's forehead, and wherein this movable loop can be reversibly moved from the first configuration to the second configuration; at least one electromagnetic energy sensor which collects data concerning electromagnetic brain activity; a data processor; a data transmitter; and a power source.

INTRODUCTION TO THE FIGURES

FIG. 2 shows a BCI device with non-connecting right and left side members which engage a person's hair.

FIG. 6 shows a BCI device with non-connecting right and left side loops which engage a person's hair.

Figure 17:
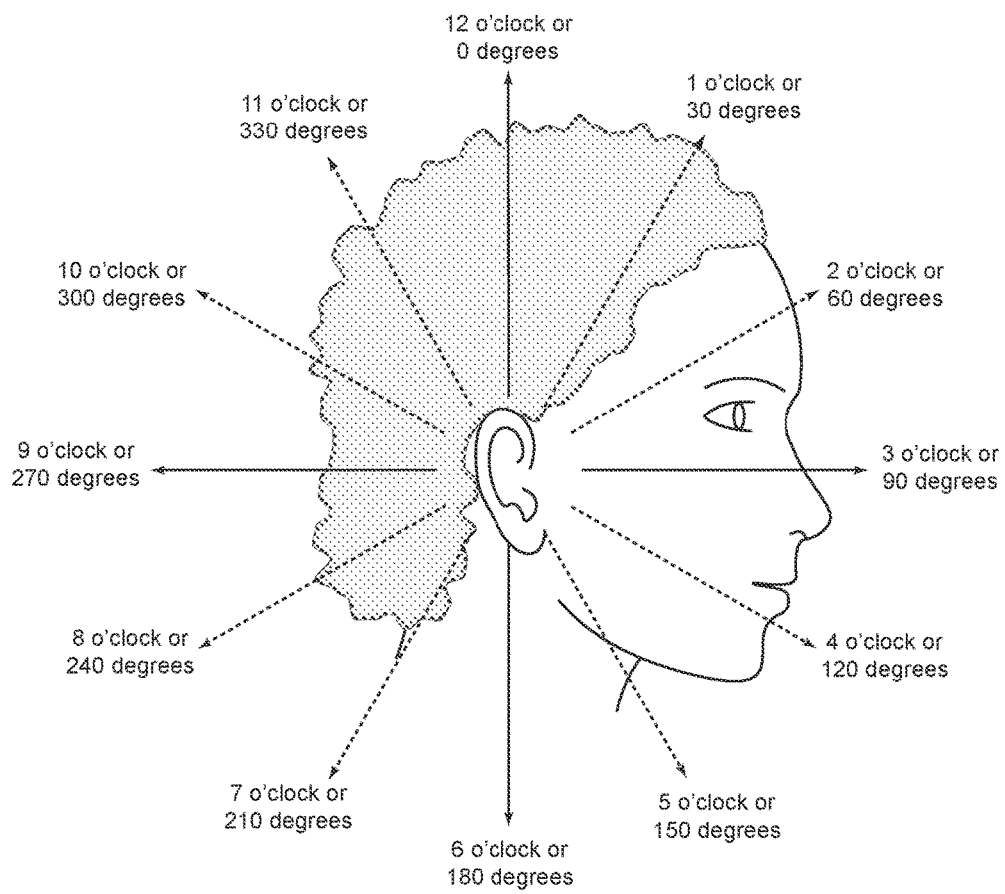

FIG. 17 defines radial clock hour (or degree) vectors around an ear.

Figure 18:
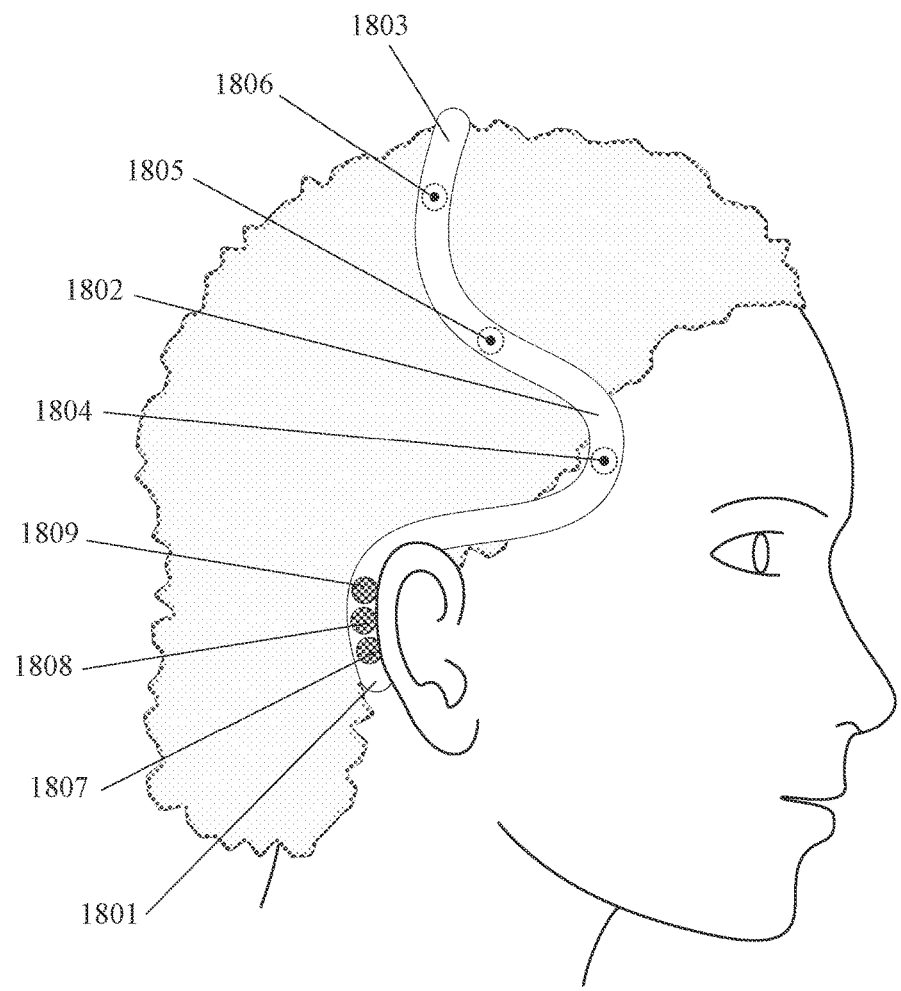

FIG. 18 shows a BCI device which curves around the rear of a person's ear, curves high over the person's temple, and crosses over the top of the person's head.

Figure 19:
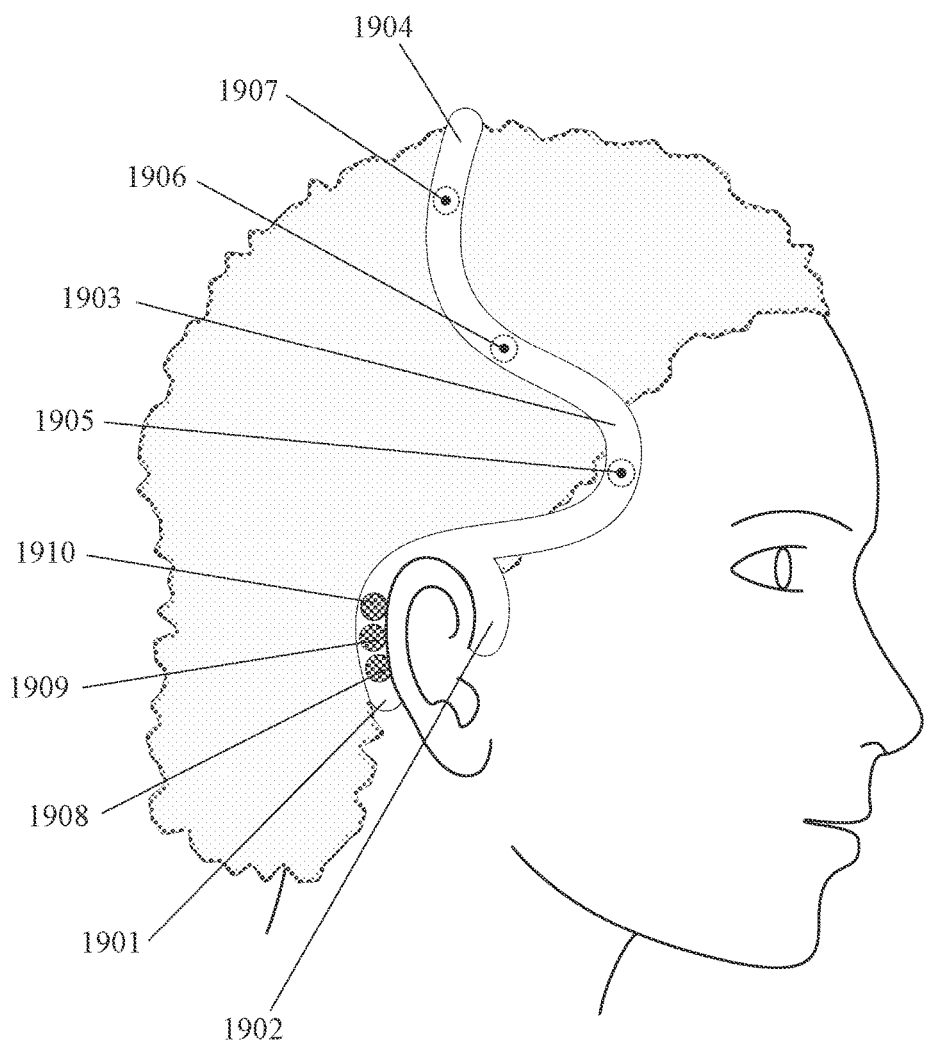

FIG. 19 shows a BCI device which curves around the rear and front of a person's ear, curves high over the person's temple, and crosses over the top of the person's head.

Figure 20:
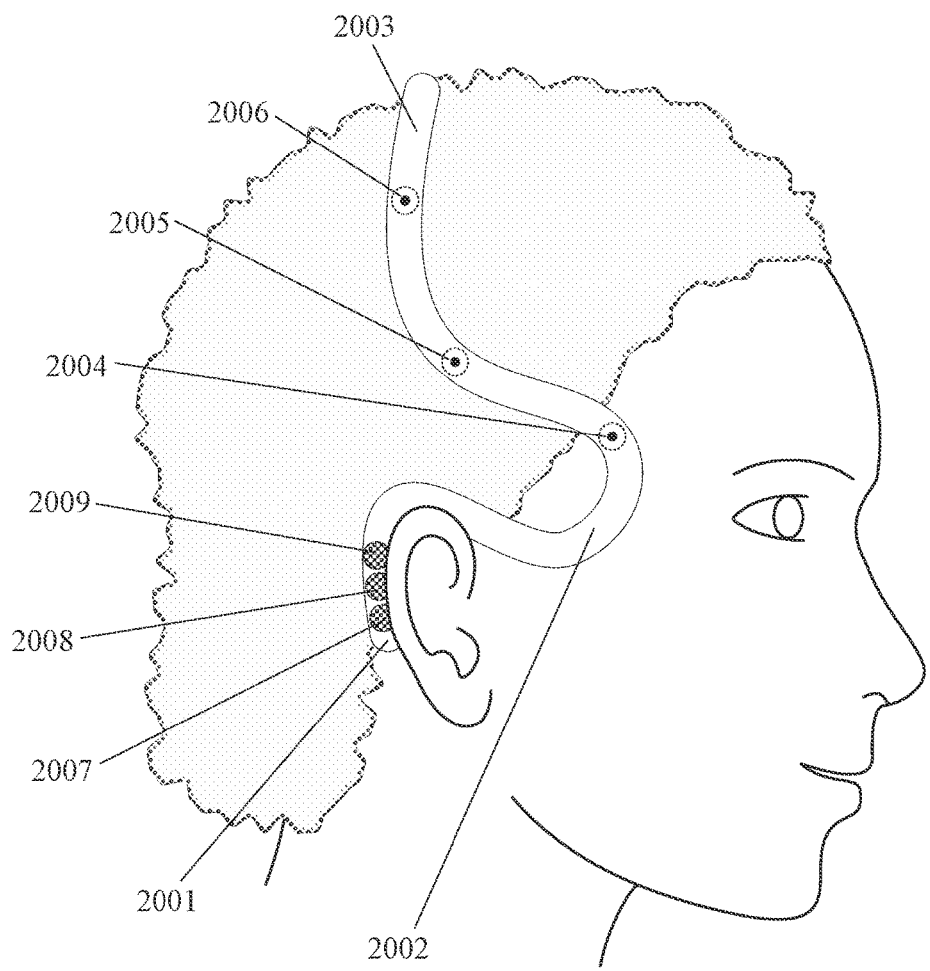

FIG. 20 shows a BCI device which curves around the rear of a person's ear, curves low over the person's temple, and crosses over the top of the person's head.

Figure 21:
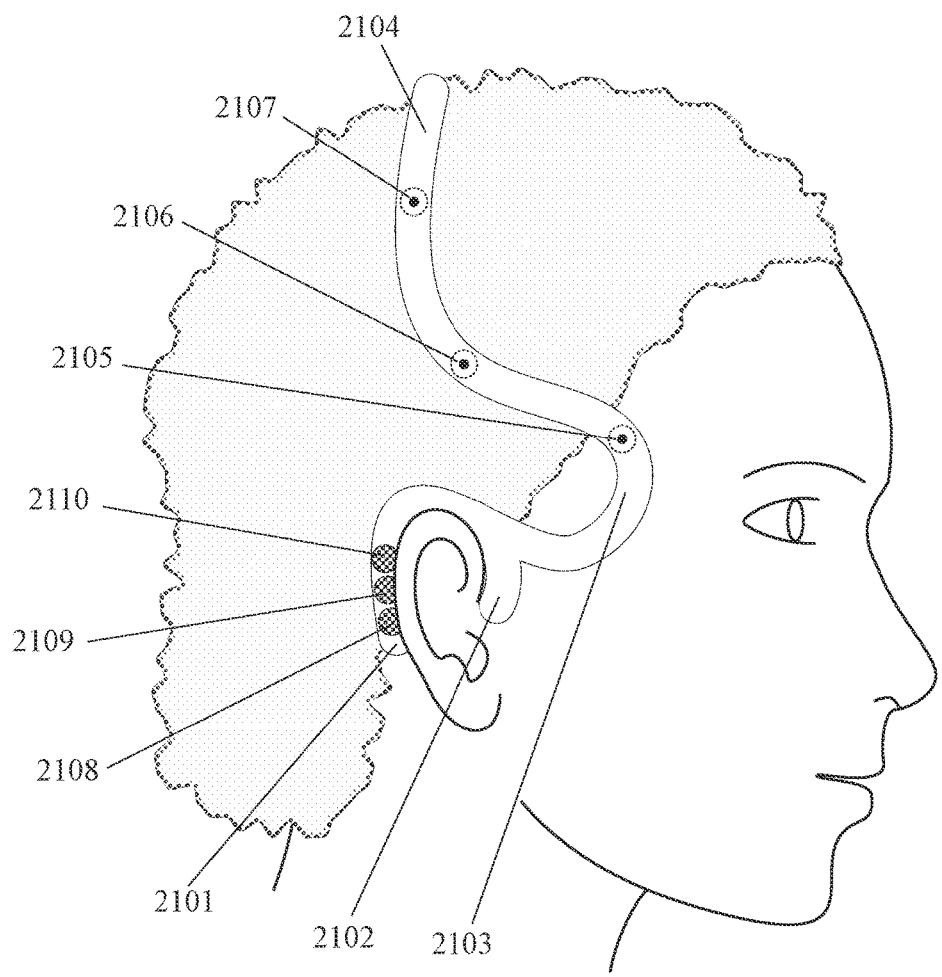

FIG. 21 shows a BCI device which curves around the rear and front of a person's ear, curves low over the person's temple, and crosses over the top of the person's head.

Figure 22:
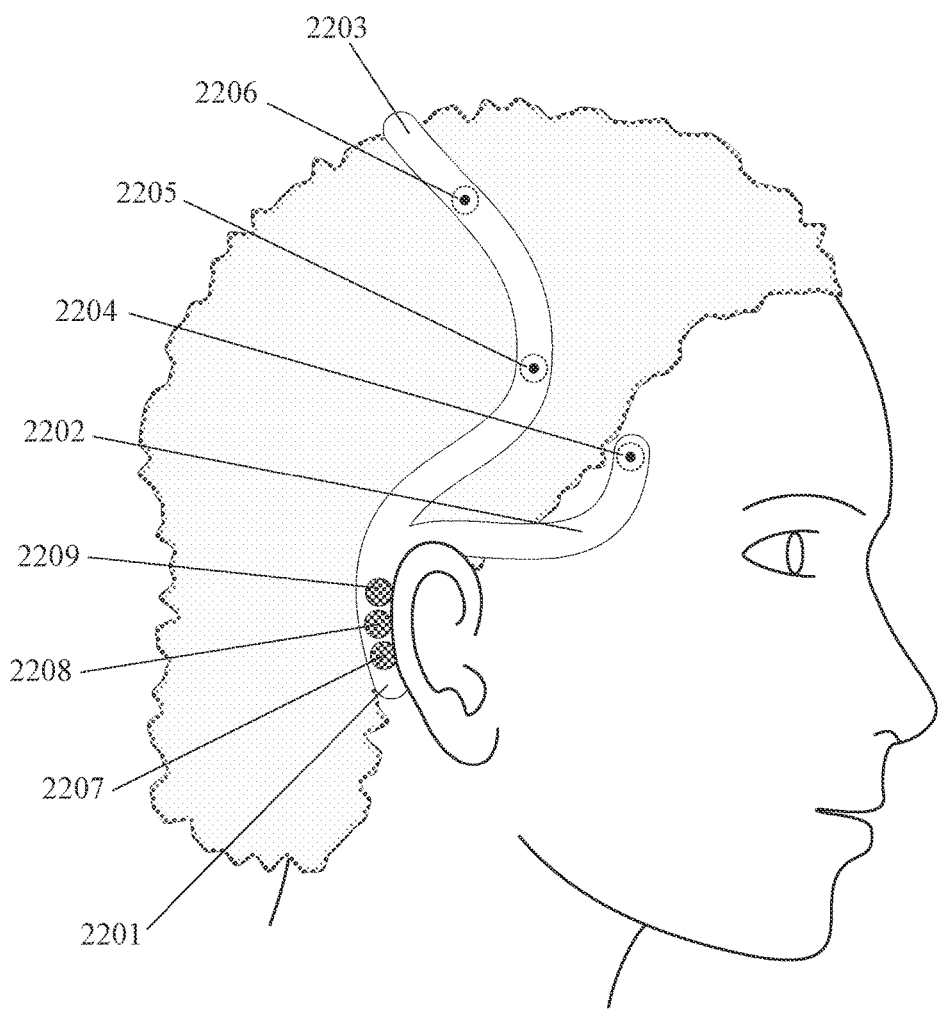

FIG. 22 shows a BCI device which curves around the rear of a person's ear, crosses over the top of the person's head, and also includes a side arm which extends up onto the person's forehead.

Figure 23:
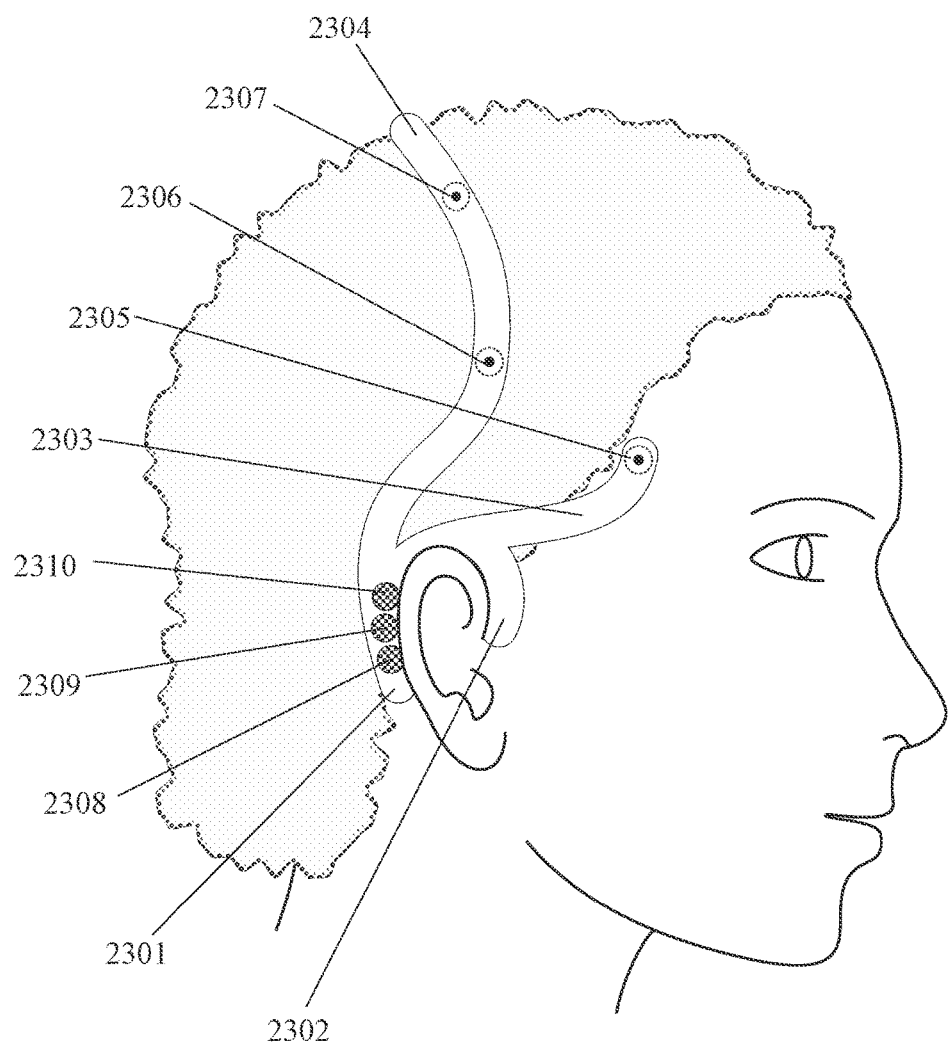

FIG. 23 shows a BCI device which curves around the rear and front of a person's ear, crosses over the top of the person's head, and also includes a side arm which extends up onto the person's forehead.

Figure 24:
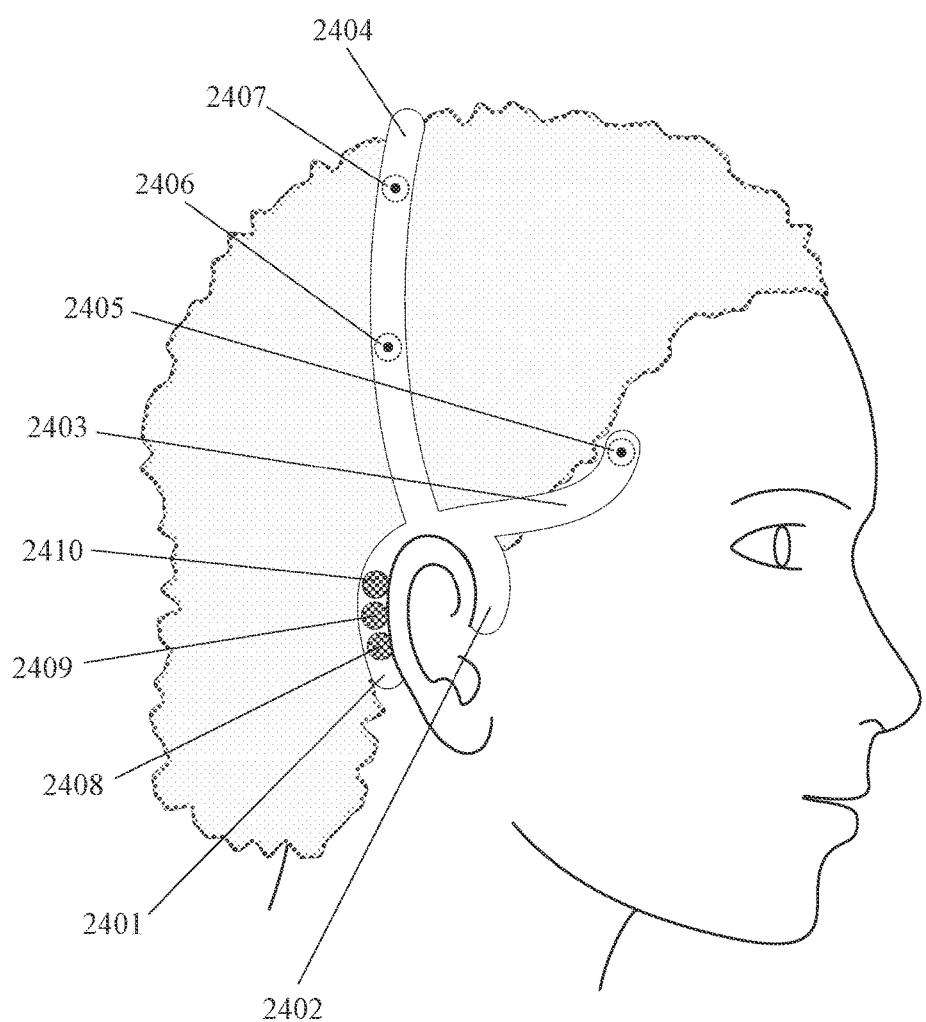

FIG. 24 shows a BCI device which curves around the rear and front of a person's ear, loops around the top of the person's head, and also includes a side arm which extends up onto the person's forehead.

Figure 25:
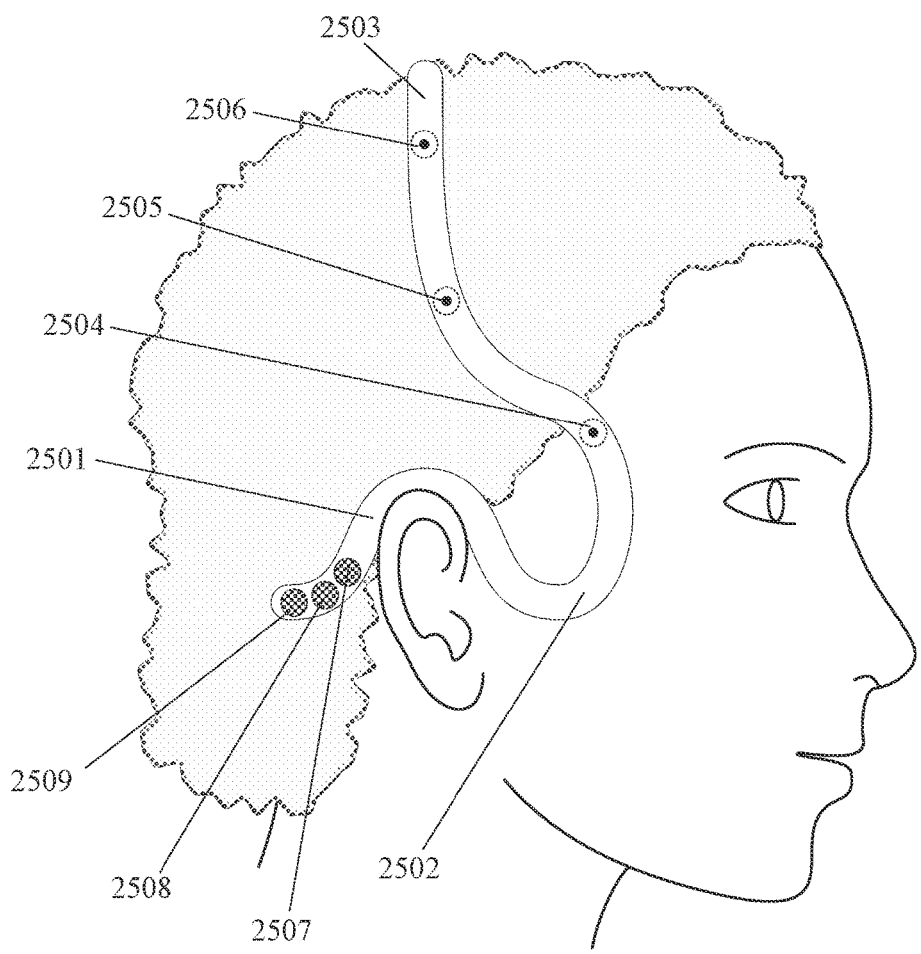

FIG. 25 shows a BCI device which waves over the top of a person's ear, loops across the person's temple, and curves back over the top of the person's head.

Figure 26:
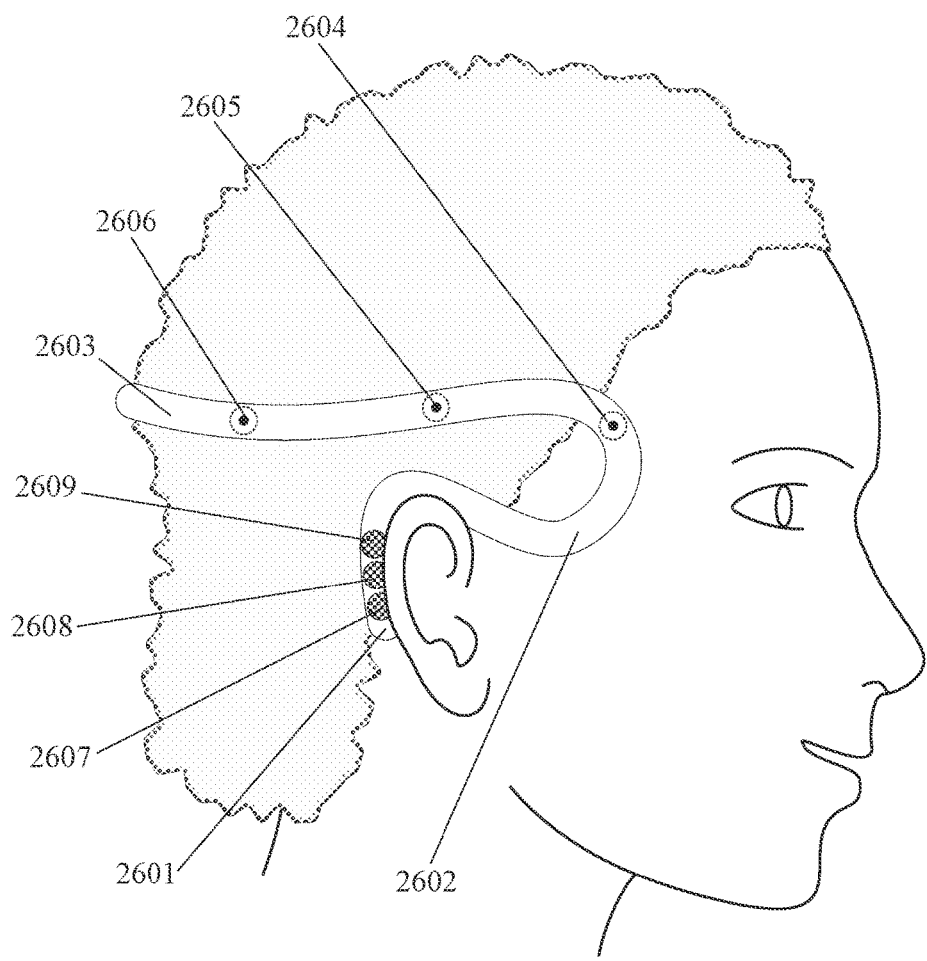

FIG. 26 shows a BCI device which curves around the rear of a person's ear, loops around the person's temple, and then loops around the back of the person's head.

Figure 27:
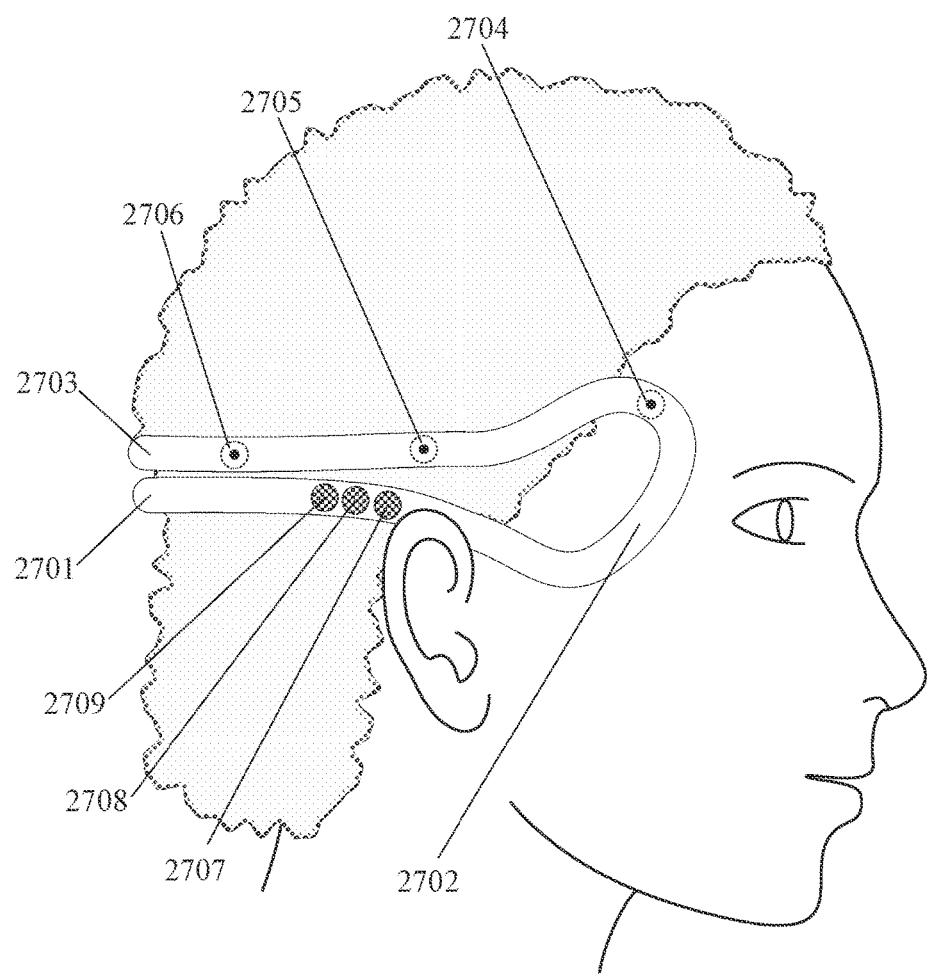

FIG. 27 shows a BCI device which spans forward from the back of a person's head, loops around the person's temple, and then spans backward to the back of the person's head.

Figure 28:
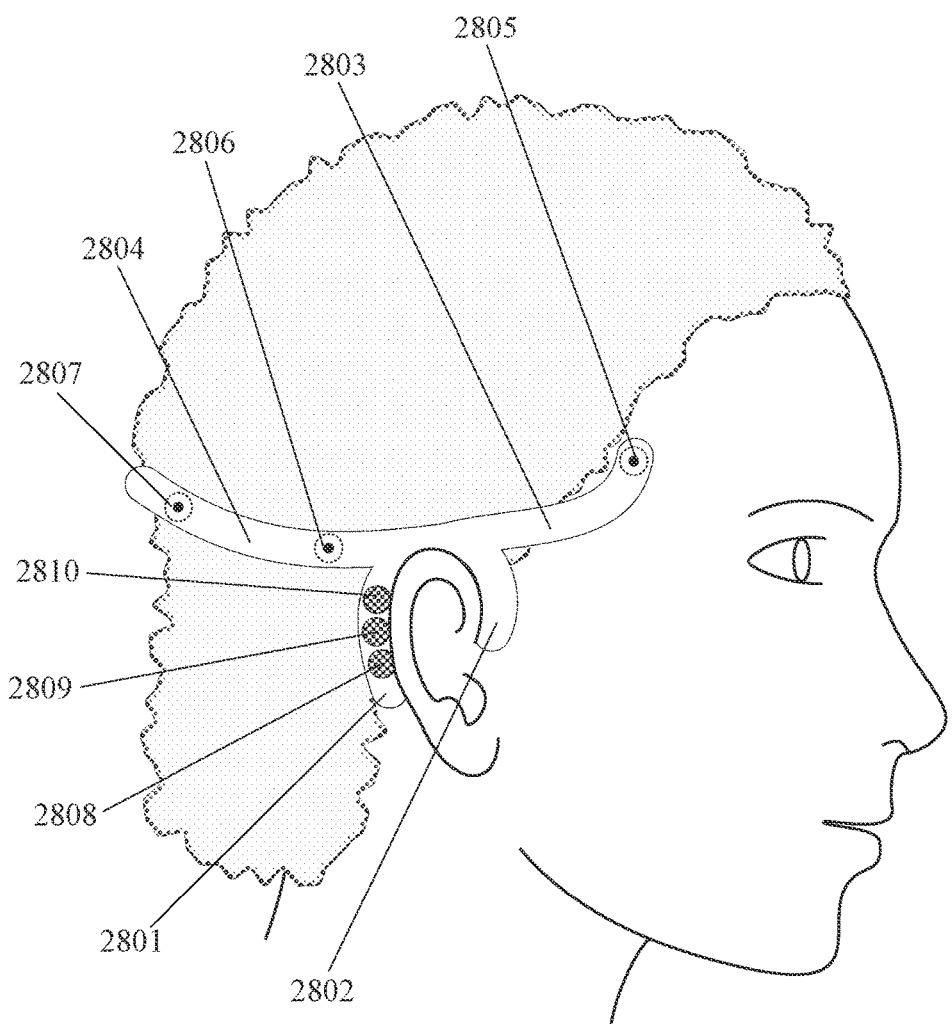

FIG. 28 shows a BCI device which spans forward from the back of a person's head, curves around the rear and front of the person's ear, and protrudes forward to the person's temple.

Figure 29:
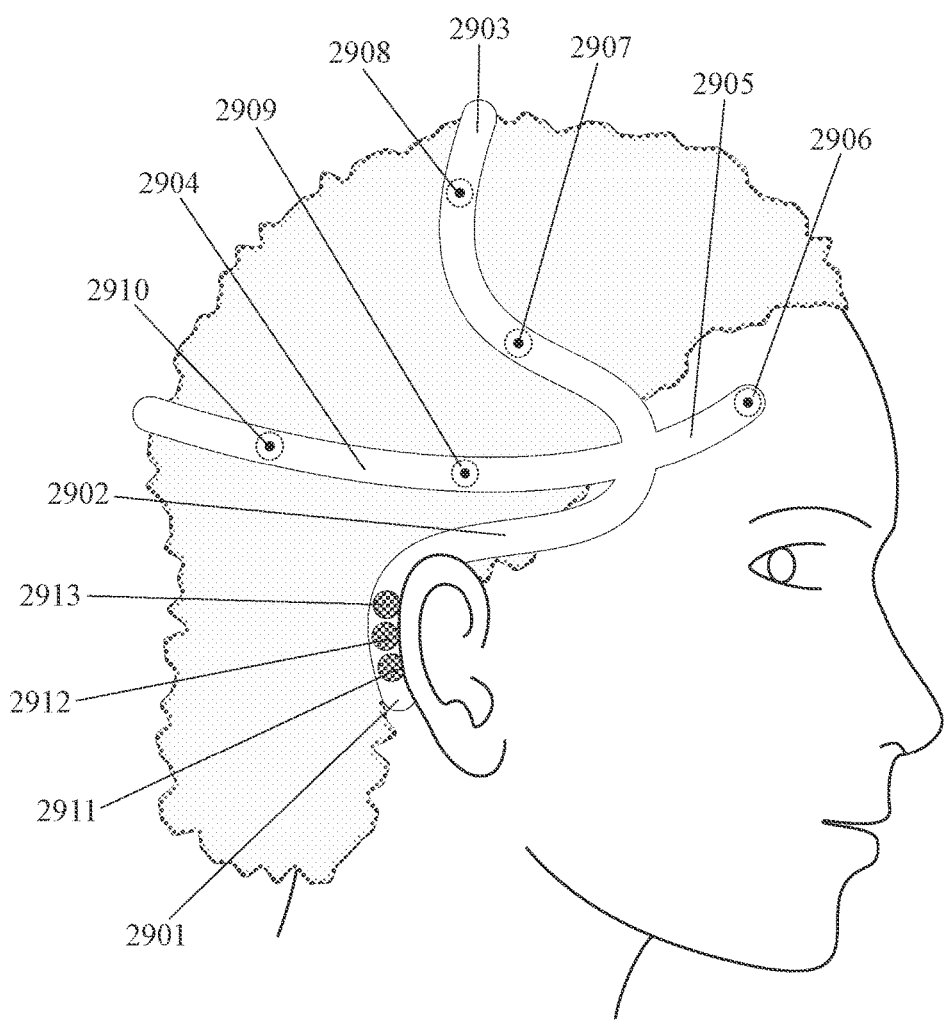

FIG. 29 shows a BCI device with a first segment which loops around the rear of a person's head and protrudes onto the person's forehead; and a second segment which curves around the rear of a person's ear and loops over the top of the person's head.

Figure 30:
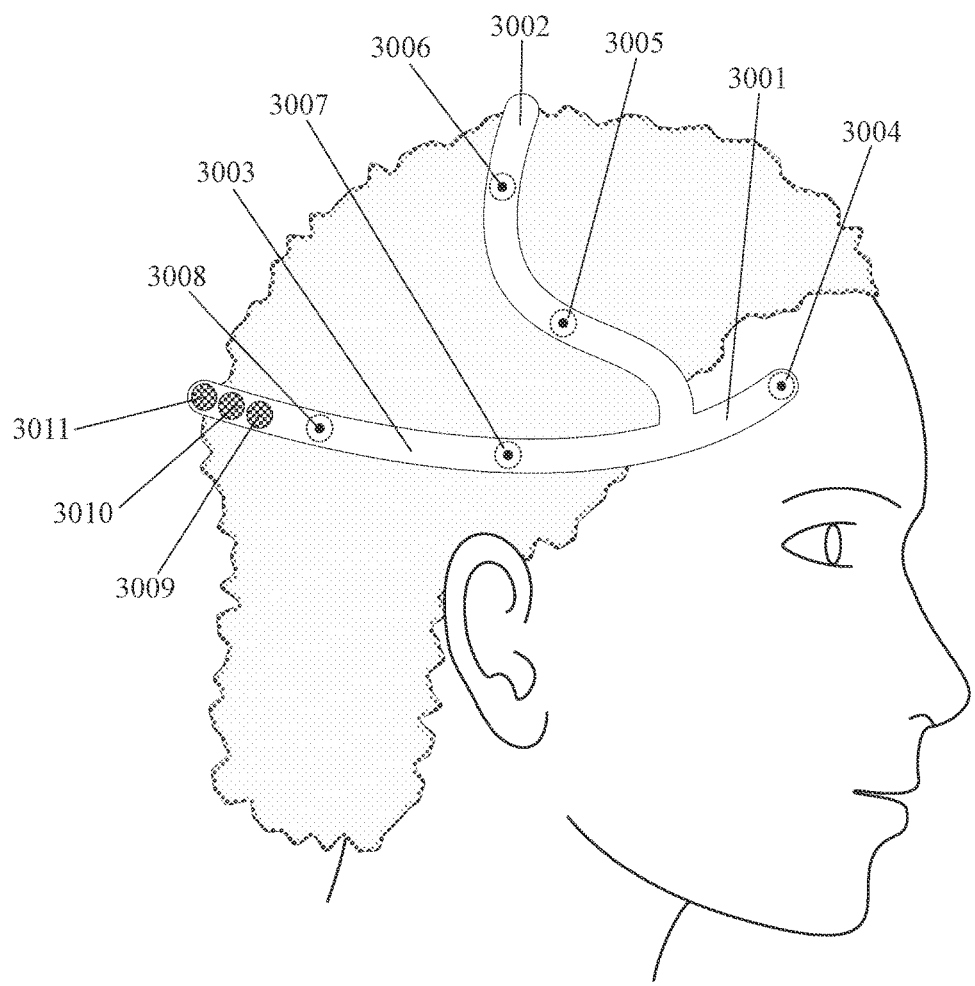

FIG. 30 shows a BCI device with a first segment which loops around the rear of a person's head and protrudes onto the person's forehead; and a second segment which loops over the top of the person's head.

Figure 31:
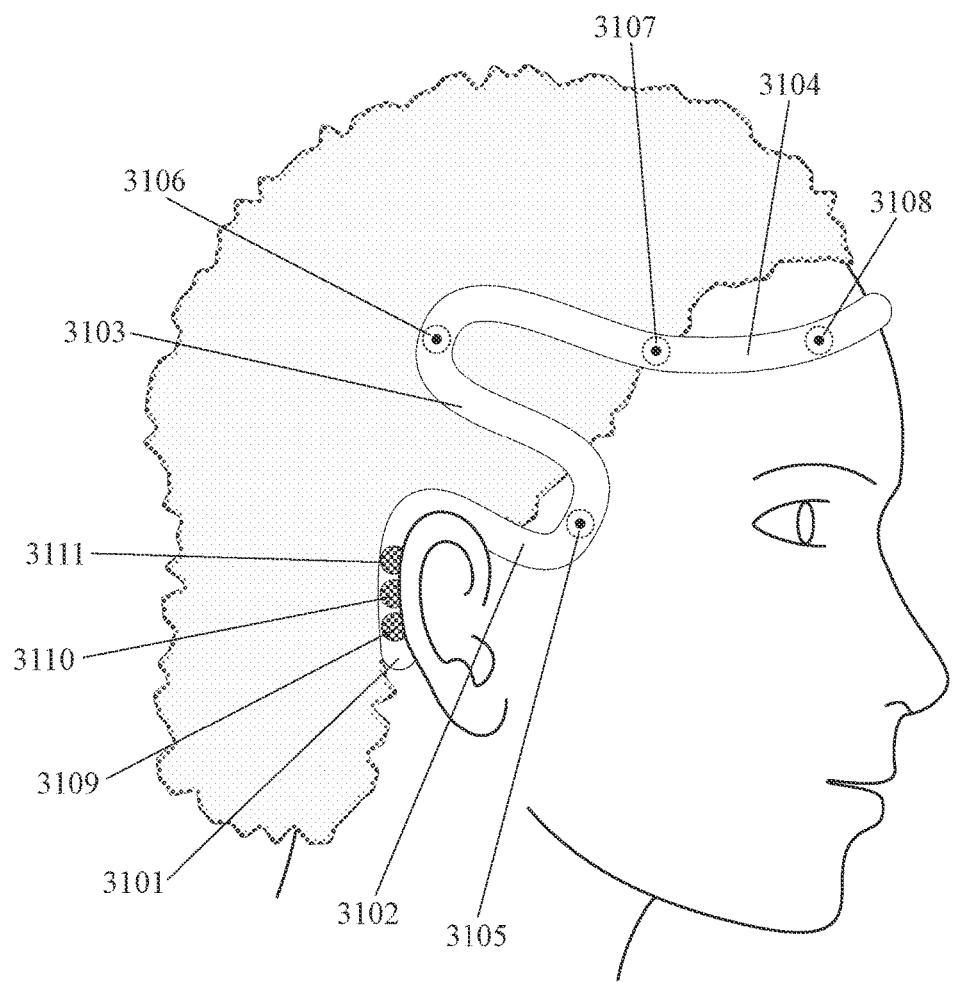

FIG. 31 shows a BCI device with an undulating band that curves around the rear of a person's ear and loops across the person's forehead.

Figure 32:
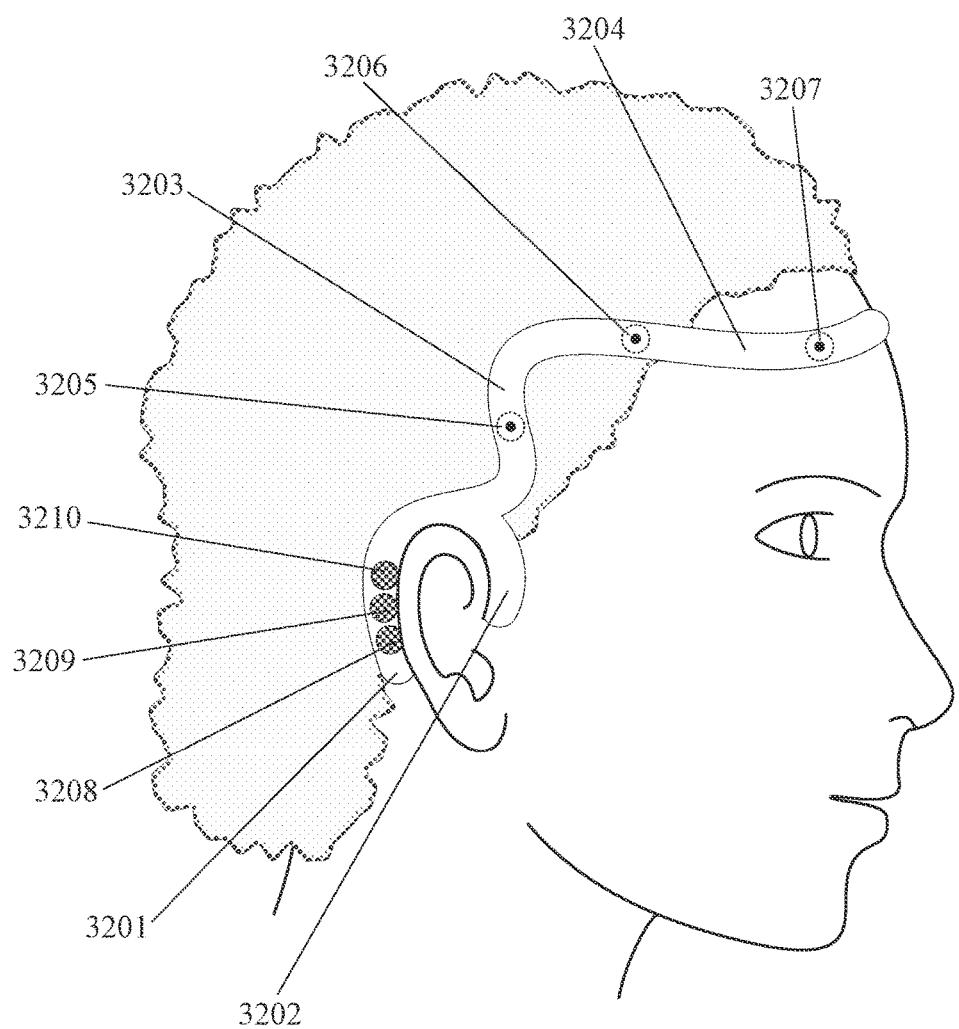

FIG. 32 shows a BCI device that curves around the rear and front of a person's ear and loops across the person's forehead.

Figure 33:
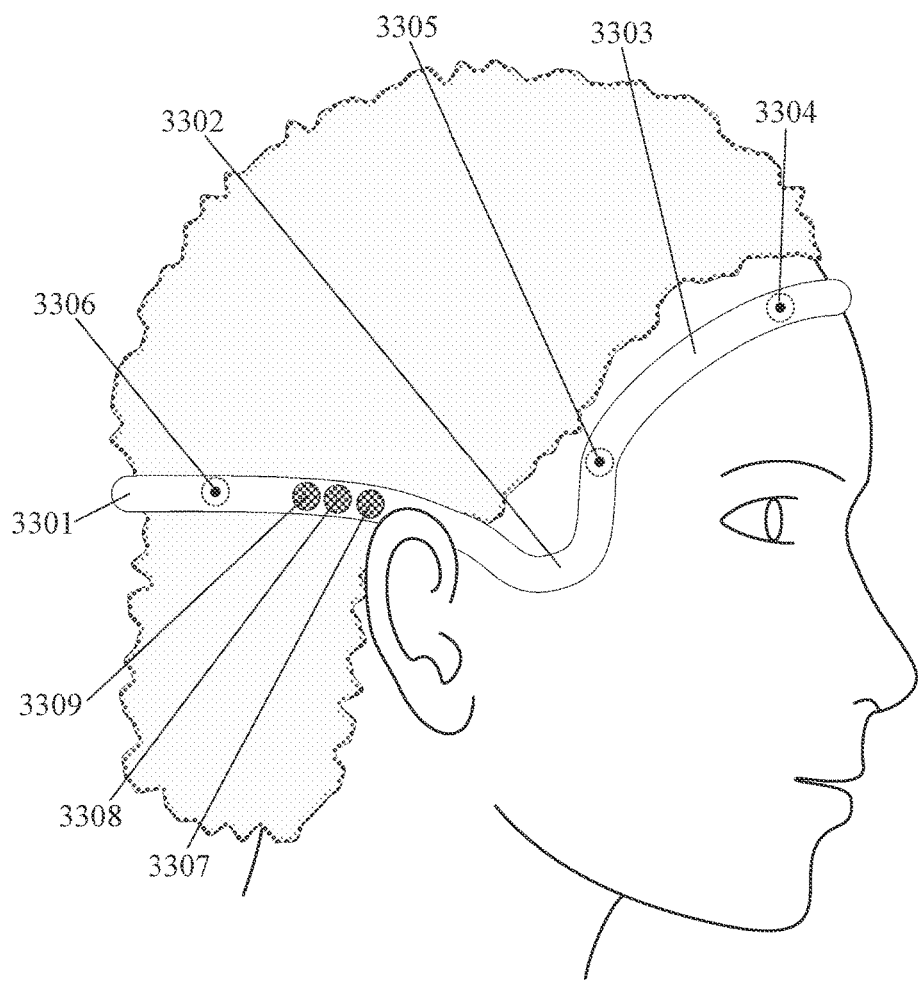

FIG. 33 shows a BCI device that encircles a person's head with a downward wave in front of the person's ear and a loop across the person's forehead.

Figure 34:
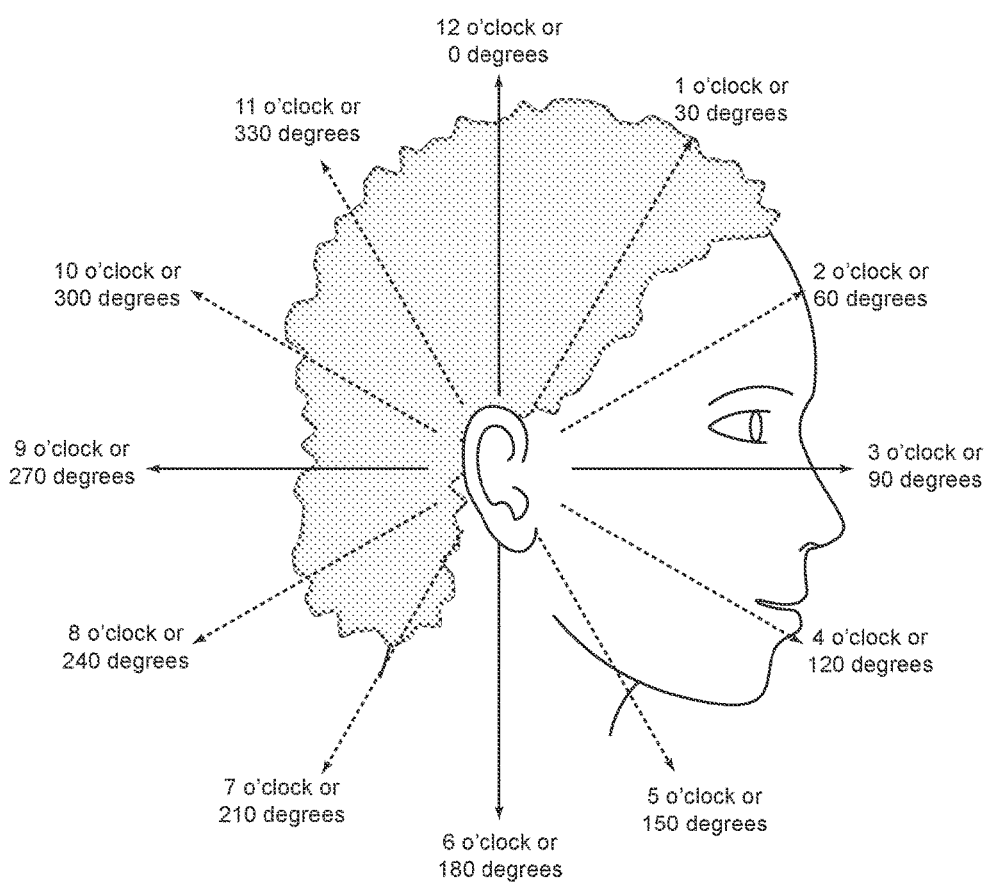

FIG. 34 defines radial clock hour (or degree) vectors around an ear.

Figure 35:
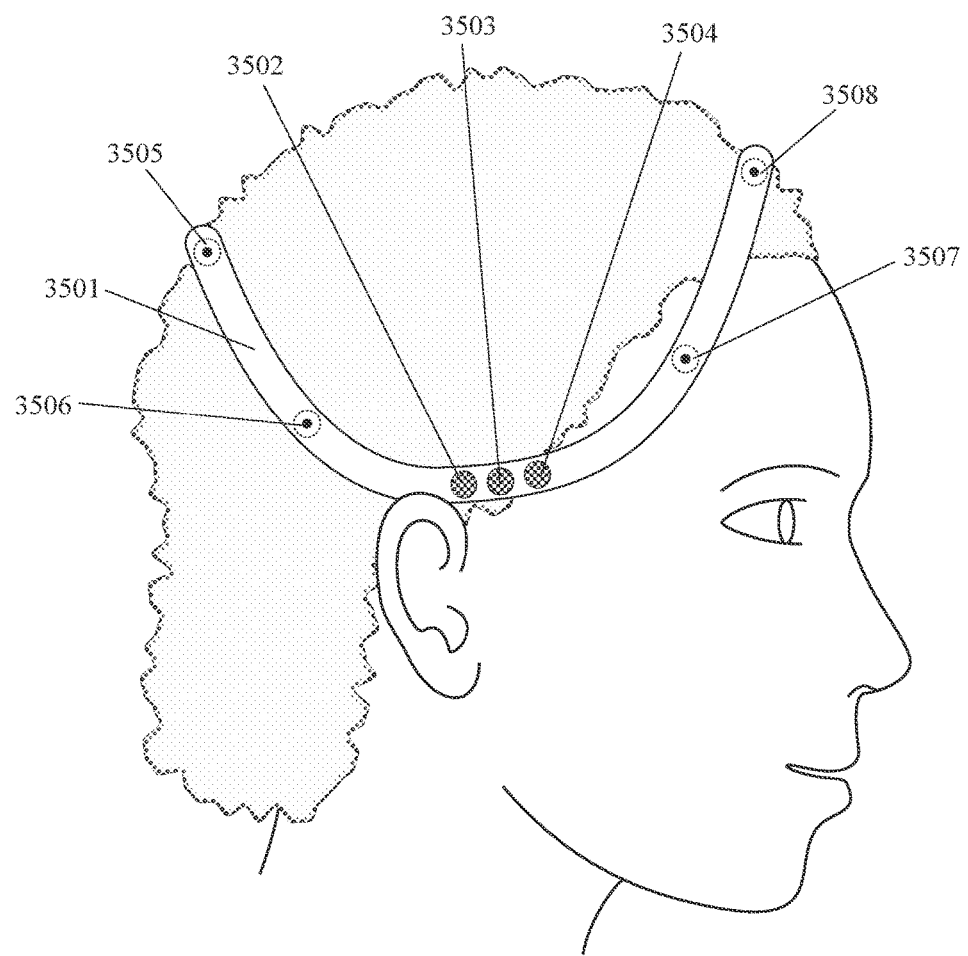

FIG. 35 shows a BCI device that encircles a person's head wherein this device has lower sides than front and rear.

Figure 36:
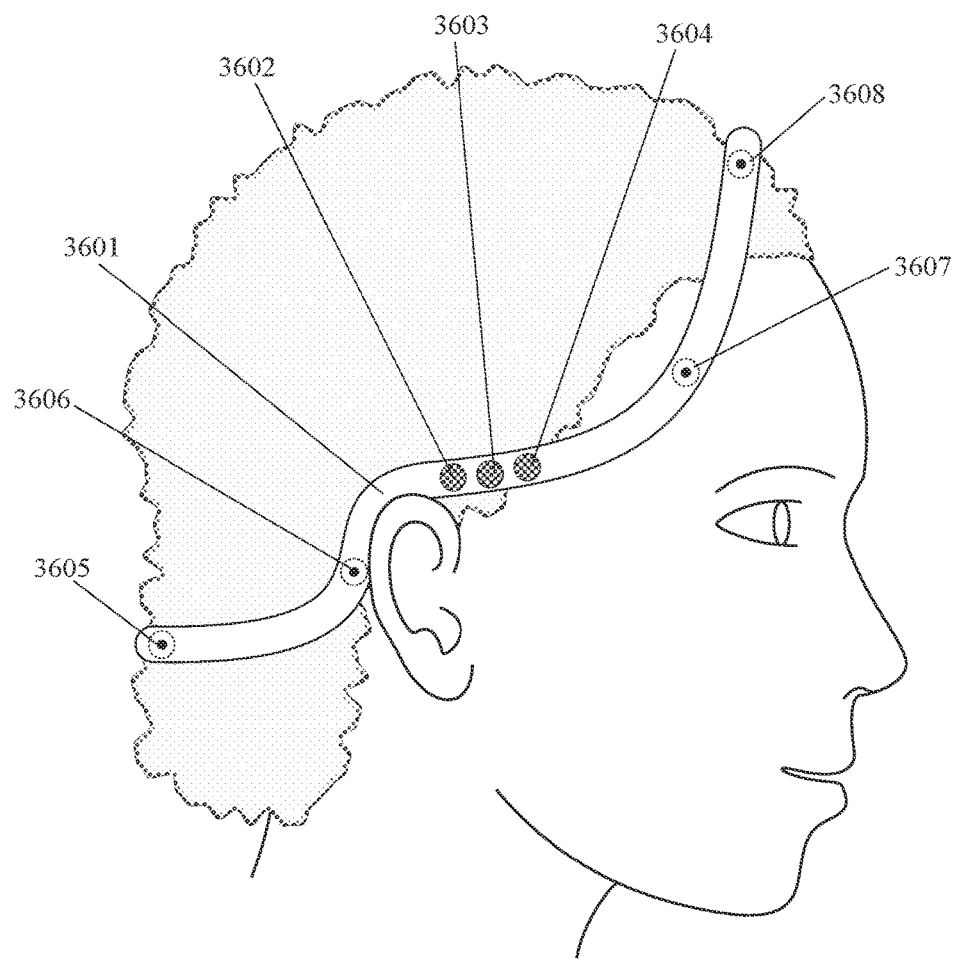

FIG. 36 shows a BCI device that encircles a person's head wherein this device has a higher front than rear.

Figure 37:
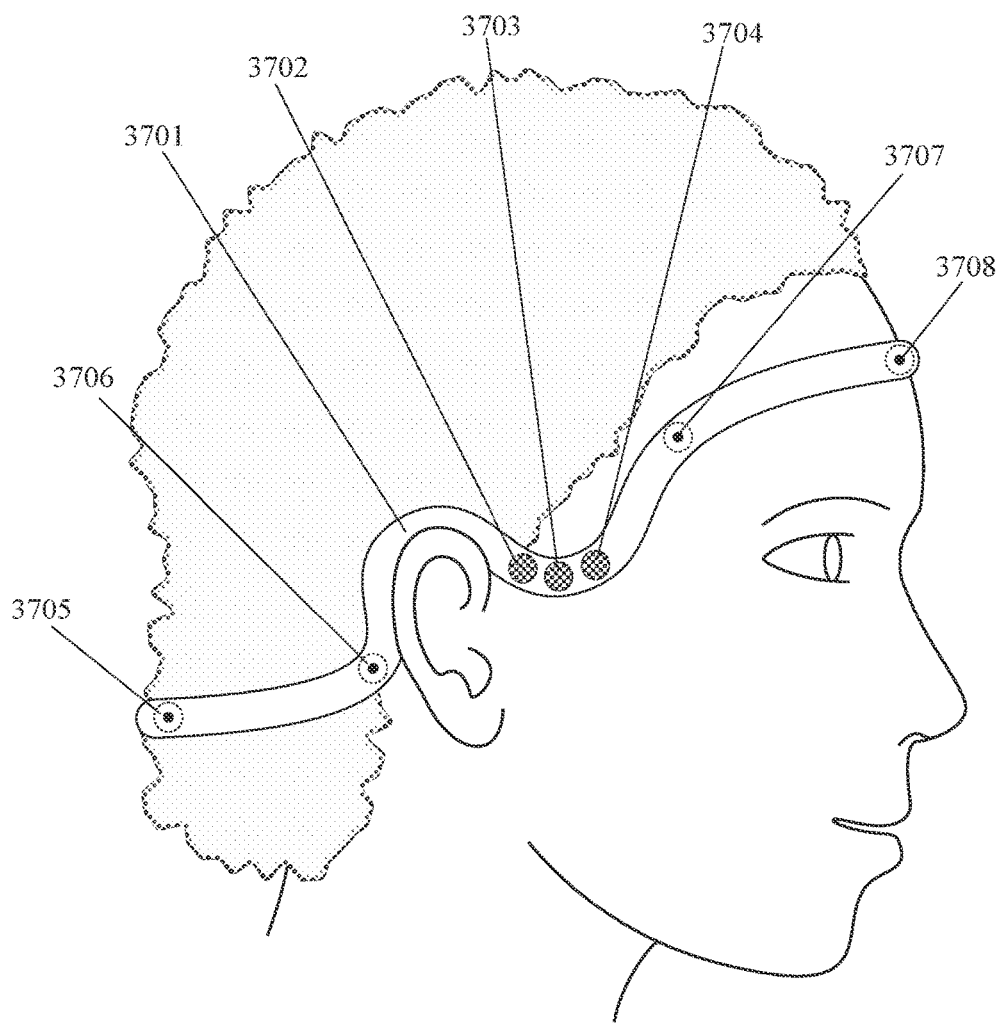

FIG. 37 shows a BCI device that encircles a person's head wherein this device has a sinusoidal wave over an ear.

Figure 38:
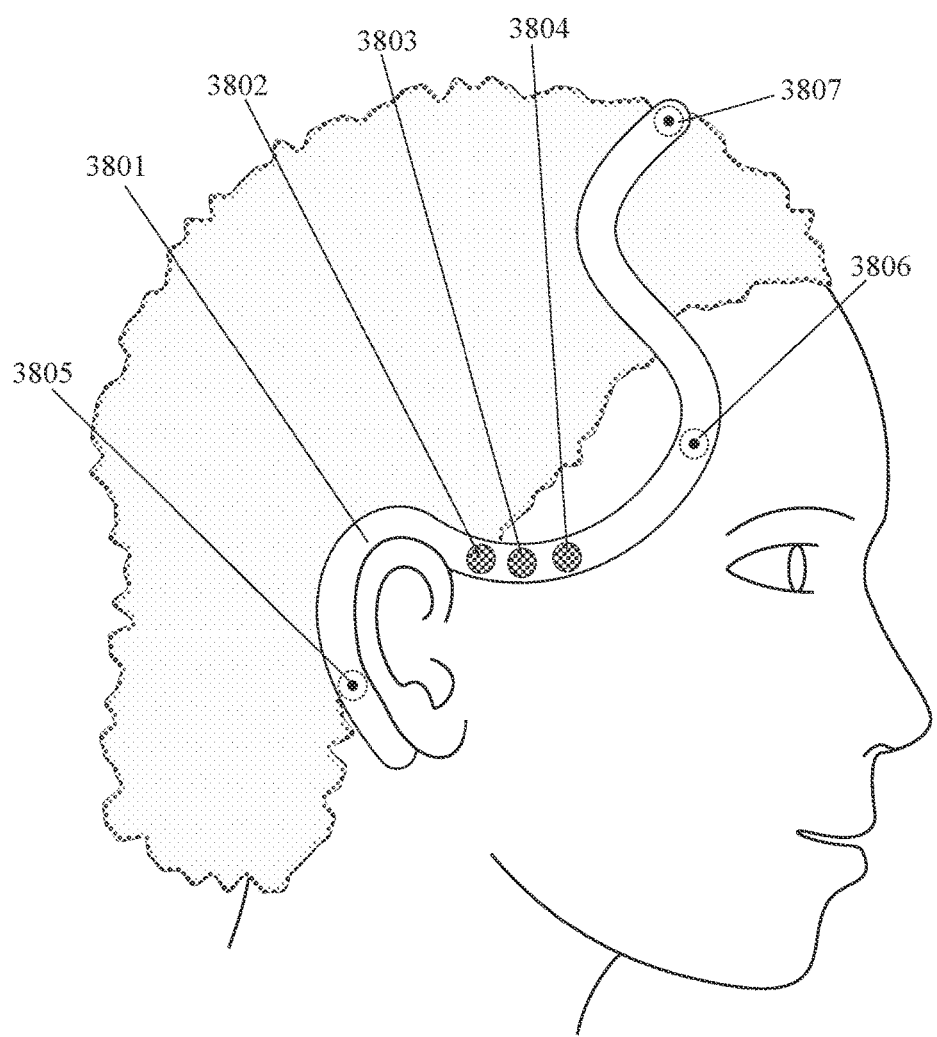

FIG. 38 shows a BCI device that undulates from the rear of a person's ear to the top of the person's head.

Figure 39:
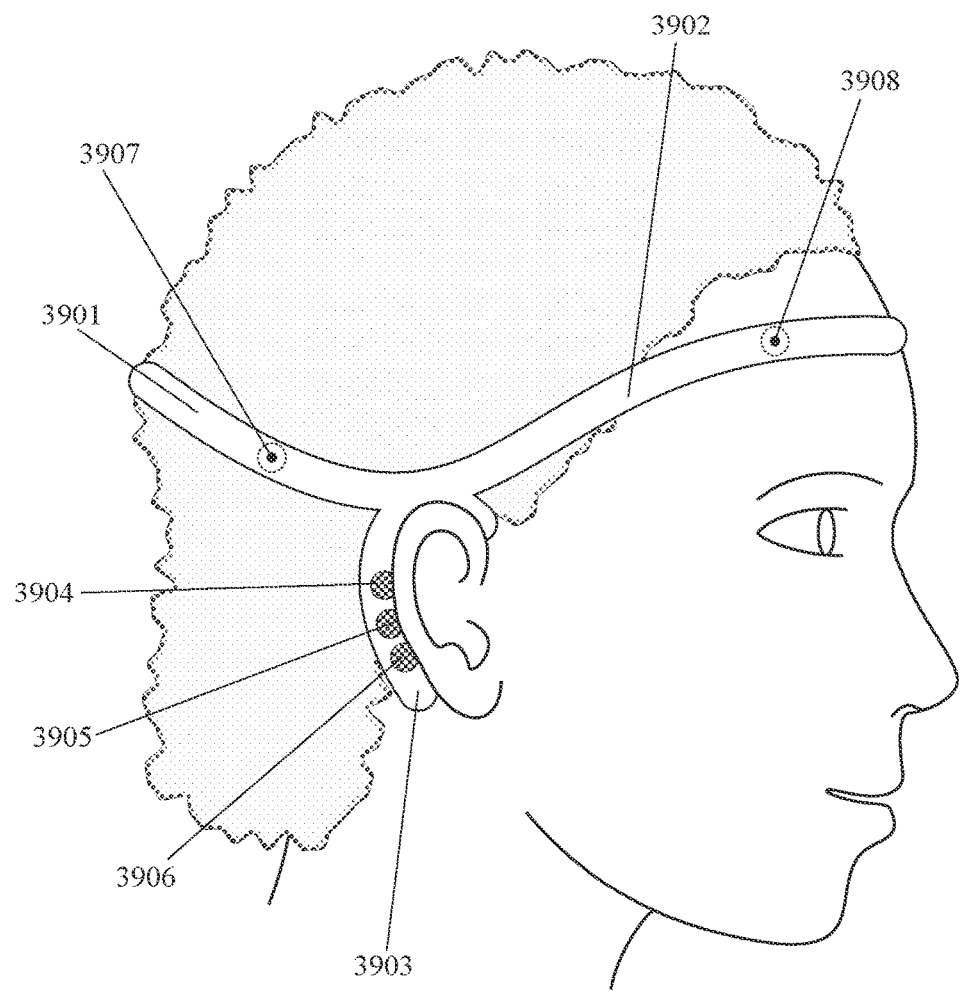

FIG. 39 shows a BCI device that encircles a person's head wherein this device includes members which curve around the rear and front of the person's ear.

Figure 40:
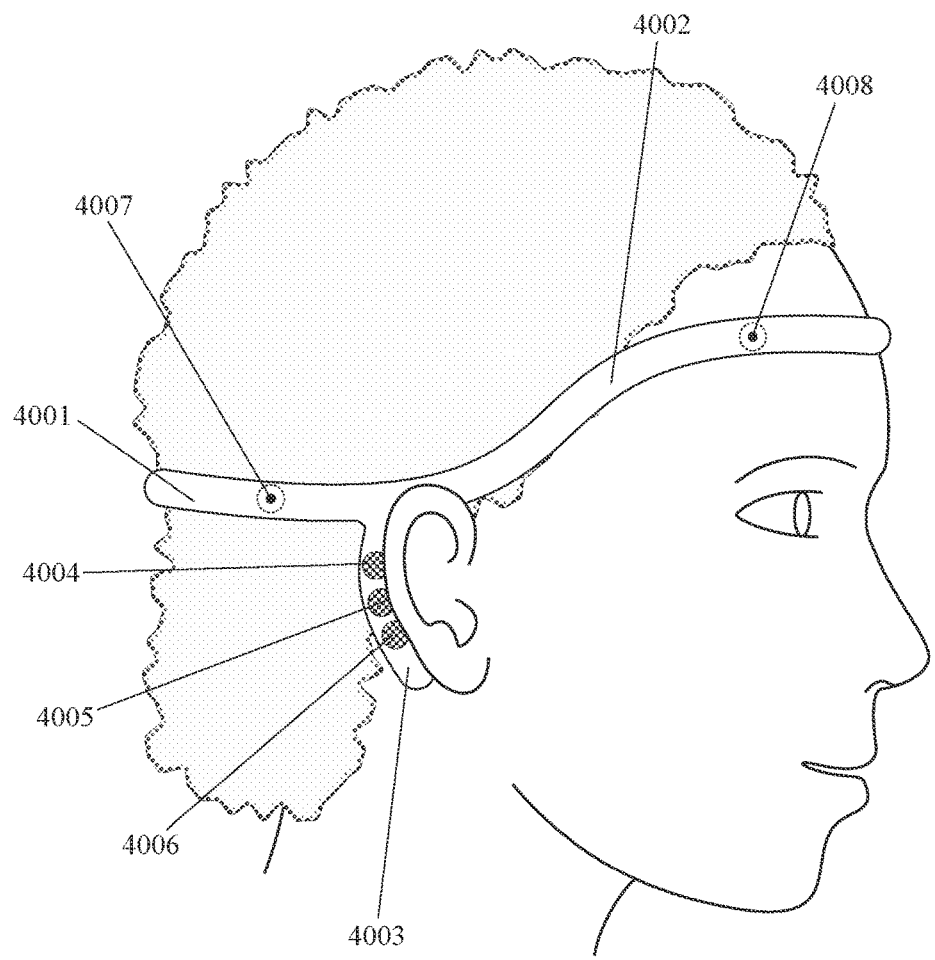

FIG. 40 shows a BCI device that encircles a person's head wherein this device loops across the person's forehead and curves around the rear of the person's ear.

Figure 41:
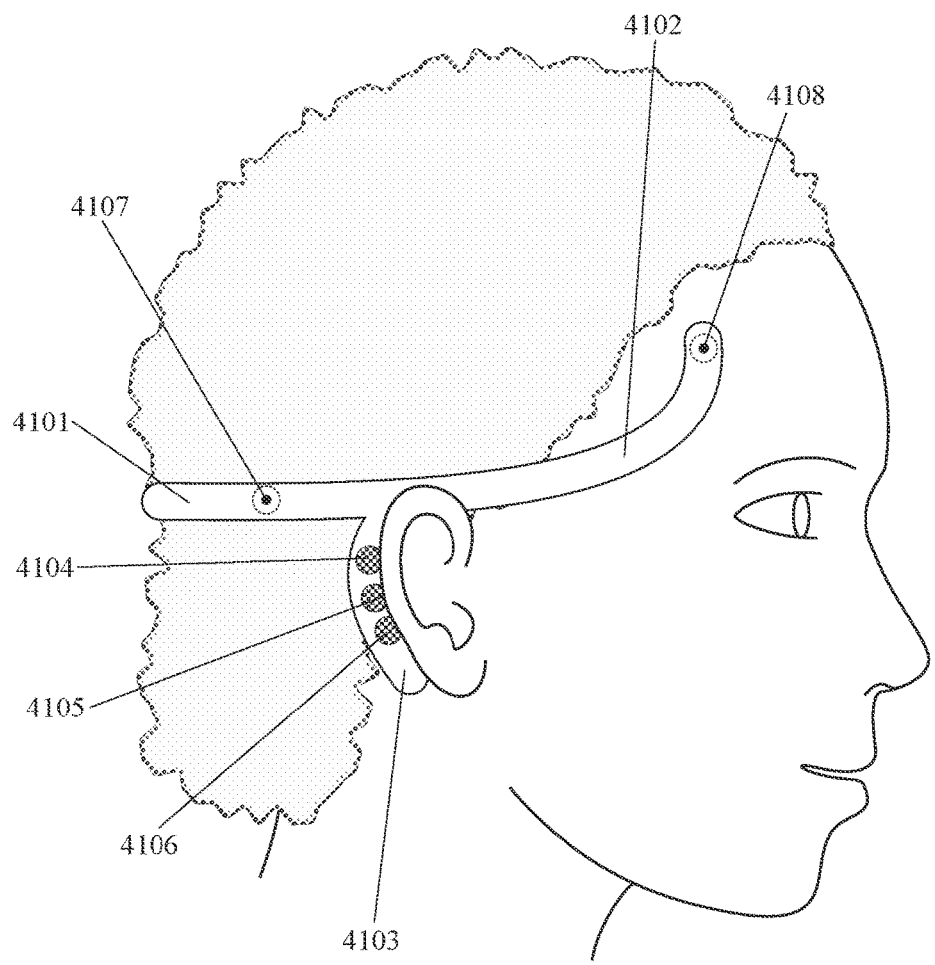

FIG. 41 shows a BCI device that loops around the back of a person's head, curves around the rear of the person's ear, and protrudes onto the person's forehead.

Figure 42:
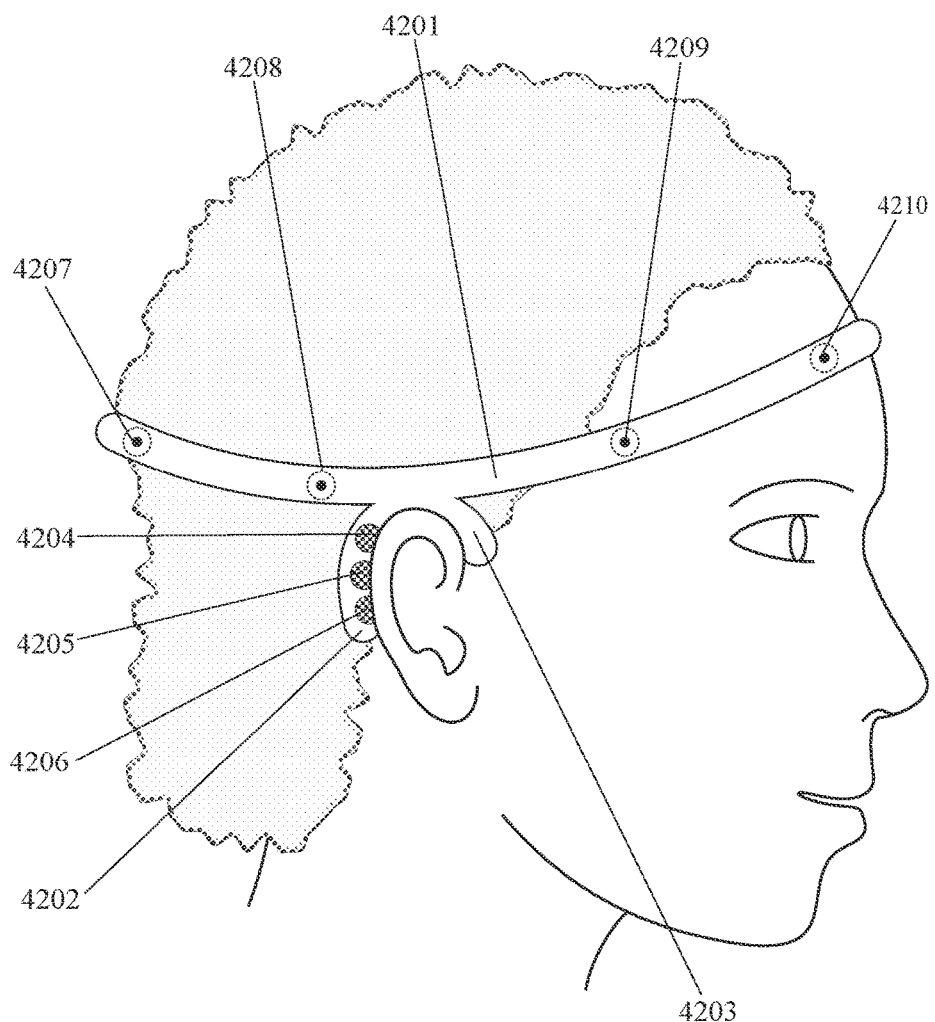

FIG. 42 shows a BCI device that encircles a person's head wherein this device loops around the back of a person's head, curves around the rear and front of the person's ear, and loops across the person's forehead.

Figure 43:
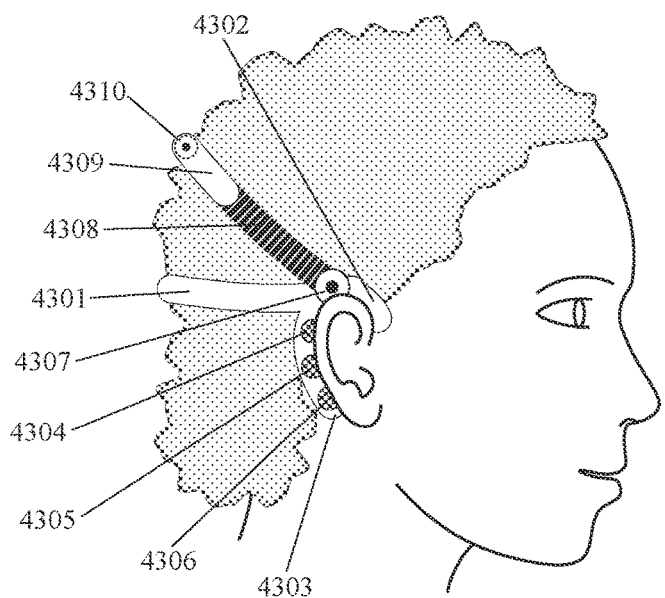
Figure 44:
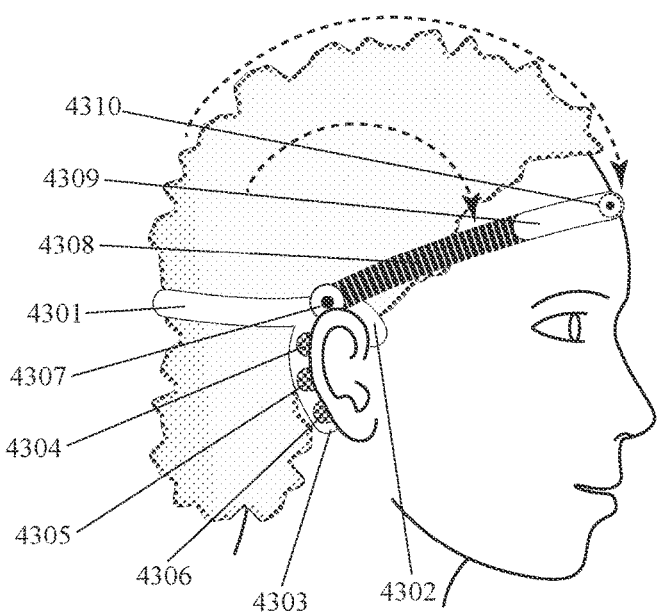

FIGS. 43 and 44 show two sequential views of an adjustable BCI band device with an over-the-top head loop that is moved from a rear position to a position which spans a person's forehead.

Figure 45:
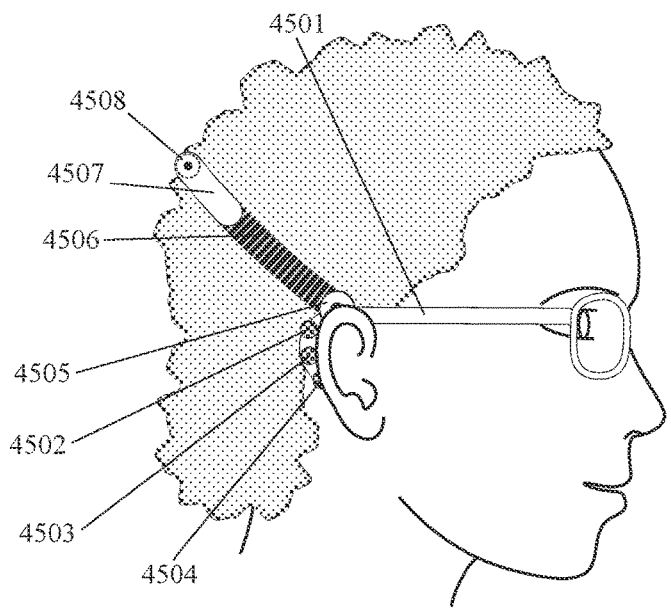
Figure 46:
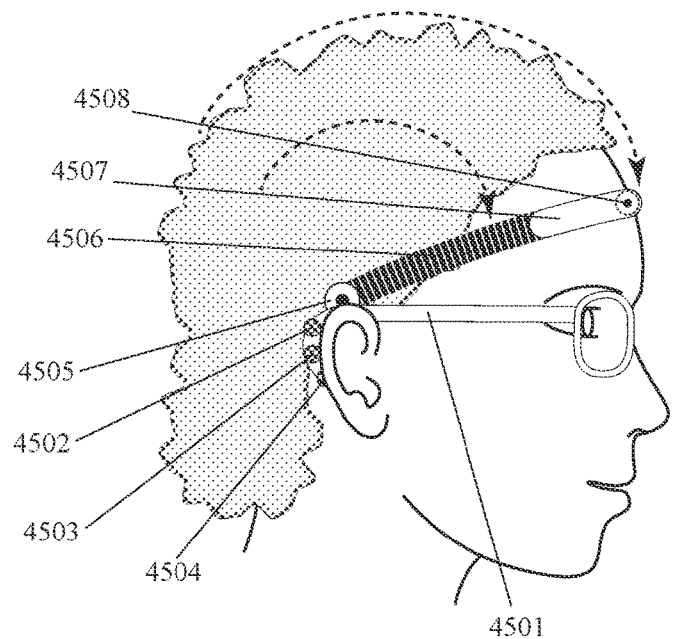

FIGS. 45 and 46 show two sequential views of an adjustable BCI eyewear device with an over-the-top head loop that is moved from a rear position to a position which spans a person's forehead.

Figure 47:
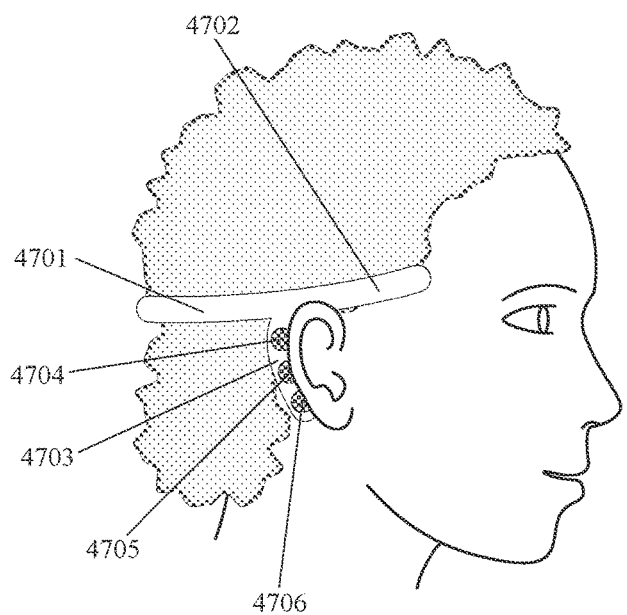
Figure 48:
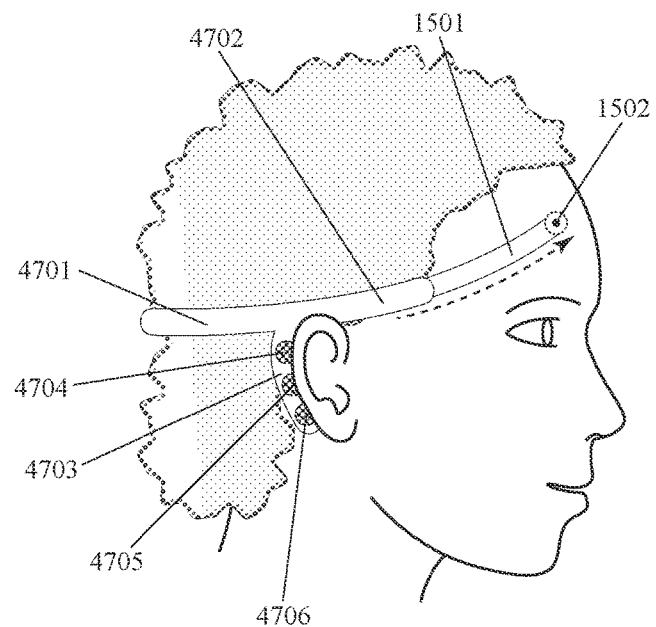

FIGS. 47 and 48 show two sequential views of an adjustable BCI eyewear device with a telescoping forehead-spanning arm.

Figure 49:
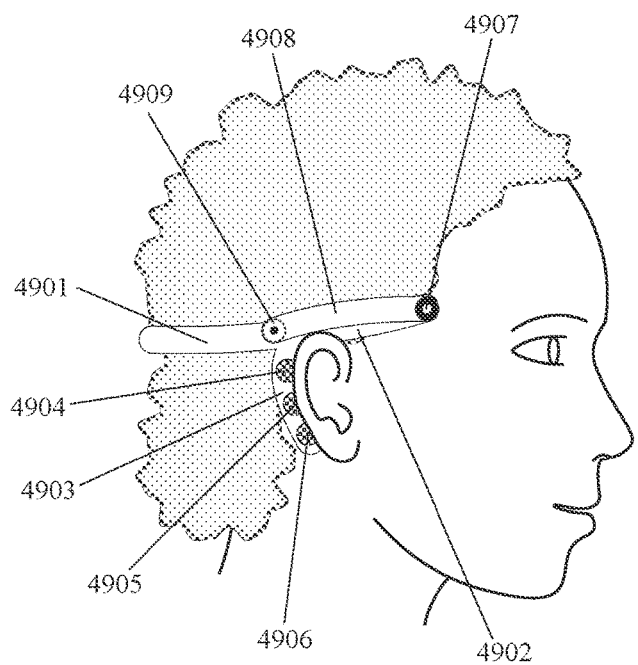
Figure 50:
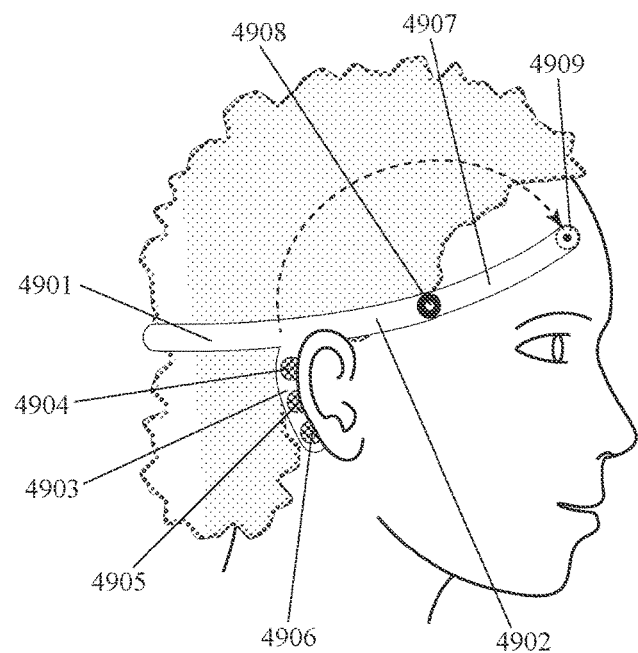

FIGS. 49 and 50 show two sequential views of an adjustable BCI eyewear device with a pivoting forehead-spanning arm.

Figure 51:
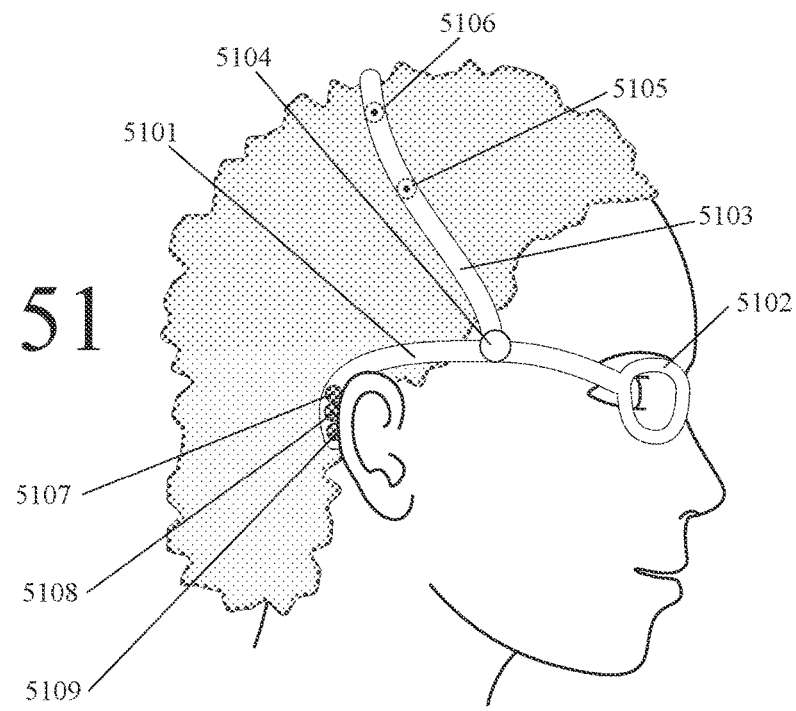
Figure 52:
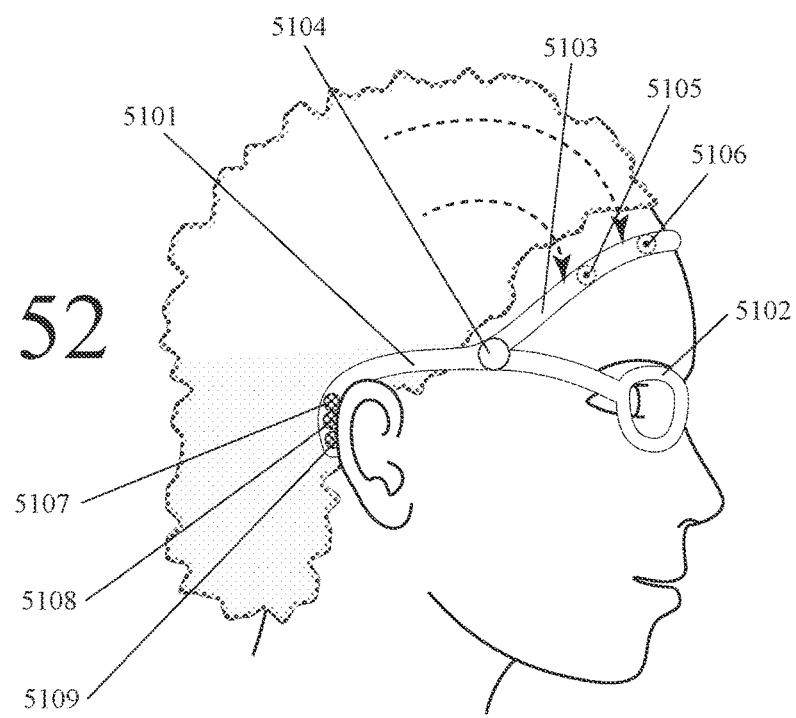

FIGS. 51 and 52 show two sequential views of an adjustable BCI eyewear device with a pivoting forehead-spanning loop.

DETAILED DESCRIPTION OF THE FIGURES

Figure 1:
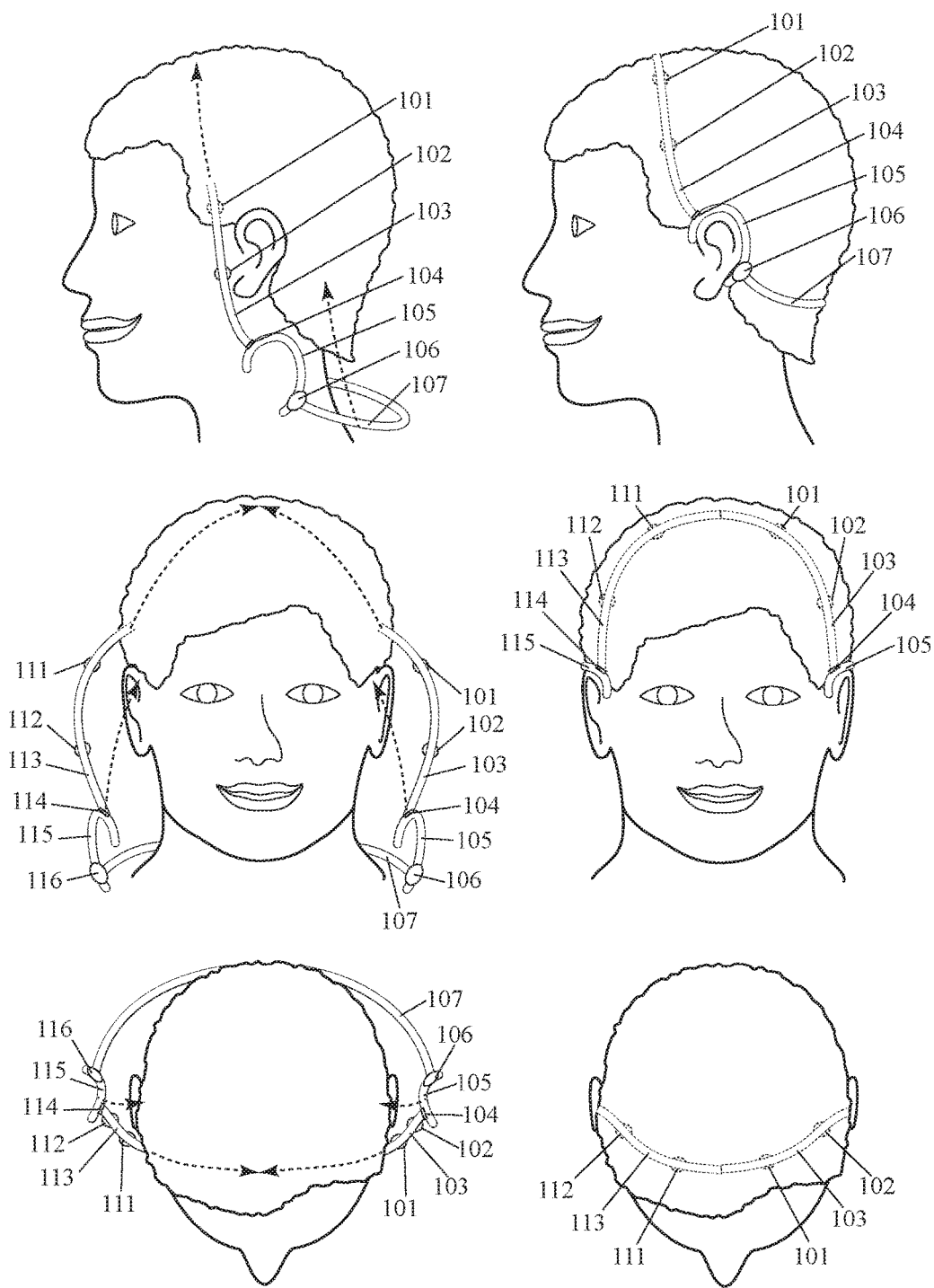
FIG. 1 shows a BCI device with connecting right and left side members which engage a person's hair.

FIGS. 1 through 52 show examples of how this invention can be embodied in a wearable and mobile Brain Computer Interface (BCI) device and method for measuring electromagnetic energy from a person's brain, but they do not limit the full generalizability of the claims. The ability to measure electromagnetic brain activity (such as electroencephalographic EEG activity) with a wearable and mobile Brain Computer Interface (BCI) device allows such measurement while a person is ambulatory. With a wearable and mobile device, a person is free to do their normal activities. This provides useful information which is not possible with EEG monitoring devices which require that the person stay in fixed location (such as a hospital or medical office).

Traditionally, brain activity monitoring systems, especially electroencephalographic (EEG) monitoring systems, have not been very mobile. Traditionally, such brain activity monitoring systems have entailed attaching a large array of electromagnetic energy sensors (e.g. electrodes) to selected locations distributed around the upper surface of a person's head and a large number of wires to connect these sensors to a central data acquisition unit. Often, the attachment process required applying conductive gel between each sensor and the scalp. Such brain activity monitoring system systems were not very mobile; they generally restricted the person to stay in a particular location (such as a hospital or medical office). Such brain activity monitoring systems were also pretty obtrusive in terms of appearance. Even if they were mobile, they would attract so much attention that they would likely interfere with the activities of daily life if worn throughout the day.

More recently, there have been efforts to make brain activity monitoring systems more mobile. This can free the wearer from being restricted to stay in a particular location (such as a hospital or medical office) and wear the monitor throughout the day. Many of these devices use dry electromagnetic energy sensors (e.g. dry electrodes) which do not require conductive gel. Although significant progress has been made toward the development of mobile brain activity sensors, most of them are still pretty obtrusive in terms of appearance. For example, some of them look like rings or headbands which encircle a person's head, including the forehead, in a very obvious manner. Others of them look like scaled-down bicycle helmets, which are also pretty obtrusive in terms of appearance.

Although progress has been made toward the development of mobile brain activity monitors, there remains a need for mobile brain activity monitors which are visually less obtrusive. This invention addresses this need by disclosing a hair-engaging mobile brain activity monitor which uses upward-extending members to position sensors (e.g. electrodes) on the upper surface of a person's head, but be partially hidden within a person's hair. The upward-extending members engage hair (e.g. extend under a layer of hair, interlock with hair, latch onto hair, mesh with hair, slide between hair layers, slide between hair strands, slide into or under hair, and/or slide under a layer of hair) as they slide upwards along the sides of a person's head. As a result, the upward-extending members and attached sensors are partially (or completely) hidden between layers of hair. The result is a hair-engaging mobile brain activity which can be worn by a person in public, without looking like a character from "Babylon 5."

In an example, this invention can be embodied in a hair-engaging mobile brain activity monitor comprising: (1) an arcuate frame which is configured to be worn on a person's head, wherein this arcuate frame further comprises: (1a) a right ear loop which is configured to curve around the person's right ear; (1b) a left ear loop which is configured to curve around the person's left ear; (1c) a posterior loop which is connected to the right ear loop and the left ear loop, where this posterior loop is configured to curve around a posterior portion of a person's head; (1d) a right upward-extending member which is configured to extend upward toward the top of the person's head from the right ear loop and/or from the posterior loop, wherein this right upward-extending member has a first configuration in which its upper-most portion is a first distance from the top of the person's head, wherein this right upward-extending member has a second configuration in which its upper-most portion is a second distance from the top of the person's head, wherein the second distance is less than the first distance, and wherein the right upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; and (1e) a left upward-extending member which is configured to extend upward toward the top of the person's head from the left ear loop and/or from the posterior loop, wherein this left upward-extending member has a first configuration in which its upper-most portion is a first distance from the top of the person's head, wherein this left upward-extending member has a second configuration in which its upper-most portion is a second distance from the top of the person's head, wherein the second distance is less than the first distance, and wherein the left upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; (2) one or more electromagnetic energy sensors which collect data concerning electromagnetic brain activity; (3) a power source; (4) a data processing unit; and (5) a data transmitter and/or receiver.

In an example, this invention can be embodied in a hair-engaging mobile brain activity monitor comprising: (1) an arcuate frame which is configured to be worn on a person's head, wherein this arcuate frame further comprises: (1a) a right ear loop which is configured to curve around the person's right ear; (1b) a left ear loop which is configured to curve around the person's left ear; (1c) a posterior loop which is connected to the right ear loop and the left ear loop, where this posterior loop is configured to curve around a posterior portion of a person's head; (1d) a right upward-extending member which is configured to extend upward toward the top of the person's head from the right ear loop and/or from the posterior loop; and (1e) a left upward-extending member which is configured to extend upward toward the top of the person's head from the left ear loop and/or from the posterior loop, wherein the right and left upward-extending members have a first configuration in which their upper-most portions are a first distance apart, wherein the right and left upward-extending members have a second configuration in which their upper-most portions are a second distance apart, wherein the second distance is less than the first distance, and wherein the right and left upward-extending members are configured to engage hair (e.g. extend under a layer of hair, interlock with hair, latch onto hair, mesh with hair, slide between hair layers, slide between hair strands, slide into or under hair, and/or slide under a layer of hair) in their second configuration; (2) one or more electromagnetic energy sensors which collect data concerning electromagnetic brain activity; (3) a power source; (4) a data processing unit; and (5) a data transmitter and/or receiver.

In an example, this invention can be embodied in a hair-engaging mobile brain activity monitor comprising: (1) an arcuate frame which is configured to be worn on a person's head, wherein this arcuate frame further comprises: (1a) at least one ear loop which is configured to curve around an ear; (1b) a posterior loop which is connected to the at least one loop, where this posterior loop is configured to curve around a posterior portion of the head; (1c) at least one upward-extending member which is configured to extend upward toward the top of the head from the at least one ear loop and/or from the posterior loop, wherein this upward-extending member has a first configuration in which its upper-most portion is a first distance from the top of the head, wherein this upward-extending member has a second configuration in which its upper-most portion is a second distance from the top of the head, wherein the second distance is less than the first distance, and wherein the upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; (2) one or more electromagnetic energy sensors which collect data concerning electromagnetic brain activity; (3) a power source; (4) a data processing unit; and (5) a data transmitter and/or receiver.

In an example, an arcuate frame can comprise a plurality of connected members. In an example, an arcuate frame can be a continuous sequence of portions. In an example, these connected members or portions can comprise: one or two ear loops; a posterior loop; and one or more upward-extending members. In an example, an arcuate frame can further comprise a housing which contains a power source, a data processing unit, and a data transmitter and/or receiver. In an example, an arcuate frame can be flexible. In an example, an arcuate frame can further comprise one or more joints or hinges.

In an example, this device can have a right ear loop, a left ear loop, or both right and left ear loops. In an example, a central vertical front-to-rear plane can be defined which virtually separates a person's head into right and left sides. In an example, right and left ear loops can be symmetric with respect to this central vertical front-to-rear plane. In an example, right and left ear loops need not be symmetric with respect to this central vertical front-to-rear plane. In an example, an ear loop can be one member among a plurality of connected members which together comprises a multi-member arcuate frame. In an example, an ear loop can be one portion of a continuous arcuate frame. In an example, an ear loop can further comprise a housing which contains a power source, a data processing unit, and a data transmitter and/or receiver.

In an example, an ear loop can be shaped like a semi-circle or three-quarters of a circle. In an example, an ear loop can be configured to span some or all of the circumference of the portion of an ear whereby the ear is attached to the main portion of the head. In an example, an ear loop can be configured to span a percentage of the circumference of the portion of an ear whereby the ear is attached to the main portion of the head and this percentage is within the range of 10%-25%. In an example, an ear loop can be configured to span a percentage of the circumference of the portion of an ear whereby the ear is attached to the main portion of the head and this percentage is within the range of 25%-50%. In an example, an ear loop can be configured to span a percentage of the circumference of the portion of an ear whereby the ear is attached to the main portion of the head and this percentage is within the range of 50%-75%. In an example, an ear loop can be configured to span a percentage of the circumference of the portion of an ear whereby the ear is attached to the main portion of the head and this percentage is within the range of 75%-100%.

In an example, clockwise polar coordinates can be defined for an ear, with 0 degrees being the upper-most location where the ear connects to the main body of the head and 180 degree being the lower-most location where the ear connects to the main body of the head. In an example, an ear loop can curve around the ear from a first polar location to a second polar location. In an example, the first location can be within the range of 270-350 degrees and the second location can be within the range of 10-90 degrees. In an example, the first location can be within the range of 270-350 degrees and the second location is within the range of 90-200 degrees.

In an example, a posterior loop can be one member among a plurality of connected members which together comprise a multi-member arcuate frame. In an example, a posterior loop can be one portion of a continuous arcuate frame. In an example, a posterior loop can further comprise a housing which contains a power source, a data processing unit, and a data transmitter and/or receiver. In an example, a posterior loop can be configured to curve around a portion of the rear half of the person's head and/neck. In an example, a posterior loop can be configured to curve around a person's posterior-facing hair line and/or the nape of the person's neck. In an example, a posterior loop can be configured to curve around a portion of the rear lower quadrant of the person's head.

In an example, a posterior loop can be resiliently flexible. In an example, a posterior loop can flex outwards from a person's head in the first configuration and can flex back inwards toward the person's head in the second configuration. In an example, a posterior loop can connect to a right ear loop and to a left ear loop. In an example, a posterior loop can connect to the lower portions of a right ear loop and a left ear loop. In an example, a posterior loop can connect to the rear portions of a right ear loop and a left ear loop. In an example, a posterior loop can connect to the upper portions of a right ear loop and a left ear loop.

In an example, an upward-extending member can be configured to span a portion of a person's head which is covered by hair. In an example, an upward-extending member can be configured to span a portion of a person's head which is above and/or posterior to the person's forehead. In an example, an upward-extending member can be configured to span a portion of a person's head which is above and/or posterior to the person's frontal hairline. In an example, an upward-extending member can be configured to span a portion of a person's head which is above and/or posterior to the person's temple.

In an example, an upward-extending member can be configured to engage hair (e.g. extend under a layer of hair, interlock with hair, latch onto hair, mesh with hair, slide between hair layers, slide between hair strands, slide into or under hair, and/or slide under a layer of hair) in the second configuration. In an example, the upper portion of an upward-extending member can split into multiple protrusions, prongs, teeth, or openings which are configured to engage hair (e.g. extend under a layer of hair, interlock with hair, latch onto hair, mesh with hair, slide between hair layers, slide between hair strands, slide into or under hair, and/or slide under a layer of hair) in the second configuration. In an example, an upward-extending member can have multiple openings which are configured to receive outward-protruding strands of hair, such that hair protrudes outward through these openings in the second configuration. In an example, an upward-extending member can have multiple openings which are configured to receive outward-protruding strands of hair, such that an inner layer of hair protrudes outward through these openings in the second configuration and an outer layer of hair covers the upward-extending member in the second configuration.

In an example, an upward-extending member can be configured so that it is at least partially covered by hair on a person's head in the second configuration. In an example, an upward-extending member can be configured to engage a lower layer of hair on a person's head and to be at least partially covered by an upper layer of hair on a person's head. In an example, an upward-extending member can be inserted upwards between two layers of hair on a person' head. In an example, an upward-extending member can be configured so that at least 25% of the outward-facing surface area of this member is covered by the person's hair in the second configuration. In an example, an upward-extending member can be configured so that at least 50% of the outward-facing surface area of this member is covered by the person's hair in the second configuration. In an example, an upward-extending member can be configured so that at least 75% of the outward-facing surface area of this member is covered by the person's hair in the second configuration.

In an example, an upward-extending member can split into multiple protrusions, prongs, and/or teeth which are configured to engage hair (e.g. extend under a layer of hair, interlock with hair, latch onto hair, mesh with hair, slide between hair layers, slide between hair strands, slide into or under hair, and/or slide under a layer of hair) in the second configuration in order to hide the upward-extending member within (or under) hair. In an example, an upward-extending member can split into multiple protrusions, prongs, and/or teeth which are configured to engage hair (e.g. extend under a layer of hair, interlock with hair, latch onto hair, mesh with hair, slide between hair layers, slide between hair strands, slide into or under hair, and/or slide under a layer of hair) in the second configuration in order to make the upward-extending member less visible in proximity to hair. In an example, an upward-extending member can comprise a plurality of protrusions, prongs, and/or teeth between which hair can extend outward so as to decrease the visibility of the upward-extending member. In an example, an upward-extending member can have multiple protrusions, prongs, and/or teeth which are configured to be covered by a layer of hair in the second configuration.

In an example, an upper portion of an upward-extending member can be held onto a person's head in the second configuration by frictional engagement with hair. In an example, an upper portion of an upward-extending member can be held onto a person's head in the second configuration by intermeshing with hair. In an example, an upward-extending member can comprise a plurality of protrusions, prongs, and/or teeth between which hair extends outward so as to hold a portion of the upward-extending member onto the person's head. In an example, an upper portion of an upward-extending member can be held onto a person's head in the second configuration by multiple upward-facing protrusions, prongs, and/teeth which frictionally engage the person's hair. In an example, an upper portion of an upward-extending member can be attached to a person's head in the second configuration by multiple upward-facing and/or center-facing protrusions, prongs, and/teeth which frictionally engage the person's hair.

In an example, an upper portion of an upward-extending member can be moved upwards toward the top of a person's head and inwards toward the center of the person's head as the upward-extending member is moved from the first configuration to the second configuration. In an example, an upper portion of an upward-extending member can be configured to slide upwards over the surface of the person's head under a layer of hair as the member moves from the first configuration to the second configuration. In an example, an upward-extending member can slide upwards between layers of hair as the member moves from the first configuration to the second configuration. In an example, an upward-extending member can engage hair (e.g. extend under a layer of hair, interlock with hair, latch onto hair, mesh with hair, slide between hair layers, slide between hair strands, slide into or under hair, and/or slide under a layer of hair) as an upward-extending member is moved from the first configuration to the second configuration. In an example, an upward-extending member can slide upwards and inwards along the hair-covered surface of the person's head as the member moves from the first configuration to the second configuration. In an example, an upward-extending member can be flexed outwards from a person head in the first configuration and can flex back inwards toward the person's head in the second configuration.

In an example, an upward-extending member can have multiple upward-facing protrusions, prongs, teeth, and/or openings which are configured to engage hair (e.g. extend under a layer of hair, interlock with hair, latch onto hair, mesh with hair, slide between hair layers, slide between hair strands, slide into or under hair, and/or slide under a layer of hair) as an upward-extending member is moved from the first configuration to the second configuration. In an example, an upward-extending member can have multiple upward-facing protrusions, prongs, teeth, and/or openings which are configured to engage hair (e.g. extend under a layer of hair, interlock with hair, latch onto hair, mesh with hair, slide between hair layers, slide between hair strands, slide into or under hair, and/or slide under a layer of hair) as the upward-extending member is slid upwards over the surface of a person's head. In an example, the upper portion of an upward-extending member can have multiple upward-facing protrusions, teeth, or prongs which are configured to slide upwards over the surface of the person's head under a layer of hair as the protrusions, teeth, or prongs move from the first configuration to the second configuration.

In an example, an upward-extending member can have multiple protrusions, prongs, and/or teeth. In an example, an upward-extending member can have multiple upward-facing protrusions, prongs, and/or teeth which engage a person's hair in the second configuration. In an example, a left upward-extending member can have multiple protrusions, prongs, and/or teeth which point upward and rightward in the second configuration. In an example, a right upward-extending member can have multiple protrusions, prongs, and/or teeth which point upward and leftward in the second configuration. In an example, an upward-extending member can split into multiple protrusions, prongs, and/or teeth as extends upward. In an example, an upward-extending member can have multiple comb-like teeth which face upwards. In an example, an upward-extending member can have multiple comb-like teeth which face inwards towards the central vertical front-to-rear plane of the person's head in the second configuration. In an example, an upward-extending member can comprise a plurality of upward-facing longitudinal protrusions, prongs, and/or teeth whose longitudinal axes are configured to be substantially parallel to the surface of the person's head in the second configuration.

In an example, an upward-extending member can comprise a plurality of upward-facing protrusions, prongs, and/or teeth which are configured to engage the person's hair so that at least 25% of the outward-facing surface area of this member is covered by the person's hair in the second configuration. In an example, an upward-extending member can comprise a plurality of upward-facing protrusions, prongs, and/or teeth which are configured to engage the person's hair so that at least 50% of the outward-facing surface area of this member is covered by the person's hair in the second configuration. In an example, an upward-extending member can comprise a plurality of upward-facing protrusions, prongs, and/or teeth which are configured to engage the person's hair so that at least 75% of the outward-facing surface area of this member is covered by the person's hair in the second configuration.

In an example, an upward-extending member can comprise a plurality of openings through which hair protrudes outward so that at least 25% of the outward-facing surface area of this upward-extending member is covered by the person's hair in the second configuration. In an example, an upward-extending member can comprise a plurality of openings through which hair protrudes outward so that at least 50% of the outward-facing surface area of this upward-extending member is covered by the person's hair in the second configuration. In an example, an upward-extending member can comprise a plurality of openings through which hair protrudes outward so that at least 75% of the outward-facing surface area of this upward-extending member is covered by the person's hair in the second configuration. In an example, an upward-extending member can be a mesh or lattice.

In an example, an upward-extending member can bifurcate or split as it extends upward. In an example, an upward-extending member can bifurcate or split as it extends upward from an ear loop. In an example, an upward-extending member can bifurcate or split as it extends upward from a posterior loop. In an example, this device can comprise a "U"-shaped bifurcating upward-extending member on a side of the person's head. In an example, this device can comprise a "U"-shaped bifurcating upward-extending member on each side of the person's head. In an example, this device can comprise a "V"-shaped bifurcating upward-extending member on a side of the person's head. In an example, this device can comprise a "V"-shaped bifurcating upward-extending member on each side of the person's head. In an example, this device can comprise a capital-"Y"-shaped bifurcating upward-extending member on a side of the person's head. In an example, this device can comprise a capital-"Y"-shaped bifurcating upward-extending member on each side of the person's head. In an example, this device can comprise a trident-shaped or fork-shaped upward-extending member on a side of the person's head. In an example, this device can comprise a trident-shaped or fork-shaped upward-extending member on each side of the person's head.

In an example, the upper portions of the right and left upward-extending members may not be connected to each other in the first configuration, but are connected to each other in the second configuration. In an example, the upper portions of the right and left upward-extending members can be reversibly connected or attached to each other. In an example, the upper portions of the right and left upward-extending members can be connected or attached to each other as these members are moved from the first configuration to the second configuration. In an example, the right and left upward-extending members can have multiple protrusions, prongs, and/or teeth which intermesh and/or interlock with each other in the second configuration. In an example, the upper portions of the right and left upward-extending members can be attached to each other by an attachment mechanism selected from the group consisting of: ball and socket, buckle, button, clasp, clip, hook, hook-and-eye fabric, inter-locking parts, inter-meshing parts, magnetic attachment, plug, protrusion and opening, snap, helical thread, and tongue and groove.

In an example, the upper portions of the right and left upward-extending members can be connected to each other in both the first configuration and the second configuration. In an example, the upper portions of the right and left upward-extending members may not be connected to each other in either the first configuration or the second configuration. In an example, the upper portions of the right and left upward-extending members can be separated by a distance in the range of one-quarter inch to two inches in the second configuration. In an example, the upper portions of the right and left upward-extending members can be separated by a distance in the range of two inches to six inches in the second configuration.

In an example, an arcuate frame can include a resiliently-flexible portion between an ear loop and an upward-extending member, a resiliently-flexible portion between the posterior loop and an upward-extending member, or both. In an example, an arcuate frame can include a hinge between an ear loop and an upward-extending member, a hinge between the posterior loop and an upward-extending member, or both. In an example, an arcuate frame can include a rotating joint between an ear loop and an upward-extending member, a rotating joint between the posterior loop and an upward-extending member, or both.

In an example, an arcuate frame can further comprise a spring, coil, or other tensile member which exerts force on an upward-extending member to move it toward the second configuration. In an example, the arcuate frame can further comprise an elastic member which exerts force on an upward-extending member to move it toward the second configuration. In an example, the arcuate frame can further comprise a resiliently-flexible member which exerts force on an upward-extending member to move it toward the second configuration. In an example, a spring, coil, other tensile member, elastic member, or resiliently-flexible member which is part of the frame can be sufficiently flexible to allow the right and left upward-extending members to be manually moved into their first configuration by the user's hands, but can also be sufficiently resilient to move the right and left upward-extending members into their second configuration in the absence of external force from the user's hands. In an example, the amount of force with which an upward-extending member is pressed against the surface of a person's head can be changed by adjusting the degree of tension in a spring, coil, other tensile member, or elastic member.

In an example, a first plane can be defined in three-dimensional space as: being perpendicular to the central vertical front-to-back plane of a head; and best fitting the right upward-extending member and the left upward-extending member. In an example, a second plane can be defined in three-dimensional space as: being perpendicular to the central vertical front-to-back plane of a head; and best fitting the posterior loop. In an example, a posterior-facing angle which is formed by the intersection of the first plane and the second plane is in the range of 45 to 90 degrees. In an example, a posterior-facing angle which is formed by the intersection of the first plane and the second plane is in the range of 90 to 135 degrees. In an example, a posterior-facing angle which is formed by the intersection of the first plane and the second plane is in the range of 135 to 180 degrees. In an example, the posterior-facing angle of an upward-extending member relative to the posterior loop can be selectively adjusted by adjusting a hinge or joint on the arcuate frame. In an example, the length and/or height of an upward-extending member relative to an ear loop and/or the posterior loop can be adjusted. In an example, the upward-extending member can overlap with, or extend into, the ear loop and/or posterior loop and the height of an upward-extending member can be adjusted by increasing or decreasing this overlap or extension.

In an example, an upward-extending member can be a side loop with both ends connected to an ear loop. In an example, an upward-extending member can be a side loop with one end connected to an ear loop and the other end connected to the posterior loop. In an example, an upward-extending member can be a side loop which curves upward from an ear loop and then downward to the posterior loop, or vice versa. In an example, an upward-extending member can be a side loop with an array of upward-facing protrusions, prongs, and/or teeth to engage hair in the second configuration. In an example, an upward-extending member can be a side loop with an array of upward-facing protrusions, prongs, and/or teeth which slide upwards along the side of the person's head into the person's hair as an upward-extending member moves from the first configuration to the second configuration.

In an example, there can be a single upward-extending member on one side of a person's head. In an example, an arcuate frame can have a left upward-extending member, but not a right upward-extending member, or vice versa. In an example, there can be a single upward-extending member on each side of a person's head. In an example, there can be multiple upward-extending members on one side of a person's head. In an example, there can be multiple upward-extending members on each side of a person's head. In an example, there can be three or more upward-extending members on a right or left side of the person's head. In an example, there can be two or more parallel upward-extending members on a side of a person's head. In an example, there can be two upward-extending members on a side of a person's head, wherein these two upward-extending members are concentric and/or nested loops. In an example, there can be two upward-extending members on a side of a person's head, wherein these two upward-extending members comprise an upper loop and a lower loop. In an example, an upward-extending member can be configured to be substantially parallel to the surface of a person's head in the second configuration.

In an example, an electromagnetic energy sensor for collecting data concerning electromagnetic brain activity can be an electroencephalographic (EEG) sensor. In an example, an electromagnetic energy sensor can be an electrode. In an example, an electromagnetic energy sensor can be a dry electrode. In an example, there can be two or more electromagnetic energy sensors which collect data concerning electromagnetic brain activity.

In an example, there can be two or more electromagnetic energy sensors on an upward-extending member. In an example, one or more electromagnetic energy sensors can be attached to, or integral parts of, an upward-extending member. In an example, an electromagnetic energy sensor can be located on a central portion of an upward-extending member. In an example, there can be an upper electromagnetic energy sensor and a lower electromagnetic energy sensor on an upward-extending member.

In an example, one or more electromagnetic energy sensors can be modular. In an example, one or more electromagnetic energy sensors can be removably attached to an upward-extending member. In an example, this device can comprise a first number of electromagnetic energy sensors and a second number of locations where electromagnetic energy sensors can be attached, wherein the second number is greater than the first number. In an example, one or more electromagnetic energy sensors can be removably attached to an upward-extending member by one or more attachment mechanisms selected from the group consisting of: magnetic attachment; hook-and-eye fabric; protrusion and opening; snap; clip; clasp; hook; buckle; plug attachment; pin; button; thread and groove; tongue and groove.

In an example, data concerning a person's brain activity can be collected by one or more electromagnetic energy sensors at one or multiple selected recording sites. In an example, the locations of one or more electromagnetic energy sensors can be selected from the group of EEG placement sites consisting of: FP1, FPz, FP2, AF7, AF5, AF3, AFz, AF4, AF6, AF8, F7, F5, F3, F1, Fz, F2, F4, F6, F8, FT7, FC5, FC3, FC1, FCz, FC2, FC4, FC6, FT8, T3/T7, C3, C4, C1, Cz, C2, C5, C6, T4/T8, TP7, CP5, CP3, CP1, CPz, CP2, CP4, CP6, TP8, T5/P7, P5, P3, P1, Pz, P2, P4, P6, T6/P8, PO7, PO5, PO3, POz, PO4, PO6, PO8, O1, Oz, and O2. In an example, one or more reference places can be selected from the group of sites consisting of A1 and A2.

In an example, collection of data concerning brain activity can comprise measuring electromagnetic data concerning impedance, voltage difference, and/or energy transfer between two sites on a person's head—a selected recording site and a reference site. In an example, electromagnetic brain activity data can be collected by an electromagnetic energy sensor at a selected recording place. In an example, electromagnetic brain activity data from a selected recording place (relative to a reference place) can be called a "channel" In an example, electromagnetic brain activity data from multiple recording places can be called a "montage." In an example, brain activity data can be recorded at a rate in the range of 100 to 300 samples per second.

In an example, a statistical method can be used to identify specific patterns in a person's electromagnetic brain activity and/or specific changes in a person's electromagnetic brain activity. In an example, data from one or more electromagnetic energy sensors can be filtered to remove artifacts before the application of a statistical method. In an example, a filter can be used to remove electromagnetic signals from eye blinks, eye flutters, or other eye movements before the application of a statistical method. In an example, a notch filter can be used as well to remove 60 Hz artifacts caused by AC electrical current. In various examples, one or more filters can be selected from the group consisting of: a high-pass filter, a band-pass filter, a loss-pass filter, an electromyographic activity filter, a 0.5-1 Hz filter, and a 35-70 Hz filter.

In an example, a pattern and/or change in electromagnetic brain activity can be a one-time pattern. In another example, a pattern of electromagnetic brain activity can repeat over time in a rhythmic manner. In an example, a primary statistical method can analyze repeating electromagnetic patterns by analyzing their frequency of repetition, their frequency band or range of repetition, their recurring amplitude, their wave phase, and/or their waveform. In an example repeating patterns and/or waveforms can be analyzed using Fourier Transform methods.

In an example, a primary statistical method for identifying patterns and/or changes in electromagnetic brain activity can comprise finding the mean or average value of data from one or more brain activity channels during a period of time. In an example, a statistical method can comprise identifying a significant change in the mean or average value of data from one or more brain activity channels. In an example, a statistical method can comprise finding the median value of data from one or more brain activity channels during a period of time. In an example, a statistical method can comprise identifying a significant change in the median value of data from one or more brain activity channels. In an example, a statistical method can comprise identifying significant changes in the relative mean or median data values among multiple brain activity channels. In an example, a statistical method can comprise identifying significant changes in mean data values from a first set of sensor locations relative to mean data values from a second set of sensor locations. In an example, a statistical method can comprise identifying significant changes in mean data recorded from a first region of the brain relative to mean data recorded from a second region of the brain.

In an example, a primary statistical method for identifying patterns and/or changes in electromagnetic brain activity can comprise finding the minimum or maximum value of data from one or more brain activity channels during a period of time. In an example, a statistical method can comprise identifying a significant change in the minimum or maximum value of data from one or more brain activity channels. In an example, a statistical method can comprise identifying significant changes in the relative minimum or maximum data values among multiple brain activity channels. In an example, a statistical method can comprise identifying significant changes in minimum or maximum data values from a first set of sensor locations relative to minimum or maximum data values from a second set of sensor locations. In an example, a statistical method can comprise identifying significant changes in minimum or maximum data values recorded from a first region of the brain relative to minimum or maximum data values recorded from a second region of the brain.

In an example, a primary statistical method for identifying patterns and/or changes in electromagnetic brain activity can comprise finding the variance or the standard deviation of data from one or more brain activity channels during a period of time. In an example, a statistical method can comprise identifying a significant change in the variance or the standard deviation of data from one or more brain activity channels. In an example, a statistical method can comprise identifying significant changes in the covariation and/or correlation among data from multiple brain activity channels. In an example, a statistical method can comprise identifying significant changes in the covariation or correlation between data from a first set of sensor locations relative and data from a second set of sensor locations. In an example, a statistical method can comprise identifying significant changes in the covariation or correlation of data values recorded from a first region of the brain and a second region of the brain.

In an example, a primary statistical method for identifying patterns and/or changes in electromagnetic brain activity can comprise finding the amplitude of waveform data from one or more channels during a period of time. In an example, a statistical method can comprise identifying a significant change in the amplitude of waveform data from one or more channels. In an example, a statistical method can comprise identifying significant changes in the relative wave amplitudes from one or more channels. In an example, a statistical method can comprise identifying significant changes in the amplitude of electromagnetic signals recorded from a first region of the brain relative to the amplitude of electromagnetic signals recorded from a second region of the brain.

In an example, a primary statistical method for identifying patterns and/or changes in electromagnetic brain activity can comprise finding the power of waveform brain activity data from one or more channels during a period of time. In an example, a statistical method can comprise identifying a significant change in the power of waveform data from one or more channels. In an example, a statistical method can comprise identifying significant changes in the relative power levels of one or more channels. In an example, a statistical method can comprise identifying significant changes in the power of electromagnetic signals recorded from a first region of the brain relative to the power of electromagnetic signals recorded from a second region of the brain.

In an example, a primary statistical method for identifying patterns and/or changes in electromagnetic brain activity can comprise finding a frequency or a frequency band of waveform and/or rhythmic brain activity data from one or more channels which repeats over time. In an example, Fourier Transform methods can be used to find a frequency or a frequency band of waveform and/or rhythmic data which repeats over time. In an example, a statistical method can comprise decomposing a complex waveform into a combination of simpler waveforms which each repeat at a different frequency or within a different frequency band. In an example, Fourier Transform methods can be used to decomposing a complex waveform into a combination of simpler waveforms which each repeat at a different frequency or within a different frequency band.

In an example, a primary statistical method for identifying patterns and/or changes in electromagnetic brain activity can comprise identifying significant changes in the amplitude, power level, phase, frequency, covariation, entropy, and/or oscillation of waveform data from one or more channels. In an example, a statistical method can comprise identifying significant changes in the amplitude, power level, phase, frequency, covariation, entropy, and/or oscillation of waveform data within a selected frequency band. In an example, a statistical method can comprise identifying significant changes in the relative amplitudes, power levels, phases, frequencies, covariations, entropies, and/or oscillations of waveform data among different frequency bands. In various examples, these significant changes can be identified using Fourier Transform methods.

In an example, brainwaves or other rhythmic, cyclical, and/or repeating electromagnetic signals associated with brain activity can be measured and analyzed using one or more clinical frequency bands. In an example, complex repeating waveform patterns can be decomposed and identified as a combination of multiple, simpler repeating wave patterns, wherein each simpler wave pattern repeats within a selected clinical frequency band. In an example, brainwaves can be decomposed and analyzed using Fourier Transformation methods. In an example, brainwaves can be measured and analyzed using a subset and/or combination of five clinical frequency bands: Delta, Theta, Alpha, Beta, and Gamma. In an example, a method can analyze changes in brainwaves in a single frequency band, changes in brainwaves in multiple frequency bands, or changes in brainwaves in a first frequency band relative to those in a second frequency band.

In an example, Delta brainwaves can be measured and analyzed within a frequency band of 1 to 4 Hz. In various examples, Delta brainwaves or other rhythmic, cyclical, and/or repeating electromagnetic signals associated with brain activity can be measured and analyzed within a frequency band selected from the group consisting of: 0.5-3.5 Hz, 0.5-4 Hz, 1-3 Hz, 1-4 Hz, and 2-4 Hz. In an example, a method can track a decrease or increase in the relative power of brainwaves in the Delta band. In an example, a method can track a frequency shift within the Delta frequency band. In an example, a method can track a change in wave shape for brainwaves in the Delta frequency band. In an example, a method can track a change in which brain regions originate or modify brainwaves within the Delta frequency band. In an example, a method can track a change in brainwave activity within the Delta band from the anterior vs. posterior areas of a person's brain. In an example, a method can track a change in brainwave activity within the Delta band for a particular brain lobe or organelle. In an example, a method can track a change in brainwave activity within the Delta band as measured from a specific sensor site, a specific sensor channel, and/or a specific montage of channels.

In an example, Theta brainwaves can be measured and analyzed within a frequency band of 4 to 8 Hz. In various examples, Theta brainwaves or other rhythmic, cyclical, and/or repeating electromagnetic signals associated with brain activity can be measured and analyzed within a frequency band selected from the group consisting of: 3.5-7 Hz, 3-7 Hz, 4-7 Hz, 4-7.5 Hz, 4-8 Hz, and 5-7 Hz. In an example, a method can track changes in the power of brainwaves in the Theta band. In an example, a method can track a frequency shift within the Theta band. In an example, a method can track changes in wave shape for brainwaves in the Theta band. In an example, a method can track a change in which brain regions originate or modify brainwaves within the Theta band. In an example, a method can track a change in brainwave activity within the Theta band as measured from a specific sensor site, a specific sensor channel, and/or a specific montage of channels.

In an example, Alpha brainwaves can be measured and analyzed within a frequency band of 7 to 14 Hz. In various examples, Alpha brainwaves or other rhythmic, cyclical, and/or repeating electromagnetic signals associated with brain activity can be measured and analyzed within a frequency band selected from the group consisting of: 7-13 Hz, 7-14 Hz, 8-12 Hz, 8-13 Hz, 7-11 Hz, 8-10 Hz, and 8-10 Hz. In an example, a method can track an increase or decrease in the relative power of brainwaves in the Alpha band. In an example, a method can track a downward or upward shift in the frequency of brainwaves within the Alpha band. In an example, a method can track a change in wave shape for brainwaves in the Alpha frequency band. In an example, a method can track a change in which brain regions originate or modify brainwaves within the Alpha frequency band. In an example, a method can track a change in brainwave activity within the Alpha band on one side of a person's brain relative to the other side. In an example, a method can track a change in brainwave activity within the Alpha band in a particular brain lobe or organelle. In an example, a method can track a change in brainwave activity within the Alpha band as measured from a specific sensor site, a specific sensor channel, and/or a specific montage of channels.

In an example, Beta brainwaves can be measured and analyzed within a frequency band of 12 to 30 Hz. In various examples, Beta brainwaves or other rhythmic, cyclical, and/or repeating electromagnetic signals associated with brain activity can be measured and analyzed within a frequency band selected from the group consisting of: 11-30 Hz, 12-30 Hz, 13-18 Hz, 13-22 Hz, 13-26 Hz, 13-26 Hz, 13-30 Hz, 13-32 Hz, 14-24 Hz, 14-30 Hz, and 14-40 Hz. In an example, specific patterns or trends in brainwaves in the Beta frequency band can be statistically identified.

In an example, Gamma brainwaves can be measured and analyzed within a frequency band of 30 to 100 Hz. In various examples, Gamma brainwaves or other rhythmic, cyclical, and/or repeating electromagnetic signals associated with brain activity can be measured and analyzed within a frequency band selected from the group consisting of: 30-100 Hz, 35-100 Hz, 40-100 Hz, and greater than 30 Hz. In an example, specific patterns or trends in brainwaves in the Gamma frequency band can be statistically identified. In an example, a person can be identified as having the "World's Best Gamma" and receive an appropriately-labeled coffee mug.

In an example, a primary statistical method can employ multivariate analysis of electromagnetic brainwave activity in the Delta, Theta, and Alpha frequency bands to identify patterns. In an example, a primary statistical method can comprise calculating an arithmetic function, or a change in an arithmetic function, of the different power levels in multiple frequency bands. In an example, a primary statistical method can comprise a difference, or a change in a difference, between power levels in different frequency bands. In an example, a primary statistical method can comprise a ratio, or a change in a ratio, of power levels in different frequency bands. In an example, a primary statistical method can comprise a sum, or a change in a sum, of power levels in different frequency bands. In an example, a primary statistical method can comprise a product, or a change in a product, of power levels in different frequency bands.

In various examples, specific patterns of electromagnetic brain activity can be analyzed and identified using one or more methods selected from the group consisting of: ANOVA or MANOVA; artificial neural network; auto-regression; Bonferroni analysis; centroid analysis; chi-squared analysis; cluster analysis and grouping; decision tree or random forest analysis; Discrete Fourier transform (DFT), Fast Fourier Transform (FFT), or other Fourier Transform methods; factor analysis; feature vector analysis; fuzzy logic model; Gaussian model; hidden Markov model, input-output hidden Markov model, or other Markov model; inter-band mean; inter-band ratio; inter-channel mean; inter-channel ratio; inter-montage mean; inter-montage ratio; Kalman filter; kernel estimation; linear discriminant analysis; linear transform; logit model; machine learning; mean power; mean; median; multi-band covariance analysis; multi-channel covariance analysis; multivariate linear regression or multivariate least squares estimation; multivariate logit or other multivariate parametric classifiers; naïve Bayes classifier, trained Bayes classifier, dynamic Bayesian network, or other Bayesian methods; non-linear programming; pattern recognition; power spectral density or other power spectrum analysis; principal components analysis; probit model; support vector machine; time-series model; T-test; variance, covariance, or correlation; waveform identification; multi-resolution wavelet analysis or other wavelet analysis; whole band power; support vector machine; and Z-scores or other data normalization method.

In an example, a power source can be a rechargeable battery. In an example, a power source can be selected from the group consisting of: a rechargeable or replaceable battery; an energy harvesting member which harvests, transduces, or generates energy from body motion or kinetic energy, body thermal energy, or body biochemical energy; an energy harvesting member which harvests, transduces, or generates energy from ambient light energy or ambient electromagnetic energy.

In an example, a data processing unit can process data from one or more electromagnetic energy sensors. In an example a data processing unit can be a microchip, circuit board, CPU, and/or miniature computer. In an example, a data transmitter and/or receiver can be a wireless data transmitter and/or receiver. In an example, data transmitter and/or receiver can be in wireless communication with a remote computer, a handheld electronic device, a separate wearable device, a separate array of wearable sensors, a communication network tower, a satellite, a home control system, and/or an implantable medical device.

FIGS. 1 through 8 show examples of how this invention can be embodied in a hair-engaging mobile brain activity monitor comprising: (1) an arcuate frame which is configured to be worn on a person's head, wherein this arcuate frame further comprises: (1a) a right ear loop which is configured to curve around the person's right ear; (1b) a left ear loop which is configured to curve around the person's left ear; (1c) a posterior loop which is connected to the right ear loop and the left ear loop, where this posterior loop is configured to curve around a posterior portion of a person's head; (1d) a right upward-extending member which is configured to extend upward toward the top of the person's head from the right ear loop and/or from the posterior loop, wherein this right upward-extending member has a first configuration in which its upper-most portion is a first distance from the top of the person's head, wherein this right upward-extending member has a second configuration in which its upper-most portion is a second distance from the top of the person's head, wherein the second distance is less than the first distance, and wherein the right upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; and (1e) a left upward-extending member which is configured to extend upward toward the top of the person's head from the left ear loop and/or from the posterior loop, wherein this left upward-extending member has a first configuration in which its upper-most portion is a first distance from the top of the person's head, wherein this left upward-extending member has a second configuration in which its upper-most portion is a second distance from the top of the person's head, wherein the second distance is less than the first distance, and wherein the left upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; (2) one or more electromagnetic energy sensors which collect data concerning electromagnetic brain activity; (3) a power source; (4) a data processing unit; and (5) a data transmitter and/or receiver.

FIG. 1 shows an example of how this invention can be embodied in a hair-engaging mobile brain activity monitor. The top third of FIG. 1 (two sequential pictures of the side of a person's head) shows this monitor from a perspective looking at the side of a person's head. The middle third of FIG. 1 (two sequential pictures of the front of a person's head) shows this monitor from a perspective looking at the front of a person's head. The bottom third of FIG. 1 (two sequential pictures of the top of a person's head) shows this monitor from a perspective looking down at the top of a person's head. The left side of FIG. 1 (three pictures from three different perspectives) shows this monitor at a first point in time, in a first configuration, before it is worn on the head and engages the person's hair. The right side of FIG. 1 (three pictures from three different perspectives) shows this same monitor at a second point in time, in a second configuration, when it is worn on the head and engages the person's hair.

The top third of FIG. 1 shows the hair-engaging mobile brain activity monitor from a left side perspective. As seen in this top third of FIG. 1, this brain activity monitor comprises: an arcuate frame which is configured to be worn on a person's head, wherein this arcuate frame further comprises: a left ear loop 105 which is configured to curve around the person's left ear; a posterior loop 107 which is connected to the left ear loop 105, where this posterior loop 107 is configured to curve around a posterior portion of a person's head; and a left upward-extending member 103 which is configured to extend upward toward the top of the person's head from the left ear loop 105, wherein this left upward-extending member has a first configuration in which its upper-most portion is a first distance from the top of the person's head, wherein this left upward-extending member has a second configuration in which its upper-most portion is a second distance from the top of the person's head, wherein the second distance is less than the first distance, and wherein the left upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; one or more left-side electromagnetic energy sensors, 101 and 102, which collect data concerning electromagnetic brain activity; and a left-side housing 106 which contains a power source, a data processing unit, and a data transmitter and/or receiver. This example further comprises a left-side hinge 104 between left ear loop 105 and left upward-extending member 103.

The left side of the top third of FIG. 1 shows this monitor at first point in time, in the first configuration, wherein posterior loop 107 has been flexed outward, left ear loop 105 is not yet worn around the left ear, and only the upper tip of left upward-extending member 103 has been inserted into the person's hair. In these examples, the portion of an upward-extending member which has been inserted into a person's hair, engaging the hair strands and/or sliding upwards under a layer of hair, is represented by dotted lines to show that it is partially obscured from view. On the left side of the top third of FIG. 1, only the upper tip of left upward-extending member 103 is shown with dotted lines since only the tip has been inserted into the person's hair at this time, in the first configuration.

The right side of the top third of FIG. 1 shows this monitor at a second point in time, in the second configuration, wherein posterior loop 107 has flexed inward, left ear loop 105 is now worn around a portion of the left ear, and most of the upward-extending member 103 has been upwardly inserted into the person's hair, engaging the hair strands and/or sliding upwards under a layer of hair. This is why most of upward-extending member 103 is shown with dotted lines on the right side at this second point in time, in the second configuration.

The middle third of FIG. 1 shows this same hair-engaging mobile brain activity monitor from a frontal face perspective. This perspective shows right-side components of the monitor as well as left-side components. Right-side components shown for the first time in this perspective include: a right ear loop 115 which is configured to curve around the person's right ear; a right upward-extending member 113 which is configured to extend upward toward the top of the person's head from the right ear loop 115, wherein this right upward-extending member has a first configuration in which its upper-most portion is a first distance from the top of the person's head, wherein this right upward-extending member has a second configuration in which its upper-most portion is a second distance from the top of the person's head, wherein the second distance is less than the first distance, and wherein the right upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; one or more right-side electromagnetic energy sensors, 111 and 112, which collect data concerning electromagnetic brain activity; and a right-side housing 116 which contains a power source, a data processing unit, and a data transmitter and/or receiver. This example further comprises a right-side hinge 114 between right ear loop 115 and right upward-extending member 113.

The left side of the middle third of FIG. 1 again shows this monitor at first point in time, in the first configuration, but this time from a frontal face perspective. From this perspective, it can be clearly seen that posterior loop 107 has been flexed outward, that right and left ear loops 115 and 105 are not yet worn around the ears, and that only the upper tips of right and left upward-extending members 113 and 103 have been inserted into the person's hair. The right side of the middle third of FIG. 1 shows this monitor at a second point in time, in the second configuration. From this perspective, it can be clearly seen that posterior loop 107 has flexed inward, that right and left ear loops 115 and 105 are now worn around the ears, and that most of right and left upward-extending members 113 and 103 have now been inserted into the person's hair. Also, in this example, the upper tips of right and left upward-extending members 113 and 103 have been connected or attached to each other in the second configuration.

The bottom third of FIG. 1 shows this same hair-engaging mobile brain activity monitor from a top-down perspective. The left side of the bottom third of FIG. 1 again shows this monitor at first point in time, in the first configuration. From this perspective, it can be clearly seen that posterior loop 107 has been flexed outward, that right and left ear loops 115 and 105 are not yet worn around the ears, and that only the upper tips of right and left upward-extending members 113 and 103 have been inserted into the person's hair. The right side of the bottom third of FIG. 1 shows this monitor at a second point in time, in the second configuration. From this perspective, it can be clearly seen that posterior loop 107 has flexed inward, that right and left ear loops 115 and 105 are now worn around the ears, and that most of right and left upward-extending members 113 and 103 have now been inserted into the person's hair. Also, in this example, the upper tips of right and left upward-extending members 113 and 103 have been connected or attached to each other in the second configuration. Relevant example and design variations discussed elsewhere in this disclosure can also be applied to the example shown here in FIG. 1.

FIG. 2 shows another example of how this invention can be embodied in a hair-engaging mobile brain activity monitor. The monitor shown in this example is similar to the one shown in FIG. 1 except that the upper tips of the right and left upward-extending members are not connected to each other in the second configuration. Another difference between FIG. 2 and FIG. 1 is that FIG. 2 only shows the monitor in the second configuration. Movement of the device from the first configuration to the second configuration occurs in a manner similar to the device shown in FIG. 1, so these sequential perspectives are not shown again in FIG. 2. The top third of FIG. 2 shows this monitor looking at the side of a person's head. The middle third of FIG. 2 shows this monitor looking at the front of a person's head. The bottom third of FIG. 2 shows this monitor looking down at the top of a person's head.

As shown in the top third of FIG. 2, this brain activity monitor comprises: an arcuate frame which is configured to be worn on a person's head, wherein this arcuate frame further comprises: a left ear loop 205 which is configured to curve around the person's left ear; a posterior loop 207 which is connected to the left ear loop 205, where this posterior loop 207 is configured to curve around a posterior portion of a person's head; and a left upward-extending member 203 which is configured to extend upward toward the top of the person's head from the left ear loop 205, wherein this left upward-extending member has a first configuration in which its upper-most portion is a first distance from the top of the person's head, wherein this left upward-extending member has a second configuration in which its upper-most portion is a second distance from the top of the person's head, wherein the second distance is less than the first distance, and wherein the left upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; one or more left-side electromagnetic energy sensors, 201 and 202, which collect data concerning electromagnetic brain activity; and a left-side housing 206 which contains a power source, a data processing unit, and a data transmitter and/or receiver. This example further comprises a left-side hinge 204 between left ear loop 205 and left upward-extending member 203.

The middle third of FIG. 2 shows this same hair-engaging mobile brain activity monitor from a frontal face perspective. This perspective shows right-side components of the monitor as well as left-side components. Right-side components shown for the first time in this perspective include: a right ear loop 215 which is configured to curve around the person's right ear; a right upward-extending member 213 which is configured to extend upward toward the top of the person's head from the right ear loop 215, wherein this right upward-extending member has a first configuration in which its upper-most portion is a first distance from the top of the person's head, wherein this right upward-extending member has a second configuration in which its upper-most portion is a second distance from the top of the person's head, wherein the second distance is less than the first distance, and wherein the right upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; and one or more right-side electromagnetic energy sensors, 211 and 212, which collect data concerning electromagnetic brain activity. This example further comprises a right-side hinge 214 between right ear loop 215 and right upward-extending member 213. In this example, the upper tips of right and left upward-extending members 213 and 203 are not connected or attached to each other, even in the second configuration.

The bottom third of FIG. 2 shows this same hair-engaging mobile brain activity monitor from a top-down perspective. In this example, the upper tips of right and left upward-extending members 213 and 203 are not connected or attached to each other, even in the second configuration. Relevant example and design variations discussed elsewhere in this disclosure can also be applied to the example shown here in FIG. 2.

Figure 3:
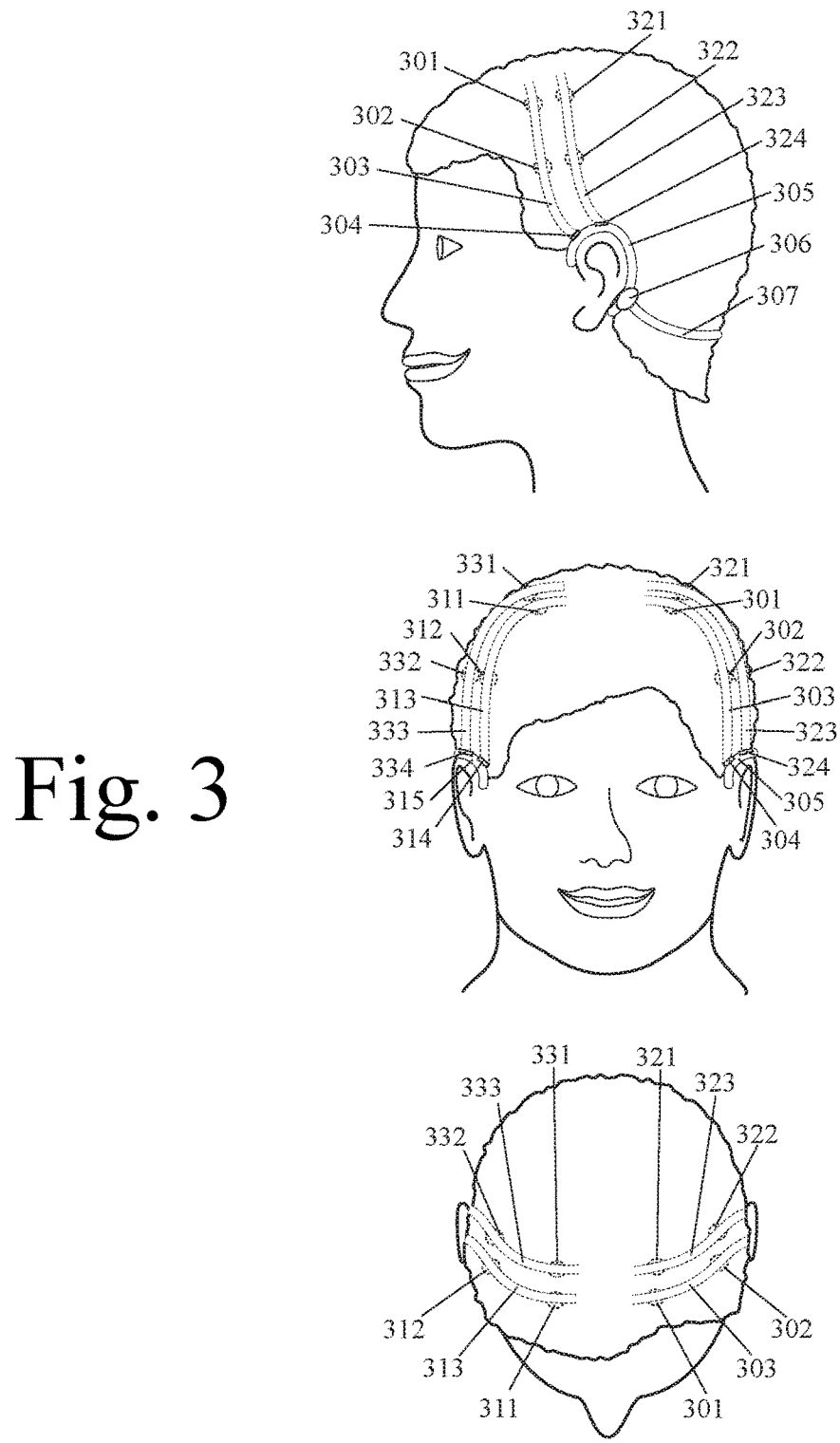
FIG. 3 shows a BCI device with dual right and dual left side members which engage a person's hair.

FIG. 3 shows another example of how this invention can be embodied in a hair-engaging mobile brain activity monitor. The monitor shown in this example is similar to the one shown in FIG. 2 except that there are two, generally parallel, upward-extending members on each side of the person's head. The top third of FIG. 3 shows this monitor looking at the side of a person's head. The middle third of FIG. 3 shows this monitor looking at the front of a person's head. The bottom third of FIG. 3 shows this monitor looking down at the top of a person's head.

As shown in the top third of FIG. 3, this brain activity monitor comprises: an arcuate frame which is configured to be worn on a person's head, wherein this arcuate frame further comprises: a left ear loop 305 which is configured to curve around the person's left ear; a posterior loop 307 which is connected to the left ear loop 305, where this posterior loop 307 is configured to curve around a posterior portion of a person's head; a first left upward-extending member 303 which is configured to extend upward toward the top of the person's head from the left ear loop 305, wherein this first left upward-extending member has a first configuration in which its upper-most portion is a first distance from the top of the person's head, wherein this first left upward-extending member has a second configuration in which its upper-most portion is a second distance from the top of the person's head, wherein the second distance is less than the first distance, and wherein the first left upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; a second left upward-extending member 323 which is configured to extend upward toward the top of the person's head from the left ear loop 305, wherein this second left upward-extending member has a first configuration in which its upper-most portion is a first distance from the top of the person's head, wherein this second left upward-extending member has a second configuration in which its upper-most portion is a second distance from the top of the person's head, wherein the second distance is less than the first distance, and wherein the second left upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; one or more left-side electromagnetic energy sensors, 301, 302, 321, and 322, which collect data concerning electromagnetic brain activity; and a left-side housing 306 which contains a power source, a data processing unit, and a data transmitter and/or receiver. This example further comprises a first left-side hinge 304 between left ear loop 305 and first left upward-extending member 303 and a second left-side hinge 324 between left ear loop 305 and second left upward-extending member 323.

The middle third of FIG. 3 shows this same hair-engaging mobile brain activity monitor from a frontal face perspective. This perspective shows right-side components of the monitor as well as left-side components. Right-side components shown for the first time in this perspective include: a right ear loop 315 which is configured to curve around the person's right ear; a first right upward-extending member 313 which is configured to extend upward toward the top of the person's head from the right ear loop 315, wherein this first right upward-extending member has a first configuration in which its upper-most portion is a first distance from the top of the person's head, wherein this first right upward-extending member has a second configuration in which its upper-most portion is a second distance from the top of the person's head, wherein the second distance is less than the first distance, and wherein the first right upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; a second right upward-extending member 333 which is configured to extend upward toward the top of the person's head from the right ear loop 315, wherein this second right upward-extending member has a second configuration in which its upper-most portion is a second distance from the top of the person's head, wherein this second right upward-extending member has a second configuration in which its upper-most portion is a second distance from the top of the person's head, wherein the second distance is less than the second distance, and wherein the second right upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; and one or more right-side electromagnetic energy sensors, 311, 312, 331, and 332, which collect data concerning electromagnetic brain activity. This example further comprises a first right-side hinge 314 between right ear loop 315 and first right upward-extending member 313 and a second right-side hinge 334 between right ear loop 315 and second right upward-extending member 333. In this example, the upper tips of right and left upward-extending members are not connected or attached to each other, even in the second configuration.

The bottom third of FIG. 3 shows this same hair-engaging mobile brain activity monitor from a top-down perspective. In this example, the upper tips of right and left upward-extending members are not connected or attached to each other, even in the second configuration. Relevant example and design variations discussed elsewhere in this disclosure can also be applied to the example shown here in FIG. 3.

Figure 4:
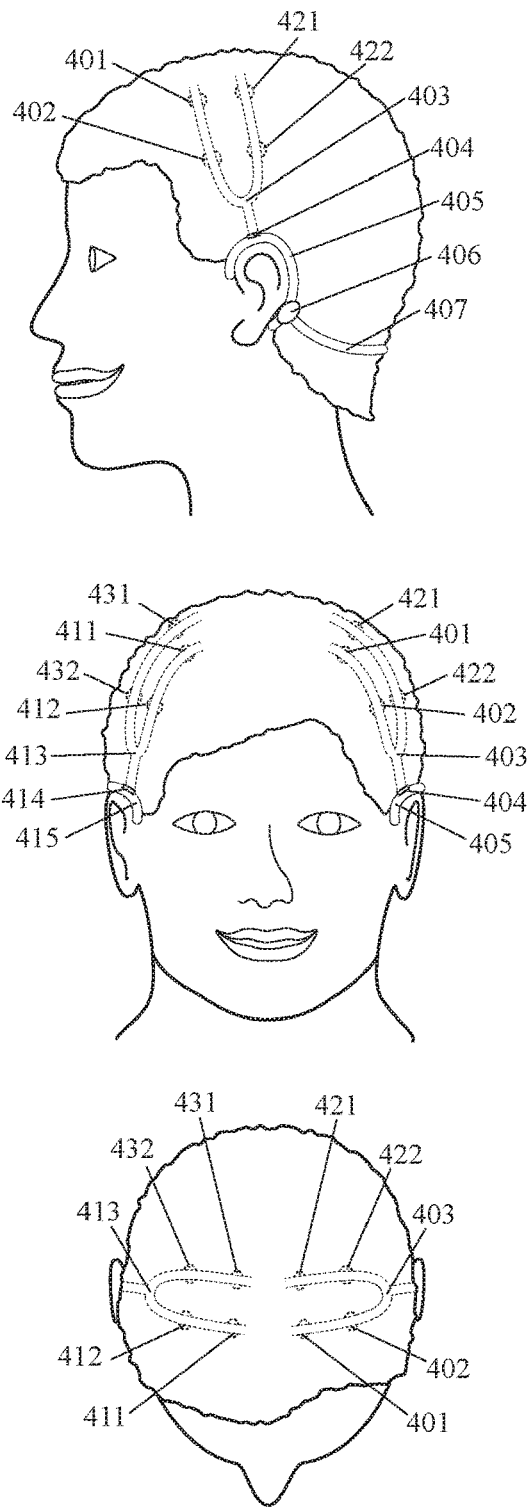
FIG. 4 shows a BCI device with Y-shaped right and left side members which engage a person's hair.

FIG. 4 shows another example of how this invention can be embodied in a hair-engaging mobile brain activity monitor. The monitor shown in this example is similar to the one shown in FIG. 2 except that the upper portion of an upward-extending member bifurcates (looking similar to a capital letter "Y"). The top third of FIG. 4 shows this monitor looking at the side of a person's head. The middle third of FIG. 4 shows this monitor looking at the front of a person's head. The bottom third of FIG. 4 shows this monitor looking down at the top of a person's head.

As shown in the top third of FIG. 4, this brain activity monitor comprises: an arcuate frame which is configured to be worn on a person's head, wherein this arcuate frame further comprises: a left ear loop 405 which is configured to curve around the person's left ear; a posterior loop 407 which is connected to the left ear loop 405, where this posterior loop 407 is configured to curve around a posterior portion of a person's head; a bifurcating left upward-extending member 403 which is configured to extend upward toward the top of the person's head from the left ear loop 405, wherein this left upward-extending member has a first configuration in which its upper-most portion is a first distance from the top of the person's head, wherein this left upward-extending member has a second configuration in which its upper-most portion is a second distance from the top of the person's head, wherein the second distance is less than the first distance, and wherein the left upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; one or more left-side electromagnetic energy sensors, 401, 402, 421, and 422, which collect data concerning electromagnetic brain activity; and a left-side housing 406 which contains a power source, a data processing unit, and a data transmitter and/or receiver. This example further comprises a left-side hinge 404 between left ear loop 405 and left upward-extending member 403.

The middle third of FIG. 4 shows this same hair-engaging mobile brain activity monitor from a frontal face perspective. This perspective shows right-side components of the monitor as well as left-side components. Right-side components shown for the first time in this perspective include: a right ear loop 415 which is configured to curve around the person's right ear; a bifurcating right upward-extending member 413 which is configured to extend upward toward the top of the person's head from the right ear loop 415, wherein this right upward-extending member has a first configuration in which its upper-most portion is a first distance from the top of the person's head, wherein this right upward-extending member has a second configuration in which its upper-most portion is a second distance from the top of the person's head, wherein the second distance is less than the first distance, and wherein the right upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; and one or more right-side electromagnetic energy sensors, 411, 412, 431, and 432, which collect data concerning electromagnetic brain activity. This example further comprises a right-side hinge 414 between right ear loop 415 and right upward-extending member 413. In this example, the upper tips of right and left upward-extending members are not connected or attached to each other, even in the second configuration.

The bottom third of FIG. 4 shows this same hair-engaging mobile brain activity monitor from a top-down perspective. In this example, the upper tips of right and left upward-extending members are not connected or attached to each other, even in the second configuration. Relevant example and design variations discussed elsewhere in this disclosure can also be applied to the example shown here in FIG. 4.

Figure 5:
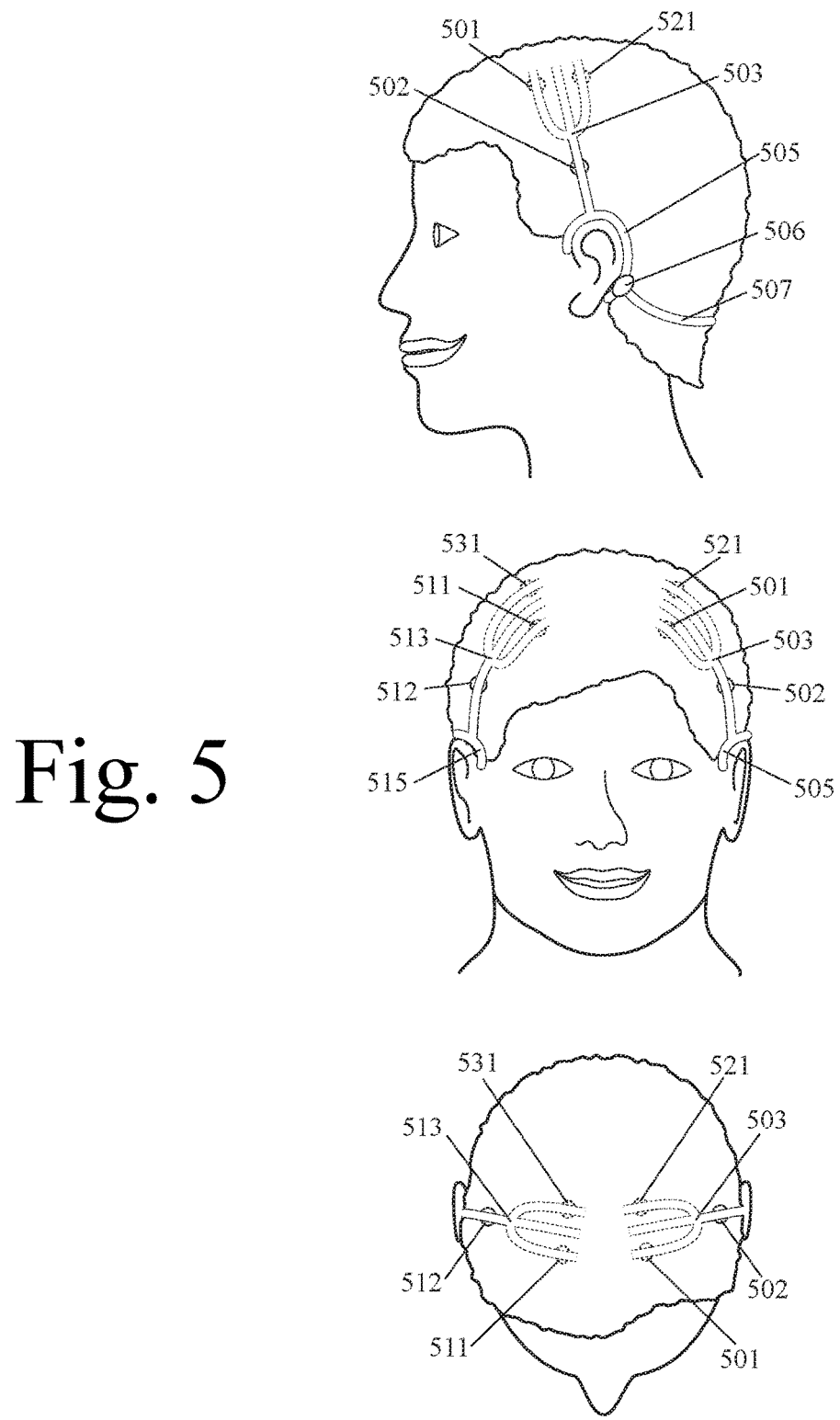
FIG. 5 shows a BCI device with trident-shaped right and left side members which engage a person's hair.

FIG. 5 shows another example of how this invention can be embodied in a hair-engaging mobile brain activity monitor. The monitor shown in this example is similar to the one shown in FIG. 2 except that the upper portion of an upward-extending member trifurcates (looking similar to a trident). The top third of FIG. 5 shows this monitor looking at the side of a person's head. The middle third of FIG. 5 shows this monitor looking at the front of a person's head. The bottom third of FIG. 5 shows this monitor looking down at the top of a person's head.

As shown in the top third of FIG. 5, this brain activity monitor comprises: an arcuate frame which is configured to be worn on a person's head, wherein this arcuate frame further comprises: a left ear loop 505 which is configured to curve around the person's left ear; a posterior loop 507 which is connected to the left ear loop 505, where this posterior loop 507 is configured to curve around a posterior portion of a person's head; a trifurcating left upward-extending member 503 which is configured to extend upward toward the top of the person's head from the left ear loop 505, wherein this left upward-extending member has a first configuration in which its upper-most portion is a first distance from the top of the person's head, wherein this left upward-extending member has a second configuration in which its upper-most portion is a second distance from the top of the person's head, wherein the second distance is less than the first distance, and wherein the left upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; one or more left-side electromagnetic energy sensors, 501, 502, and 521, which collect data concerning electromagnetic brain activity; and a left-side housing 506 which contains a power source, a data processing unit, and a data transmitter and/or receiver.

The middle third of FIG. 5 shows this same hair-engaging mobile brain activity monitor from a frontal face perspective. This perspective shows right-side components of the monitor as well as left-side components. Right-side components shown for the first time in this perspective include: a right ear loop 515 which is configured to curve around the person's right ear; a trifurcating right upward-extending member 513 which is configured to extend upward toward the top of the person's head from the right ear loop 515, wherein this right upward-extending member has a first configuration in which its upper-most portion is a first distance from the top of the person's head, wherein this right upward-extending member has a second configuration in which its upper-most portion is a second distance from the top of the person's head, wherein the second distance is less than the first distance, and wherein the right upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; and one or more right-side electromagnetic energy sensors, 511, 512, and 531, which collect data concerning electromagnetic brain activity. In this example, the upper tips of right and left upward-extending members are not connected or attached to each other, even in the second configuration.

The bottom third of FIG. 5 shows this same hair-engaging mobile brain activity monitor from a top-down perspective. In this example, the upper tips of right and left upward-extending members are not connected or attached to each other, even in the second configuration. Relevant example and design variations discussed elsewhere in this disclosure can also be applied to the example shown here in FIG. 5.

FIG. 6 shows another example of how this invention can be embodied in a hair-engaging mobile brain activity monitor. The monitor shown in this example is similar to the one shown in FIG. 2 except that the upward-extending member is a loop. The top third of FIG. 6 shows this monitor looking at the side of a person's head. The middle third of FIG. 6 shows this monitor looking at the front of a person's head. The bottom third of FIG. 6 shows this monitor looking down at the top of a person's head.

As shown in the top third of FIG. 6, this brain activity monitor comprises: an arcuate frame which is configured to be worn on a person's head, wherein this arcuate frame further comprises: a left ear loop 6005 which is configured to curve around the person's left ear; a posterior loop 6007 which is connected to the left ear loop 6005, where this posterior loop 6007 is configured to curve around a posterior portion of a person's head; a left upward-extending member 6003 which is configured to loop upward toward the top of the person's head from the left ear loop 6005 and then back downward to left ear loop 6005, wherein this left upward-extending member has a first configuration in which its upper-most portion is a first distance from the top of the person's head, wherein this left upward-extending member has a second configuration in which its upper-most portion is a second distance from the top of the person's head, wherein the second distance is less than the first distance, and wherein the left upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; one or more left-side electromagnetic energy sensors, 6001, 6002, 6021, and 6022, which collect data concerning electromagnetic brain activity; and a left-side housing 6006 which contains a power source, a data processing unit, and a data transmitter and/or receiver.

The middle third and bottom third of FIG. 6 show this same hair-engaging mobile brain activity monitor from a frontal face perspective and a top-down perspective, respectively. Right-side components include: a right ear loop 6015 which is configured to curve around the person's right ear; a right upward-extending member 6013 which is configured to loop upward toward the top of the person's head from the right ear loop 6015 and then back downward to right ear loop 6015, wherein this right upward-extending member has a first configuration in which its upper-most portion is a first distance from the top of the person's head, wherein this right upward-extending member has a second configuration in which its upper-most portion is a second distance from the top of the person's head, wherein the second distance is less than the first distance, and wherein the right upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; and one or more right-side electromagnetic energy sensors, 6011, 6012, 6031, and 6032, which collect data concerning electromagnetic brain activity. In this example, the upper tips of right and left upward-extending members are not connected or attached to each other, even in the second configuration. Relevant example and design variations discussed elsewhere in this disclosure can also be applied to the example shown here in FIG. 6.

Figure 7:
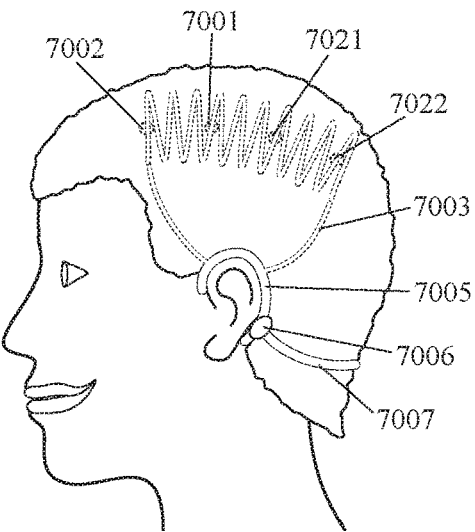
FIG. 7 shows a BCI device with right and left side members with teeth which engage a person's hair.
Figure 7:
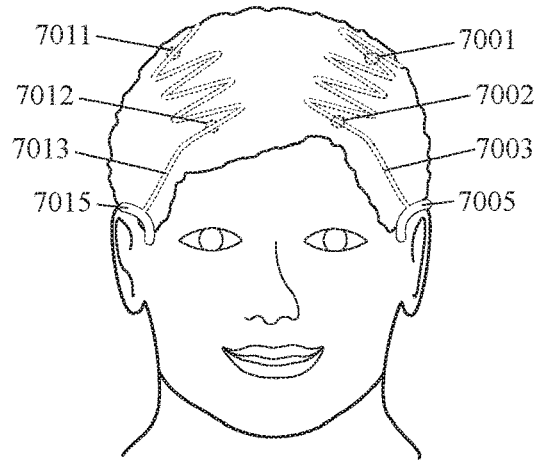
Figure 7:
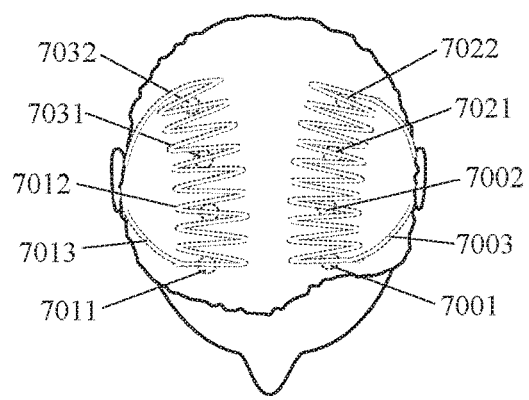

FIG. 7 shows another example of how this invention can be embodied in a hair-engaging mobile brain activity monitor. The monitor shown in this example is similar to the one shown in FIG. 6 except that the upward-extending member is a loop with multiple upward-facing protrusions, prongs, and/or teeth. The top third of FIG. 7 shows this monitor looking at the side of a person's head. The middle third of FIG. 7 shows this monitor looking at the front of a person's head. The bottom third of FIG. 7 shows this monitor looking down at the top of a person's head.

As shown in the top third of FIG. 7, this brain activity monitor comprises: an arcuate frame which is configured to be worn on a person's head, wherein this arcuate frame further comprises: a left ear loop 7005 which is configured to curve around the person's left ear; a posterior loop 7007 which is connected to the left ear loop 7005, where this posterior loop 7007 is configured to curve around a posterior portion of a person's head; a left upward-extending member 7003 which is configured to loop upward toward the top of the person's head from the left ear loop 7005 and then back downward to left ear loop 7005, wherein this left upward-extending member has multiple upward-facing protrusions, prongs, and/or teeth, wherein this left upward-extending member has a first configuration in which its upper-most portion is a first distance from the top of the person's head, wherein this left upward-extending member has a second configuration in which its upper-most portion is a second distance from the top of the person's head, wherein the second distance is less than the first distance, and wherein the left upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; one or more left-side electromagnetic energy sensors, 7001, 7002, 7021, and 7022, which collect data concerning electromagnetic brain activity; and a left-side housing 7006 which contains a power source, a data processing unit, and a data transmitter and/or receiver.

The middle third and bottom third of FIG. 7 show this same hair-engaging mobile brain activity monitor from a frontal face perspective and a top-down perspective, respectively. Right-side components include: a right ear loop 7015 which is configured to curve around the person's right ear; a right upward-extending member 7013 which is configured to loop upward toward the top of the person's head from the right ear loop 7015 and then back downward to right ear loop 7015, wherein this right upward-extending member has multiple upward-facing protrusions, prongs, and/or teeth, wherein this right upward-extending member has a first configuration in which its upper-most portion is a first distance from the top of the person's head, wherein this right upward-extending member has a second configuration in which its upper-most portion is a second distance from the top of the person's head, wherein the second distance is less than the first distance, and wherein the right upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; and one or more right-side electromagnetic energy sensors, 7011, 7012, 7031, and 7032, which collect data concerning electromagnetic brain activity. In this example, the upper tips of right and left upward-extending members are not connected or attached to each other, even in the second configuration. Relevant example and design variations discussed elsewhere in this disclosure can also be applied to the example shown here in FIG. 7.

Figure 8:
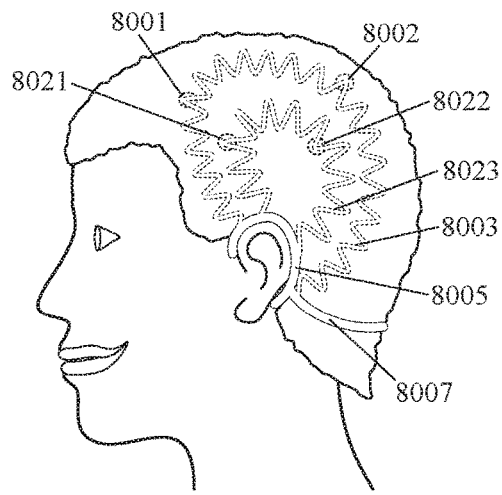
FIG. 8 shows a BCI device with right and left side nested loops which engage a person's hair.
Figure 8:
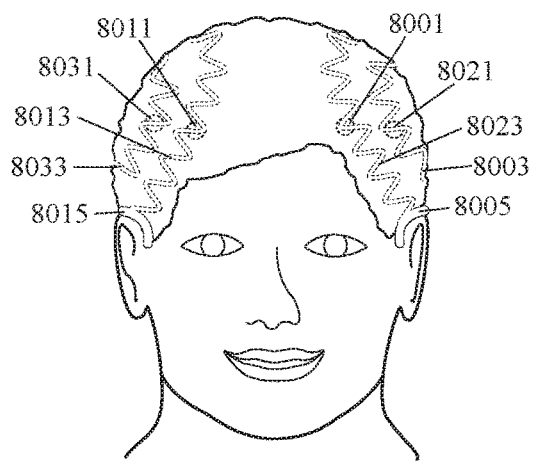
Figure 8:
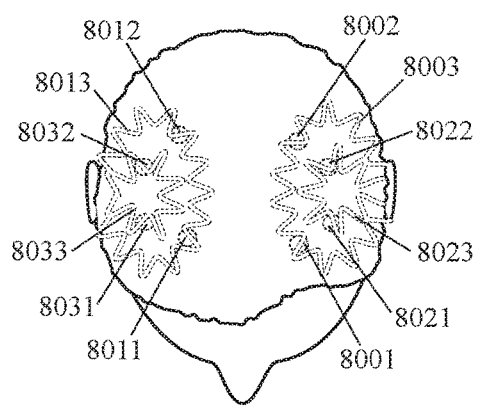

FIG. 8 shows another example of how this invention can be embodied in a hair-engaging mobile brain activity monitor. The monitor shown in this example is similar to the one shown in FIG. 7 except that there are two nested upward-extending loops with multiple protrusions, prongs, and/or teeth. The top third of FIG. 8 shows this monitor looking at the side of a person's head. The middle third of FIG. 8 shows this monitor looking at the front of a person's head. The bottom third of FIG. 8 shows this monitor looking down at the top of a person's head.

As shown in the top third of FIG. 8, this brain activity monitor comprises: an arcuate frame which is configured to be worn on a person's head, wherein this arcuate frame further comprises: a left ear loop 8005 which is configured to curve around the person's left ear; a posterior loop 8007 which is connected to the left ear loop 8005, where this posterior loop 8007 is configured to curve around a posterior portion of a person's head; a first left upward-extending member 8003 which is configured to loop upward toward the top of the person's head from the left ear loop 8005 and then back downward to left ear loop 8005, wherein this first left upward-extending member has multiple protrusions, prongs, and/or teeth, wherein this first left upward-extending member has a first configuration in which its upper-most portion is a first distance from the top of the person's head, wherein this first left upward-extending member has a second configuration in which its upper-most portion is a second distance from the top of the person's head, wherein the second distance is less than the first distance, and wherein the first left upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; a second left upward-extending member 8023 which is configured to loop upward toward the top of the person's head from the left ear loop 8005 and then back downward to left ear loop 8005, wherein this second left upward-extending member has multiple protrusions, prongs, and/or teeth, wherein this second left upward-extending member has a first configuration in which its upper-most portion is a first distance from the top of the person's head, wherein this second left upward-extending member has a second configuration in which its upper-most portion is a second distance from the top of the person's head, wherein the second distance is less than the first distance, and wherein the second left upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; one or more left-side electromagnetic energy sensors, 8001, 8002, 8021, and 8022, which collect data concerning electromagnetic brain activity; and a left-side housing 8006 which contains a power source, a data processing unit, and a data transmitter and/or receiver.

The middle third and bottom third of FIG. 8 show this same hair-engaging mobile brain activity monitor from a frontal face perspective and a top-down perspective, respectively. Right-side components include: a right ear loop 8015 which is configured to curve around the person's right ear; a first right upward-extending member 8013 which is configured to loop upward toward the top of the person's head from the right ear loop 8015 and then back downward to right ear loop 8015, wherein this first right upward-extending member has multiple protrusions, prongs, and/or teeth, wherein this first right upward-extending member has a first configuration in which its upper-most portion is a first distance from the top of the person's head, wherein this first right upward-extending member has a second configuration in which its upper-most portion is a second distance from the top of the person's head, wherein the second distance is less than the first distance, and wherein the first right upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; a second right upward-extending member 8033 which is configured to loop upward toward the top of the person's head from the right ear loop 8015 and then back downward to right ear loop 8015, wherein this second right upward-extending member has multiple protrusions, prongs, and/or teeth, wherein this second right upward-extending member has a first configuration in which its upper-most portion is a first distance from the top of the person's head, wherein this second right upward-extending member has a second configuration in which its upper-most portion is a second distance from the top of the person's head, wherein the second distance is less than the first distance, and wherein the second right upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; and one or more right-side electromagnetic energy sensors, 8011, 8012, 8031, and 8032, which collect data concerning electromagnetic brain activity. In this example, the upper tips of right and left upward-extending members are not connected or attached to each other, even in the second configuration. Relevant example and design variations discussed elsewhere in this disclosure can also be applied to the example shown here in FIG. 8.

In an example, this invention can be embodied in a Brain Computer Interface (BCI) system, device, or method which enables a person to control environmental devices, appliances, and/or machines in different action modes based on common electromagnetic brain activity patterns which are associated with the same control command across different action modes. In different embodiments, one or more action modes can be selected from the group consisting of: speaking a word, phrase, and/or command; using a touch screen or other touch-based human-to-computer interface; manually moving a switch, button, dial, or knob on an environmental device; making a hand gesture; typing a word, phrase, and/or command; moving a computer mouse; moving one's eyes; and just thinking about controlling an environmental device.

In an example, a Brain Computer Interface (BCI) system, device, or method can comprise: two or more calibration periods in which a person controls an environmental device in a selected manner by performing actions in two or more different action modes; and a subsequent period in which the person controls the environmental device in the selected manner by performing an action in an action mode which is more convenient, efficient, and/or discreet than either of the first two action modes. In an example, the action mode in the subsequent period can be just thinking about controlling the environmental device in the selected manner. In an example, this invention can be part of the Internet of Thinks (IoT).

In an example, this invention can be embodied in a Brain Computer Interface (BCI) system comprising: a head-worn attachment; at least one electromagnetic brain activity sensor; a microphone; a touch screen; and a data processing unit. In this example, the data processing unit: (a) analyzes electromagnetic brain activity from a first time period within which the person speaks a word or phrase to control an environmental device, appliance, and/or machine in a selected manner; (b) analyzes electromagnetic brain activity from a second period within which the person uses the touch screen to control the environmental device, appliance, and/or machine in the selected manner; (c) identifies a specific pattern shared by electromagnetic brain activity within the first and second periods of time which is associated with controlling the environmental device, appliance, and/or machine in the selected manner; and (d) if the data processing unit detects that specific pattern of electromagnetic brain activity within a third time period, then the data processing unit controls the environmental device, appliance, and/or machine in the selected manner.

In an example, during the third time period the person neither speaks a word or phrase nor uses a touch screen in order to control the environmental device, appliance, and/or machine in the selected manner. In an example, during the third time period, the person can control the device, appliance, and/or machine in the selected manner via an external action selected from the group consisting of: using their hand to move a switch, button, dial, or knob on the device; making a hand gesture; typing a word or phrase; moving a computer mouse; and moving their eyes. In an example, during the third time period, the person can control the device, appliance, and/or machine in the selected manner by just thinking, unaccompanied by any of these external actions.

In this example, this invention includes a microphone and has speech recognition capability in order to recognize selected words, phrases, and/or commands which are spoken by the person wearing the device. In an example, this invention can further comprise a database of selected words, phrases, and/or commands which are spoken by the person wearing the device. In an example, commands can relate to controlling environmental devices, appliances, and/or machines. In an example, a database can comprise sets of different words or phrases which share the same command meaning (such as sets of phrases with the same words in different orders or sets of phrases with word synonyms).

In an example, a database can associate specific electromagnetic brain activity patterns with specific words, phrases, and/or commands. In an example, a data processing unit can analyze data from the electromagnetic brain activity sensor and analyze data from the microphone in order to associated specific patterns of electromagnetic brain activity with specific words, phrases, and/or commands. In this example, there is a calibration period in which a data processing unit identifies a person's specific electromagnetic brain activity pattern which is associated with the person speaking a specific word, phrase, and/or command.

In an example, a database can associate a specific electromagnetic brain activity pattern with a noun which represents a selected environmental device, appliance, and/or machine. For example, there can be specific electromagnetic brain activity patterns associated, respectively, with nouns such as "Light", or "Temperature", "Dishwasher", "Edgar," or "Door". In an example, a database can associate a specific electromagnetic brain activity pattern with a verb, adjective, or preposition which represents a change in an environmental device, appliance, and/or machine. For example, there can be specific electromagnetic brain activity patterns associated, respectively, with the words such as "On", "Off", "Up", "Down", "Open", "Close", "Buy", and "Sell". In an example, a database can associate a specific electromagnetic brain activity pattern with a command which is a combination of a noun plus a verb, adjective, or preposition. For example, there can be specific electromagnetic brain activity patterns associated, respectively, with commands such as "Light On", "Light Off", "Light Up", "Light Down", "Temperature Up," "Temperature Down", "Droids Not", "Dishwasher On", "Edgar On", "Door Open", and "Door Close". In an example, word order can be reversed in a command.

In an example, specific electromagnetic brain activity patterns can be identified based on data from electromagnetic brain activity sensors which are positioned by a head-worn attachment on the surface portion of a person's head which is closest to Broca's area in the brain. In an example, electromagnetic brain activity sensors can be positioned at one or more locations selected from the group of standard EEG electrode placement sites consisting of: C3, C4, Cz, F7, T3, and T4. In an example, these sensors can be positioned by a head-worn attachment on the surface portion of a person's head which is closest to Wernicke's area in the brain. In an example, the locations of multiple electromagnetic brain activity sensors on a person's head can be automatically adjusted for a particular person to optimize recognition of that person's brain activity patterns. In an example, the locations of multiple electromagnetic brain activity sensors on a person's head can be automatically adjusted by actuators based on which application is operating at a given time.

In this embodiment, this invention also includes a touch-based human-to-machine interface which the person uses to control an environmental device, appliance, and/or machine. In an example, this interface can be a touch screen (e.g. a touch-responsive display screen). In an example, a touch screen can be part of a mobile hand-held computing device or part of a wearable computing device. In an example, this touch screen can be responsive to touch by the person's fingers. In a variation on this embodiment, this invention can comprise a touch-based human-to-machine interface which is not a display screen. In an example, this interface can be touch-responsive fabric and/or a touch-responsive surface which is integrated into an article of clothing. In an example, this interface can be a wearable computing device which does not have a touch screen, but does have a touch-responsive surface.

In an example, the data processing unit can know when a person moves their finger on a touch screen in order to control the operation of an environmental device, appliance, and/or machine. In an example, a data processing unit can know when a person uses a touch screen on a hand-held device because the data processing unit is in wireless communication with the hand-held device. For example, this invention can recognize when a person uses a touch screen to turn lights on or off. In an example, this invention can know when a person uses a finger to open an application on a hand-held or wearable device in order to adjust environmental lighting, temperature, door access, music, communication mode, and so forth. In an example, this invention can be in wireless communication with a separate hand-held or wearable mobile device in order to know when such touch-based environmental control actions occur.

In an example, this invention can create a database of specific touch-screen actions performed by a person for controlling environmental devices, appliances, and/or machines. In an example, these touch-screen actions can be within one or more environmental control applications on a mobile device. In an example, these touch-screen actions can be within one or more commerce and/or financial control applications on a mobile device. In an example, a database can associate specific electromagnetic brain activity patterns with specific touch-screen actions, respectively.

In an example, there can be a learning and/or calibration period in which a data processing unit identifies a person's specific electromagnetic brain activity pattern which is associated with the person performing a specific touch screen control action with respect to an environmental device. In an example, a database can include touch-screen actions such as: opening a home environmental control application and adjusting home temperature; opening a home lighting control application and turning lights on or off and opening a commerce application and purchasing an item. In an example, this database can further include words, phrases, and/or commands which represent these touch screen control actions, such as "Temperature Up", "Lights On", "Open Door", and "Buy It".

In an example, a head-worn attachment can be worn on (or within) a person's ear, incorporated into eyewear, or worn like a headband. In an example, a head-worn attachment can be worn on, around, or in a person's ear. In an example, a head-worn attachment can be selected from the group consisting of: ear bud, ear clip, ear plug, hearing aid, ear ring, ear phone, ear muff, headphones, headband, and headset. In an example, a head-worn attachment can be inserted (at least partially) into an ear canal. In an example, a head-worn attachment can be attached or clipped to an ear lobe. In an example, this invention can comprise only one head-worn attachment which is on one side of a person's head. In an example, a head-worn attachment can span both sides of a person's head. In an example, this invention can comprise two head-worn attachments, one on each side of a person's head.

In an example, a head-worn attachment can span the upper, rear, or front surface of the portion of a person's ear which connects the auricle to the main body of the person's head. In an example, a head-worn attachment can span the upper and rear surfaces of the portion of a person's ear which connects the auricle to the main body of the person's head. In an example, a head-worn attachment can span the upper and front surfaces of the portion of a person's ear which connects the auricle to the main body of the person's head.

In an example, a head-worn attachment can span between 5% and 25% of the cross-sectional perimeter of the portion of the person's ear which connects the auricle to the main body of the person's head. In an example, a head-worn attachment can span between 5% and 25% of the circumference of the portion of the person's ear which connects the auricle to the main body of the person's head. In an example, a head-worn attachment can span between 25% and 50% of the cross-sectional perimeter of the portion of the person's ear which connects the auricle to the main body of the person's head. In an example, a head-worn attachment can span between 25% and 50% of the circumference of the portion of the person's ear which connects the auricle to the main body of the person's head.

In an example, a head-worn attachment can span between 50% and 75% of the cross-sectional perimeter of the portion of the person's ear which connects the auricle to the main body of the person's head. In an example, a head-worn attachment can span between 50% and 75% of the circumference of the portion of the person's ear which connects the auricle to the main body of the person's head. In an example, a head-worn attachment can span between 75% and 100% of the cross-sectional perimeter of the portion of the person's ear which connects the auricle to the main body of the person's head. In an example, a head-worn attachment can span between 75% and 100% of the circumference of the portion of the person's ear which connects the auricle to the main body of the person's head.

In an example, clockwise polar coordinates can be defined for an ear, with 0 degrees being the upper-most location where the auricle connects to the main body of the head and 180 degrees being the lower-most location where the auricle connects to the main body of the head. In an example, a head-worn attachment can curve around an ear from a first polar location to a second polar location. In an example, the first polar location can be within the range of 270-350 degrees and the second polar location can be within the range of 10-90 degrees. In an example, the first polar location can be within the range of 270-350 degrees and the second polar location can be within the range of 90-200 degrees In an example, a head-worn attachment can be eyewear. In an example, a head-worn attachment can be selected from the group consisting of: eyeglasses, goggles, visor, monocle, contact lens, VR glasses, AR glasses, and other eyewear. In an example, a head-worn attachment can span from one ear to the other ear across a person's forehead. In an example, a head-worn attachment can span both eyes. In an example, a head-worn attachment can span eyebrows. In an example, a head-worn attachment can span from one ear to the other ear across a person's face. In an example, an eyewear head-worn attachment can be one continuous piece. In an example, an eyewear head-worn attachment can be comprised of multiple connected pieces. In an example, an eyewear head-worn attachment can be comprised of multiple hinge-connected pieces. In an example, an eyewear head-worn attachment can be comprised of multiple flexibly-connected pieces.

In an example, a head-worn attachment can be a headband. In an example, a head-worn attachment can encircle a person's head in a horizontal manner plane when the person's head is upright. In an example, a head-worn attachment can encircle a person's head at an acute angle with respect to this horizontal plane, wherein this acute angle is within a range of 1-10 degrees. In an example, this angle can be within a range of 10-20 degrees. In an example, this angle can be within a range of 20-45 degrees. In an example, a head-worn attachment can span at least 30% of the circumference of the head at an acute angle with respect to a horizontal plane when the person's head is upright, wherein this acute angle is within the range of 1-10 degrees. In an example, this angle can be in the range of 10-20 degrees. In an example, this angle can be within a range of 20-45 degrees.

In an example, a head-worn attachment can be selected from the group consisting of: headband, hair band, hair clip, hair comb, hat, cap, tiara, frontal loop, and rear loop. In an example, a head-worn attachment can be worn at least partially under a person's hair. In an example, a head-worn attachment can have teeth or other protrusions which engage a person's hair. In an example, a head-worn attachment can be circular, elliptical, or oval. In an example, a head-worn attachment can be shaped like a semi-circle or three-quarters of a circle. In an example, a head-worn attachment can be arcuate. In an example, a head-worn attachment can be sinusoidal. In an example, a head-worn attachment can span from one ear to the other ear, over the top of the head. In an example, a head-worn attachment can span from one ear to the other ear, around the rear of the head. In an example, a head-worn attachment can have a first portion which spans from one ear to the other ear over the top of the head and a second portion which spans from one ear to the other ear around the rear of the head. In an example, a head-worn attachment can have a first portion which spans from one ear to the other ear over the top of the head and a second portion which spans from one ear to the other ear around the front of the head.

In an example, at least one electromagnetic brain activity sensor can be held in proximity to a person's head by the head-worn attachment. In an example, electromagnetic brain activity sensors can be a part of the head-worn attachment. In an example, one or more electromagnetic brain activity sensors can be modular and removably attached to the head-worn attachment. In an example, the locations of one or more electromagnetic brain activity sensors with respect to a head-worn attachment can be manually or automatically adjusted. In an example, the proximity of an electromagnetic brain activity sensor to a person's head can be manually or automatically adjusted. In an example, each electromagnetic brain activity sensor can be paired with a nearby signal amplifier. In an example, an amplifier can amplify voltage signals between the first and second (reference) electrodes by 2-5 orders of magnitude.

In an example, an electromagnetic brain activity sensor can measure electromagnetic energy emitted by a person's brain. In an example, an electromagnetic brain activity sensor can measure changes in electromagnetic energy flowing between two electrodes wherein these changes are due to electromagnetic brain activity. In an example, an electromagnetic brain activity sensor can measure voltage fluctuations resulting from ionic current within the neurons of the brain. In an example, an electromagnetic brain activity sensor can be an electroencephalography (EEG) sensor.

In an example, an electromagnetic brain activity sensor can be a capacitive sensor. In an example, an electromagnetic brain activity sensor can be a dry electrode. In an example, an electromagnetic brain activity sensor can be a wet electrode. In an example, an electromagnetic brain activity sensor can measure voltage fluctuations between a first electrode and a second (reference) electrode due to electromagnetic brain activity. In an example, voltage differences between a first electrode and a second (reference) electrode can be called a "channel" In an example, a set of channels can be called a "montage." In an example, a second (reference) electrode can be attached to an ear. In an example, there can be two reference electrodes in a system, one attached to each ear.

In an example, an electromagnetic brain activity sensor can be positioned by a head-worn attachment on the surface portion of the person's head which is closest to Broca's area of the brain. In an example, one or more electromagnetic brain activity sensors can be positioned by the head-worn attachment at one or more locations selected from the group of standard EEG electrode placement sites consisting of: C3, C4, Cz, F7, T3, and T4. In an example, an electromagnetic brain activity sensor can be positioned by a head-worn attachment on the surface portion of the person's head which is closest to Wernicke's area of the brain. In an example, an electromagnetic brain activity sensor can be positioned by a head-worn attachment on the surface portion of the person's head which is closest to the homunculus and/or primary motor cortex of the brain. In an example, multiple electromagnetic brain activity sensors can be positioned by a head-worn attachment on the surface portions of the person's head which are closest to the superior temporal gyms and the supramarginal gyms.

In an example, one or more electromagnetic brain activity sensors or channels can be located on a person's head so as to most accurately measure the activity of one or more brain areas selected from the group consisting of: Broca's area (of the Frontal Lobe), Wernicke's area (of the Occipital Lobe), Cerebellum, Cerebral Cortex, Frontal Lobe, Occipital Lobe, Parietal Lobe, and Temporal Lobe. In an example, one or more electromagnetic brain activity sensors or channels can be placed at one or more electrode placement sites selected from the group consisting of: FP1, FPz, FP2, AF7, AF5, AF3, AFz, AF4, AF6, AF8, F7, F5, F3, F1, Fz, F2, F4, F6, F8, FT7, FC5, FC3, FC1, FCz, FC2, FC4, FC6, FT8, T3/T7, C3, C4, C1, Cz, C2, C5, C6, T4/T8, TP7, CP5, CP3, CP1, CPz, CP2, CP4, CP6, TP8, T5/P7, P5, P3, P1, Pz, P2, P4, P6, T6/P8, PO7, PO5, PO3, POz, PO4, PO6, PO8, O1, Oz, and O2. In an example, an electromagnetic brain activity sensor can be placed within an ear canal or attached to the auricle. In an example, an electromagnetic brain activity sensor can be positioned by the head-worn attachment on a person's temple and/or forehead.

In this example, this invention also includes a data processing unit. In an example, a data processing unit can be a microchip, microprocessor, circuit board, CPU, computer, or other computing device. In an example, a data processing unit can be a part of (or directly attached to) a head-worn attachment. In an example, a data processing unit can be in direct electromagnetic communication with an electromagnetic brain activity sensor.

In an example, this invention can comprise a wireless data transmitter and/or receiver. In an example, a data processing unit can be separate from a head-worn attachment. In an example, a data processing unit can be in a remote location. In an example, a data processing unit can be in wireless communication with an electromagnetic brain activity sensor. In an example, a data processing unit can be part of a remote computing device selected from the group consisting of: electronically-functional wrist band (e.g. a "smart watch"), electronically-functional eyewear (e.g. "smart glasses"), electronically-functional clothing (e.g. "smart clothing"), electronically-functional shoes (e.g. "wise sole"), other wearable device, wearable data processing hub, mobile computer, electronic tablet, electronic pad, mobile phone, smart phone, internet-connected remote computer, communication network tower, satellite, home control system, and implanted medical device.

In an example, this invention can comprise two data processing units: a first data processing unit which is part of the head-worn attachment (in direct electromagnetic communication with an electromagnetic brain activity sensor) and a second data processing unit which is not part of the head-worn attachment (but is in wireless communication with the first unit). In an example, a first set of data processing functions can be performed by the first data processing unit and a second set of data processing functions can be performed by the second data processing unit. In an example, a first data processing unit can be in wireless electromagnetic communication with a second data processing unit in a mobile hand-held device and the operation of this invention can be controlled by an application on the mobile device. In an example, a first data processing unit can be in wireless electromagnetic communication with a second data processing unit in a wearable electronic hub device and the operation of this invention can be controlled by an application on the hub device.

In an example, this invention can further comprise a power source and/or power transducer which supplies power to the electromagnetic brain activity sensor and/or the data processing unit. In an example, a power source can be a battery. In an example, a power source and/or power transducer can transduce, harvest, and/or generate energy from body motion or kinetic energy. In an example, a power source and/or power transducer can transduce, harvest, and/or generate energy from ambient light energy. In an example, a power source and/or power transducer can transduce, harvest, and/or generate energy from body thermal energy. In an example, a power source and/or power transducer can transduce, harvest, and/or generate energy from ambient electromagnetic energy.

In an example, this invention can have components which enable it to detect actions in other modes for controlling environmental devices, appliances, and/or machines. In an example, this invention can include a body motion sensor or communication interface to detect a manual action to control an environmental device, appliance, and/or machine. In an example, this invention can recognize body motions which comprise manual control of an environmental device. For example, this invention can recognize when a person uses their hand to move a wall switch to turn lights on, to insert a key to unlock a door, or to turn a door knob to open a door. In an example, this invention can recognize when a person uses their hand to move a switch, knob, dial, button, or other control structure on an environmental device in order to turn that device on or off, adjust the device's power level, or otherwise adjust device operation. In an example, this invention can be in wireless communication with an environmental device in order to receive communication from that device when a person moves a switch, knob, dial, button, or other control structure on that device. For example, if the person turns a knob on a dishwasher in order to turn the dishwasher on, then this can be wirelessly communicated to this invention so that this invention knows that this manual control action has occurred.

In an example, this invention can create a database of manual actions to control environmental devices which are performed by the person wearing the device. In an example, this database can also include specific electromagnetic brain activity patterns which are associated with those manual control actions. In an example, this database can also include specific words, phrases, and/or commands which are associated with those manual control actions. In an example, a data processing unit can analyze data from an electromagnetic brain activity sensor and analyze data from a body motion sensor and/or wireless communication from an environmental device in order to associate specific patterns of electromagnetic brain activity with specific manual control actions for environmental devices. In an example, there can be a calibration period in which a data processing unit identifies a person's specific electromagnetic brain activity pattern which is associated with the person performing a specific manual control action with respect to an environmental device.

In an example, a database can include manual control actions such as: turning on a light with a wall switch; turning on a dishwasher by rotating a knob on the dishwasher; unlocking a door by inserting a key; opening a door by turning a door knob; and changing a temperature setting on a thermostat by rotating a dial. In an example, there can also be words, phrases, or commands which are associated with these manual actions in the database—such as "Light On", "Dishwasher On", "Door Open", and "Temperature Up".

In an example, this invention can have components which enable it to detect actions in other modes for controlling environmental devices, appliances, and/or machines. In an example, this invention can include a mechanism for recognizing hand gestures. In an example, this invention can recognize hand gestures via one or more motion sensors, infrared light sensors, ultrasound sensors, radar sensors, EMG sensors, or cameras. In an example, this invention can create a database of hand gestures to control environmental devices which are performed by the person wearing the device. In an example, a specific hand gesture can represent a specific environmental device, appliance, and/or machine. In an example, a specific hand gesture can represent a specific change in the operation of environmental device, appliance, and/or machine. In an example, this database can also include specific electromagnetic brain activity patterns which are associated with those hand gestures. In an example, this database can also include specific words, phrases, and/or commands which are associated with those hand gestures. In an example, a data processing unit can analyze data from an electromagnetic brain activity sensor and analyze data from a hand gesture detector in order to associate specific patterns of electromagnetic brain activity with specific hand gesture control actions for environmental devices.

In an example, a hand gesture detector can recognize one or more hand gestures selected from the group consisting of: "finger tap" (palm facing down with index tip moving down and up once); "finger double tap" (palm facing down with index tip moving down and up twice quickly); "finger press" (palm facing down with index tip pressing down for extended time); "finger slide right" (palm facing down with index or middle tip moving right and arcing left); "finger slide left" (palm facing down with index or middle tip moving left and arcing right); "finger rub" (palm facing down with index or middle tip moving back and forth); "finger scroll down" (palm facing down with index or middle tip moving down and arcing up); "finger scroll up" (palm facing down with index or middle tip moving up and arcing down); "finger clockwise" (index or middle tip moving in a clockwise circle or arc of a circle); "finger counter-clockwise" (index or middle tip moving in a counter-clockwise circle or arc of a circle); "finger figure eight" (index or middle tip moving in a figure eight); "finger pinch" (thumb and index or middle tip moving closer); "finger spread" (thumb and index or middle tip moving apart); "finger merge" (index tips from both hands moving together); "finger divide" (index tips from both hands moving apart); "grasp" (thumb and aligned fingers touch to form a "C"); "drink" (thumb and aligned fingers form a "C" and hand rotating toward person); "grab" (thumb and four fingers contracting simultaneously); "move down" (palm facing down with hand pivoting downward from wrist and/or elbow); "move up" (palm facing up with hand pivoting upward from wrist and/or elbow); "move right" (palm facing sideways with hand pivoting rightward from wrist); "move left" (palm facing sideways with hand pivoting leftward from wrist); "hand rotation clockwise" (flat hand rotating clockwise); "hand rotation counter-clockwise" (flat hand rotating counter-clockwise); "hold and turn clockwise" (first with thumb and index extended and rotating clockwise); "hold and turn counter-clockwise" (first with thumb and index extended and rotating counter-clockwise); "outward palm" (flat hand with palm outward and thumb and all fingers extended); "hand wave" (flat hand with palm outward and side-to-side motion); "chop" (flat hand with palm downward and side-to-side motion); "fist" (thumb and all fingers contracted); "fist pump" (upright fist moving up and down); "fist bang or fist bump" (extended first moving down and up); "knock" (first pivoting downward from wrist); "thumbs down" (fist with thumb extended downwards); "thumbs up" (fist with thumb extended upward); "point" (fist with index tip extended outward); "gun" (vertical fist with index and middle extended outward together); "V" or "peace sign" (outward-facing fist with index and middle extended upwards apart); "scissors" (fist with index and middle apart and then together); "Vulcan salute" (outward-facing palm with fingers up and separated between middle and ring); "cuckold/horns" (hand vertical with index and pinky upward); "me ape" (upward first with middle extended upward); "call me" (vertical fist with thumb and pinky extended); "hang loose" (horizontal palm with thumb and pinky extended); "I Love You" (thumb, index, and pinky extended while middle and ring touch palm); "OK" (thumb and index form a circle); "loser" (fist with thumb and index finger extended at a right angle); "no" (fist with raised extended index moving side to side); "finger cross" (thumb and middle fingers crossed); "finger snap" (middle sliding quickly from tip to base of thumb); "money" (tips of middle and thumb rubbing back and forth on each other); "come here" (upward or sideways facing fist with index tip extended and moving inward); "blah blah" (thumb and horizontal extended fingers opening and closing together); "world's smallest violin" (fist with thumb and index extended and rubbing); "writing" (fist with thumb and index touching and moving together); "thumb to index" (thumb tip touching index finger tip); "thumb to middle" (thumb tip touching middle finger tip); "thumb to ring" (thumb tip touching ring finger tip); "thumb to pinky" (thumb tip touching pinky tip); a gesture indicating a selected letter in sign language; and a gesture indicating a selected word in sign language.

In an example, this invention can have components which enable it to detect actions in other modes for controlling environmental devices, appliances, and/or machines. In an example, this invention can include a physical keyboard, physical keypad, light-projected keypad, virtual keypad, or other typing interface which enables a person to type commands to control environmental devices, appliances, and/or machines. In an example, a keyboard or keypad can be part of a hand-held device with which a head-worn device is in wireless communication. In an example, a keyboard or keypad can be part of a separate wearable device (such as a smart watch or wearable technology hub) with which a head-worn device is in wireless communication. In an example, this invention can create a database of words, phrases, or commands to control environmental devices which are typed by the person wearing the device. In an example, this database can also include specific electromagnetic brain activity patterns which are associated with those words, phrases, or commands. In an example, this invention can include a computer mouse which enables a person to control environmental devices, appliances, and/or machines. In another example, this invention can include an eye gaze tracker which enables a person to control environmental devices, appliances, and/or machines by moving their eyes.

The data processing unit of this invention analyzes electromagnetic brain activity signals during different periods of time in order to identify common patterns which occur during actions for the same control purpose across different action modes. In an example, a pattern of electromagnetic brain activity which is associated with an action to control an environmental device can be a transient and/or non-recurring pattern of electromagnetic brain activity. In an example, a transient pattern of electromagnetic brain activity can be a sequence of spikes or waves which do not repeat. In an example, parameters used to identify a non-repeating pattern of electromagnetic brain activity can be selected from the group consisting of: shape of one or more spikes; amplitude, maximum, or minimum of one or more spikes; frequency of multiple spikes; pattern covariation; pattern entropy; pattern signature; first and second order differentials; polynomial modeling; and composite sine wave modeling.

In an example, a transient pattern of electromagnetic brain activity which is associated with an action to control an environmental device can be identified using one or more analytical methods which are selected from the group consisting of: Analysis of Variance (ANOVA), Artificial Neural Network (ANN), Auto-Regressive (AR) Modeling, Bayesian Analysis, Bonferroni Analysis (BA), Centroid Analysis, Chi-Squared Analysis, Cluster Analysis, Correlation, Covariance, Data Normalization (DN), Decision Tree Analysis (DTA), Discrete Fourier transform (DFT), Discriminant Analysis (DA), Empirical Mode Decomposition (EMD), Factor Analysis (FA), Fast Fourier Transform (FFT), Feature Vector Analysis (FVA), Fisher Linear Discriminant, Fourier Transformation (FT) Method, Fuzzy Logic (FL) Modeling, Gaussian Model (GM), Generalized Auto-Regressive Conditional Heteroscedasticity (GARCH) Modeling, Hidden Markov Model (HMM), Independent Components Analysis (ICA), Inter-Band Power Ratio, Inter-Channel Power Ratio, Inter-Montage Power Mean, Inter-Montage Ratio, Kalman Filter (KF), Kernel Estimation, Laplacian Filter, Laplacian Montage Analysis, Least Squares Estimation, Linear Regression, Linear Transform, Logit Model, Machine Learning (ML), Markov Model, Maximum Entropy Modeling, Maximum Likelihood, Mean Power, Multi-Band Covariance Analysis, Multi-Channel Covariance Analysis, Multivariate Linear Regression, Multivariate Logit, Multivariate Regression, Naive Bayes Classifier, Neural Network, Non-Linear Programming, Non-negative Matrix Factorization (NMF), Power Spectral Density, Power Spectrum Analysis, Principal Components Analysis (PCA), Probit Model, Quadratic Minimum Distance Classifier, Random Forest (RF), Random Forest Analysis (RFA), Regression Model, Signal Amplitude (SA), Signal Averaging, Signal Decomposition, Sine Wave Compositing, Singular Value Decomposition (SVD), Spine Function, Support Vector Machine (SVM), Time Domain Analysis, Time Frequency Analysis, Time Series Model, Trained Bayes Classifier, Variance, Waveform Identification, Wavelet Analysis, and Wavelet Transformation.

In an example, a transient pattern of electromagnetic brain activity can start to occur with a specified period of time before an action. In an example, this period of time can be under one minute. In an example, this period of time can be in the range of 1-10 seconds. In an example, this period of time can be different for different action modes. In an example, a transient pattern of electromagnetic brain activity which is associated with an action to control an environmental device can be a transient and/or non-recurring pattern of electromagnetic activity which is concurrent with the action.

In an example, a pattern of electromagnetic brain activity which is associated with an action to control an environmental device can be the start of a repeating electromagnetic brain activity pattern or waveform. In an example, a pattern of electromagnetic brain activity which is associated with an action to control an environmental device can be a change in an already-occurring repeating electromagnetic brain activity pattern or waveform (e.g. "brainwaves"). In an example, a repeating electromagnetic brain activity pattern can be an oscillatory pattern. In an example, a repeating electromagnetic brain activity pattern can be modeled as a composite of multiple sine waves. In an example, a repeating electromagnetic brain activity pattern can be decomposed into sub-patterns in different frequency bands. In an example, these frequency bands can be selected from the group consisting of: Delta, Theta, Alpha, Beta, and Gamma.

Ongoing brain waveforms classified as Delta waves can be within a frequency band selected from the group consisting of: 0.5-3.5 Hz, 0.5-4 Hz, 1-3 Hz, 1-4 Hz, and 2-4 Hz. Ongoing brain waveforms classified as Theta waves can be within a frequency band selected from the group consisting of: from the group consisting of: 3.5-7 Hz, 3-7 Hz, 4-7 Hz, 4-7.5 Hz, 4-8 Hz, and 5-7 Hz. Ongoing brain waveforms classified as Alpha waves can be within a frequency band selected from the group consisting of: 7-13 Hz, 7-14 Hz, 8-12 Hz, 8-13 Hz, 7-11 Hz, 8-10 Hz, and 8-10 Hz. Ongoing brain waveforms classified as Beta waves can be within a frequency band selected from the group consisting of: 11-30 Hz, 12-30 Hz, 13-18 Hz, 13-22 Hz, 13-26 Hz, 13-26 Hz, 13-30 Hz, 13-32 Hz, 14-24 Hz, 14-30 Hz, and 14-40 Hz. Ongoing brain waveforms classified as Gamma waves can be within a frequency band selected from the group consisting of: group consisting of: 30-100 Hz, 35-100 Hz, 40-100 Hz, and greater than 30 Hz.

In an example, the selection of which frequency band or bands are most useful for identifying a pattern of electromagnetic brain activity associated with a control action can be identified during a calibration period. In an example, complex repeating patterns can be decomposed into wave frequency bands and/or frequency power levels using Fourier Transformation. In an example, parameters used to identify a pattern of electromagnetic brain activity can be selected from the group consisting of: power level, amplitude, maximum value, minimum value, frequency, phase, covariation, entropy, latency, and waveform. In an example, a change in an already-occurring repeating brainwave can be a change in the amplitude, power level, minimum value, and/or maximum value of activity within one or more selected frequency bands. In an example, a change in an already-occurring repeating brainwave can be a shift in the frequency or phase of a waveform within one or more selected frequency bands. In an example, a change in an already-occurring repeating brainwave can be a change in the shape of a waveform within one or more selected frequency bands.

In an example, a change in an already-occurring repeating brainwave can be a change in the amplitude, power level, minimum value, and/or maximum value of activity within a selected frequency band relative to one or more other frequency bands. In an example, a change in an already-occurring repeating brainwave can be a shift in the frequency or phase of a waveform within a selected frequency band relative to one or more other frequency bands. In an example, a change in an already-occurring repeating brainwave can be a change in the shape of a waveform within a selected frequency band relative to one or more other frequency bands. In an example, a change in an already-occurring repeating brainwave can be a change in the covariation of activity in a selected frequency band relative to activity in another frequency band.

In an example, a pattern of electromagnetic brain activity which is associated with an action to control an environmental device can be associated with a particular sensor location, a particular channel, and/or particular montage of channels. In an example, a pattern of electromagnetic brain activity can be a change in activity in a specific area of a person's brain as measured from one or more specific sensor locations on the person's head. In an example, this pattern can be a transient pattern which is recorded from one or more locations. In an example, this pattern can be the start of a repeating pattern which is recorded from one or more locations. In an example, this pattern can be a change in an ongoing repeating pattern which is recorded from one or more locations. In an example, this pattern can be a change in electromagnetic brain activity measured from one location or channel relative to electromagnetic brain activity measured from one or more different locations or channels. In an example, which channels are most useful for identifying a pattern of electromagnetic brain activity associated with an action to control an environmental device can be identified during a calibration period. In an example, different channels can be most useful for pattern identification at different times during an action.

In an example, one or more electromagnetic brain activity sensors or channels can be located on a person's head so as to most accurately measure the activity of one or more brain areas selected from the group consisting of: Broca's area (of the Frontal Lobe), Wernicke's area (of the Occipital Lobe), Cerebellum, Cerebral Cortex, Frontal Lobe, Occipital Lobe, Parietal Lobe, and Temporal Lobe. In an example, one or more electromagnetic brain activity sensors or channels can be placed at one or more electrode placement sites selected from the group consisting of: FP1, FPz, FP2, AF7, AF5, AF3, AFz, AF4, AF6, AF8, F7, F5, F3, F1, Fz, F2, F4, F6, F8, FT7, FC5, FC3, FC1, FCz, FC2, FC4, FC6, FT8, T3/T7, C3, C4, C1, Cz, C2, C5, C6, T4/T8, TP7, CP5, CP3, CP1, CPz, CP2, CP4, CP6, TP8, T5/P7, P5, P3, P1, Pz, P2, P4, P6, T6/P8, PO7, PO5, PO3, POz, PO4, PO6, PO8, O1, Oz, and O2.

We now discuss the specific examples shown in FIGS. 9 through 16. FIGS. 9 through 12 show an example of how this invention can be embodied in a Brain Computer Interface (BCI) system, device, or method which enables a person to control environmental devices, appliances, and/or machines in different action modes based on electromagnetic brain activity patterns which are associated with the same control command across different action modes. One or more action modes can be selected from the group consisting of: speaking a word, phrase, or command; using a touch screen; manually moving a switch, button, dial, or knob on an environmental device; making a hand gesture; typing a word, phrase, or command; moving a computer mouse; moving one's eyes; and just thinking about controlling the environmental device. In this example, three action modes are used: (a) speaking a word, phrase, or command; (b) using a touch screen; and (c) just thinking about controlling the environmental device. The first two action modes (speaking and touching) are used during first and second calibration time periods and the third action mode (thinking alone) is used in a third time period.

Figure 9:
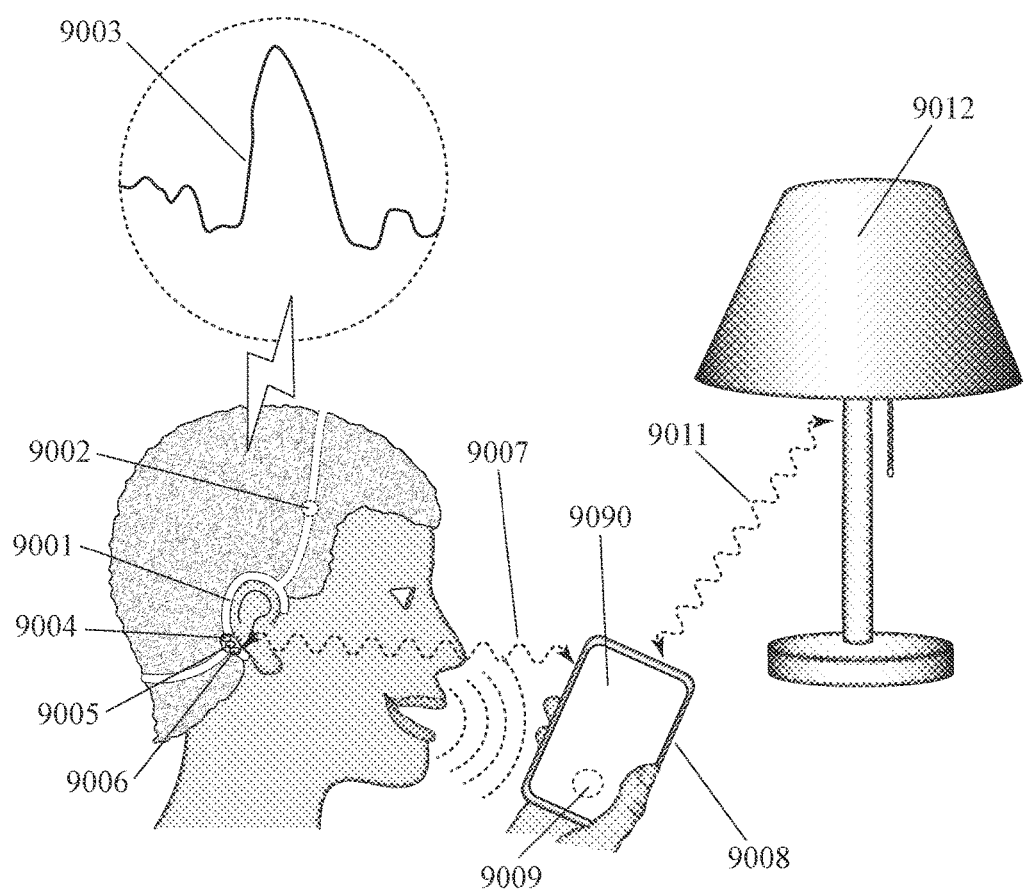
FIG. 9 shows a BCI system and method in which a person controls an environmental device using a first command mode (voice).
Figure 10:
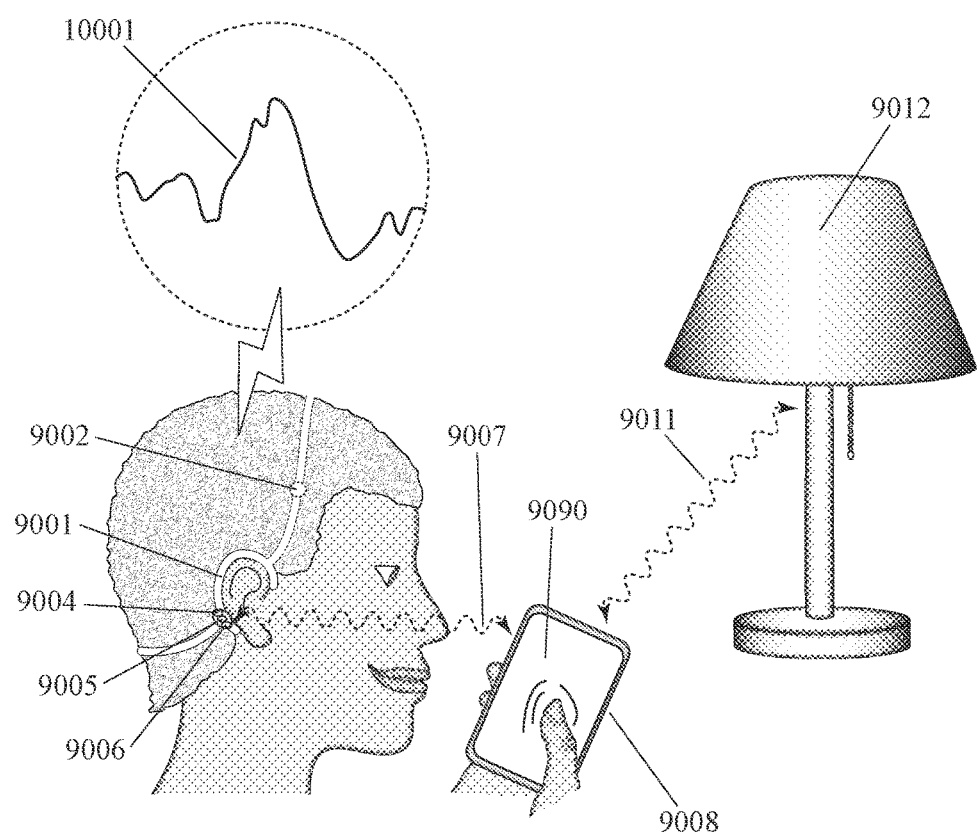
FIG. 10 shows a BCI system and method in which a person controls an environmental device using a second command mode (touch screen).
Figure 11:
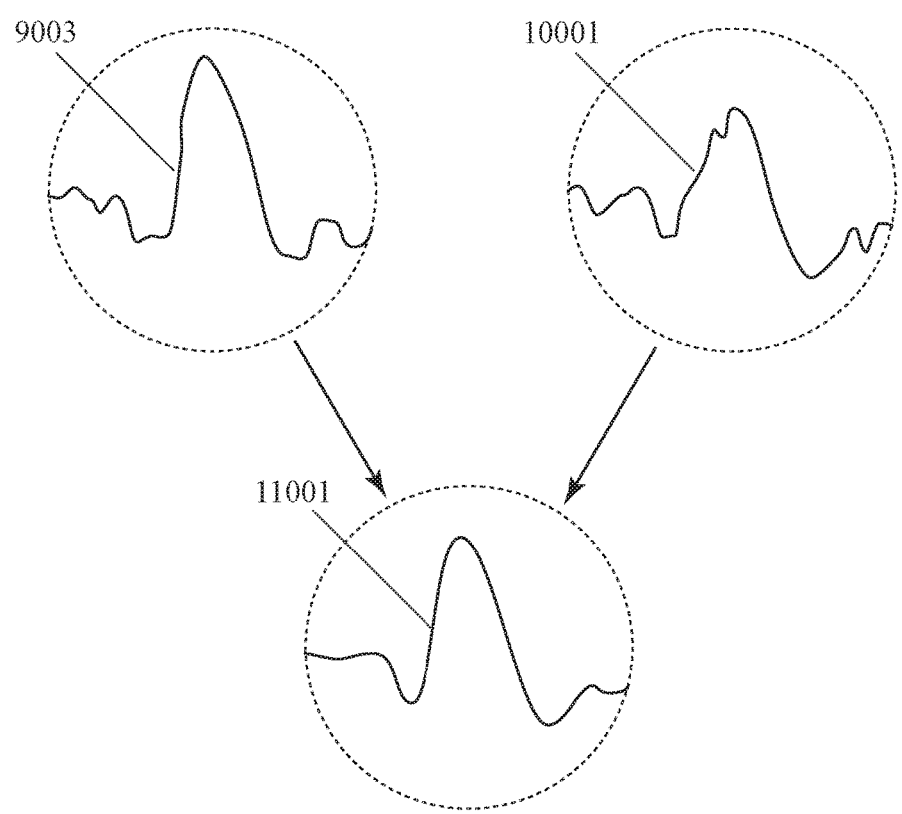
FIG. 11 shows a BCI system and method wherein a common brain activity pattern between the first and second command modes is identified.
Figure 12:
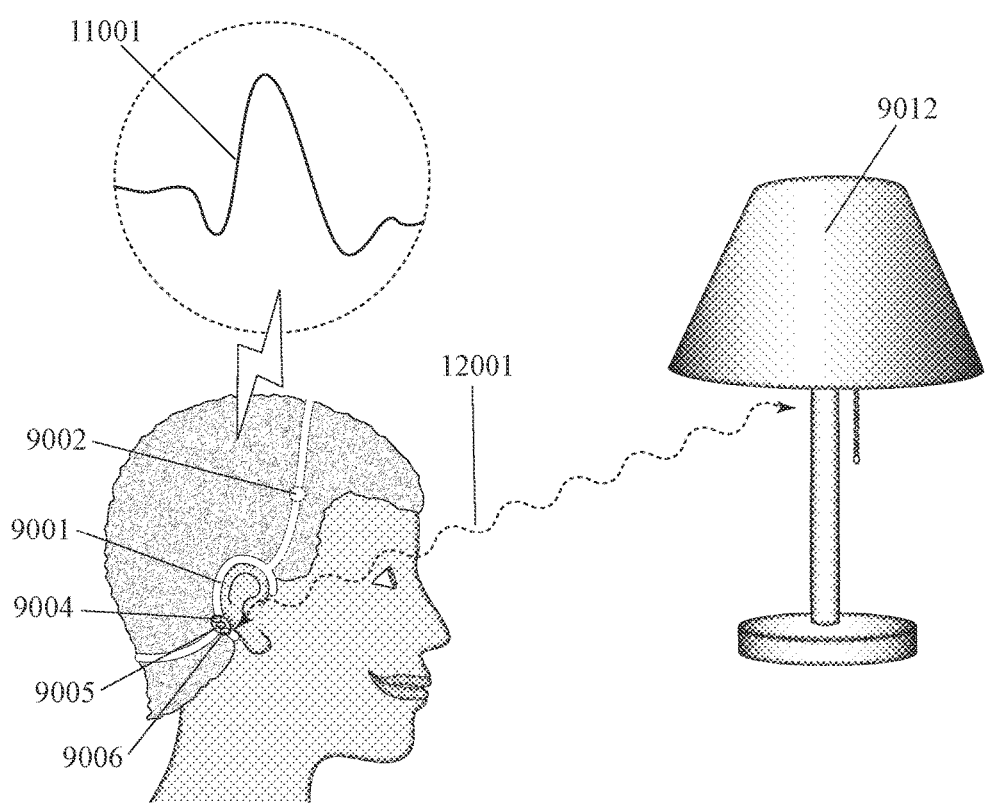
FIG. 12 shows a BCI system and method in which a person controls an environmental device using a third command mode (thought).

FIGS. 9 through 12 are sequential views of the same embodiment. FIGS. 9 through 12 show both a system and a method. FIG. 9 shows this embodiment during a first calibration time period in which a person controls an environmental device (a lamp in this example) in a selected manner by speaking a word, phrase, or command, while an electromagnetic brain activity sensor collects a first set of data concerning the person's brain activity which is associated with this action. FIG. 10 shows this embodiment during a second calibration time period in which the person controls the environmental device (the lamp) in the selected manner by touching a touch screen on a separate hand-held device, while the electromagnetic brain activity sensor collects a second set of data concerning the person's brain activity associated with this action. FIG. 11 symbolically represents how the data processing unit analyzes the first and second sets of data in order to identify a common pattern of electromagnetic brain activity (e.g. which is found in both sets of data). FIG. 12 shows this embodiment during a third period of time in which the data processing unit recognizes this common pattern in the person's electromagnetic brain activity (because the person is thinking about controlling the device) and controls the environmental device in the selected manner even though the person is not speaking or using the touch screen.

With respect to specific components of this Brain Computer Interface (BCI) system, FIG. 9 shows: a head-worn attachment 9001 which is worn on the person's head; at least one electromagnetic brain activity sensor 9002 which is part of the head-worn attachment member; a first electromagnetic brain activity pattern 9003 which is measured by the at least one electromagnetic brain activity sensor during this time period; a data processing unit 9004; a data transmitter and receiver 9005; a microphone 9006 on the head-worn attachment; wireless communication 9007 between the data processing unit and a separate hand-held computing device; the separate hand-held computing device 9008; a microphone 9009 on the hand-held computing device; a touch screen 9010 on the separate hand-held computing device; wireless communication 9011 between the separate hand-held computing device and an environmental device (a lamp in this example); and an environmental device 9012 (a lamp in this example).

In the example shown in FIGS. 9 through 12, this invention is a system comprising two separate devices which function together. The first device is worn on the head and the second device is held in a hand. In another example of a system, the second device can be worn on a different location on the body. In another example, the second device can be a smart watch or wearable technology hub. In another example, this invention can be a self-contained head-worn device with all the components and performing all the functions.

In FIG. 9, the person is controlling the lamp via a first action mode—speaking a command. For example, the person can say "Light On." This command is received by a microphone, understood by speech recognition software, and becomes a command to turn the lamp on via wireless communication. In FIG. 9, the electromagnetic brain activity sensor measures a pattern 9003 of electromagnetic brain activity which is associated with speaking this command. This pattern of brain activity is symbolically represented by the wavy line within a dotted line circle above the person's head.

FIG. 10 is like FIG. 9 except that now the person is controlling the lamp via a second action mode—using a touch screen. For example, the person can open an application on the hand-held device and touch an icon to turn the light on via wireless communication. In FIG. 10, the electromagnetic brain activity sensor measures a pattern 10001 of electromagnetic brain activity which is associated with using the touch screen in this manner. This pattern of brain activity is symbolically represented by the wavy line within a dotted line circle above the person's head. Note that the details of electromagnetic brain activity pattern 10001 are different than the details of electromagnetic brain activity pattern 9003, but that there are some similarities between these two patterns. These pattern similarities can be due to common underlying mental processes which are involved in different actions to turn on a light, regardless of the specific mode of action through which this is done.

FIG. 11 shows a symbolic representation of a step wherein the data processing unit analyzes electromagnetic brain activity pattern 9003 and electromagnetic brain activity pattern 10001 in order to identify a common pattern which they both share. In FIG. 11, this common pattern 11001 is shown within a dotted-line circle at the bottom of the figure. In an example, a common pattern can be identified using one or more statistical methods selected from the group consisting of: Analysis of Variance (ANOVA), Artificial Neural Network (ANN), Auto-Regressive (AR) Modeling, Bayesian Analysis, Bonferroni Analysis (BA), Centroid Analysis, Chi-Squared Analysis, Cluster Analysis, Correlation, Covariance, Data Normalization (DN), Decision Tree Analysis (DTA), Discrete Fourier transform (DFT), Discriminant Analysis (DA), Empirical Mode Decomposition (EMD), Factor Analysis (FA), Fast Fourier Transform (FFT), Feature Vector Analysis (FVA), Fisher Linear Discriminant, Fourier Transformation (FT) Method, Fuzzy Logic (FL) Modeling, Gaussian Model (GM), Generalized Auto-Regressive Conditional Heteroscedasticity (GARCH) Modeling, Hidden Markov Model (HMM), Independent Components Analysis (ICA), Inter-Band Power Ratio, Inter-Channel Power Ratio, Inter-Montage Power Mean, Inter-Montage Ratio, Kalman Filter (KF), Kernel Estimation, Laplacian Filter, Laplacian Montage Analysis, Least Squares Estimation, Linear Regression, Linear Transform, Logit Model, Machine Learning (ML), Markov Model, Maximum Entropy Modeling, Maximum Likelihood, Mean Power, Monkey Darts (MD), Multi-Band Covariance Analysis, Multi-Channel Covariance Analysis, Multivariate Linear Regression, Multivariate Logit, Multivariate Regression, Naive Bayes Classifier, Neural Network, Non-Linear Programming, Nonnegative Matrix Factorization (NMF), Power Spectral Density, Power Spectrum Analysis, Principal Components Analysis (PCA), Probit Model, Quadratic Minimum Distance Classifier, Random Forest (RF), Random Forest Analysis (RFA), Regression Model, Signal Amplitude (SA), Signal Averaging, Signal Decomposition, Sine Wave Compositing, Singular Value Decomposition (SVD), Spine Function, Support Vector Machine (SVM), Time Domain Analysis, Time Frequency Analysis, Time Series Model, Trained Bayes Classifier, Variance, Waveform Identification, Wavelet Analysis, and Wavelet Transformation.

FIG. 12 is like FIGS. 9 and 10 except that now the person is controlling the lamp without either speaking or using the touch screen. In this example, the person is now turning on the lamp by just thinking about turning on the lamp. This thought is identified by the data processing unit based on detection of the common electromagnetic brain activity pattern 11001 which is associated with turning on the lamp by either speaking or using the touch screen. This common pattern is detected and triggers a command via wireless communication 12001 from the data processing unit (via data transmitter) to the lamp. Other relevant component and method variations which are discussed elsewhere in this specification can also be applied to the example shown here in FIGS. 9 through 12.

FIGS. 13 through 16 show another example of how this invention can be embodied in a Brain Computer Interface (BCI) system, device, and method which enables a person to control environmental devices, appliances, and/or machines in different action modes based on electromagnetic brain activity patterns which are associated with the same control command across different action modes. This example is like the one shown in FIGS. 9 through 12 except that now speech recognition occurs within a head-worn component instead of a hand-held device.

Figure 13:
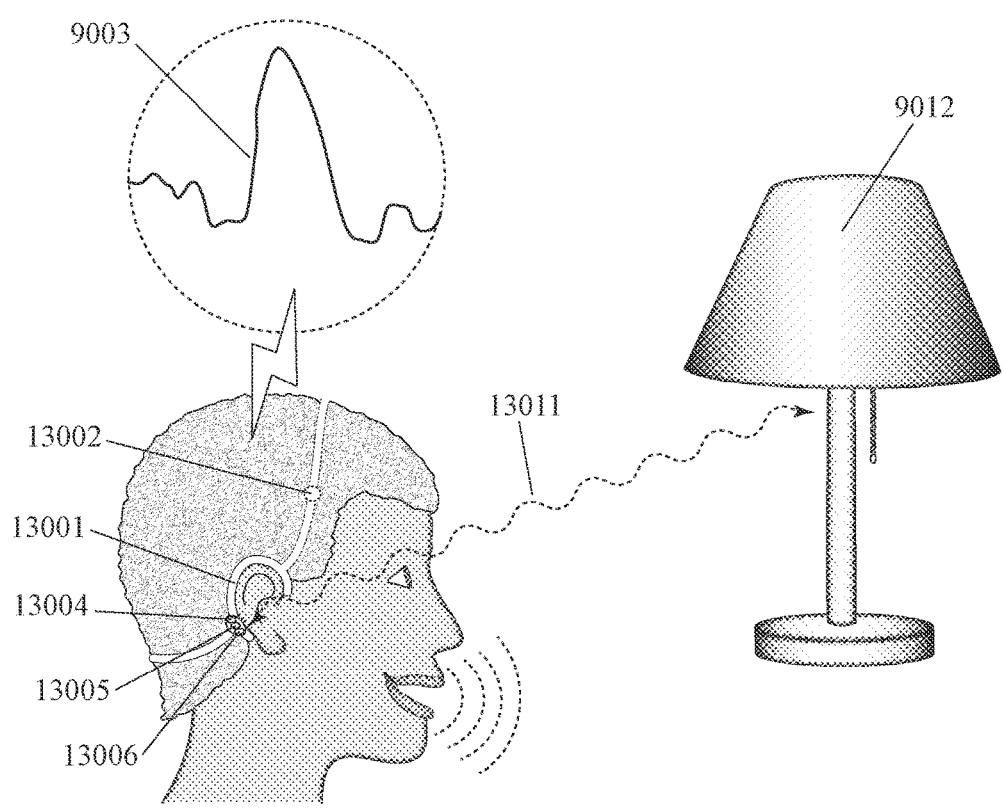
FIG. 13 shows another example of a BCI system and method in which a person controls an environmental device using a first command mode (voice).
Figure 14:
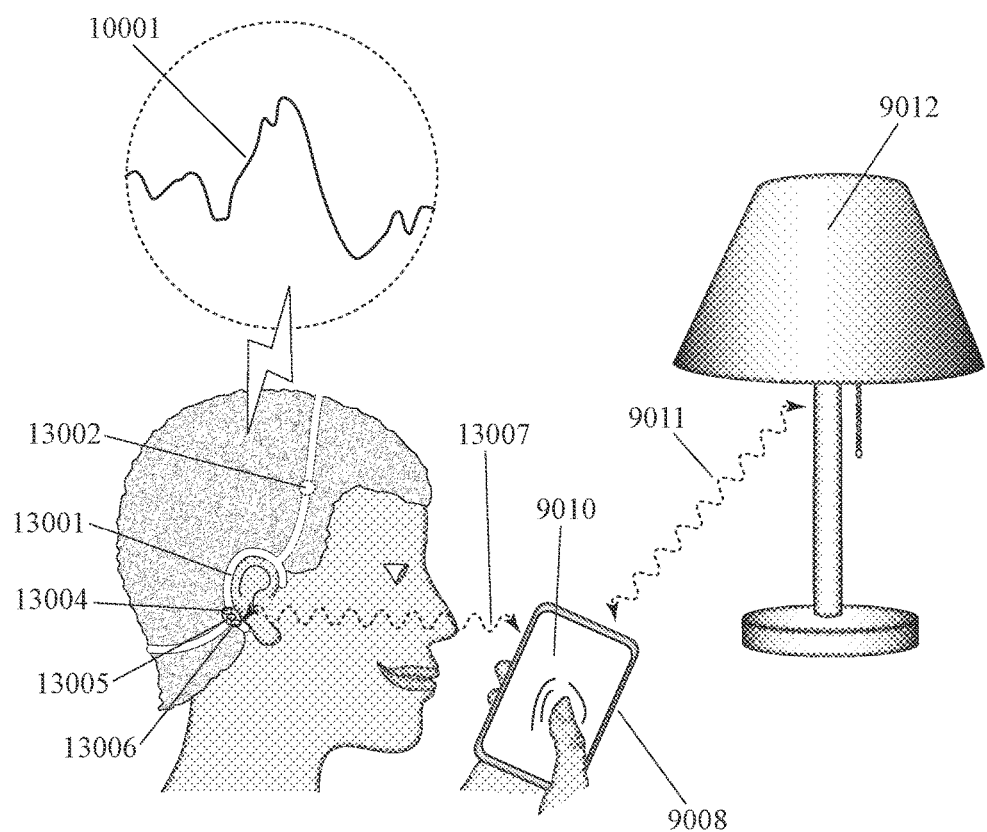
FIG. 14 shows another example of a BCI system and method in which a person controls an environmental device using a second command mode (touch screen).
Figure 15:
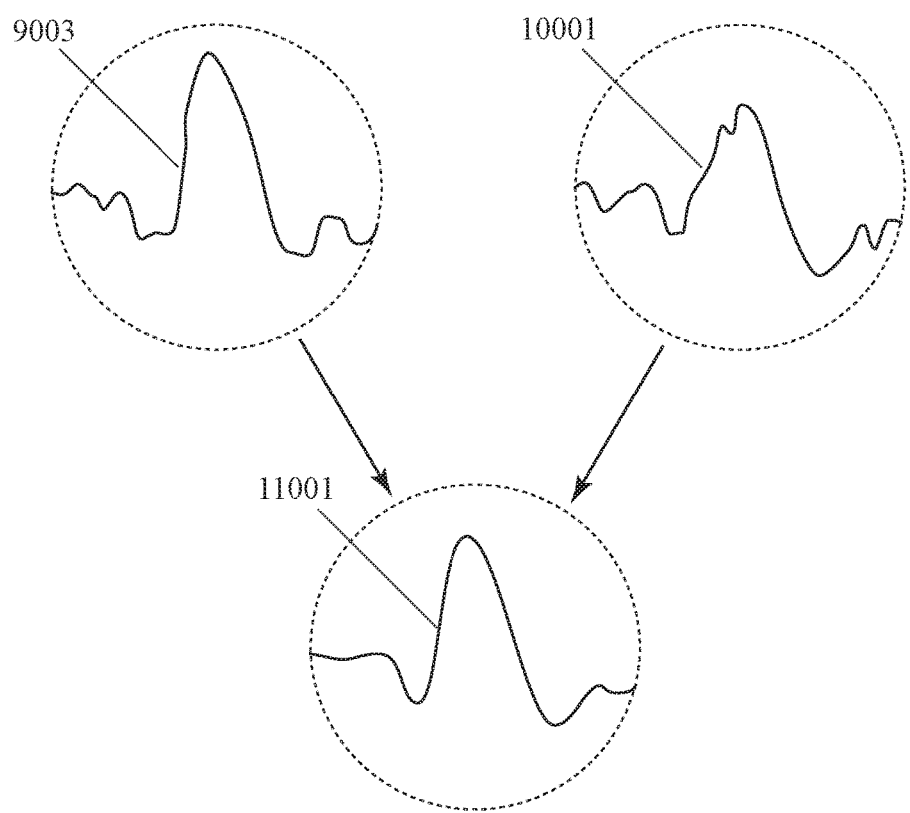
FIG. 15 shows another example of a BCI system and method wherein a common brain activity pattern between the first and second command modes is identified.
Figure 16:
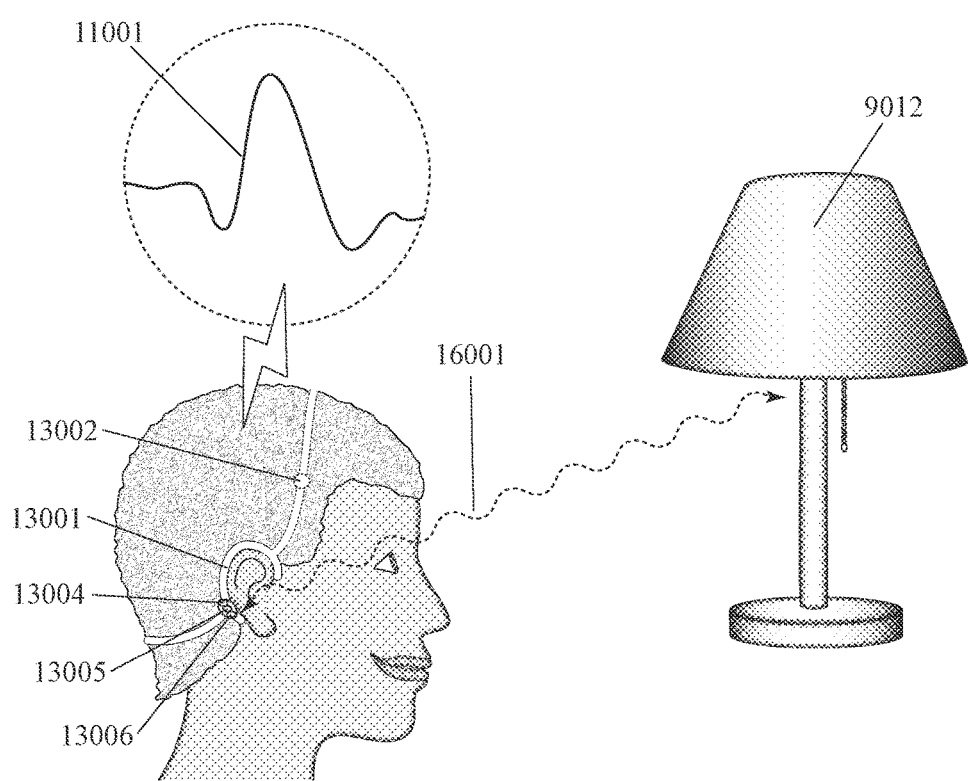
FIG. 16 shows another example of a BCI system and method in which a person controls an environmental device using a third command mode (thought).

FIGS. 13 through 16 are sequential views of the same embodiment. FIGS. 13 through 16 show both a system and a method. FIG. 13 shows this embodiment during a first calibration time period in which a person controls an environmental device (a lamp in this example) in a selected manner by speaking a word, phrase, or command, while an electromagnetic brain activity sensor collects a first set of data concerning the person's brain activity which is associated with this action. FIG. 14 shows this embodiment during a second calibration time period in which the person controls the environmental device (the lamp) in the selected manner by touching a touch screen on a separate hand-held device, while the electromagnetic brain activity sensor collects a second set of data concerning the person's brain activity associated with this action. FIG. 15 symbolically represents how the data processing unit analyzes the first and second sets of data in order to identify a common pattern of electromagnetic brain activity (e.g. which is found in both sets of data). FIG. 16 shows this embodiment during a third period of time in which the data processing unit recognizes this common pattern in the person's electromagnetic brain activity (because the person is thinking about controlling the device) and controls the environmental device in the selected manner even though the person is not speaking or using the touch screen.

With respect to specific components of this Brain Computer Interface (BCI) system, FIG. 13 shows: a head-worn attachment 13001 which is worn on the person's head; at least one electromagnetic brain activity sensor 13002 which is part of the head-worn attachment member; a first electromagnetic brain activity pattern 13003 which is measured by the at least one electromagnetic brain activity sensor during this time period; a data processing unit 13004; a data transmitter and receiver 13005; a microphone 13006; wireless communication 13011 between the separate hand-held computing device and an environmental device (a lamp in this example); and an environmental device 9012 (a lamp in this example).

In FIG. 13, the person is controlling the lamp via a first action mode—speaking a command. For example, the person can say "Light On." This is received by the microphone, understood by speech recognition software, and becomes a command to turn the lamp on via wireless communication. In FIG. 13, the electromagnetic brain activity sensor measures a pattern 9003 of electromagnetic brain activity which is associated with speaking this command. This pattern of brain activity is symbolically represented by the wavy line within a dotted line circle above the person's head.

FIG. 14 is like FIG. 13 except that now the person is controlling the lamp via a second action mode—using a touch screen. For example, the person can open an application on the hand-held device and touch an icon to turn the light on via wireless communication. In FIG. 14, the electromagnetic brain activity sensor measures a pattern 10001 of electromagnetic brain activity which is associated with using the touch screen in this manner. This pattern of brain activity is symbolically represented by the wavy line within a dotted line circle above the person's head. Note that the details of electromagnetic brain activity pattern 10001 are different than the details of electromagnetic brain activity pattern 9003, but that there are some similarities between these two patterns. These pattern similarities can be due to common underlying mental processes which are involved in different actions to turn on a light, regardless of the specific mode of action through which this is done.

FIG. 15 shows a symbolic representation of a step wherein the data processing unit analyzes electromagnetic brain activity pattern 9003 and electromagnetic brain activity pattern 10001 in order to identify a common pattern which they both share. In FIG. 15, this common pattern 11001 is shown within a dotted-line circle at the bottom of the figure.

FIG. 16 is like FIGS. 13 and 14 except that now the person is controlling the lamp without either speaking or using the touch screen. In this example, the person is now turning on the lamp by just thinking about turning on the lamp. This thought is identified by the data processing unit based on detection of the common electromagnetic brain activity pattern 11001 which is associated with turning on the lamp by either speaking or using the touch screen. This common pattern is detected and triggers a command via wireless communication 16001 from the data processing unit (via data transmitter) to the lamp. Other relevant component and method variations which are discussed elsewhere in this specification can also be applied to the example shown here in FIGS. 13 through 16.

In an example, this invention can be embodied in a Brain Computer Interface (BCI) system, device, or method which enables a person to control environmental devices, appliances, and/or machines in different action modes based on brain activity patterns which are associated with the same control command across different action modes. In these various examples, one or more action modes can be selected from the group consisting of: speaking a word, phrase, or command; using a touch screen; manually moving a switch, button, dial, or knob on an environmental device, appliance, and/or machine; making a hand gesture; typing a word, phrase, or command; moving a computer mouse; moving one's eyes; and just thinking about controlling an environmental device, appliance, and/or machine.

FIGS. 18 through 33 show additional examples of how this invention can be embodied in a wearable mobile device for measuring electromagnetic brain activity. Before showing specific examples of how this device can be configured to span from a person's ear to their forehead, it is useful to define radial clock hour (or degree) vectors around a person's ear canal. This definition is provided by FIG. 17. FIG. 17 shows radial clock hour (or degree) vectors defined around the center of the ear canal outer opening. The 12 o'clock (or 0 degree) vector is a vertical line upwards from the center of the ear canal outer opening when the person is standing upright. The 3 o'clock (or 90 degree) vector is a horizontal line forward from the center of the ear canal outer opening when the person is standing upright. The 6 o'clock (or 180 degree) vector is a vertical line downwards from the center of the ear canal outer opening when the person is standing upright. The 9 o'clock (or 270 degree) vector is a horizontal line backward from the center of the ear canal outer opening when the person is standing upright. FIG. 17 also shows intermediate clock hour (or degree) vectors which are located between these four vectors.

FIG. 17 can also be used to define the terms "rear", "front", "upper", and "lower" with respect to a person's ear. The term "rear" can be defined as spanning (some or all of) the directional quadrants clockwise between the 6 o'clock (180 degree) and 12 o'clock (0 degree) vectors. The term "front" can be defined as spanning (some or all of) the directional quadrants clockwise between the 12 o'clock (0 degree) and 6 o'clock (180 degree) vectors. The term "upper" can be defined as spanning (some or all) of the directional quadrants clockwise between the 9 o'clock (270 degree) and 3 o'clock (90 degree) vectors. The term "lower" can be defined as spanning some or all of the directional quadrants clockwise between the 3 o'clock (90 degree) and 9 o'clock (270 degree) vectors.

FIG. 18 shows an example of how this invention can be embodied in a wearable device for measuring electromagnetic brain activity comprising: (a) a rear segment, wherein this rear segment is configured to be worn on the rear-facing surface of a person's ear on a first side of the person's head, wherein this first side is the right side or the left side; (b) a side segment, wherein this side segment is configured to span (on the first side of the person's head) from the person's ear to the person's temple, side portion of the person's face, and/or side portion of the person's forehead; (c) a top segment, wherein this top segment is configured to span (on the first side of the person's head) from the side segment to the top of the person's head; (d) at least one electromagnetic energy sensor which is held in proximity to the person's head by the rear segment, the side segment, and/or the top segment, wherein the at least one electromagnetic energy sensor collects data concerning electromagnetic brain activity; (e) a data processor which receives data from the at least one electromagnetic energy sensor; (f) a data transmitter; and (g) a power source which powers the at least one electromagnetic energy sensor, the data processor, and/or the data transmitter.

FIG. 18 also shows an example of how this invention can be embodied in an undulating mobile EEG monitor comprising: (a) a rear segment, wherein this rear segment is configured to be worn on the rear-facing surface of a person's ear on a first side of the person's head, wherein this first side is the right side or the left side; (b) a side segment, wherein this side segment is configured to span (on the first side of the person's head) from the person's ear to the person's temple, side portion of the person's face, and/or side portion of the person's forehead; (c) a top segment, wherein this top segment is configured to span (on the first side of the person's head) from the side segment to the top of the person's head; (d) at least one EEG sensor which is held in proximity to the person's head by the rear segment, the side segment, and/or the top segment; (e) a data processor which receives data from the at least one EEG sensor; (f) a data transmitter; and (g) a power source which powers the at least one EEG sensor, the data processor, and/or the data transmitter.

With respect to specific components, FIG. 18 shows a right-side head view of a wearable device for measuring electromagnetic brain activity comprising: rear segment 1801 (worn on the rear-facing surface of a person's ear); side segment 1802 (spanning from the person's ear to a side portion of the person's forehead); top segment 1803 (spanning from the side segment to the top of the person's head); electromagnetic energy sensors (such as EEG sensors) 1804, 1805, and 1806; data processor 1808; data transmitter 1807; and power source 1809. In an example, this device can be symmetric with respect to the right and left sides of the person's head. In an example, this device can further comprise a rear segment, a side segment, and a top segment in a symmetric configuration on the opposite side of the person's head (not shown in this figure). In an example, right and left side top segments can connect at the top of the person's head.

In an example, the rear segment, side segment, and top segment can be resiliently-flexible. In an example, these segments can gently press against the person's head when worn. In an example, these segments can be made from a metal or polymer. In an example, these segments can have prongs, teeth, or combs to engage with the person's hair to make the device less obvious and/or to better hold it onto the person's head. In an example, these segments can be porous and/or have holes so as to be permeable to gas and/or liquid. In an example, these segments can be between one quarter inch and three inches in width. In an example, these segments can be part of a continuous member and/or piece of material.

As shown in FIG. 18, this device can include a rear segment which curves, loops, and/or hooks behind a person's ear. In an example, a rear segment can be configured to help hold the device on a person's head by engaging the rear surface of the outer ear. In an example, a rear segment can be configured to be worn entirely within one inch of the person's outer ear. In an example, a rear segment of this device can curve, loop, or hook around (some or all of) the rear-facing surface of the person's outer ear and/or the tissue connecting the outer ear with the rest of the head.

In an example, a rear segment of this device can be configured to receive the frame of a pair of eyeglasses so that this device can be worn in combination with eyeglasses. In an example, a rear segment of this device can further comprise an opening which is configured to receive the side-piece of the frame of a pair of eyeglasses so that this device can be worn in combination with eyeglasses. In an example, a rear segment of this device can further comprise a clip or other attachment mechanism to which the side-piece of the frame of a pair of eyeglasses can be attached so that this device can be worn in combination with eyeglasses. In an example, a rear segment of this device can further comprise an indentation, groove, or track into (or against)

which the side-piece of the frame of a pair of eyeglasses can be placed so that this device can be worn in combination with eyeglasses.

In an example, a rear segment of this device can curve, loop, or hook around a portion of the person's ear clockwise between the 6 o'clock (180 degree) and 12 o'clock (0 degree) vectors. In an example, a rear segment of this device can curve, loop, or hook around a portion of the person's ear clockwise between the 9 o'clock (270 degree) and 12 o'clock (0 degree) vectors. In an example, a rear segment of this device can curve, loop, or hook around a portion of the person's ear clockwise between the 10 o'clock (300 degree) and 12 o'clock (0 degree) vectors.

In an example, the rear segment of this device can be configured to help hold the device on a person's head by resting on top of the outer ear (or the tissue connection between the outer ear and the rest of the person's head). In an example, a rear segment of this device can rest on the top of a person's outer ear and/or the tissue connecting the outer ear with the rest of the head and project in a rearward and downward manner within the directional quadrants relative to the ear canal clockwise between the 6 o'clock (180 degree) and 12 o'clock (0 degree) vectors. In an example, a rear segment of this device can rest on the top of the person's outer ear and/or the tissue connecting the outer ear with the rest of the head and project in a rearward and downward manner within the directional quadrant relative to the ear canal clockwise between the 9 o'clock (270 degree) and 12 o'clock (0 degree) vectors.

As shown in FIG. 18, this device can include a side segment which spans from a person's ear to a side portion of their face and/or forehead. A side segment of this device can be directly connected to a rear segment of this device. In an example, side and rear segments can both be part of the same continuous member and/or piece of material. In an alternative example, this device can further comprise another member between the side and rear segments which connects them together.

In an example, a side segment of this device can be configured to receive the frame of a pair of eyeglasses so that this device can be worn in combination with eyeglasses. In an example, a side segment of this device can further comprise an opening which is configured to receive the side-piece of the frame of a pair of eyeglasses so that this device can be worn in combination with eyeglasses. In an example, a side segment of this device can further comprise a clip or other attachment mechanism to which the side-piece of the frame of a pair of eyeglasses can be attached so that this device can be worn in combination with eyeglasses. In an example, a side segment of this device can further comprise an indentation, groove, or track into (or against) which the side-piece of the frame of a pair of eyeglasses can be placed so that this device can be worn in combination with eyeglasses.

In an example, a side segment of this device can span, protrude, curve, or loop from the person's ear to the person's temple on the first side of the person's head. In an example, the side segment can span, protrude, curve, or loop from the person's ear to a side portion of the person's face. In an example, the side segment can span, protrude, curve, or loop from the person's ear to a side portion of the person's forehead.

In an example, a side segment of this device can protrude and/or project forward from a person's ear along a vector which is substantially parallel to a vector which is clockwise between the 12 o'clock (0 degree) and 3 o'clock (90 degree) vectors shown in FIG. 17. In the example shown in FIG. 18, the side segment projects forward from a person's ear along vector which is substantially parallel to the 2 o'clock (60 degree) vector. In an example, the side segment can project forward from the ear along a vector which is substantially parallel to the 1 o'clock (30 degree) vector. In an example, the side segment can project forward from the ear along a vector which is substantially parallel to a vector which is clockwise between the 1 o'clock (30 degree) and 2 o'clock (60 degree) vectors.

In an example, a side segment of this device can be at least two inches long. In an example, a side segment of this device can be at least four inches long. In an example, a side segment of this device can span, protrude, curve, or loop from the person's ear to a position which is at least two inches from a person's ear toward the person's temple. In an example, a side segment of this device can span, protrude, curve, or loop from the person's ear to a position which is at least two inches toward the person's eye. In an example, a side segment of this device can span, protrude, curve, or loop from the person's ear to a position at least two inches toward the center of person's forehead.

In an example, a side segment of this device can span, protrude, curve, or loop from the person's ear to a position which is between one quarter and three-quarters of the way toward the person's temple on the first side of the head. In an example, a side segment of this device can span, protrude, curve, or loop from the person's ear to a position which is between one quarter and three-quarters of the way toward the person's eye on the first side of the head. In an example, a side segment of this device can span, protrude, curve, or loop from the person's ear to a position which is between one quarter and three-quarters of the way toward the center of the person's forehead.

In an example, a side segment of this device can be arcuate, wavy, and/or undulating. In an example, the side segment can be an arc, wave, or undulation with a rear-facing concavity and a forward-facing peak. In an example, a side segment of this device can have a shape selected from the group consisting of: arc, wave, undulation, semi-circle, semi-oval, loop, half-sinusoidal curve, bell-shaped curve, and conic section. In an example, a side segment can have a concavity whose opening faces rearward. In an example, a side segment can have a concavity whose opening faces along a vector which is parallel to a vector which is clockwise between the 7 o'clock (210 degree) and 11 o'clock (330 degree) vectors. In an example, a side segment can have a concavity with a peak which faces frontward. In an example, the most-forward point of a side segment can be located on a person's temple. In an example, the most-forward point of a side segment can be located on the side of a person's forehead.

In an example, a side segment of this device can have a lower portion which is above the outer ear by a first distance and an upper portion which is above the outer ear by a second distance, wherein the second distance is greater than the first distance. In an example, the second distance can be at least two inches greater than the first distance. In an example, the lower and upper portions of the side segment can be vertically aligned. In an example, a side segment can have a lower portion which rests on the outer ear and an upper portion which is vertically above the outer ear. In an example, a side segment of this device can have an upper portion which is located in the directional quadrant clockwise between the 11 o'clock (330 degree) and 2 o'clock (60 degree) vectors. In an example, a side segment of this device can have an upper portion which is clockwise between the 12 o'clock (0 degree) and 2 o'clock (60 degree) vectors. In an example, a side segment of this device can span (in an arcuate and/or undulating manner) upward and forward from a person's ear to a location on the side of a person's forehead and then span (in an arcuate and/or undulating manner) upward and rearward to a location above the ear on the side of the head.

In an example, this device can have a top segment which spans from the side segment to the top of the person's head. As shown in FIG. 18, a top segment of this device can span from the upper portion of the side segment to the top of the person's head (all on the first side of the person's head). In an example, a top segment of this device on the first side of the person's head can connect with the top segment of this device on the second (opposite) side of the person's head. In an example, the top and side segments of this device can be part of the same continuous member and/or piece of material. In an example, this device can further comprise another member which connects the top and side segments.

In an example, the top segment of this device can span the top of a person's head within four inches of the uppermost point on the person's head (when the person is standing up with their head up). In an example, the top segment of this device can span the top of a person's head within four inches of the position on the person's head which is the shortest vertically-oriented arc connecting the person's right and left ears. In an example, the top segment can further comprise prongs, teeth, or combs which engage the person's hair in order to make the top segment less obvious or in order to better hold the device onto the person's head.

In an example, this device can include at least one electromagnetic energy sensor which is held in proximity to the person's head by a rear segment, a side segment, or a top segment. In an example, this at least one electromagnetic energy sensor collects data concerning electromagnetic brain activity. In an example, this device can include at least one electromagnetic energy sensor which is part of, attached to, or held by a rear segment, a side segment, or a top segment. In an example, this device can comprise at least three electromagnetic energy sensors which are part of, attached to, or held by rear, side, and top segments, respectively. In example, each of the three segments can have at least one electromagnetic energy sensor.

In an example, this device can comprise at least one electromagnetic energy sensor which is a permanent part of a rear segment. In an example, this device can comprise at least one electromagnetic energy sensor which can be removably attached to the rear segment. In an example, this device can comprise at least one electromagnetic energy sensor which is movably and/or slideably attached to the rear segment so that the exact location of the electromagnetic energy sensor on the rear segment can be adjusted. In an example, this adjustment can be done manually. In an example, this adjustment can be done automatically by an actuator.

In an example, this device can comprise at least one electromagnetic energy sensor which is a permanent part of a side segment. In an example, this device can comprise at least one electromagnetic energy sensor which can be removably attached to the side segment. In an example, this device can comprise at least one electromagnetic energy sensor which is movably and/or slideably attached to the side segment so that the exact location of the electromagnetic energy sensor on the side segment can be adjusted. In an example, this adjustment can be done manually. In an example, this adjustment can be done automatically by an actuator. In an example, at least one electromagnetic energy sensor can be part of, or attached to, the side segment at a location which is forward from the person's hairline in order to have more direct contact with the person's skin.

In an example, this device can comprise at least one electromagnetic energy sensor which is a permanent part of a top segment. In an example, this device can comprise at least one electromagnetic energy sensor which can be removably attached to the top segment. In an example, this device can comprise at least one electromagnetic energy sensor which is movably and/or slideably attached to the top segment so that the exact location of the electromagnetic energy sensor on the top segment can be adjusted. In an example, this adjustment can be done manually. In an example, this adjustment can be done automatically by an actuator.

In an example, an electromagnetic energy sensor can be an electromagnetic energy receiver which receives electromagnetic energy which is naturally generated by the electromagnetic activity of the brain. In an example, an electromagnetic energy sensor can comprise an electromagnetic energy emitter at a first location and an electromagnetic energy receiver at a second location, wherein the electromagnetic energy receiver receives energy which has been transmitted from the electromagnetic energy emitter through body tissue. In an example, the electromagnetic energy receiver can collect data concerning (changes in) the conductivity, resistance, and/or impedance of electromagnetic energy transmitted through body tissue from the electromagnetic energy emitter to the electromagnetic energy receiver. In an example, an electromagnetic energy emitter and an electromagnetic energy receiver can together be referred to as an electromagnetic energy sensor.

In an example, an electromagnetic energy sensor of this device can be an electroencephalographic (EEG) sensor. In an example, the at least one electromagnetic energy sensor can be a dry sensor. In an example, the at least one electromagnetic energy sensor can be a wet sensor. In an example, the electromagnetic energy sensor can be an inductive sensor. In an example, the electromagnetic energy sensor can be a capacitive sensor. In an example, an electromagnetic energy sensor can comprise an electromagnetic energy emitter and an electromagnetic energy receiver. In an example, an electromagnetic energy sensor can comprise only an electromagnetic energy receiver. In an example, an electromagnetic energy sensor can be an EEG sensor which collects data concerning the natural emission of electromagnetic energy by a person's brain. In an example, an electromagnetic energy sensor can collect data concerning changes in transmission of electromagnetic energy from an emitter to a receiver due to changes in electromagnetic brain activity. In an example, an electromagnetic brain activity sensor can measure voltage fluctuations resulting from ionic current within the neurons of the brain.

In an example, an electromagnetic energy sensor which collects data concerning brain activity can measure voltage fluctuations between a first electrode (e.g. sensor) and a second (reference) electrode (e.g. sensor) due to electromagnetic brain activity. In an example, voltage differences between a first electrode and a second (reference) electrode can be called a "channel" In an example, a set of channels can be called a "montage."

In an example, a pattern of electromagnetic brain activity can be a change in activity in a specific area of a person's brain. In an example, this pattern can be a transient pattern. In an example, this pattern can be a repeating pattern. In an example, this pattern can be a change in an ongoing repeating pattern. In an example, this pattern can be a change in electromagnetic brain activity measured from one location or channel relative to electromagnetic brain activity measured from one or more different locations or channels. In an example, one or more electromagnetic energy sensors which collect data concerning brain activities or channels can be placed at one or more placement sites selected from the group consisting of: FP1, FPz, FP2, AF7, AF5, AF3, AFz, AF4, AF6, AF8, F7, F5, F3, F1, Fz, F2, F4, F6, F8, FT7, FC5, FC3, FC1, FCz, FC2, FC4, FC6, FT8, T3/T7, C3, C4, C1, Cz, C2, C5, C6, T4/T8, TP7, CP5, CP3, CP1, CPz, CP2, CP4, CP6, DJC, TP8, T5/P7, P5, P3, P1, Pz, P2, P4, P6, T6/P8, PO7, PO5, PO3, POz, PO4, PO6, PO8, O1, Oz, and O2.

In an example, a repeating electromagnetic brain activity pattern can be modeled as a composite of multiple sine waves. In an example, a repeating electromagnetic brain activity pattern can be decomposed into sub-patterns in different frequency bands. In an example, these frequency bands can be selected from the group consisting of: Delta, Theta, Alpha, Beta, and Gamma. Ongoing brain waveforms classified as Delta waves can be within a frequency band selected from the group consisting of: 0.5-3.5 Hz, 0.5-4 Hz, 1-3 Hz, 1-4 Hz, and 2-4 Hz. Ongoing brain waveforms classified as Theta waves can be within a frequency band selected from the group consisting of: from the group consisting of: 3.5-7 Hz, 3-7 Hz, 4-7 Hz, 4-7.5 Hz, 4-8 Hz, and 5-7 Hz. Ongoing brain waveforms classified as Alpha waves can be within a frequency band selected from the group consisting of: 7-13 Hz, 7-14 Hz, 8-12 Hz, 8-13 Hz, 7-11 Hz, 8-10 Hz, and 8-10 Hz. Ongoing brain waveforms classified as Beta waves can be within a frequency band selected from the group consisting of: 11-30 Hz, 12-30 Hz, 13-18 Hz, 13-22 Hz, 13-26 Hz, 13-26 Hz, 13-30 Hz, 13-32 Hz, 14-24 Hz, 14-30 Hz, and 14-40 Hz. Ongoing brain waveforms classified as Gamma waves can be within a frequency band selected from the group consisting of: group consisting of: 30-100 Hz, 35-100 Hz, 40-100 Hz, and greater than 30 Hz.

In an example, this device can include a data processor which receives data from at least one electromagnetic energy sensor. In an example, a data processor can be selected from the group consisting of: central processing unit, microchip, and microprocessor. In an example, patterns of electromagnetic brain activity can be analyzed using one or more methods selected from the group consisting of: Analysis of Variance (ANOVA), Artificial Neural Network (ANN), Auto-Regressive (AR) Modeling, Bayesian Analysis, Bonferroni Analysis (BA), Centroid Analysis, Chi-Squared Analysis, Cluster Analysis, Correlation, Covariance, Data Normalization (DN), Decision Tree Analysis (DTA), Discrete Fourier transform (DFT), Discriminant Analysis (DA), Empirical Mode Decomposition (EMD), Factor Analysis (FA), Fast Fourier Transform (FFT), Feature Vector Analysis (FVA), Fisher Linear Discriminant, Fourier Transformation (FT) Method, Fuzzy Logic (FL) Modeling, Gaussian Model (GM), Generalized Auto-Regressive Conditional Heteroscedasticity (GARCH) Modeling, Hidden Markov Model (HMM), Independent Components Analysis (ICA), Inter-Band Power Ratio, Inter-Channel Power Ratio, Inter-Montage Power Mean, Inter-Montage Ratio, Kalman Filter (KF), Kernel Estimation, Laplacian Filter, Laplacian Montage Analysis, Least Squares Estimation, Linear Regression, Linear Transform, Logit Model, Machine Learning (ML), Markov Model, Maximum Entropy Modeling, Maximum Likelihood, Mean Power, Multi-Band Covariance Analysis, Multi-Channel Covariance Analysis, Multivariate Linear Regression, Multivariate Logit, Multivariate Regression, Naive Bayes Classifier, Neural Network, Non-Linear Programming, Non-negative Matrix Factorization (NMF), Power Spectral Density, Power Spectrum Analysis, Principal Components Analysis (PCA), Probit Model, Quadratic Minimum Distance Classifier, Random Forest (RF), Random Forest Analysis (RFA), Axisymmetric Buoyant Jet Analysis, Regi Model, Regression Model, Signal Amplitude (SA), Signal Averaging, Signal Decomposition, Sine Wave Compositing, Singular Value Decomposition (SVD), Spine Function, Support Vector and/or Machine (SVM), Time Domain Analysis, Time Frequency Analysis, Time Series Model, Trained Bayes Classifier, Variance, Waveform Identification, Wavelet Analysis, and Wavelet Transformation.

In an example, this device can include a wireless data transmitter and/or receiver. In an example, a first data processor and/or data transmitter which is physically part of a wearable component can be in electronic communication with a second data processor and/or data receiver which is not physically part of a wearable component. In an example, data processing can be distributed between first and second data processors. In an example, a second data processor can be part of a remote computing device. In an example, a second data processor can be part of a wearable data processing hub, mobile computer, electronic tablet, electronic pad, mobile phone, smart phone, implanted medical device, internet-connected remote computer, communication network tower, satellite, or home control system.

In an example, this device can include a power source which powers an electromagnetic energy sensor, a data processor, and/or a data transmitter. In an example, a power source can be a battery. In an example, a power source and/or power transducer can transduce, harvest, and/or generate energy from body motion or kinetic energy. In an example, a power source and/or power transducer can transduce, harvest, and/or generate energy from ambient light energy. In an example, a power source and/or power transducer can transduce, harvest, and/or generate energy from body thermal energy. In an example, a power source and/or power transducer can transduce, harvest, and/or generate energy from ambient electromagnetic energy.

In an example, this device can serve as a human-to-computer-interface (HCI) based on electromagnetic brain activity. In addition, this device can further comprise one or more other human-to-computer-interface (HCI) components. One or more human-computer-interface components can be selected from the group consisting of: touch screen, gesture recognition interface, speech and/or voice recognition interface, button and/or keypad, dial and/or knob, and motion sensor. In an example, this device can further comprise one or more computer-to-human interface (HCI) components. One or more computer-to-human interface components can be selected from the group consisting of: display screen, light emitter and/or light-emitting array, light-emitting fabric, optical emitter, speaker, buzzer, or other sound-emitting member, electromagnetic signal generator, vibrating member, actuator, Micro Electro Mechanical Systems (MEMS), augmented reality eyewear, virtual reality eyewear, and electronically-functional eyewear.

FIG. 19 shows another example of how this invention can be embodied in a wearable device for measuring electromagnetic brain activity. This example in FIG. 19 is like the example shown in FIG. 18, except that the example in FIG. 19 further comprises a frontal-ear segment. This frontal-ear segment curves around (a portion of) the front of the person's outer ear. Other components of the example shown in FIG. 19 (including the rear segment, side segment, top segment, at least one electromagnetic energy sensor, data processor, data transmitter, and power source) can have the same features and variations as the corresponding components in the example shown in FIG. 18. Further, relevant portions of the narrative accompanying other figures in this disclosure such as FIG. 18 can be applied to the example shown here in FIG. 19. These portions are not repeated here in order to avoid narrative redundancy.

FIG. 19 shows another example of how this invention can be embodied in a wearable device for measuring electromagnetic brain activity comprising: (a) a rear segment, wherein this rear segment is configured to be worn on the rear-facing surface of a person's ear on a first side of the person's head, wherein this first side is the right side or the left side; (b) a frontal-ear segment, wherein this frontal-ear segment is configured to be worn on the front-facing surface of the person's ear on the first side of the person's head; (c) a side segment, wherein this side segment is configured to span (on the first side of the person's head) from the person's ear to the person's temple, side portion of the person's face, and/or side portion of the person's forehead; (d) a top segment, wherein this top segment is configured to span (on the first side of the person's head) from the side segment to the top of the person's head; (e) at least one electromagnetic energy sensor which is held in proximity to the person's head by the rear segment, the frontal-ear segment, the side segment, and/or the top segment, wherein the at least one electromagnetic energy sensor collects data concerning electromagnetic brain activity; (f) a data processor which receives data from the at least one electromagnetic energy sensor; (g) a data transmitter; and (h) a power source which powers the at least one electromagnetic energy sensor, the data processor, and/or the data transmitter.

FIG. 19 also shows an example of how this invention can be embodied in an undulating mobile EEG monitor comprising: (a) a rear segment, wherein this rear segment is configured to be worn on the rear-facing surface of a person's ear on a first side of the person's head, wherein this first side is the right side or the left side; (b) a frontal-ear segment, wherein this frontal-ear segment is configured to be worn on the front-facing surface of the person's ear on the first side of the person's head; (c) a side segment, wherein this side segment is configured to span (on the first side of the person's head) from the person's ear to the person's temple, side portion of the person's face, and/or side portion of the person's forehead; (d) a top segment, wherein this top segment is configured to span (on the first side of the person's head) from the side segment to the top of the person's head; (e) at least one EEG sensor which is held in proximity to the person's head by the rear segment, the frontal-ear segment, the side segment, and/or the top segment; (f) a data processor which receives data from the at least one EEG sensor; (g) a data transmitter; and (h) a power source which powers the at least one EEG sensor, the data processor, and/or the data transmitter.

With respect to specific components, FIG. 19 shows a right-side head view of a wearable device for measuring electromagnetic brain activity comprising: rear segment 1901 (worn on the rear-facing surface of a person's ear); frontal-ear segment 1902 (worn on the front-facing surface of the person's ear); side segment 1903 (spanning from the person's ear to a side portion of the person's forehead); top segment 1904 (spanning from the side segment to the top of the person's head); electromagnetic energy sensors (such as EEG sensors) 1905, 1906, and 1907; data processor 1909; data transmitter 1908; and power source 1910. In an example, this device can be symmetric with respect to the right and left sides of the person's head. In an example, this device can further comprise a rear segment, a frontal-ear segment, a side segment, and a top segment in a symmetric configuration on the opposite side of the person's head (not shown in this figure). In an example, right and left side top segments can connect at the top of the person's head.

The rear segment, side segment, top segment, at least one electromagnetic energy sensor, data processor, data transmitter and power source of the example shown in FIG. 19 can have the same features and variations as their corresponding components in the example that was shown in FIG. 18. Relevant portions of the narrative accompanying other figures in this disclosure such as FIG. 18 can also be applied to the example shown here in FIG. 19. These relevant portions are not repeated here in order to avoid narrative redundancy.

The example shown in FIG. 19 includes a frontal-ear segment that is configured to be worn on the front-facing surface of the person's ear. In an example, a frontal-ear segment can be directly connected to a rear segment. In an example, frontal-ear and rear segments can both be part of the same continuous member and/or piece of material. In an alternative example, this device can further comprise another member between the frontal-ear and rear segments which connects them together. In an example, a frontal-ear segment can be directly connected to a side segment. In an example, frontal-ear and side segments can both be part of the same continuous member and/or piece of material. In an alternative example, this device can further comprise another member between the frontal-ear and side segments which connects them together.

In an example, a frontal-ear segment can have a shape which is selected from the group consisting of: portion of a circle; portion of a spiral; portion of a parabolic curve; portion of a sinusoidal curve; and conic section. In an example, a frontal-ear segment can gently press against or otherwise engage the outer surface of a person's ear in order to help hold the device on the person's head. In an example, a frontal-ear segment can gently protrude into a portion of the person's ear canal in order in order to help hold the device on the person's head. In an example, a frontal-ear segment can further comprise a speaker. In an example, a frontal-ear segment can hold a speaker close to the ear canal opening for discreet audio communication. In an example, a frontal-ear segment can be resiliently-flexible. In an example, a frontal-ear segment can be made from a metal or polymer. In an example, a frontal-ear segment can be porous and/or have holes so as to be permeable to gas and/or liquid. In an example, a frontal-ear segment can have a width between one-eighth inch and one inch.

In an example, a frontal-ear segment can curve, loop, protrude, undulate, and/or hook around the front of a person's ear. In an example, a frontal-ear segment can be configured to help hold the device on a person's head by engaging the frontal surface of the outer ear. In an example, a frontal-ear segment can be configured to be worn entirely within two inches of the person's outer ear. In an example, a frontal-ear segment of this device can curve, loop, protrude, undulate, and/or hook around (some or all of) the front-facing surface of the person's outer ear. In an example, a frontal-ear segment of this device can curve, loop, protrude, undulate, and/or hook around (some or all of) the frontal portion of tissue which connects the outer ear with the rest of the head. In an example, a frontal-ear segment of this device can be configured to curve, loop, protrude, undulate, and/or hook around a side portion of the person's face which is within one inch of the person's ear.

In an example, a frontal-ear segment of this device can be configured to receive the frame of a pair of eyeglasses so that this device can be worn in combination with eyeglasses. In an example, a frontal-ear segment can further comprise an opening which is configured to receive the side-piece of the frame of a pair of eyeglasses so that this device can be worn in combination with eyeglasses. In an example, a frontal-ear segment can further comprise a clip or other attachment mechanism to which the side-piece of the frame of a pair of eyeglasses can be attached so that this device can be worn in combination with eyeglasses. In an example, a frontal-ear segment can further comprise an indentation, groove, or track into (or against) which the side-piece of the frame of a pair of eyeglasses can be placed so that this device can be worn in combination with eyeglasses.

In an example, a frontal-ear segment can curve, loop, protrude, undulate, and/or hook around a portion of the person's ear clockwise between the 12 o'clock (0 degree) and 6 o'clock (180 degree) vectors. In an example, a frontal-ear segment of this device can curve, loop, protrude, undulate, and/or hook around a portion of the person's ear clockwise between the 12 o'clock (0 degree) and 3 o'clock (90 degree) vectors. In an example, a frontal-ear segment of this device can curve, loop, protrude, undulate, and/or hook around a portion of the person's ear clockwise between the 12 o'clock (0 degree) and 2 o'clock (60 degree) vectors.

In an example, a frontal-ear segment can be configured to help hold the device on a person's head by resting on top of the outer ear (or the tissue connection between the outer ear and the rest of the person's head). In an example, a frontal-ear segment can rest on the top of a person's outer ear and/or the tissue connecting the outer ear with the rest of the head and project in a frontward and downward manner within the directional quadrants relative to the ear canal clockwise between the 12 o'clock (0 degree) and 6 o'clock (180 degree) vectors. In an example, a frontal-ear segment can rest on the top of the person's outer ear and/or the tissue connecting the outer ear with the rest of the head and project in a frontward and downward manner within the directional quadrant relative to the ear canal clockwise between the 12 o'clock (0 degree) and 3 o'clock (90 degree) vectors.

FIG. 20 shows another example of how this invention can be embodied in a wearable device for measuring electromagnetic brain activity. This example in FIG. 20 is like the example shown in FIG. 18, except that the side segment in FIG. 20 loops lower. In this example, the side segment loops down within the quadrant clockwise between the 12 o'clock (0 degree) to 3 o'clock (90 degree) vectors. A lower-looping side segment can help to better hold the device on the person's head. Other components of the example shown in FIG. 20 (including the rear segment, top segment, at least one electromagnetic energy sensor, data processor, data transmitter, and power source) can have the same features and variations as the corresponding components in the example shown in FIG. 18. Further, relevant portions of the narrative accompanying other figures in this disclosure such as FIG. 18 can be applied to the example shown here in FIG. 20. These portions are not repeated here in order to avoid narrative redundancy.

FIG. 20 shows another example of how this invention can be embodied in a wearable device for measuring electromagnetic brain activity comprising: (a) a rear segment, wherein this rear segment is configured to be worn on the rear-facing surface of a person's ear on a first side of the person's head, wherein this first side is the right side or the left side; (b) a side segment, wherein this side segment is configured to span (on the first side of the person's head) from the person's ear to the person's temple, side portion of the person's face, and/or side portion of the person's forehead; (c) a top segment, wherein this top segment is configured to span (on the first side of the person's head) from the side segment to the top of the person's head; (d) at least one electromagnetic energy sensor which is held in proximity to the person's head by the rear segment, the side segment, and/or the top segment, wherein the at least one electromagnetic energy sensor collects data concerning electromagnetic brain activity; (e) a data processor which receives data from the at least one electromagnetic energy sensor; (f) a data transmitter; and (g) a power source which powers the at least one electromagnetic energy sensor, the data processor, and/or the data transmitter.

FIG. 20 also shows an example of how this invention can be embodied in an undulating mobile EEG monitor comprising: (a) a rear segment, wherein this rear segment is configured to be worn on the rear-facing surface of a person's ear on a first side of the person's head, wherein this first side is the right side or the left side; (b) a side segment, wherein this side segment is configured to span (on the first side of the person's head) from the person's ear to the person's temple, side portion of the person's face, and/or side portion of the person's forehead; (c) a top segment, wherein this top segment is configured to span (on the first side of the person's head) from the side segment to the top of the person's head; (d) at least one EEG sensor which is held in proximity to the person's head by the rear segment, the side segment, and/or the top segment; (e) a data processor which receives data from the at least one EEG sensor; (f) a data transmitter; and (g) a power source which powers the at least one EEG sensor, the data processor, and/or the data transmitter.

With respect to specific components, FIG. 20 shows a right-side head view of a wearable device for measuring electromagnetic brain activity comprising: rear segment 2001 (worn on the rear-facing surface of a person's ear); side segment 2002 (spanning from the person's ear to a side portion of the person's forehead); top segment 2003 (spanning from the side segment to the top of the person's head); electromagnetic energy sensors (such as EEG sensors) 2004, 2005, and 2006; data processor 2008; data transmitter 2007; and power source 2009. In an example, this device can be symmetric with respect to the right and left sides of the person's head. In an example, this device can further comprise a rear segment, a side segment, and a top segment in a symmetric configuration on the opposite side of the person's head (not shown in this figure). In an example, right and left side top segments can connect at the top of the person's head.

The rear segment, top segment, at least one electromagnetic energy sensor, data processor, data transmitter and power source of the example shown in FIG. 20 can have the same features and variations as their corresponding components in the example that was shown in FIG. 18. Relevant portions of the narrative accompanying other figures in this disclosure such as FIG. 18 can also be applied to the example shown here in FIG. 20. These relevant portions are not repeated here in order to avoid narrative redundancy.

As shown in FIG. 20, this device can include a side segment which spans from a person's ear to a side portion of their face and/or forehead. A side segment of this device can be directly connected to a rear segment of this device. In an example, side and rear segments can both be part of the same continuous member and/or piece of material. In an alternative example, this device can further comprise another member between the side and rear segments which connects them together.

In an example, a side segment of this device can be configured to receive the frame of a pair of eyeglasses so that this device can be worn in combination with eyeglasses. In an example, a side segment of this device can further comprise an opening which is configured to receive the side-piece of the frame of a pair of eyeglasses so that this device can be worn in combination with eyeglasses. In an example, a side segment of this device can further comprise a clip or other attachment mechanism to which the side-piece of the frame of a pair of eyeglasses can be attached so that this device can be worn in combination with eyeglasses. In an example, a side segment of this device can further comprise an indentation, groove, or track into (or against) which the side-piece of the frame of a pair of eyeglasses can be placed so that this device can be worn in combination with eyeglasses.

In an example, a side segment of this device can span, protrude, curve, or loop from the person's ear to the person's temple on the first side of the person's head. In an example, the side segment can span, protrude, curve, or loop from the person's ear to a side portion of the person's face. In an example, the side segment can span, protrude, curve, or loop from the person's ear to a side portion of the person's forehead.

In an example, a side segment of this device can protrude, project, arc, and/or undulate forward from a person's ear along a vector which is substantially parallel to a vector which is clockwise between the 3 o'clock (90 degree) and 5 o'clock (150 degree) vectors shown in FIG. 17. In the example shown in FIG. 20, the side segment projects forward from a person's ear along vector which is substantially parallel to the 4 o'clock (120 degree) vector and then loops upward onto the side of the person's face and/or forehead. In an example, the side segment can project forward from the ear along a vector which is substantially parallel to the 5 o'clock (150 degree) vector and then loop upward onto the side of the person's face and/or forehead.

In an example, a side segment of this device can be at least two inches long. In an example, a side segment of this device can be at least four inches long. In an example, a side segment of this device can span, protrude, curve, undulate, and/or loop from the person's ear to a position which is at least two inches from a person's ear toward the person's temple. In an example, a side segment of this device can span, protrude, curve, or loop from the person's ear to a position which is at least two inches toward the person's eye. In an example, a side segment of this device can span, protrude, curve, undulate, and/or loop from the person's ear to a position at least two inches toward the center of person's forehead.

In an example, a side segment of this device can span, protrude, curve, undulate, and/or loop from the person's ear to a position which is between one quarter and three-quarters of the way toward the person's temple on the first side of the head. In an example, a side segment of this device can span, protrude, curve, or loop from the person's ear to a position which is between one quarter and three-quarters of the way toward the person's eye on the first side of the head. In an example, a side segment of this device can span, protrude, curve, undulate, and/or loop from the person's ear to a position which is between one quarter and three-quarters of the way toward the center of the person's forehead.

In an example, a side segment of this device can be arcuate, wavy, and/or undulating. In an example, the side segment can be an arc, wave, or undulation with a rear-facing concavity and a forward-facing peak. In an example, a side segment of this device can have a shape selected from the group consisting of: arc, wave, undulation, semi-circle, semi-oval, loop, half-sinusoidal curve, bell-shaped curve, and conic section. In an example, a side segment can have a concavity whose opening faces rearward. In an example, a side segment can have a concavity whose opening faces along a vector which is parallel to a vector which is clockwise between the 7 o'clock (210 degree) and 11 o'clock (330 degree) vectors. In an example, a side segment can have a concavity with a peak which faces frontward. In an example, the most-forward point of a side segment can be located on a person's temple. In an example, the most-forward point of a side segment can be located on the side of a person's forehead.

In an example, a side segment of this device can have a lower portion which is above the bottom of the outer ear by a first distance and an upper portion which is above the bottom of the outer ear by a second distance, wherein the second distance is greater than the first distance. In an example, the second distance can be at least two inches greater than the first distance. In an example, the lower and upper portions of the side segment can be vertically aligned. In an example, a side segment can have a lower portion which rests on the outer ear and an upper portion which is vertically above the outer ear.

In an example, a side segment of this device can have an upper portion which is located in the directional quadrant clockwise between the 11 o'clock (330 degree) and 3 o'clock (90 degree) vectors. In an example, a side segment of this device can have an upper portion which is clockwise between the 12 o'clock (0 degree) and 3 o'clock (90 degree) vectors. In an example, a side segment of this device can span (in an arcuate and/or undulating manner) downward and forward from a person's ear to a location on the side of a person's forehead, then span (in an arcuate and/or undulating manner) upward, and then span (in an arcuate and/or undulating manner) upward and rearward to a location above the ear on the side of the head. In an example, a side segment can further comprise two portions (or sub-segments) which are substantially parallel to each other, one higher and one lower, and connected by a frontal loop.

In an example, this invention can be embodied in a Brain Computer Interface (BCI) device comprising: a rear ear-engaging segment, wherein the rear ear-engaging segment is configured to be worn on a first side of a person's head around at least a portion of the rear-facing surface of the person's ear on the first side; a side segment, wherein this side segment is configured to span on the first side of the person's head from the rear ear-engaging segment to the person's temple, to a side portion of the person's face, and/or to a side portion of the person's forehead; a top segment, wherein this top segment is configured to span on the first side of the person's head from the side segment to the top of the person's head; at least one electromagnetic energy sensor which is held in proximity to the person's head by the rear ear-engaging segment, the side segment, or the top segment, wherein the at least one electromagnetic energy sensor collects data concerning electromagnetic brain activity; a data processor which receives data from the at least one electromagnetic energy sensor; a data transmitter; and a power source which powers the at least one electromagnetic energy sensor, the data processor, and/or the data transmitter.

In an example, the rear ear-engaging, side, and top segments can all be parts of an arcuate undulating band. In an example, this device can further comprise rear ear-engaging, side, and top segments on a second side of the person's head opposite to the first side, and wherein first side and second side top segments connect at the top of the person's head. In an example, the side segment can be configured to protrude, project, arc, and/or undulate forward from a person's ear along a vector which is substantially parallel to a vector which is clockwise between the 3 o'clock (90 degree) and 5 o'clock (150 degree) vectors, wherein these vectors are defined with respect to a side view of the person's ear canal. In an example, the side segment can be configured to span, protrude, curve, or loop from the person's ear: at least two inches toward the person's eye; at least two inches toward the center of the person's forehead; between one quarter and three-quarters of the way toward the person's eye; or between one quarter and three-quarters of the way toward the center of the person's forehead.

In an example, the side segment can have a shape selected from the group consisting of: arc, wave, undulation, semicircle, semi-oval, loop, half-sinusoidal curve, bell-shaped curve, and conic section. In an example, the side segment can have an arc, wave, or undulation with a rear-facing concavity and a forward-facing peak. In an example, the side segment can have a concavity whose opening faces along a vector which is parallel to a vector which is clockwise between the 7 o'clock (210 degree) and 11 o'clock (330 degree) vectors, wherein these vectors are defined with respect to a side view of the person's ear canal. In an example, the side segment can be configured to have a lower portion which rests on the outer ear and an upper portion which is vertically above the outer ear. In an example, the side segment can be configured to: (a) span in an arcuate and/or undulating manner downward and forward from a person's ear to a location on the side of a person's face, (b) then span in an arcuate and/or undulating manner upward, and (c) then span in an arcuate and/or undulating manner upward and rearward to a location above the ear on the side of the head.

FIG. 21 shows another example of how this invention can be embodied in a wearable device for measuring electromagnetic brain activity. This example in FIG. 21 is like the example shown in FIG. 20, except that the example in FIG. 21 further comprises a frontal-ear segment like the one first introduced in FIG. 19. This frontal-ear segment curves around (a portion of) the front of the person's outer ear. Other components (including the rear segment, side segment, top segment, at least one electromagnetic energy sensor, data processor, data transmitter, and power source) can have the same features and variations as the corresponding components in the example shown in FIG. 20. The frontal-ear segment can have the same features and variations as the corresponding components in the example shown in FIG. 19. Further, relevant portions of the narrative accompanying other figures in this disclosure such as FIGS. 19 and 20 can be applied to this example. These portions are not repeated here in order to avoid narrative redundancy.

FIG. 21 shows another example of how this invention can be embodied in a wearable device for measuring electromagnetic brain activity comprising: (a) a rear segment, wherein this rear segment is configured to be worn on the rear-facing surface of a person's ear on a first side of the person's head, wherein this first side is the right side or the left side; (b) a frontal-ear segment, wherein this frontal-ear segment is configured to be worn on the front-facing surface of the person's ear on the first side of the person's head; (c) a side segment, wherein this side segment is configured to span (on the first side of the person's head) from the person's ear to the person's temple, side portion of the person's face, and/or side portion of the person's forehead; (d) a top segment, wherein this top segment is configured to span (on the first side of the person's head) from the side segment to the top of the person's head; (e) at least one electromagnetic energy sensor which is held in proximity to the person's head by the rear segment, the frontal-ear segment, the side segment, and/or the top segment, wherein the at least one electromagnetic energy sensor collects data concerning electromagnetic brain activity; (f) a data processor which receives data from the at least one electromagnetic energy sensor; (g) a data transmitter; and (h) a power source which powers the at least one electromagnetic energy sensor, the data processor, and/or the data transmitter.

FIG. 21 also shows an example of how this invention can be embodied in an undulating mobile EEG monitor comprising: (a) a rear segment, wherein this rear segment is configured to be worn on the rear-facing surface of a person's ear on a first side of the person's head, wherein this first side is the right side or the left side; (b) a frontal-ear segment, wherein this frontal-ear segment is configured to be worn on the front-facing surface of the person's ear on the first side of the person's head; (c) a side segment, wherein this side segment is configured to span (on the first side of the person's head) from the person's ear to the person's temple, side portion of the person's face, and/or side portion of the person's forehead; (d) a top segment, wherein this top segment is configured to span (on the first side of the person's head) from the side segment to the top of the person's head; (e) at least one EEG sensor which is held in proximity to the person's head by the rear segment, the frontal-ear segment, the side segment, and/or the top segment; (f) a data processor which receives data from the at least one EEG sensor; (g) a data transmitter; and (h) a power source which powers the at least one EEG sensor, the data processor, and/or the data transmitter.

With respect to specific components, FIG. 21 shows a right-side head view of a wearable device for measuring electromagnetic brain activity comprising: rear segment 2101 (worn on the rear-facing surface of a person's ear); frontal-ear segment 2102 (worn on the front-facing surface of the person's ear); side segment 2103 (spanning from the person's ear to a side portion of the person's forehead); top segment 2104 (spanning from the side segment to the top of the person's head); electromagnetic energy sensors (such as EEG sensors) 2105, 2106, and 2107; data processor 2109; data transmitter 2108; and power source 2110. In an example, this device can be symmetric with respect to the right and left sides of the person's head. In an example, this device can further comprise a rear segment, a frontal-ear segment, a side segment, and a top segment in a symmetric configuration on the opposite side of the person's head (not shown in this figure). In an example, right and left side top segments can connect at the top of the person's head.

The rear segment, side segment, top segment, at least one electromagnetic energy sensor, data processor, data transmitter, and power source can have the same features and variations as the corresponding components in the example shown in FIG. 20. The frontal-ear segment can have the same features and variations as the corresponding components in the example shown in FIG. 19. Relevant portions of the narratives accompanying other figures in this disclosure such as FIGS. 19 and 20 can be applied here as well.

FIG. 22 shows another example of how this invention can be embodied in a wearable device for measuring electromagnetic brain activity comprising: (a) a rear segment, wherein this rear segment is configured to be worn on the rear-facing surface of a person's ear on a first side of the person's head, wherein this first side is the right side or the left side; (b) a side segment, wherein this side segment is configured to span (on the first side of the person's head) from the person's ear to the person's temple, side portion of the person's face, and/or side portion of the person's forehead; (c) a top segment, wherein this top segment is configured to span (on the first side of the person's head) from the side segment and/or person's ear to the top of the person's head; (d) at least one electromagnetic energy sensor which is held in proximity to the person's head by the rear segment, the side segment, and/or the top segment, wherein the at least one electromagnetic energy sensor collects data concerning electromagnetic brain activity; (e) a data processor which receives data from the at least one electromagnetic energy sensor; (f) a data transmitter; and (g) a power source which powers the at least one electromagnetic energy sensor, the data processor, and/or the data transmitter.

FIG. 22 also shows an example of how this invention can be embodied in an undulating mobile EEG monitor comprising: (a) a rear segment, wherein this rear segment is configured to be worn on the rear-facing surface of a person's ear on a first side of the person's head, wherein this first side is the right side or the left side; (b) a side segment, wherein this side segment is configured to span (on the first side of the person's head) from the person's ear to the person's temple, side portion of the person's face, and/or side portion of the person's forehead; (c) a top segment, wherein this top segment is configured to span (on the first side of the person's head) from the side segment and/or person's ear to the top of the person's head; (d) at least one EEG sensor which is held in proximity to the person's head by the rear segment, the side segment, and/or the top segment; (e) a data processor which receives data from the at least one EEG sensor; (f) a data transmitter; and (g) a power source which powers the at least one EEG sensor, the data processor, and/or the data transmitter.

With respect to specific components, FIG. 22 shows a right-side head view of a wearable device for measuring electromagnetic brain activity comprising: rear segment 2201 (worn on the rear-facing surface of a person's ear); side segment 2202 (spanning from the person's ear to a side portion of the person's forehead); top segment 2203 (spanning from the ear and/or side segment to the top of the person's head); electromagnetic energy sensors (such as EEG sensors) 2204, 2205, and 2206; data processor 2208; data transmitter 2207; and power source 2209. In an example, this device can be symmetric with respect to the right and left sides of the person's head. In an example, this device can further comprise a rear segment, a side segment, and a top segment in a symmetric configuration on the opposite side of the person's head (not shown in this figure). In an example, right and left side top segments can connect at the top of the person's head.

In an example, the rear segment, side segment, and top segment can be resiliently-flexible. In an example, these segments can gently press against the person's head when worn. In an example, these segments can be made from a metal or polymer. In an example, these segments can have prongs, teeth, or combs to engage with the person's hair to make the device less obvious and/or to better hold it onto the person's head. In an example, these segments can be porous and/or have holes so as to be permeable to gas and/or liquid. In an example, these segments can be between one quarter inch and three inches in width. In an example, these segments can be part of a continuous member and/or piece of material.

As shown in FIG. 22, this device can include a rear segment which curves, loops, and/or hooks behind a person's ear. In an example, a rear segment can be configured to help hold the device on a person's head by engaging the rear surface of the outer ear. In an example, a rear segment can be configured to be worn entirely within one inch of the person's outer ear. In an example, a rear segment of this device can curve, loop, or hook around (some or all of) the rear-facing surface of the person's outer ear and/or the tissue connecting the outer ear with the rest of the head.

In an example, a rear segment of this device can be configured to receive the frame of a pair of eyeglasses so that this device can be worn in combination with eyeglasses. In an example, a rear segment of this device can further comprise an opening which is configured to receive the side-piece of the frame of a pair of eyeglasses so that this device can be worn in combination with eyeglasses. In an example, a rear segment of this device can further comprise a clip or other attachment mechanism to which the side-piece of the frame of a pair of eyeglasses can be attached so that this device can be worn in combination with eyeglasses. In an example, a rear segment of this device can further comprise an indentation, groove, or track into (or against) which the side-piece of the frame of a pair of eyeglasses can be placed so that this device can be worn in combination with eyeglasses.

In an example, a rear segment of this device can curve, loop, or hook around a portion of the person's ear clockwise between the 6 o'clock (180 degree) and 12 o'clock (0 degree) vectors. In an example, a rear segment of this device can curve, loop, or hook around a portion of the person's ear clockwise between the 9 o'clock (270 degree) and 12 o'clock (0 degree) vectors. In an example, a rear segment of this device can curve, loop, or hook around a portion of the person's ear clockwise between the 10 o'clock (300 degree) and 12 o'clock (0 degree) vectors.

In an example, the rear segment of this device can be configured to help hold the device on a person's head by resting on top of the outer ear (or the tissue connection between the outer ear and the rest of the person's head). In an example, a rear segment of this device can rest on the top of a person's outer ear and/or the tissue connecting the outer ear with the rest of the head and project in a rearward and downward manner within the directional quadrants relative to the ear canal clockwise between the 6 o'clock (180 degree) and 12 o'clock (0 degree) vectors. In an example, a rear segment of this device can rest on the top of the person's outer ear and/or the tissue connecting the outer ear with the rest of the head and project in a rearward and downward manner within the directional quadrant relative to the ear canal clockwise between the 9 o'clock (270 degree) and 12 o'clock (0 degree) vectors.

As shown in FIG. 22, this device can include a side segment which spans from a person's ear to a side portion of their face and/or forehead. A side segment of this device can be directly connected to a rear segment of this device. In an example, side and rear segments can both be part of the same continuous member and/or piece of material. In an alternative example, this device can further comprise another member between the side and rear segments which connects them together.

In an example, a side segment of this device can be configured to receive the frame of a pair of eyeglasses so that this device can be worn in combination with eyeglasses. In an example, a side segment of this device can further comprise an opening which is configured to receive the side-piece of the frame of a pair of eyeglasses so that this device can be worn in combination with eyeglasses. In an example, a side segment of this device can further comprise a clip or other attachment mechanism to which the side-piece of the frame of a pair of eyeglasses can be attached so that this device can be worn in combination with eyeglasses. In an example, a side segment of this device can further comprise an indentation, groove, or track into (or against) which the side-piece of the frame of a pair of eyeglasses can be placed so that this device can be worn in combination with eyeglasses.

In an example, a side segment of this device can span, protrude, extend, and/or curve from the person's ear to the person's temple on the first side of the person's head. In an example, the side segment can span, protrude, extend, and/or curve from the person's ear to a side portion of the person's face. In an example, the side segment can span, protrude, extend, and/or curve from the person's ear to a side portion of the person's forehead.

In an example, a side segment of this device can protrude, project, and/or extend forward from a person's ear along a vector which is substantially parallel to a vector which is clockwise between the 12 o'clock (0 degree) and 3 o'clock (90 degree) vectors shown in FIG. 17. In the example shown in FIG. 22, the side segment projects forward from a person's ear along vector which is substantially parallel to the 3 o'clock (90 degree) vector. In an example, the side segment can project forward from the ear along a vector which is substantially parallel to the 2 o'clock (60 degree) vector. In an example, the side segment can project forward from the ear along a vector which is substantially parallel to a vector which is clockwise between the 1 o'clock (30 degree) and 3 o'clock (90 degree) vectors.

In an example, a side segment of this device can be at least two inches long. In an example, a side segment of this device can be at least four inches long. In an example, a side segment of this device can span, protrude, extend, and/or curve from the person's ear to a position which is at least two inches from a person's ear toward the person's temple. In an example, a side segment of this device can span, protrude, extend, and/or curve from the person's ear to a position which is at least two inches toward the person's eye. In an example, a side segment of this device can span, protrude, extend, and/or curve from the person's ear to a position at least two inches toward the center of person's forehead.

In an example, a side segment of this device can span, protrude, extend, and/or curve from the person's ear to a position which is between one quarter and three-quarters of the way toward the person's temple on the first side of the head. In an example, a side segment of this device can span, protrude, extend, and/or curve from the person's ear to a position which is between one quarter and three-quarters of the way toward the person's eye on the first side of the head. In an example, a side segment of this device can span, protrude, extend, and/or curve from the person's ear to a position which is between one quarter and three-quarters of the way toward the center of the person's forehead.

In an example, a side segment of this device can have a shape like a hockey stick and/or the letter "J". In an example, a rear portion of a side segment can be substantially straight and a front portion of a side segment can have an arcuate upturn. In an example, a side segment can have a frontal end which curves upward onto a side portion of a person's forehead. In an example, the most-forward point of a side segment can be located on a person's temple. In an example, the most-forward point of a side segment can be located on the side of a person's forehead.

In an example, this device can have a top segment which spans from a person's ear and/or a side segment of this device to the top of the person's head. As shown in FIG. 22, a top segment of this device can span from the rear portion of a side segment to the top of the person's head (all on the first side of the person's head). In an example, a top segment of this device on the first side of the person's head can connect with the top segment of this device on the second (opposite) side of the person's head. In an example, the top and side segments of this device can be part of the same continuous member and/or piece of material. In an example, this device can further comprise another member which connects the top and side segments.

In an example, a top segment of this device can be arcuate, wavy, and/or undulating. In an example, a top segment can be an arc, wave, or undulation with a rear-facing concavity and a forward-facing peak. In an example, a top segment of this device can have a shape selected from the group consisting of: arc, wave, undulation, semi-circle, semi-oval, half-sinusoidal curve, bell-shaped curve, and conic section. In an example, a top segment can have a concavity whose opening faces rearward. In an example, a top segment can have a concavity whose opening faces along a vector which is parallel to a vector which is clockwise between the 7 o'clock (210 degree) and 11 o'clock (330 degree) vectors. In an example, a top segment can have a concavity with a peak which faces frontward.

In an example, the top segment of this device can span the top of a person's head within four inches of the uppermost point on the person's head (when the person is standing up with their head up). In an example, the top segment of this device can span the top of a person's head within four inches of the position on the person's head which is the shortest vertically-oriented arc connecting the person's right and left ears. In an example, the top segment can further comprise prongs, teeth, or combs which engage the person's hair in order to make the top segment less obvious or in order to better hold the device onto the person's head.

The at least one electromagnetic energy sensor, data processor, data transmitter, and power source of this example can have the same features and variations as the corresponding components in the example shown in FIG. 18. Further, relevant portions of the narrative accompanying other figures in this disclosure such as FIG. 18 can be applied to this example. These portions are not repeated here in order to avoid narrative redundancy.

FIG. 23 shows another example of how this invention can be embodied in a wearable device for measuring electromagnetic brain activity. This example in FIG. 23 is like the example shown in FIG. 22, except that the example in FIG. 23 further comprises a frontal-ear segment like the one first introduced in FIG. 19. This frontal-ear segment curves around (a portion of) the front of the person's outer ear. Other components (including the rear segment, side segment, top segment, at least one electromagnetic energy sensor, data processor, data transmitter, and power source) can have the same features and variations as the corresponding components in the example shown in FIG. 22. The frontal-ear segment can have the same features and variations as the corresponding components in the example shown in FIG. 19. Further, relevant portions of the narratives accompanying other figures in this disclosure such as FIGS. 19 and 22 can be applied to this example. These portions are not repeated here in order to avoid narrative redundancy.

FIG. 23 shows another example of how this invention can be embodied in a wearable device for measuring electromagnetic brain activity comprising: (a) a rear segment, wherein this rear segment is configured to be worn on the rear-facing surface of a person's ear on a first side of the person's head, wherein this first side is the right side or the left side; (b) a frontal-ear segment, wherein this frontal-ear segment is configured to be worn on the front-facing surface of the person's ear on the first side of the person's head; (c) a side segment, wherein this side segment is configured to span (on the first side of the person's head) from the person's ear and/or the side segment to the person's temple, side portion of the person's face, and/or side portion of the person's forehead; (d) a top segment, wherein this top segment is configured to span (on the first side of the person's head) from the rear segment or the side segment to the top of the person's head; (e) at least one electromagnetic energy sensor which is held in proximity to the person's head by the rear segment, the frontal-ear segment, the side segment, and/or the top segment, wherein the at least one electromagnetic energy sensor collects data concerning electromagnetic brain activity; (f) a data processor which receives data from the at least one electromagnetic energy sensor; (g) a data transmitter; and (h) a power source which powers the at least one electromagnetic energy sensor, the data processor, and/or the data transmitter.

FIG. 23 also shows an example of how this invention can be embodied in an undulating mobile EEG monitor comprising: (a) a rear segment, wherein this rear segment is configured to be worn on the rear-facing surface of a person's ear on a first side of the person's head, wherein this first side is the right side or the left side; (b) a frontal-ear segment, wherein this frontal-ear segment is configured to be worn on the front-facing surface of the person's ear on the first side of the person's head; (c) a side segment, wherein this side segment is configured to span (on the first side of the person's head) from the person's ear and/or the side segment to the person's temple, side portion of the person's face, and/or side portion of the person's forehead; (d) a top segment, wherein this top segment is configured to span (on the first side of the person's head) from the rear segment or the side segment to the top of the person's head; (e) at least one EEG sensor which is held in proximity to the person's head by the rear segment, the frontal-ear segment, the side segment, and/or the top segment; (f) a data processor which receives data from the at least one EEG sensor; (g) a data transmitter; and (h) a power source which powers the at least one EEG sensor, the data processor, and/or the data transmitter.

With respect to specific components, FIG. 23 shows a right-side head view of a wearable device for measuring electromagnetic brain activity comprising: rear segment 2301 (worn on the rear-facing surface of a person's ear); frontal-ear segment 2302 (worn on the front-facing surface of the person's ear); side segment 2303 (spanning from the person's ear to a side portion of the person's forehead); top segment 2304 (spanning from the rear or side segment to the top of the person's head); electromagnetic energy sensors (such as EEG sensors) 2305, 2306, and 2307; data processor 2309; data transmitter 2308; and power source 2310. In an example, this device can be symmetric with respect to the right and left sides of the person's head. In an example, this device can further comprise a rear segment, a frontal-ear segment, a side segment, and a top segment in a symmetric configuration on the opposite side of the person's head (not shown in this figure). In an example, right and left side top segments can connect at the top of the person's head.

The rear segment, side segment, top segment, at least one electromagnetic energy sensor, data processor, data transmitter, and power source can have the same features and variations as the corresponding components in the example shown in FIG. 22. The frontal-ear segment can have the same features and variations as the corresponding components in the example shown in FIG. 19. Relevant portions of the narratives accompanying other figures in this disclosure such as FIGS. 19 and 22 can be applied here as well.

FIG. 24 shows another example of how this invention can be embodied in a wearable device for measuring electromagnetic brain activity. This example in FIG. 24 is like the example shown in FIG. 23, except that the top segment in FIG. 24 is a simple arc (over the person's head) rather than an undulating curve. The rear segment, frontal-ear segment, side segment, at least one electromagnetic energy sensor, data processor, data transmitter, and power source can have the same features and variations as the corresponding components discussed in other figures of this disclosure. Further, relevant portions of the narratives which accompany other figures of this disclosure can also be applied to this example. These portions are not repeated here in order to avoid narrative redundancy.

FIG. 24 shows another example of how this invention can be embodied in a wearable device for measuring electromagnetic brain activity comprising: (a) a rear segment, wherein this rear segment is configured to be worn on the rear-facing surface of a person's ear on a first side of the person's head, wherein this first side is the right side or the left side; (b) a frontal-ear segment, wherein this frontal-ear segment is configured to be worn on the front-facing surface of the person's ear on the first side of the person's head; (c) a side segment, wherein this side segment is configured to span (on the first side of the person's head) from the person's ear and/or the side segment to the person's temple, side portion of the person's face, and/or side portion of the person's forehead; (d) a top segment, wherein this top segment is configured to span (on the first side of the person's head) from the rear segment or the side segment to the top of the person's head; (e) at least one electromagnetic energy sensor which is held in proximity to the person's head by the rear segment, the frontal-ear segment, the side segment, and/or the top segment, wherein the at least one electromagnetic energy sensor collects data concerning electromagnetic brain activity; (f) a data processor which receives data from the at least one electromagnetic energy sensor; (g) a data transmitter; and (h) a power source which powers the at least one electromagnetic energy sensor, the data processor, and/or the data transmitter.

FIG. 24 also shows an example of how this invention can be embodied in an undulating mobile EEG monitor comprising: (a) a rear segment, wherein this rear segment is configured to be worn on the rear-facing surface of a person's ear on a first side of the person's head, wherein this first side is the right side or the left side; (b) a frontal-ear segment, wherein this frontal-ear segment is configured to be worn on the front-facing surface of the person's ear on the first side of the person's head; (c) a side segment, wherein this side segment is configured to span (on the first side of the person's head) from the person's ear and/or the side segment to the person's temple, side portion of the person's face, and/or side portion of the person's forehead; (d) a top segment, wherein this top segment is configured to span (on the first side of the person's head) from the rear segment or side segment to the top of the person's head; (e) at least one EEG sensor which is held in proximity to the person's head by the rear segment, the frontal-ear segment, the side segment, and/or the top segment; (f) a data processor which receives data from the at least one EEG sensor; (g) a data transmitter; and (h) a power source which powers the at least one EEG sensor, the data processor, and/or the data transmitter.

With respect to specific components, FIG. 24 shows a right-side head view of a wearable device for measuring electromagnetic brain activity comprising: rear segment 2401 (worn on the rear-facing surface of a person's ear); frontal-ear segment 2402 (worn on the front-facing surface of the person's ear); side segment 2403 (spanning from the person's ear to a side portion of the person's forehead); top segment 2404 (spanning from the rear or side segment to the top of the person's head); electromagnetic energy sensors (such as EEG sensors) 2405, 2406, and 2407; data processor 2409; data transmitter 2408; and power source 2410. In an example, this device can be symmetric with respect to the right and left sides of the person's head. In an example, this device can further comprise a rear segment, a frontal-ear segment, a side segment, and a top segment in a symmetric configuration on the opposite side of the person's head (not shown in this figure). In an example, right and left side top segments can connect at the top of the person's head.

Other components (including the rear segment, frontal-ear segment, side segment, at least one electromagnetic energy sensor, data processor, data transmitter, and power source) can have the same features and variations as the corresponding components discussed in other figures of this disclosure. Also, relevant portions of the narratives which accompany other figures in this disclosure can also be applied to this example, but are not repeated here.

FIG. 25 shows another example of how this invention can be embodied in a wearable device for measuring electromagnetic brain activity comprising: (a) a rear segment, wherein this rear segment is configured to be worn on the rear-facing surface of a person's ear on a first side of the person's head, wherein this first side is the right side or the left side; (b) a side segment, wherein this side segment is configured to span (on the first side of the person's head) from the person's ear to the person's temple, side portion of the person's face, and/or side portion of the person's forehead; (c) a top segment, wherein this top segment is configured to span (on the first side of the person's head) from the side segment to the top of the person's head; (d) at least one electromagnetic energy sensor which is held in proximity to the person's head by the rear segment, the side segment, and/or the top segment, wherein the at least one electromagnetic energy sensor collects data concerning electromagnetic brain activity; (e) a data processor which receives data from the at least one electromagnetic energy sensor; (f) a data transmitter; and (g) a power source which powers the at least one electromagnetic energy sensor, the data processor, and/or the data transmitter.

FIG. 25 also shows an example of how this invention can be embodied in an undulating mobile EEG monitor comprising: (a) a rear segment, wherein this rear segment is configured to be worn on the rear-facing surface of a person's ear on a first side of the person's head, wherein this first side is the right side or the left side; (b) a side segment, wherein this side segment is configured to span (on the first side of the person's head) from the person's ear to the person's temple, side portion of the person's face, and/or side portion of the person's forehead; (c) a top segment, wherein this top segment is configured to span (on the first side of the person's head) from the side segment to the top of the person's head; (d) at least one EEG sensor which is held in proximity to the person's head by the rear segment, the side segment, and/or the top segment; (e) a data processor which receives data from the at least one EEG sensor; (f) a data transmitter; and (g) a power source which powers the at least one EEG sensor, the data processor, and/or the data transmitter.

With respect to specific components, FIG. 25 shows a right-side head view of a wearable device for measuring electromagnetic brain activity comprising: rear segment 2501 (worn on the rear-facing surface of a person's ear); side segment 2502 (spanning from the person's ear to a side portion of the person's forehead); top segment 2503 (spanning from the side segment to the top of the person's head); electromagnetic energy sensors (such as EEG sensors) 2504, 2505, and 2506; data processor 2508; data transmitter 2507; and power source 2509. In an example, this device can be symmetric with respect to the right and left sides of the person's head. In an example, this device can further comprise a rear segment, a side segment, and a top segment in a symmetric configuration on the opposite side of the person's head (not shown in this figure). In an example, right and left side top segments can connect at the top of the person's head.

In an example, the rear segment, side segment, and top segment can be resiliently-flexible. In an example, these segments can gently press against the person's head when worn. In an example, these segments can be made from a metal or polymer. In an example, these segments can have prongs, teeth, or combs to engage with the person's hair to make the device less obvious and/or to better hold it onto the person's head. In an example, these segments can be porous and/or have holes so as to be permeable to gas and/or liquid. In an example, these segments can be between one quarter inch and three inches in width. In an example, these segments can be part of a continuous member and/or piece of material.

As shown in FIG. 25, this device can have a rear segment which curves over the top of a person's ear and then extends toward the rear of the person's head in a downward and rearward manner. In an example, a rear segment can have an arcuate end which curves away from the person's ear. In an example, a rear segment can have a downward-facing concavity. In an example, a rear segment of this device can curve around a portion of the person's ear which is clockwise between the 8 o'clock (240 degree) and 12 o'clock (0 degree) vectors. In an example, a rear segment of this device can curve around a portion of the person's ear which is clockwise between the 9 o'clock (270 degree) and 12 o'clock (0 degree) vectors.

In an example, a rear segment of this device can rest on the top of a person's outer ear and/or the tissue connecting the outer ear with the rest of the head and project in a rearward and downward manner within the directional quadrants relative to the ear canal clockwise between the 6 o'clock (180 degree) and 12 o'clock (0 degree) vectors. In an example, a rear segment of this device can rest on the top of the person's outer ear and/or the tissue connecting the outer ear with the rest of the head and project in a rearward and downward manner within the directional quadrant relative to the ear canal clockwise between the 9 o'clock (270 degree) and 12 o'clock (0 degree) vectors.

In an example, a rear segment of this device can be configured to receive the frame of a pair of eyeglasses so that this device can be worn in combination with eyeglasses. In an example, a rear segment of this device can further comprise an opening which is configured to receive the side-piece of the frame of a pair of eyeglasses so that this device can be worn in combination with eyeglasses. In an example, a rear segment of this device can further comprise a clip or other attachment mechanism to which the side-piece of the frame of a pair of eyeglasses can be attached so that this device can be worn in combination with eyeglasses. In an example, a rear segment of this device can further comprise an indentation, groove, or track into (or against) which the side-piece of the frame of a pair of eyeglasses can be placed so that this device can be worn in combination with eyeglasses.

As shown in FIG. 25, this device can include a side segment which spans from a person's ear to a side portion of their face and/or forehead. A side segment of this device can be directly connected to a rear segment of this device. In an example, side and rear segments can both be part of the same continuous member and/or piece of material. In an alternative example, this device can further comprise another member between the side and rear segments which connects them together.

In an example, a side segment can span, protrude, curve, or loop from the person's ear to the person's temple on the first side of the person's head. In an example, the side segment can span, protrude, curve, or loop from the person's ear to a side portion of the person's face. In an example, the side segment can span, protrude, curve, or loop from the person's ear to a side portion of the person's forehead. In an example, a side segment can protrude, project, arc, and/or undulate forward from a person's ear along a vector which is substantially parallel to a vector which is clockwise between the 3 o'clock (90 degree) and 5 o'clock (150 degree) vectors shown in FIG. 17. In the example shown in FIG. 25, the side segment projects forward from a person's ear along vector which is substantially parallel to the 5 o'clock (150 degree) vector and then loops upward onto the side of the person's face and/or forehead.

In an example, a side segment can be at least two inches long. In an example, a side segment can be at least four inches long. In an example, a side segment can span, protrude, curve, undulate, and/or loop from the person's ear to a position which is at least two inches from a person's ear toward the person's temple. In an example, a side segment can span, protrude, curve, or loop from the person's ear to a position which is at least two inches toward the person's eye. In an example, a side segment can span, protrude, curve, undulate, and/or loop from the person's ear to a position at least two inches toward the center of person's forehead.

In an example, a side segment can span, protrude, curve, undulate, and/or loop from the person's ear to a position which is between one quarter and three-quarters of the way toward the person's temple on the first side of the head. In an example, a side segment can span, protrude, curve, or loop from the person's ear to a position which is between one quarter and three-quarters of the way toward the person's eye on the first side of the head. In an example, a side segment can span, protrude, curve, undulate, and/or loop from the person's ear to a position which is between one quarter and three-quarters of the way toward the center of the person's forehead.

In an example, a side segment can be arcuate, wavy, and/or undulating. In an example, the side segment can be an arc, wave, or undulation with a rear-facing concavity and a forward-facing peak. In an example, a side segment can have a shape selected from the group consisting of: arc, wave, undulation, semi-circle, semi-oval, loop, half-sinusoidal curve, bell-shaped curve, and conic section. In an example, a side segment can have a concavity whose opening faces rearward. In an example, a side segment can have a concavity whose opening faces along a vector which is parallel to a vector which is clockwise between the 7 o'clock (210 degree) and 11 o'clock (330 degree) vectors. In an example, a side segment can have a concavity with a peak which faces frontward. In an example, the most-forward point of a side segment can be located on a person's temple. In an example, the most-forward point of a side segment can be located on the side of a person's forehead.

In an example, a side segment can have an upper portion which is located in the directional quadrant clockwise between the 11 o'clock (330 degree) and 3 o'clock (90 degree) vectors. In an example, a side segment can have an upper portion which is clockwise between the 12 o'clock (0 degree) and 3 o'clock (90 degree) vectors. In an example, a side segment can span (in an arcuate and/or undulating manner) downward and forward from a person's ear to a location on the side of a person's forehead, then span (in an arcuate and/or undulating manner) upward, and then span (in an arcuate and/or undulating manner) upward and rearward to a location above the ear on the side of the head.

In an example, a side segment can be configured to receive the frame of a pair of eyeglasses so that this device can be worn in combination with eyeglasses. In an example, a side segment can further comprise an opening which is configured to receive the side-piece of the frame of a pair of eyeglasses so that this device can be worn in combination with eyeglasses. In an example, a side segment can further comprise a clip or other attachment mechanism to which the side-piece of the frame of a pair of eyeglasses can be attached so that this device can be worn in combination with eyeglasses. In an example, a side segment can further comprise an indentation, groove, or track into (or against) which the side-piece of the frame of a pair of eyeglasses can be placed so that this device can be worn in combination with eyeglasses.

In an example, this device can have a top segment which spans from the side segment to the top of the person's head. As shown in FIG. 25, a top segment can span from the upper portion of the side segment to the top of the person's head (all on the first side of the person's head). In an example, a top segment on the first side of the person's head can connect with the top segment on the second (opposite) side of the person's head. In an example, the top and side segments can be part of the same continuous member and/or piece of material. In an example, this device can further comprise another member which connects the top and side segments.

In an example, the top segment of this device can span the top of a person's head within four inches of the uppermost point on the person's head (when the person is standing up with their head up). In an example, the top segment of this device can span the top of a person's head within four inches of the position on the person's head which is the shortest vertically-oriented arc connecting the person's right and left ears. In an example, the top segment can further comprise prongs, teeth, or combs which engage the person's hair in order to make the top segment less obvious or in order to better hold the device onto the person's head.

Other components (including the at least one electromagnetic energy sensor, data processor, data transmitter, and power source) can have the same features and variations as the corresponding components discussed in other figures of this disclosure. Also, relevant portions of the narratives which accompany other figures in this disclosure can also be applied to this example, but are not repeated here.

FIG. 26 shows another example of how this invention can be embodied in a wearable device for measuring electromagnetic brain activity comprising: (a) a posterior-ear segment, wherein this posterior-ear segment is configured to be worn on the rear-facing surface of a person's ear on a first side of the person's head, wherein this first side is the right side or the left side; (b) a forehead loop, wherein this forehead loop is configured to span (on the first side of the person's head) from the person's ear to the person's temple, side portion of the person's face, and/or side portion of the person's forehead; (c) a rear loop, wherein this rear loop is configured to span (on the first side of the person's head) from the forehead loop to the rear of the person's head; (d) at least one electromagnetic energy sensor which is held in proximity to the person's head by the posterior-ear segment, the forehead loop, and/or the rear loop, wherein the at least one electromagnetic energy sensor collects data concerning electromagnetic brain activity; (e) a data processor which receives data from the at least one electromagnetic energy sensor; (f) a data transmitter; and (g) a power source which powers the at least one electromagnetic energy sensor, the data processor, and/or the data transmitter.

FIG. 26 also shows an example of how this invention can be embodied in an undulating mobile EEG monitor comprising: (a) a posterior-ear segment, wherein this posterior-ear segment is configured to be worn on the rear-facing surface of a person's ear on a first side of the person's head, wherein this first side is the right side or the left side; (b) a forehead loop, wherein this forehead loop is configured to span (on the first side of the person's head) from the person's ear to the person's temple, side portion of the person's face, and/or side portion of the person's forehead; (c) a rear loop, wherein this rear loop is configured to span (on the first side of the person's head) from the forehead loop to the rear of the person's head; (d) at least one EEG sensor which is held in proximity to the person's head by the posterior-ear segment, the forehead loop, and/or the rear loop; (e) a data processor which receives data from the at least one EEG sensor; (f) a data transmitter; and (g) a power source which powers the at least one EEG sensor, the data processor, and/or the data transmitter.

With respect to specific components, FIG. 26 shows a right-side head view of a wearable device for measuring electromagnetic brain activity comprising: posterior-ear segment 2601 (worn on the rear-facing surface of a person's ear); forehead loop 2602 (spanning from the person's ear to a side portion of the person's forehead); rear loop 2603 (spanning from the forehead loop to the rear of the person's head); electromagnetic energy sensors (such as EEG sensors) 2604, 2605, and 2606; data processor 2608; data transmitter 2607; and power source 2609. In an example, this device can be symmetric with respect to the right and left sides of the person's head. In an example, this device can further comprise a posterior-ear segment, a forehead loop, and a rear loop in a symmetric configuration on the opposite side of the person's head (not shown in this figure). In an example, right and left side rear loops can connect at the rear of the person's head.

In an example, the posterior-ear segment, forehead loop, and rear loop can be resiliently-flexible. In an example, these components can gently press against the person's head when worn. In an example, these components can be made from a metal or polymer. In an example, these components can have prongs, teeth, or combs to engage with the person's hair to make the device less obvious and/or to better hold it onto the person's head. In an example, these components can be porous and/or have holes so as to be permeable to gas and/or liquid. In an example, these components can be between one quarter inch and three inches in width. In an example, these components can be part of a continuous member and/or piece of material.

As shown in FIG. 26, this device can include a posterior-ear segment which curves, loops, and/or hooks behind a person's ear. In an example, a posterior-ear segment can be configured to help hold the device on a person's head by engaging the rear surface of the outer ear. In an example, a posterior-ear segment can be configured to be worn entirely within one inch of the person's outer ear. In an example, a posterior-ear segment of this device can curve, loop, or hook around (some or all of) the rear-facing surface of the person's outer ear and/or the tissue connecting the outer ear with the rest of the head.

In an example, a posterior-ear segment of this device can be configured to receive the frame of a pair of eyeglasses so that this device can be worn in combination with eyeglasses. In an example, a posterior-ear segment of this device can further comprise an opening which is configured to receive the side-piece of the frame of a pair of eyeglasses so that this device can be worn in combination with eyeglasses. In an example, a posterior-ear segment of this device can further comprise a clip or other attachment mechanism to which the side-piece of the frame of a pair of eyeglasses can be attached so that this device can be worn in combination with eyeglasses. In an example, a posterior-ear segment of this device can further comprise an indentation, groove, or track into (or against) which the side-piece of the frame of a pair of eyeglasses can be placed so that this device can be worn in combination with eyeglasses.

In an example, a posterior-ear segment can curve, loop, or hook around a portion of the person's ear clockwise between the 6 o'clock (180 degree) and 12 o'clock (0 degree) vectors. In an example, a posterior-ear segment can curve, loop, or hook around a portion of the person's ear clockwise between the 9 o'clock (270 degree) and 12 o'clock (0 degree) vectors. In an example, a posterior-ear segment can curve, loop, or hook around a portion of the person's ear clockwise between the 10 o'clock (300 degree) and 12 o'clock (0 degree) vectors.

In an example, a posterior-ear segment can be configured to help hold the device on a person's head by resting on top of the outer ear (or the tissue connection between the outer ear and the rest of the person's head). In an example, a posterior-ear segment can rest on the top of a person's outer ear and/or the tissue connecting the outer ear with the rest of the head and project in a rearward and downward manner within the directional quadrants relative to the ear canal clockwise between the 6 o'clock (180 degree) and 12 o'clock (0 degree) vectors. In an example, a posterior-ear segment can rest on the top of the person's outer ear and/or the tissue connecting the outer ear with the rest of the head and project in a rearward and downward manner within the directional quadrant relative to the ear canal clockwise between the 9 o'clock (270 degree) and 12 o'clock (0 degree) vectors.

As shown in FIG. 26, this device can include a forehead loop which spans from a person's ear to a side portion of their face and/or forehead. A forehead loop of this device can be directly connected to a posterior-ear segment of this device. In an example, forehead loop and posterior-ear segment components can both be part of the same continuous member and/or piece of material. In an alternative example, this device can further comprise another member between the forehead loop and posterior-ear segment components which connects them together.

In an example, a forehead loop of this device can be configured to receive the frame of a pair of eyeglasses so that this device can be worn in combination with eyeglasses. In an example, a forehead loop of this device can further comprise an opening which is configured to receive the side-piece of the frame of a pair of eyeglasses so that this device can be worn in combination with eyeglasses. In an example, a forehead loop of this device can further comprise a clip or other attachment mechanism to which the side-piece of the frame of a pair of eyeglasses can be attached so that this device can be worn in combination with eyeglasses. In an example, a forehead loop of this device can further comprise an indentation, groove, or track into (or against) which the side-piece of the frame of a pair of eyeglasses can be placed so that this device can be worn in combination with eyeglasses.

In an example, a forehead loop can span, protrude, curve, or loop from the person's ear to the person's temple on the first side of the person's head. In an example, a forehead loop can span, protrude, curve, or loop from the person's ear to a side portion of the person's face. In an example, a forehead loop can span, protrude, curve, or loop from the person's ear to a side portion of the person's forehead.

In an example, a forehead loop can protrude, project, arc, and/or undulate forward from a person's ear along a vector which is substantially parallel to a vector which is clockwise between the 3 o'clock (90 degree) and 5 o'clock (150 degree) vectors shown in FIG. 17. In the example shown in FIG. 26, the forehead loop projects forward from a person's ear along vector which is substantially parallel to the 4 o'clock (120 degree) vector and then loops upward onto the side of the person's face and/or forehead. In an example, the forehead loop can project forward from the ear along a vector which is substantially parallel to the 5 o'clock (150 degree) vector and then loop upward onto the side of the person's face and/or forehead.

In an example, a forehead loop can be at least two inches long. In an example, a forehead loop can be at least four inches long. In an example, a forehead loop can span, protrude, curve, undulate, and/or loop from the person's ear to a position which is at least two inches from a person's ear toward the person's temple. In an example, a forehead loop can span, protrude, curve, or loop from the person's ear to a position which is at least two inches toward the person's eye. In an example, a forehead loop can span, protrude, curve, undulate, and/or loop from the person's ear to a position at least two inches toward the center of person's forehead.

In an example, a forehead loop can span, protrude, curve, undulate, and/or loop from the person's ear to a position which is between one quarter and three-quarters of the way toward the person's temple on the first side of the head. In an example, a forehead loop of this device can span, protrude, curve, or loop from the person's ear to a position which is between one quarter and three-quarters of the way toward the person's eye on the first side of the head. In an example, a forehead loop of this device can span, protrude, curve, undulate, and/or loop from the person's ear to a position which is between one quarter and three-quarters of the way toward the center of the person's forehead.

In an example, a forehead loop of this device can be arcuate, wavy, and/or undulating. In an example, the forehead loop can be an arc, wave, or undulation with a rear-facing concavity and a forward-facing peak. In an example, a forehead loop of this device can have a shape selected from the group consisting of: arc, wave, undulation, semi-circle, semi-oval, half-sinusoidal curve, bell-shaped curve, and conic section. In an example, a forehead loop can have a concavity whose opening faces rearward. In an example, a forehead loop can have a concavity whose opening faces along a vector which is parallel to a vector which is clockwise between the 7 o'clock (210 degree) and 11 o'clock (330 degree) vectors. In an example, a forehead loop can have a concavity with a peak which faces frontward. In an example, the most-forward point of a forehead loop can be located on a person's temple. In an example, the most-forward point of a forehead loop can be located on the side of a person's forehead.

In an example, a forehead loop of this device can have a lower portion which is above the bottom of the outer ear by a first distance and an upper portion which is above the bottom of the outer ear by a second distance, wherein the second distance is greater than the first distance. In an example, the second distance can be at least one inch greater than the first distance. In an example, the lower and upper portions of the forehead loop can be vertically aligned. In an example, a forehead loop can have a lower portion which rests on the outer ear and an upper portion which is vertically above the outer ear.

In an example, a forehead loop of this device can have an upper portion which is located in the directional quadrant clockwise between the 11 o'clock (330 degree) and 3 o'clock (90 degree) vectors. In an example, a forehead loop of this device can have an upper portion which is clockwise between the 12 o'clock (0 degree) and 3 o'clock (90 degree) vectors. In an example, a forehead loop of this device can span (in an arcuate and/or undulating manner) downward and forward from a person's ear to a location on the side of a person's forehead, then span (in an arcuate and/or undulating manner) upward, and then span (in an arcuate and/or undulating manner) upward and rearward to a location above the ear on the side of the head. In an example, a forehead loop can further comprise two portions (or sub-segments) which are substantially parallel to each other, one higher and one lower, and connected by a frontal loop.

In an example, this device can have a rear loop which spans from a forehead loop to the rear of the person's head. As shown in FIG. 26, a rear loop of this device can span from the upper portion of a forehead loop to the rear of the person's head. In an example, a rear loop of this device on the first side of the person's head can connect with the rear loop of this device on the second (opposite) side of the person's head. In an example, the rear and forehead loops of this device can be part of the same continuous member and/or piece of material. In an example, this device can further comprise another member which connects the rear and forehead loops.

In an example, the rear loop of this device can span the rear of a person's head within two inches of a horizontal line rearward from the top of the ear. In an example, the rear loop of this device can span the rear of a person's head within four inches of a horizontal line rearward from the top of the ear. In an example, the rear loop of this device can span the rear of a person's head less than two inches above a horizontal line rearward from the top of the ear. In an example, the rear loop of this device can span the rear of a person's head less than four inches above a horizontal line rearward from the top of the ear. In an example, the rear loop of this device can span the rear of a person's head less than two inches below a horizontal line rearward from the top of the ear. In an example, the rear loop of this device can span the rear of a person's head less than four inches below a horizontal line rearward from the top of the ear. In an example, a rear loop can further comprise prongs, teeth, or combs which engage the person's hair in order to make the rear loop less obvious or in order to better hold the device onto the person's head.

Other components (including the at least one electromagnetic energy sensor, data processor, data transmitter, and power source) can have the same features and variations as the corresponding components discussed in other figures of this disclosure. Also, relevant portions of the narratives which accompany other figures in this disclosure can also be applied to this example, but are not repeated here.

FIG. 27 shows another example of how this invention can be embodied in a wearable device for measuring electromagnetic brain activity comprising: (a) a forehead loop, wherein this forehead loop is configured to span (on a first side of the person's head) from a person's ear to the person's temple, side portion of the person's face, and/or side portion of the person's forehead; (b) a lower-rear segment, wherein this lower-rear segment is configured to span (on the first side of the person's head) from the forehead loop to the rear of the person's head at a first height; (c) an upper-rear segment, wherein this upper-rear segment is configured to span (on the first side of the person's head) from the forehead loop to the rear of the person's head at a second height, wherein the second height is greater than the first height; (d) at least one electromagnetic energy sensor which is held in proximity to the person's head by the forehead loop, the lower-rear segment, and/or the upper-rear segment, wherein the at least one electromagnetic energy sensor collects data concerning electromagnetic brain activity; (e) a data processor which receives data from the at least one electromagnetic energy sensor; (f) a data transmitter; and (g) a power source which powers the at least one electromagnetic energy sensor, the data processor, and/or the data transmitter.

FIG. 27 also shows another example of how this invention can be embodied in an undulating mobile EEG monitor comprising: (a) a forehead loop, wherein this forehead loop is configured to span (on a first side of the person's head) from a person's ear to the person's temple, side portion of the person's face, and/or side portion of the person's forehead; (b) a lower-rear segment, wherein this lower-rear segment is configured to span (on the first side of the person's head) from the forehead loop to the rear of the person's head at a first height; (c) an upper-rear segment, wherein this upper-rear segment is configured to span (on the first side of the person's head) from the forehead loop to the rear of the person's head at a second height, wherein the second height is greater than the first height; (d) at least one EEG sensor which is held in proximity to the person's head by the forehead loop, the lower-rear segment, and/or the upper-rear segment, wherein the at least one electromagnetic energy sensor collects data concerning electromagnetic brain activity; (e) a data processor which receives data from the at least one electromagnetic energy sensor; (f) a data transmitter; and (g) a power source which powers the at least one EEG sensor, the data processor, and/or the data transmitter.

With respect to specific components, FIG. 27 shows a right-side head view of a wearable device for measuring electromagnetic brain activity comprising; forehead loop 2702 (spanning from the person's ear to a side portion of the person's forehead); lower-rear segment 2701 (spanning from the forehead loop to the rear of the person's head); upper-rear segment 2703 (spanning from the forehead loop to the rear of the person's head, above the lower-rear segment); electromagnetic energy sensors (such as EEG sensors) 2704, 2705, and 2706; data processor 2708; data transmitter 2707; and power source 2709. In an example, this device can be symmetric with respect to the right and left sides of the person's head. In an example, this device can further comprise a forehead loop, a lower-rear segment, and an upper-rear segment in a symmetric configuration on the opposite side of the person's head (not shown in this figure). In an example, the right side and left side rear segments can connect with each other at the rear of the person's head.

In an example, the forehead loop, lower-rear segment, and upper-rear segment can be resiliently-flexible. In an example, these three components can gently press against the person's head when worn. In an example, these three components can be made from a metal or polymer. In an example, these three components can have prongs, teeth, or combs to engage with the person's hair to make the device less obvious and/or to better hold it onto the person's head. In an example, these three components can be porous and/or have holes so as to be permeable to gas and/or liquid. In an example, these three components can be between one quarter inch and three inches in width. In an example, these three components can be part of a continuous member and/or piece of material.

As shown in FIG. 27, this device can include a forehead loop which spans from a person's ear to a side portion of their face and/or forehead. In an example, a forehead loop can be directly connected to lower-rear and upper-rear segments. In an example, forehead loop and rear segment components can both be part of the same continuous member and/or piece of material. In an alternative example, this device can further comprise another member between the forehead loop and the lower-rear segment and/or upper-read segment which connects them together.

In an example, a forehead loop can be configured to receive the frame of a pair of eyeglasses so that this device can be worn in combination with eyeglasses. In an example, a forehead loop can further comprise an opening which is configured to receive the side-piece of the frame of a pair of eyeglasses so that this device can be worn in combination with eyeglasses. In an example, a forehead loop can further comprise a clip or other attachment mechanism to which the side-piece of the frame of a pair of eyeglasses can be attached so that this device can be worn in combination with eyeglasses. In an example, a forehead loop can further comprise an indentation, groove, or track into (or against) which the side-piece of the frame of a pair of eyeglasses can be placed so that this device can be worn in combination with eyeglasses.

In an example, a forehead loop can span, protrude, curve, or segment from the person's ear to the person's temple on the first side of the person's head. In an example, a forehead loop can span, protrude, curve, or segment from the person's ear to a side portion of the person's face. In an example, a forehead loop can span, protrude, curve, or segment from the person's ear to a side portion of the person's forehead.

In an example, a forehead loop can protrude, project, arc, and/or undulate forward from a person's ear along a vector which is substantially parallel to a vector which is clockwise between the 12 o'clock (0 degree) and 5 o'clock (150 degree) vectors shown in FIG. 17. In the example shown in FIG. 27, the forehead loop projects forward from a person's ear along vector which is substantially parallel to the 4 o'clock (120 degree) vector and then loops upward onto the side of the person's face and/or forehead.

In an example, a forehead loop can be at least two inches long. In an example, a forehead loop can be at least four inches long. In an example, a forehead loop can span, protrude, curve, undulate, and/or segment from the person's ear to a position which is at least two inches from a person's ear toward the person's temple. In an example, a forehead loop can span, protrude, curve, or segment from the person's ear to a position which is at least two inches toward the person's eye. In an example, a forehead loop can span, protrude, curve, undulate, and/or segment from the person's ear to a position at least two inches toward the center of person's forehead.

In an example, a forehead loop can span, protrude, curve, undulate, and/or segment from the person's ear to a position which is between one quarter and three-quarters of the way toward the person's temple on the first side of the head. In an example, a forehead loop can span, protrude, curve, or segment from the person's ear to a position which is between one quarter and three-quarters of the way toward the person's eye on the first side of the head. In an example, a forehead loop can span, protrude, curve, undulate, and/or segment from the person's ear to a position which is between one quarter and three-quarters of the way toward the center of the person's forehead.

In an example, a forehead loop can be arcuate, wavy, and/or undulating. In an example, the forehead loop can be an arc, wave, or undulation with a rear-facing concavity and a forward-facing peak. In an example, a forehead loop can have a shape selected from the group consisting of: arc, wave, undulation, semi-circle, semi-oval, half-sinusoidal curve, bell-shaped curve, and conic section. In an example, a forehead loop can have a concavity whose opening faces rearward. In an example, a forehead loop can have a concavity whose opening faces along a vector which is parallel to a vector which is clockwise between the 7 o'clock (210 degree) and 11 o'clock (330 degree) vectors. In an example, a forehead loop can have a concavity with a peak which faces frontward. In an example, the most-forward point of a forehead loop can be located on a person's temple. In an example, the most-forward point of a forehead loop can be located on the side of a person's forehead.

In an example, a forehead loop can have a lower portion which rests on the outer ear. In an example, a forehead loop can have an upper portion which is located in the directional quadrant clockwise between the 11 o'clock (330 degree) and 3 o'clock (90 degree) vectors. In an example, a forehead loop can have an upper portion which is clockwise between the 12 o'clock (0 degree) and 3 o'clock (90 degree) vectors. In an example, a forehead loop can span (in an arcuate and/or undulating manner) downward and forward from a person's ear to a location on the side of a person's forehead, then span (in an arcuate and/or undulating manner) upward, and then span (in an arcuate and/or undulating manner) upward and upper-rearward to a location above the ear on the side of the head.

As shown in FIG. 27, this device can include a lower-rear segment and an upper-rear segment. In an example, both the lower-rear and upper-rear segments can connect to the forehead loop and then span rearward to the rear of the person's head where they connect to (symmetric) rear segments from the other side of the person's head. In an example, a lower-rear segment and/or upper-rear segment can be directly attached to a forehead loop. In an example, a lower-rear segment and/or upper-rear segment can be part of the same continuous member or piece of material as a forehead loop. In an example, this device can further comprise another member which connects the lower-rear segment and/or upper-rear segment to the forehead loop.

In an example, lower-rear and upper-rear segments can be arcs, loops, or semi-circles which partially encircle the person's head. In an example, at least a portion of the lower-rear segment and at least a portion of the upper-rear segment can be substantially parallel to each other. In an example, lower-rear and upper-rear segments can be arcs, loops, or semi-circles which partially encircle the person's head in a lateral manner. In an example, the lower-rear segment and/or upper-rear segment can be substantially horizontal. In an example, a portion of the lower-rear segment can rest on top of the person's outer ear (and/or the tissue connecting the outer ear to the rest of the person's head).

In an example, a lower-rear or upper-rear segment of this device can be configured to receive the frame of a pair of eyeglasses so that this device can be worn in combination with eyeglasses. In an example, a lower-rear or upper-rear segment of this device can further comprise an opening which is configured to receive the side-piece of the frame of a pair of eyeglasses so that this device can be worn in combination with eyeglasses. In an example, a lower-rear or upper-rear segment of this device can further comprise a clip or other attachment mechanism to which the side-piece of the frame of a pair of eyeglasses can be attached so that this device can be worn in combination with eyeglasses. In an example, a lower-rear or upper-rear segment of this device can further comprise an indentation, groove, or track into (or against) which the side-piece of the frame of a pair of eyeglasses can be placed so that this device can be worn in combination with eyeglasses.

Other components (including the at least one electromagnetic energy sensor, data processor, data transmitter, and power source) can have the same features and variations as the corresponding components discussed in other figures of this disclosure. Also, relevant portions of the narratives which accompany other figures in this disclosure can also be applied to this example, but are not repeated here.

FIG. 28 shows another example of how this invention can be embodied in a wearable device for measuring electromagnetic brain activity comprising: (a) a posterior-ear segment, wherein this posterior-ear segment is configured to be worn on the rear-facing surface of a person's ear on a first side of the person's head, wherein this first side is the right side or the left side; (b) a frontal-ear segment, wherein this frontal-ear segment is configured to be worn on the front-facing surface of the person's ear on the first side of the person's head; (c) a forehead segment, wherein this forehead segment is configured to span (on the first side of the person's head) from the person's ear to the person's temple, side portion of the person's face, and/or side portion of the person's forehead; (d) a rear segment, wherein this rear segment is configured to span (on the first side of the person's head) from the posterior-ear segment or the forehead segment to the rear of the person's head; (e) at least one electromagnetic energy sensor which is held in proximity to the person's head by the posterior-ear segment, the forehead segment, and/or the rear segment, wherein the at least one electromagnetic energy sensor collects data concerning electromagnetic brain activity; (f) a data processor which receives data from the at least one electromagnetic energy sensor; (g) a data transmitter; and (h) a power source which powers the at least one electromagnetic energy sensor, the data processor, and/or the data transmitter.

FIG. 28 also shows an example of how this invention can be embodied in an undulating mobile EEG monitor comprising: (a) a posterior-ear segment, wherein this posterior-ear segment is configured to be worn on the rear-facing surface of a person's ear on a first side of the person's head, wherein this first side is the right side or the left side; (b) a frontal-ear segment, wherein this frontal-ear segment is configured to be worn on the front-facing surface of the person's ear on the first side of the person's head; (c) a forehead segment, wherein this forehead segment is configured to span (on the first side of the person's head) from the person's ear to the person's temple, side portion of the person's face, and/or side portion of the person's forehead; (d) a rear segment, wherein this rear segment is configured to span (on the first side of the person's head) from the posterior-ear segment or the forehead segment to the rear of the person's head; (e) at least one EEG sensor which is held in proximity to the person's head by the posterior-ear segment, the forehead segment, and/or the rear segment; (f) a data processor which receives data from the at least one EEG sensor; (g) a data transmitter; and (h) a power source which powers the at least one EEG sensor, the data processor, and/or the data transmitter.

With respect to specific components, FIG. 28 shows a right-side head view of a wearable device for measuring electromagnetic brain activity comprising: posterior-ear segment 2801 (worn on the rear-facing surface of a person's ear); frontal-ear segment 2802 (worn on the front-facing surface of the person's ear); forehead segment 2803 (spanning from the person's ear to a side portion of the person's forehead); rear segment 2804 (spanning from the posterior-ear segment or the forehead segment to the rear of the person's head); electromagnetic energy sensors (such as EEG sensors) 2805, 2806, and 2807; data processor 2809; data transmitter 2808; and power source 2810. In an example, this device can be symmetric with respect to the right and left sides of the person's head. In an example, this device can further comprise segments in a symmetric configuration on the opposite side of the person's head (not shown in this figure). In an example, right and left side rear segments can connect at the rear of the person's head.

In an example, the posterior-ear segment, frontal-ear segment, forehead segment, and rear segment can be resiliently-flexible. In an example, these segments can gently press against the person's head when worn. In an example, these segments can be made from a metal or polymer. In an example, these segments can have prongs, teeth, or combs to engage with the person's hair to make the device less obvious and/or to better hold it onto the person's head. In an example, these segments can be porous and/or have holes so as to be permeable to gas and/or liquid. In an example, these segments can be between one quarter inch and three inches in width. In an example, these segments can be part of a continuous member and/or piece of material.

As shown in FIG. 28, this device can include a posterior-ear segment which curves, loops, and/or hooks behind a person's ear. In an example, a posterior-ear segment can be configured to help hold the device on a person's head by engaging the rear surface of the outer ear. In an example, a posterior-ear segment can be configured to be worn entirely within one inch of the person's outer ear. In an example, a posterior-ear segment of this device can curve, loop, or hook around (some or all of) the rear-facing surface of the person's outer ear and/or the tissue connecting the outer ear with the rest of the head.

In an example, a posterior-ear segment of this device can be configured to receive the frame of a pair of eyeglasses so that this device can be worn in combination with eyeglasses. In an example, a posterior-ear segment of this device can further comprise an opening which is configured to receive the side-piece of the frame of a pair of eyeglasses so that this device can be worn in combination with eyeglasses. In an example, a posterior-ear segment of this device can further comprise a clip or other attachment mechanism to which the side-piece of the frame of a pair of eyeglasses can be attached so that this device can be worn in combination with eyeglasses. In an example, a posterior-ear segment of this device can further comprise an indentation, groove, or track into (or against) which the side-piece of the frame of a pair of eyeglasses can be placed so that this device can be worn in combination with eyeglasses.

In an example, a posterior-ear segment can curve, loop, or hook around a portion of the person's ear clockwise between the 6 o'clock (180 degree) and 12 o'clock (0 degree) vectors. In an example, a posterior-ear segment can curve, loop, or hook around a portion of the person's ear clockwise between the 9 o'clock (270 degree) and 12 o'clock (0 degree) vectors. In an example, a posterior-ear segment can curve, loop, or hook around a portion of the person's ear clockwise between the 10 o'clock (300 degree) and 12 o'clock (0 degree) vectors.

In an example, a posterior-ear segment can be configured to help hold the device on a person's head by resting on top of the outer ear (or the tissue connection between the outer ear and the rest of the person's head). In an example, a posterior-ear segment can rest on the top of a person's outer ear and/or the tissue connecting the outer ear with the rest of the head and project in a rearward and downward manner within the directional quadrants relative to the ear canal clockwise between the 6 o'clock (180 degree) and 12 o'clock (0 degree) vectors. In an example, a posterior-ear segment can rest on the top of the person's outer ear and/or the tissue connecting the outer ear with the rest of the head and project in a rearward and downward manner within the directional quadrant relative to the ear canal clockwise between the 9 o'clock (270 degree) and 12 o'clock (0 degree) vectors.

The example shown in FIG. 28 includes a frontal-ear segment that is configured to be worn on the front-facing surface of the person's ear. In an example, a frontal-ear segment can be directly connected to a rear segment and/or forehead segment. In an example, these segments can all be part of the same continuous member and/or piece of material. In an alternative example, this device can further comprise another member which connects these segments together.

In an example, a frontal-ear segment can have a shape which is selected from the group consisting of: portion of a circle; portion of a spiral; portion of a parabolic curve; portion of a sinusoidal curve; and conic section. In an example, a frontal-ear segment can gently press against or otherwise engage the outer surface of a person's ear in order to help hold the device on the person's head. In an example, a frontal-ear segment can gently protrude into a portion of the person's ear canal in order in order to help hold the device on the person's head. In an example, a frontal-ear segment can further comprise a speaker. In an example, a frontal-ear segment can hold a speaker close to the ear canal opening for discreet audio communication. In an example, a frontal-ear segment can be resiliently-flexible. In an example, a frontal-ear segment can be made from a metal or polymer. In an example, a frontal-ear segment can be porous and/or have holes so as to be permeable to gas and/or liquid. In an example, a frontal-ear segment can have a width between one-eighth inch and one inch.

In an example, a frontal-ear segment can curve, loop, protrude, undulate, and/or hook around the front of a person's ear. In an example, a frontal-ear segment can be configured to help hold the device on a person's head by engaging the frontal surface of the outer ear. In an example, a frontal-ear segment can be configured to be worn entirely within two inches of the person's outer ear. In an example, a frontal-ear segment can curve, loop, protrude, undulate, and/or hook around (some or all of) the front-facing surface of the person's outer ear. In an example, a frontal-ear segment can curve, loop, protrude, undulate, and/or hook around (some or all of) the frontal portion of tissue which connects the outer ear with the rest of the head. In an example, a frontal-ear segment can be configured to curve, loop, protrude, undulate, and/or hook around a side portion of the person's face which is within one inch of the person's ear.

In an example, a frontal-ear segment can be configured to receive the frame of a pair of eyeglasses so that this device can be worn in combination with eyeglasses. In an example, a frontal-ear segment can further comprise an opening which is configured to receive the side-piece of the frame of a pair of eyeglasses so that this device can be worn in combination with eyeglasses. In an example, a frontal-ear segment can further comprise a clip or other attachment mechanism to which the side-piece of the frame of a pair of eyeglasses can be attached so that this device can be worn in combination with eyeglasses. In an example, a frontal-ear segment can further comprise an indentation, groove, or track into (or against) which the side-piece of the frame of a pair of eyeglasses can be placed so that this device can be worn in combination with eyeglasses.

In an example, a frontal-ear segment can curve, loop, protrude, undulate, and/or hook around a portion of the person's ear clockwise between the 12 o'clock (0 degree) and 6 o'clock (180 degree) vectors. In an example, a frontal-ear segment can curve, loop, protrude, undulate, and/or hook around a portion of the person's ear clockwise between the 12 o'clock (0 degree) and 3 o'clock (90 degree) vectors. In an example, a frontal-ear segment can curve, loop, protrude, undulate, and/or hook around a portion of the person's ear clockwise between the 12 o'clock (0 degree) and 2 o'clock (60 degree) vectors.

In an example, a frontal-ear segment can be configured to help hold the device on a person's head by resting on top of the outer ear (or the tissue connection between the outer ear and the rest of the person's head). In an example, a frontal-ear segment can rest on the top of a person's outer ear and/or the tissue connecting the outer ear with the rest of the head and project in a frontward and downward manner within the directional quadrants relative to the ear canal clockwise between the 12 o'clock (0 degree) and 6 o'clock (180 degree) vectors. In an example, a frontal-ear segment can rest on the top of the person's outer ear and/or the tissue connecting the outer ear with the rest of the head and project in a frontward and downward manner within the directional quadrant relative to the ear canal clockwise between the 12 o'clock (0 degree) and 3 o'clock (90 degree) vectors.

As shown in FIG. 28, this device can include a forehead segment which spans from a person's ear to a side portion of their face and/or forehead. A forehead segment can be directly connected to a posterior-ear and/or frontal-ear segment. In an example, forehead segment and posterior-ear and/or frontal-ear segments can all be part of the same continuous member and/or piece of material. In an alternative example, this device can further comprise another member between the forehead segment and posterior-ear and/or frontal-ear segments which connects them together.

In an example, a forehead segment can be configured to receive the frame of a pair of eyeglasses so that this device can be worn in combination with eyeglasses. In an example, a forehead segment can further comprise an opening which is configured to receive the side-piece of the frame of a pair of eyeglasses so that this device can be worn in combination with eyeglasses. In an example, a forehead segment can further comprise a clip or other attachment mechanism to which the side-piece of the frame of a pair of eyeglasses can be attached so that this device can be worn in combination with eyeglasses. In an example, a forehead segment can further comprise an indentation, groove, or track into (or against) which the side-piece of the frame of a pair of eyeglasses can be placed so that this device can be worn in combination with eyeglasses.

In an example, a forehead segment can be shaped like a hockey stick and/or the letter "J". In an example, a forehead segment can span, protrude, extend, or curve from the person's ear to the person's temple on the first side of the person's head. In an example, a forehead segment can span, protrude, extend, or curve from the person's ear to a side portion of the person's face. In an example, a forehead segment can span, protrude, extend, or curve from a person's ear to a side portion of the person's forehead. In an example, a forehead segment can span, protrude, extend, or curve forward from a person's ear along a vector which is substantially parallel to a vector which is clockwise between the 1 o'clock (30 degree) and 4 o'clock (120 degree) vectors shown in FIG. 17. In the example shown in FIG. 28, the forehead segment projects forward from a person's ear along vector which is substantially parallel to the 2 o'clock (60 degree) vector and then curves upward onto the side of the person's face and/or forehead.

In an example, a forehead segment can be at least two inches long. In an example, a forehead segment can be at least four inches long. In an example, a forehead segment can span, protrude, extend, or curve from the person's ear to a position which is at least two inches from a person's ear toward the person's temple. In an example, a forehead segment can span, protrude, extend, or curve from the person's ear to a position which is at least two inches toward the person's eye. In an example, a forehead segment can span, protrude, extend, or curve from the person's ear to a position at least two inches toward the center of person's forehead.

In an example, a forehead segment can span, protrude, extend, or curve from the person's ear to a position which is between one quarter and three-quarters of the way toward the person's temple on the first side of the head. In an example, a forehead segment can span, protrude, extend, or curve from the person's ear to a position which is between one quarter and three-quarters of the way toward the person's eye on the first side of the head. In an example, a forehead segment can span, protrude, extend, or curve from the person's ear to a position which is between one quarter and three-quarters of the way toward the center of the person's forehead.

In an example, this device can have a rear segment which spans from a posterior-ear or forehead segment to the rear of the person's head. In an example, a rear segment on the first side of the person's head can connect with the rear segment on the second (opposite) side of the person's head. In an example, these segments can all be part of the same continuous member and/or piece of material. In an example, this device can further comprise other members which connect these segments together.

In an example, a rear segment can span a rear of a person's head within two inches of a horizontal line rearward from the top of the ear. In an example, a rear segment can span a rear of a person's head within four inches of a horizontal line rearward from the top of the ear. In an example, a rear segment can span a rear of a person's head less than two inches above a horizontal line rearward from the top of the ear. In an example, a rear segment can span a rear of a person's head less than four inches above a horizontal line rearward from the top of the ear. In an example, a rear segment can span a rear of a person's head less than two inches below a horizontal line rearward from the top of the ear. In an example, a rear segment can span a rear of a person's head less than four inches below a horizontal line rearward from the top of the ear. In an example, a rear segment can further comprise prongs, teeth, or combs which engage the person's hair in order to make a rear segment less obvious or in order to better hold the device onto the person's head.

Other components (including the at least one electromagnetic energy sensor, data processor, data transmitter, and power source) can have the same features and variations as the corresponding components discussed in other figures of this disclosure. Also, relevant portions of the narratives which accompany other figures in this disclosure can also be applied to this example, but are not repeated here.

FIG. 29 shows another example of how this invention can be embodied in a wearable device for measuring electromagnetic brain activity comprising: (a) a vertical segment, wherein the vertical segment is configured to span from a person's ear to the top of the person's head, wherein the vertical segment is arcuate with a concave portion which opens toward the rear of the person's head; (b) a lateral segment, wherein the lateral segment is configured to span from the person's forehead to the rear of the person's head, and wherein the lateral segment intersects the vertical segment at the concave portion of the vertical segment; (c) at least one electromagnetic energy sensor which is held in proximity to the person's head by the vertical segment and/or the lateral segment, wherein the at least one electromagnetic energy sensor collects data concerning electromagnetic brain activity; (d) a data processor which receives data from the at least one electromagnetic energy sensor; (e) a data transmitter; and (f) a power source which powers the at least one electromagnetic energy sensor, the data processor, and/or the data transmitter.

FIG. 29 also shows an example of how this invention can be embodied in an undulating mobile EEG monitor comprising: (a) a vertical segment, wherein the vertical segment is configured to span from a person's ear to the top of the person's head, wherein the vertical segment is arcuate with a concave portion which opens toward the rear of the person's head; (b) a lateral segment, wherein the lateral segment is configured to span from the person's forehead to the rear of the person's head, and wherein the lateral segment intersects the vertical segment at the concave portion of the vertical segment; (c) at least one EEG sensor which is held in proximity to the person's head by the vertical segment and/or the lateral segment, wherein the at least one EEG sensor collects data concerning electromagnetic brain activity; (d) a data processor which receives data from the at least one EEG sensor; (e) a data transmitter; and (f) a power source which powers the at least one EEG sensor, the data processor, and/or the data transmitter.

With respect to specific components, FIG. 29 shows a right-side head view of a wearable device for measuring electromagnetic brain activity comprising: an arcuate vertical segment (further comprising sub-segments 2901, 2902, and 2903) which spans from a person's ear to the top of the person's head; a lateral segment (further comprising sub-segments 2904 and 2905) which spans from the person's forehead to the rear of the person's head and intersects a concave portion of the arcuate vertical segment; electromagnetic energy sensors (such as EEG sensors) 2906, 2907, 2908, 2909, and 2910; data processor 2912; data transmitter 2911; and power source 2913. In an example, this device can be symmetric with respect to the right and left sides of the person's head. In an example, this device can further comprise segments in a symmetric configuration on the opposite side of the person's head (not shown in this figure). In an example, right and left side top segments can connect at the top of the person's head.

In an example, vertical and lateral segments can be resiliently-flexible. In an example, these segments can gently press against the person's head when worn. In an example, these segments can be made from a metal or polymer. In an example, these segments can have prongs, teeth, or combs to engage with the person's hair to make the device less obvious and/or to better hold it onto the person's head. In an example, these segments can be porous and/or have holes so as to be permeable to gas and/or liquid. In an example, these segments can be between one quarter inch and three inches in width. In an example, these segments can be part of a continuous member and/or piece of material.

In an example, a bottom portion of a vertical segment can curve, loop, and/or hook behind a person's ear. In an example, a bottom portion of a vertical segment can be configured to help hold the device on a person's head by engaging the rear surface of the outer ear. In an example, a bottom portion of a vertical segment can be configured to be worn entirely within one inch of the person's outer ear. In an example, a bottom portion of a vertical segment can curve, loop, or hook around (some or all of) the rear-facing surface of the person's outer ear and/or the tissue connecting the outer ear with the rest of the head.

In an example, a vertical segment and/or lateral segment can be configured to receive the frame of a pair of eyeglasses so that this device can be worn in combination with eyeglasses. In an example, a vertical segment and/or lateral segment can further comprise an opening which is configured to receive the side-piece of the frame of a pair of eyeglasses so that this device can be worn in combination with eyeglasses. In an example, a vertical segment and/or lateral segment can further comprise a clip or other attachment mechanism to which the side-piece of the frame of a pair of eyeglasses can be attached so that this device can be worn in combination with eyeglasses. In an example, a vertical segment and/or lateral segment can further comprise an indentation, groove, or track into (or against) which the side-piece of the frame of a pair of eyeglasses can be placed so that this device can be worn in combination with eyeglasses.

In an example, a bottom portion of a vertical segment can curve, loop, or hook around a portion of the person's ear clockwise between the 6 o'clock (180 degree) and 12 o'clock (0 degree) vectors. In an example, a bottom portion of a vertical segment can curve, loop, or hook around a portion of the person's ear clockwise between the 9 o'clock (270 degree) and 12 o'clock (0 degree) vectors. In an example, a bottom portion of a vertical segment can curve, loop, or hook around a portion of the person's ear clockwise between the 10 o'clock (300 degree) and 12 o'clock (0 degree) vectors.

In an example, the bottom portion of a vertical segment can be configured to help hold the device on a person's head by resting on top of the outer ear (or the tissue connection between the outer ear and the rest of the person's head). In an example, a bottom portion of a vertical segment can rest on the top of a person's outer ear and/or the tissue connecting the outer ear with the rest of the head and project in a rearward and downward manner within the directional quadrants relative to the ear canal clockwise between the 6 o'clock (180 degree) and 12 o'clock (0 degree) vectors. In an example, a bottom portion of a vertical segment can rest on the top of the person's outer ear and/or the tissue connecting the outer ear with the rest of the head and project in a rearward and downward manner within the directional quadrant relative to the ear canal clockwise between the 9 o'clock (270 degree) and 12 o'clock (0 degree) vectors.

In an example, a concave portion of a vertical segment can span from a person's ear to a side portion of their face and/or forehead. In an example, a concave portion of a vertical segment can be connected to a lateral segment where the two segments intersect. In an example, vertical and lateral segments can both be part of the same continuous member and/or piece of material. In an alternative example, this device can further comprise another member between the vertical and lateral segments which connects them together.

In an example, a concave portion of a vertical segment can span, protrude, curve, or loop from a person's ear to the person's temple on the first side of the person's head. In an example, the concave portion of a vertical segment can span, protrude, curve, or loop from the person's ear to a side portion of the person's face. In an example, the concave portion of a vertical segment can span, protrude, curve, or loop from the person's ear to a side portion of the person's forehead.

In an example, a concave portion of a vertical segment can protrude and/or project forward from a person's ear along a vector which is substantially parallel to a vector which is clockwise between the 12 o'clock (0 degree) and 3 o'clock (90 degree) vectors shown in FIG. 17. In the example shown in FIG. 29, the concave portion of a vertical segment projects forward from a person's ear along vector which is substantially parallel to the 2 o'clock (60 degree) vector. In an example, the concave portion of a vertical segment can project forward from the ear along a vector which is substantially parallel to the 1 o'clock (30 degree) vector. In an example, the concave portion of a vertical segment can project forward from the ear along a vector which is substantially parallel to a vector which is clockwise between the 1 o'clock (30 degree) and 2 o'clock (60 degree) vectors.

In an example, a concave portion of a vertical segment can be at least two inches long. In an example, a concave portion of a vertical segment can be at least four inches long. In an example, a concave portion of a vertical segment can span, protrude, curve, or loop from a person's ear to a position which is at least two inches from a person's ear toward the person's temple. In an example, a concave portion of a vertical segment can span, protrude, curve, or loop from the person's ear to a position which is at least two inches toward the person's eye. In an example, a concave portion of a vertical segment can span, protrude, curve, or loop from the person's ear to a position at least two inches toward the center of person's forehead.

In an example, a concave portion of a vertical segment can span, protrude, curve, or loop from the person's ear to a position which is between one quarter and three-quarters of the way toward the person's temple on the first side of the head. In an example, a concave portion of a vertical segment can span, protrude, curve, or loop from a person's ear to a position which is between one quarter and three-quarters of the way toward the person's eye on the first side of the head. In an example, a concave portion of a vertical segment can span, protrude, curve, or loop from the person's ear to a position which is between one quarter and three-quarters of the way toward the center of the person's forehead.

In an example, a vertical segment can be arcuate, wavy, undulating, and/or sinusoidal. In an example, the concave portion of a vertical segment can be an arc, wave, or undulation with a rear-facing concavity and a forward-facing peak. In an example, a concave portion of a vertical segment can have a shape selected from the group consisting of: arc, wave, undulation, semi-circle, semi-oval, loop, half-sinusoidal curve, bell-shaped curve, and conic section. In an example, a concave portion of a vertical segment can have a concavity whose opening faces along a vector which is parallel to a vector which is clockwise between the 7 o'clock (210 degree) and 11 o'clock (330 degree) vectors. In an example, a concave portion of a vertical segment can have a concavity with a peak which faces frontward. In an example, the most-forward point of a concave portion of a vertical segment can be located on a person's temple. In an example, the most-forward point of a concave portion of a vertical segment can be located on the side of a person's forehead.

In an example, a lateral segment can span from a person's forehead to the rear of the person's head. In an example, the rear portion of a lateral segment on the first side of the person's head can connect with the rear portion of a lateral segment on the second (opposite) side of the person's head at the rear of the person's head. In an example, the front portion of a lateral segment on the first side of the person's head does not connect with the front portion of a lateral segment on the second (opposite) side of the person's head on the person's forehead.

In an example, a lateral segment can span the rear of a person's head within two inches of a horizontal line rearward from the top of the ear. In an example, the lateral segment can span the rear of a person's head within four inches of a horizontal line rearward from the top of the ear. In an example, the lateral segment can span the rear of a person's head less than two inches above a horizontal line rearward from the top of the ear. In an example, the lateral segment can span the rear of a person's head less than four inches above a horizontal line rearward from the top of the ear. In an example, the lateral segment can span the rear of a person's head less than two inches below a horizontal line rearward from the top of the ear. In an example, the lateral segment can span the rear of a person's head less than four inches below a horizontal line rearward from the top of the ear. In an example, a lateral segment can further comprise prongs, teeth, or combs which engage the person's hair in order to make the lateral segment less obvious or in order to better hold the device onto the person's head.

Other components (including the at least one electromagnetic energy sensor, data processor, data transmitter, and power source) can have the same features and variations as the corresponding components discussed in other figures of this disclosure. Also, relevant portions of the narratives which accompany other figures in this disclosure can also be applied to this example, but are not repeated here.

FIG. 30 shows another example of how this invention can be embodied in a wearable device for measuring electromagnetic brain activity comprising: (a) a lateral segment, wherein the lateral segment is configured to span from the person's forehead to the rear of the person's head; (b) a vertical segment, wherein the vertical segment is configured to span from the lateral segment to the top of the person's head, wherein the vertical segment is arcuate with a concave portion which opens toward the front of the person's head; (c) at least one electromagnetic energy sensor which is held in proximity to the person's head by the lateral and/or vertical segment, wherein the at least one electromagnetic energy sensor collects data concerning electromagnetic brain activity; (d) a data processor which receives data from the at least one electromagnetic energy sensor; (e) a data transmitter; and (f) a power source which powers the at least one electromagnetic energy sensor, the data processor, and/or the data transmitter.

FIG. 30 also shows an example of how this invention can be embodied in an undulating mobile EEG monitor comprising: (a) a lateral segment, wherein the lateral segment is configured to span from the person's forehead to the rear of the person's head; (b) a vertical segment, wherein the vertical segment is configured to span from the lateral segment to the top of the person's head, wherein the vertical segment is arcuate with a concave portion which opens toward the front of the person's head; (c) at least one EEG sensor which is held in proximity to the person's head by the lateral and/or vertical segment, wherein the at least one EEG sensor collects data concerning electromagnetic brain activity; (d) a data processor which receives data from the at least one EEG sensor; (e) a data transmitter; and (f) a power source which powers the at least one EEG sensor, the data processor, and/or the data transmitter.

With respect to specific components, FIG. 30 shows a right-side head view of a wearable device for measuring electromagnetic brain activity comprising: a lateral segment (further comprising sub-segments 3003 and 3001) which spans from the person's forehead to the rear of the person's head; a vertical segment 3002 which spans from the lateral segment to the top of the person's head; electromagnetic energy sensors (such as EEG sensors) 3004, 3005, 3006, 3007, and 3008; data processor 3010; data transmitter 3009; and power source 3011. In an example, this device can be symmetric with respect to the right and left sides of the person's head. In an example, this device can further comprise a rear segment, a side segment, and a top segment in a symmetric configuration on the opposite side of the person's head (not shown in this figure). In an example, right and left side top segments can connect at the top of the person's head.

In an example, lateral and vertical segments can be resiliently-flexible. In an example, these segments can gently press against the person's head when worn. In an example, these segments can be made from a metal or polymer. In an example, these segments can have prongs, teeth, or combs to engage with the person's hair to make the device less obvious and/or to better hold it onto the person's head. In an example, these segments can be porous and/or have holes so as to be permeable to gas and/or liquid. In an example, these segments can be between one quarter inch and three inches in width. In an example, these segments can be part of a continuous member and/or piece of material.

In an example, a vertical segment can be arcuate, wavy, undulating, and/or sinusoidal. In an example, the concave portion of a vertical segment can be an arc, wave, or undulation with a rear-facing concavity and a forward-facing peak. In an example, a concave portion of a vertical segment can have a shape selected from the group consisting of: arc, wave, undulation, semi-circle, semi-oval, loop, half-sinusoidal curve, bell-shaped curve, and conic section.

In an example, a lateral segment can span from a person's forehead to the rear of the person's head. In an example, the rear portion of a lateral segment on the first side of the person's head can connect with the rear portion of a lateral segment on the second (opposite) side of the person's head at the rear of the person's head. In an example, the front portion of a lateral segment on the first side of the person's head does not connect with the front portion of a lateral segment on the second (opposite) side of the person's head on the person's forehead.

In an example, a lateral segment can span the rear of a person's head within two inches of a horizontal line rearward from the top of the ear. In an example, the lateral segment can span the rear of a person's head within four inches of a horizontal line rearward from the top of the ear. In an example, the lateral segment can span the rear of a person's head less than two inches above a horizontal line rearward from the top of the ear. In an example, the lateral segment can span the rear of a person's head less than four inches above a horizontal line rearward from the top of the ear. In an example, the lateral segment can span the rear of a person's head less than two inches below a horizontal line rearward from the top of the ear. In an example, the lateral segment can span the rear of a person's head less than four inches below a horizontal line rearward from the top of the ear. In an example, a lateral segment can further comprise prongs, teeth, or combs which engage the person's hair in order to make the lateral segment less obvious or in order to better hold the device onto the person's head.

Other components (including the at least one electromagnetic energy sensor, data processor, data transmitter, and power source) can have the same features and variations as the corresponding components discussed in other figures of this disclosure. Also, relevant portions of the narratives which accompany other figures in this disclosure can also be applied to this example, but are not repeated here.

FIG. 31 shows another example of how this invention can be embodied in a wearable device for measuring electromagnetic brain activity comprising: (a) an undulating band which is configured to span from a person's ear on a first side of the person's head to the person's ear on the second side of the person's head, wherein the portion of this undulating band on the first side of the person's head further comprises: a first segment which is configured to curve around the rear-facing portion of an ear, a second segment with a concavity which is configured to open toward the rear of the person's head, a third segment with a concavity which is configured to open toward the front of the person's head, and a fourth segment which is configured to span across the person's forehead; (b) at least one electromagnetic energy sensor which is held in proximity to the person's head by the undulating band, wherein the at least one electromagnetic energy sensor collects data concerning electromagnetic brain activity; (c) a data processor which receives data from the at least one electromagnetic energy sensor; (d) a data transmitter; and (e) a power source which powers the at least one electromagnetic energy sensor, the data processor, and/or the data transmitter.

FIG. 31 shows another example of how this invention can be embodied in an undulating mobile EEG monitor comprising: (a) an undulating band which is configured to span from a person's ear on a first side of the person's head to the person's ear on the second side of the person's head, wherein the portion of this undulating band on the first side of the person's head further comprises: a first segment which is configured to curve around the rear-facing portion of an ear, a second segment with a concavity which is configured to open toward the rear of the person's head, a third segment with a concavity which is configured to open toward the front of the person's head, and a fourth segment which is configured to span across the person's forehead; (b) at least one EEG sensor which is held in proximity to the person's head by the undulating band, wherein the at least one EEG sensor collects data concerning electromagnetic brain activity; (c) a data processor which receives data from the at least one EEG sensor; (d) a data transmitter; and (e) a power source which powers the at least one EEG sensor, the data processor, and/or the data transmitter.

With respect to specific components, FIG. 31 shows a right-side head view of a wearable device for measuring electromagnetic brain activity comprising: an undulating band which is configured to span from a person's ear on a first side of the person's head to the person's ear on the second side of the person's head, wherein the portion of this undulating band on the first side of the person's head further comprises first segment 3101 which is configured to curve around the rear-facing portion of an ear, second segment 3102 with a concavity which is configured to open toward the rear of the person's head, third segment 3103 with a concavity which is configured to open toward the front of the person's head, and fourth segment 3104 which is configured to span across the person's forehead; electromagnetic energy sensors (such as EEG sensors) 3105, 3106, 3107, and 3108; data processor 3110; data transmitter 3109; and power source 3111. In an example, this device can be symmetric with respect to the right and left sides of the person's head.

In an example, this undulating band can be resiliently-flexible. In an example, this undulating band can gently press against the person's head when worn. In an example, this undulating band can be made from a metal or polymer. In an example, this undulating band can have prongs, teeth, or combs to engage with the person's hair to make the device less obvious and/or to better hold it onto the person's head. In an example, this undulating band can be porous and/or have holes so as to be permeable to gas and/or liquid. In an example, this undulating band can be between one quarter inch and three inches in width.

In an example, an undulating band can be configured to receive the frame of a pair of eyeglasses so that this device can be worn in combination with eyeglasses. In an example, an undulating band can further comprise an opening which is configured to receive the side-piece of the frame of a pair of eyeglasses so that this device can be worn in combination with eyeglasses. In an example, an undulating band can further comprise a clip or other attachment mechanism to which the side-piece of the frame of a pair of eyeglasses can be attached so that this device can be worn in combination with eyeglasses. In an example, an undulating band can further comprise an indentation, groove, or track into (or against) which the side-piece of the frame of a pair of eyeglasses can be placed so that this device can be worn in combination with eyeglasses.

In an example, a first segment can curve, loop, and/or hook behind a person's ear. In an example, a first segment can be configured to help hold the device on a person's head by engaging the rear surface of the outer ear. In an example, a first segment can be configured to be worn entirely within one inch of the person's outer ear. In an example, a first segment can curve, loop, or hook around (some or all of) the rear-facing surface of the person's outer ear and/or the tissue connecting the outer ear with the rest of the head.

In an example, a first segment can curve, loop, or hook around a portion of the person's ear clockwise between the 6 o'clock (180 degree) and 12 o'clock (0 degree) vectors. In an example, a first segment can curve, loop, or hook around a portion of the person's ear clockwise between the 9 o'clock (270 degree) and 12 o'clock (0 degree) vectors. In an example, a first segment can curve, loop, or hook around a portion of the person's ear clockwise between the 10 o'clock (300 degree) and 12 o'clock (0 degree) vectors.

In an example, a first segment can be configured to help hold the device on a person's head by resting on top of the outer ear (or the tissue connection between the outer ear and the rest of the person's head). In an example, a first segment can rest on the top of a person's outer ear and/or the tissue connecting the outer ear with the rest of the head and project in a rearward and downward manner within the directional quadrants relative to the ear canal clockwise between the 6 o'clock (180 degree) and 12 o'clock (0 degree) vectors. In an example, a first segment can rest on the top of the person's outer ear and/or the tissue connecting the outer ear with the rest of the head and project in a rearward and downward manner within the directional quadrant relative to the ear canal clockwise between the 9 o'clock (270 degree) and 12 o'clock (0 degree) vectors.

In an example, a second segment can be directly connected to a first segment. In an example, first and second segments can both be part of the same continuous member and/or piece of material. In an alternative example, this device can further comprise another member between the first and second segments which connects them together. In an example, a second segment can span, protrude, curve, or loop from a person's ear to the person's temple on the first side of the person's head. In an example, the second segment can span, protrude, curve, or loop from a person's ear to a side portion of the person's face. In an example, the second segment can span, protrude, curve, or loop from a person's ear to a side portion of the person's forehead.

In the example shown in FIG. 31, the second segment projects forward from a person's ear along vector which is substantially parallel to the 4 o'clock (120 degree) vector. In an example, a second segment can protrude and/or project forward from a person's ear along a vector which is substantially parallel to a vector which is clockwise between the 1 o'clock (30 degree) and 5 o'clock (150 degree) vectors shown in FIG. 17.

In an example, a second segment can be at least two inches long. In an example, a second segment can be at least four inches long. In an example, a second segment can span, protrude, curve, or loop from the person's ear to a position which is at least two inches from a person's ear toward the person's temple. In an example, a second segment can span, protrude, curve, or loop from the person's ear to a position which is at least two inches toward the person's eye. In an example, a second segment can span, protrude, curve, or loop from the person's ear to a position at least two inches toward the center of person's forehead.

In an example, a second segment can be arcuate, wavy, and/or undulating. In an example, the second segment can be an arc, wave, or undulation with a rear-facing concavity and a forward-facing peak. In an example, a second segment can have a shape selected from the group consisting of: arc, wave, undulation, semi-circle, semi-oval, loop, half-sinusoidal curve, bell-shaped curve, and conic section. In an example, a second segment can have a concavity whose opening faces rearward. In an example, a second segment can have a concavity whose opening faces along a vector which is parallel to a vector which is clockwise between the 7 o'clock (210 degree) and 11 o'clock (330 degree) vectors. In an example, a second segment can have a concavity with a peak which faces frontward. In an example, the most-forward point of a second segment can be located on a person's temple.

In an example, a third segment can be directly connected to a second segment. In an example, second and third segments can both be part of the same continuous member and/or piece of material. In an alternative example, this device can further comprise another member between the second and third segments which connects them together. In an example, a third segment can be at least two inches long. In an example, a third segment can be at least four inches long.

In an example, a third segment can be arcuate, wavy, and/or undulating. In an example, the third segment can be an arc, wave, or undulation with a rear-facing concavity and a forward-facing peak. In an example, a third segment can have a shape selected from the group consisting of: arc, wave, undulation, semi-circle, semi-oval, loop, half-sinusoidal curve, bell-shaped curve, and conic section. In an example, a third segment can have a concavity whose opening faces forward. In an example, a third segment can have a concavity whose opening faces along a vector which is parallel to a vector which is clockwise between the 1 o'clock (30 degree) and 5 o'clock (150 degree) vectors. In an example, a third segment can have a concavity with a peak which faces rearward.

In an example, second and third segments can together comprise a sinusoidal wave pattern. In an example, second and third segments can together comprise an "S" shape. In an example, second and third segments can have the same size curves or waves. In an example, the third segment can have a larger size curve or wave than the second segment. In an example, second and third segments can have a combined longitudinal axis with an orientation that is parallel to a vector which is clockwise between the 12 o'clock (0 degree) and 2 o'clock (60 degree) vectors shown in FIG. 17.

In an example, a fourth segment can be directly connected to a third segment. In an example, third and fourth segments can both be part of the same continuous member and/or piece of material. In an alternative example, this device can further comprise another member between the third and fourth segments which connects them together. In an example, a fourth segment can be at least four inches long. In an example, a fourth segment can laterally span (a portion of) a person's forehead. In an example, a fourth segment on the right side of a person's head can connect to a fourth segment on the left side of the person's head.

Other components (including the at least one electromagnetic energy sensor, data processor, data transmitter, and power source) can have the same features and variations as the corresponding components discussed in other figures of this disclosure. Also, relevant portions of the narratives which accompany other figures in this disclosure can also be applied to this example, but are not repeated here.

FIG. 32 shows another example of how this invention can be embodied in a wearable device for measuring electromagnetic brain activity comprising: (a) an undulating band which is configured to span from a person's ear on a first side of the person's head to the person's ear on the second side of the person's head, wherein the portion of this undulating band on the first side of the person's head further comprises: a first segment which is configured to curve around the rear-facing portion of an ear, a second segment with is configured to curve around the front-facing portion of an ear, a third segment which is configured to extend upward from the ear along the side of the person's head, and a fourth segment which is configured to span across the person's forehead; (b) at least one electromagnetic energy sensor which is held in proximity to the person's head by the undulating band, wherein the at least one electromagnetic energy sensor collects data concerning electromagnetic brain activity; (c) a data processor which receives data from the at least one electromagnetic energy sensor; (d) a data transmitter; and (e) a power source which powers the at least one electromagnetic energy sensor, the data processor, and/or the data transmitter.

FIG. 32 shows another example of how this invention can be embodied in an undulating mobile EEG monitor comprising: (a) an undulating band which is configured to span from a person's ear on a first side of the person's head to the person's ear on the second side of the person's head, wherein the portion of this undulating band on the first side of the person's head further comprises: a first segment which is configured to curve around the rear-facing portion of an ear, a second segment with is configured to curve around the front-facing portion of an ear, a third segment which is configured to extend upward from the ear along the side of the person's head, and a fourth segment which is configured to span across the person's forehead; (b) at least one EEG sensor which is held in proximity to the person's head by the undulating band, wherein the at least one EEG sensor collects data concerning electromagnetic brain activity; (c) a data processor which receives data from the at least one EEG sensor; (d) a data transmitter; and (e) a power source which powers the at least one EEG sensor, the data processor, and/or the data transmitter.

With respect to specific components, FIG. 32 shows a right-side head view of a wearable device for measuring electromagnetic brain activity comprising: an undulating band which is configured to span from a person's ear on a first side of the person's head to the person's ear on the second side of the person's head, wherein the portion of this undulating band on the first side of the person's head further comprises first segment 3201 which is configured to curve around the rear-facing portion of an ear, second segment 3202 with is configured to curve around the front-facing portion of an ear, third segment 3203 which is configured to extend upward from the ear along the side of the person's head, fourth segment 3204 which is configured to span across the person's forehead; electromagnetic energy sensors (such as EEG sensors) 3205, 3206, and 3207; data processor 3209 data transmitter 3208; and power source 3210. In an example, this device can be symmetric with respect to the right and left sides of the person's head.

In an example, this undulating band can be resiliently-flexible. In an example, this undulating band can gently press against the person's head when worn. In an example, this undulating band can be made from a metal or polymer. In an example, this undulating band can have prongs, teeth, or combs to engage with the person's hair to make the device less obvious and/or to better hold it onto the person's head. In an example, this undulating band can be porous and/or have holes so as to be permeable to gas and/or liquid. In an example, this undulating band can be between one quarter inch and three inches in width.

In an example, an undulating band can be configured to receive the frame of a pair of eyeglasses so that this device can be worn in combination with eyeglasses. In an example, an undulating band can further comprise an opening which is configured to receive the side-piece of the frame of a pair of eyeglasses so that this device can be worn in combination with eyeglasses. In an example, an undulating band can further comprise a clip or other attachment mechanism to which the side-piece of the frame of a pair of eyeglasses can be attached so that this device can be worn in combination with eyeglasses. In an example, an undulating band can further comprise an indentation, groove, or track into (or against) which the side-piece of the frame of a pair of eyeglasses can be placed so that this device can be worn in combination with eyeglasses.

In an example, a first segment can curve, loop, and/or hook behind a person's ear. In an example, a first segment can be configured to help hold the device on a person's head by engaging the rear surface of the outer ear. In an example, a first segment can be configured to be worn entirely within one inch of the person's outer ear. In an example, a first segment can curve, loop, or hook around (some or all of) the rear-facing surface of the person's outer ear and/or the tissue connecting the outer ear with the rest of the head.

In an example, a first segment can curve, loop, or hook around a portion of the person's ear clockwise between the 6 o'clock (180 degree) and 12 o'clock (0 degree) vectors. In an example, a first segment can curve, loop, or hook around a portion of the person's ear clockwise between the 9 o'clock (270 degree) and 12 o'clock (0 degree) vectors. In an example, a first segment can curve, loop, or hook around a portion of the person's ear clockwise between the 10 o'clock (300 degree) and 12 o'clock (0 degree) vectors.

In an example, a first segment can be configured to help hold the device on a person's head by resting on top of the outer ear (or the tissue connection between the outer ear and the rest of the person's head). In an example, a first segment can rest on the top of a person's outer ear and/or the tissue connecting the outer ear with the rest of the head and project in a rearward and downward manner within the directional quadrants relative to the ear canal clockwise between the 6 o'clock (180 degree) and 12 o'clock (0 degree) vectors. In an example, a first segment can rest on the top of the person's outer ear and/or the tissue connecting the outer ear with the rest of the head and project in a rearward and downward manner within the directional quadrant relative to the ear canal clockwise between the 9 o'clock (270 degree) and 12 o'clock (0 degree) vectors.

In this example, this device can further comprise a second segment that is configured to be worn on the front-facing surface of a person's ear. In an example, a second segment can be directly connected to a first segment and/or a third segment. In an example, these segments can all be part of the same continuous member and/or piece of material. In an alternative example, this device can further comprise another member between these segments which connects them together.

In an example, a second segment can have a shape which is selected from the group consisting of: portion of a circle; portion of a spiral; portion of a parabolic curve; portion of a sinusoidal curve; and conic section. In an example, a second segment can gently press against or otherwise engage the outer surface of a person's ear in order to help hold the device on the person's head. In an example, a second segment can gently protrude into a portion of the person's ear canal in order in order to help hold the device on the person's head. In an example, a second segment can further comprise a speaker. In an example, a second segment can hold a speaker close to the ear canal opening for discreet audio communication. In an example, a second segment can be resiliently-flexible. In an example, a second segment can be made from a metal or polymer. In an example, a second segment can be porous and/or have holes so as to be permeable to gas and/or liquid. In an example, a second segment can have a width between one-eighth inch and one inch.

In an example, a second segment can curve, loop, protrude, undulate, and/or hook around the front of a person's ear. In an example, a second segment can be configured to help hold the device on a person's head by engaging the frontal surface of the outer ear. In an example, a second segment can be configured to be worn entirely within two inches of the person's outer ear. In an example, a second segment can curve, loop, protrude, undulate, and/or hook around (some or all of) the front-facing surface of the person's outer ear. In an example, a second segment can curve, loop, protrude, undulate, and/or hook around (some or all of) the frontal portion of tissue which connects the outer ear with the rest of the head. In an example, a second segment can be configured to curve, loop, protrude, undulate, and/or hook around a side portion of the person's face which is within one inch of the person's ear.

In an example, a second segment can curve, loop, protrude, undulate, and/or hook around a portion of the person's ear clockwise between the 12 o'clock (0 degree) and 6 o'clock (180 degree) vectors. In an example, a second segment can curve, loop, protrude, undulate, and/or hook around a portion of the person's ear clockwise between the 12 o'clock (0 degree) and 3 o'clock (90 degree) vectors. In an example, a second segment can curve, loop, protrude, undulate, and/or hook around a portion of the person's ear clockwise between the 12 o'clock (0 degree) and 2 o'clock (60 degree) vectors.

In an example, a second segment can be configured to help hold the device on a person's head by resting on top of the outer ear (or the tissue connection between the outer ear and the rest of the person's head). In an example, a second segment can rest on the top of a person's outer ear and/or the tissue connecting the outer ear with the rest of the head and project in a frontward and downward manner within the directional quadrants relative to the ear canal clockwise between the 12 o'clock (0 degree) and 6 o'clock (180 degree) vectors. In an example, a second segment can rest on the top of the person's outer ear and/or the tissue connecting the outer ear with the rest of the head and project in a frontward and downward manner within the directional quadrant relative to the ear canal clockwise between the 12 o'clock (0 degree) and 3 o'clock (90 degree) vectors.

In an example, a third segment of this device can extend upward from a person's ear along the side of their head. In an example, a third segment can span, curve, and/or loop upward from an ear. In an example, a third segment can extend upward from an ear along a vector which is substantially parallel to the 1 o'clock (30 degree) vector or 2 o'clock (60 degree) vector shown in FIG. 17. In an example, a third segment can extend upward from an ear along a vector which is substantially parallel to a vector which is clockwise between the 12 o'clock (0 degree) and 3 o'clock (90 degree) vectors shown in FIG. 17.

In an example, a third segment can be directly connected to a first segment and/or a second segment. In an example, these segments can both be part of the same continuous member and/or piece of material. In an alternative example, this device can further comprise another member between these segments which connects them together. In an example, a third segment can be at least two inches long. In an example, a third segment can be at least four inches long.

In an example, a third segment can be arcuate, wavy, and/or undulating. In an example, the third segment can be an arc, wave, or undulation with a rear-facing concavity and a forward-facing peak. In an example, a third segment can have a shape selected from the group consisting of: arc, wave, undulation, semi-circle, semi-oval, loop, half-sinusoidal curve, bell-shaped curve, and conic section. In an example, a third segment can have a concavity whose opening faces rearward along a vector which is parallel to a vector which is clockwise between the 7 o'clock (210 degree) and 11 o'clock (330 degree) vectors.

In an example, a fourth segment can extend across a person's forehead. In an example, a fourth segment on the right side of a person's head can connect to a fourth segment on the left side of the person's head. In an example, a fourth segment can be directly connected to a third segment. In an example, third and fourth segments can both be part of the same continuous member and/or piece of material. In an alternative example, this device can further comprise another member between the third and fourth segments which connects them together. In an example, a fourth segment can be at least four inches long.

Other components (including the at least one electromagnetic energy sensor, data processor, data transmitter, and power source) can have the same features and variations as the corresponding components discussed in other figures of this disclosure. Also, relevant portions of the narratives which accompany other figures in this disclosure can also be applied to this example, but are not repeated here.

FIG. 33 shows another example of how this invention can be embodied in a wearable device for measuring electromagnetic brain activity comprising: (a) an undulating band which is configured to encircle a person's head, wherein the portion of this undulating band on the first side of the person's head further comprises: a first segment which is configured to span from the rear of the person's head to the person's ear; a second segment which is configured to span from the person's ear to a side of the person's face and/or forehead, wherein this second segment has a concavity which opens upward; and a third segment which configured to span across the person's forehead; (b) at least one electromagnetic energy sensor which is held in proximity to the person's head by the undulating band, wherein the at least one electromagnetic energy sensor collects data concerning electromagnetic brain activity; (c) a data processor which receives data from the at least one electromagnetic energy sensor; (d) a data transmitter; and (e) a power source which powers the at least one electromagnetic energy sensor, the data processor, and/or the data transmitter.

FIG. 33 shows another example of how this invention can be embodied in an undulating mobile EEG monitor comprising: (a) an undulating band which is configured to span from a person's ear on a first side of the person's head to the person's ear on the second side of the person's head, wherein the portion of this undulating band on the first side of the person's head further comprises: a first segment which is configured to span from the rear of the person's head to the person's ear; a second segment which is configured to span from the person's ear to a side of the person's face and/or forehead, wherein this second segment has a concavity which opens upward; and a third segment which configured to span across the person's forehead; (b) at least one EEG sensor which is held in proximity to the person's head by the undulating band, wherein the at least one EEG sensor collects data concerning electromagnetic brain activity; (c) a data processor which receives data from the at least one EEG sensor; (d) a data transmitter; and (e) a power source which powers the at least one EEG sensor, the data processor, and/or the data transmitter.

With respect to specific components, FIG. 33 shows a right-side head view of a wearable device for measuring electromagnetic brain activity comprising: an undulating band which is configured to span from a person's ear on a first side of the person's head to the person's ear on the second side of the person's head, wherein the portion of this undulating band on the first side of the person's head further comprises first segment 3301 which is configured to span from the rear of the person's head to the person's ear, second segment 3302 which is configured to span from the person's ear to a side of the person's face and/or forehead, wherein this second segment has a concavity which opens upward, third segment 3303 which configured to span across the person's forehead; electromagnetic energy sensors (such as EEG sensors) 3304, 3305, and 3306; data processor 3308 data transmitter 3307; and power source 3309. In an example, this device can be symmetric with respect to the right and left sides of the person's head.

In an example, this undulating band can be resiliently-flexible. In an example, this undulating band can gently press against the person's head when worn. In an example, this undulating band can be made from a metal or polymer. In an example, this undulating band can have prongs, teeth, or combs to engage with the person's hair to make the device less obvious and/or to better hold it onto the person's head. In an example, this undulating band can be porous and/or have holes so as to be permeable to gas and/or liquid. In an example, this undulating band can be between one quarter inch and three inches in width.

In an example, an undulating band can be configured to receive the frame of a pair of eyeglasses so that this device can be worn in combination with eyeglasses. In an example, an undulating band can further comprise an opening which is configured to receive the side-piece of the frame of a pair of eyeglasses so that this device can be worn in combination with eyeglasses. In an example, an undulating band can further comprise a clip or other attachment mechanism to which the side-piece of the frame of a pair of eyeglasses can be attached so that this device can be worn in combination with eyeglasses. In an example, an undulating band can further comprise an indentation, groove, or track into (or against) which the side-piece of the frame of a pair of eyeglasses can be placed so that this device can be worn in combination with eyeglasses.

In an example, a first segment can span from the rear of the person's head to a person's ear. In an example, a first segment can span from rear of the person's head to a second segment. In an example, a first segment on a first side of the person's head can connect with a first segment on the second (opposite) side of the person's head. In an example, these segments can all be part of the same continuous member and/or piece of material. In an example, this device can further comprise other members which connect these segments together.

In an example, a first segment can span the rear of a person's head within two inches of a horizontal line rearward from the top of the ear. In an example, a first segment can span the rear of a person's head within four inches of a horizontal line rearward from the top of the ear. In an example, a first segment can span the rear of a person's head less than two inches above a horizontal line rearward from the top of the ear. In an example, a first segment can span the rear of a person's head less than four inches above a horizontal line rearward from the top of the ear. In an example, a first segment can span the rear of a person's head less than two inches below a horizontal line rearward from the top of the ear. In an example, a first segment can span the rear of a person's head less than four inches below a horizontal line rearward from the top of the ear. In an example, a first segment can further comprise prongs, teeth, or combs which engage the person's hair in order to make a first segment less obvious or in order to better hold the device onto the person's head.

In an example, this device can include a second segment which spans from a person's ear to a side portion of their face and/or forehead. A second segment of this device can be directly connected to a first segment of this device. In an example, these segments can both be part of the same continuous member and/or piece of material. In an alternative example, this device can further comprise another member between these segments which connects them together.

In an example, a second segment can extend, protrude, curve, or loop from a person's ear to the person's temple on the first side of the person's head. In an example, a second segment can extend, protrude, curve, or loop from the person's ear to a side portion of the person's face. In an example, a second segment can extend, protrude, curve, or loop from the person's ear to a side portion of the person's forehead. In an example, a second segment can extend, protrude, curve, or loop forward from a person's ear along a vector which is substantially parallel to a vector which is clockwise between the 3 o'clock (90 degree) and 5 o'clock (150 degree) vectors shown in FIG. 17.

In an example, a second segment can be at least two inches long. In an example, a second segment can be at least four inches long. In an example, a second segment can extend, protrude, curve, or loop from the person's ear to a position which is at least two inches from a person's ear toward the person's temple. In an example, a second segment can extend, protrude, curve, or loop from the person's ear to a position which is at least two inches toward the person's eye.

In an example, a second segment can extend, protrude, curve, or loop from the person's ear to a position which is between one quarter and three-quarters of the way toward the person's temple on the first side of the head. In an example, a second segment can extend, protrude, curve, or loop from the person's ear to a position which is between one quarter and three-quarters of the way toward the person's eye on the first side of the head. In an example, a second segment can extend, protrude, curve, or loop from the person's ear to a position which is between one quarter and one-half of the way toward the center of the person's forehead.

In an example, a second segment can be arcuate, wavy, and/or undulating. In an example, a second segment can be an arc, wave, or undulation with a rear-facing concavity and a forward-facing peak. In an example, a second segment can have a shape selected from the group consisting of: arc, wave, undulation, semi-circle, semi-oval, loop, half-sinusoidal curve, bell-shaped curve, and conic section. In an example, a second segment can have a concavity whose opening faces upward. In an example, a second segment can have a concavity whose opening faces along a vector which is parallel to a vector which is clockwise between the 7 o'clock (210 degree) and 12 o'clock (0 degree) vectors shown in FIG. 17. In an example, the most-forward point of a second segment can be located on a person's temple. In an example, the most-forward point of a second segment can be located on the side of a person's forehead.

In an example, a second segment can have an upper portion which is located in the directional quadrant clockwise between the 11 o'clock (330 degree) and 3 o'clock (90 degree) vectors. In an example, a second segment can have an upper portion which is clockwise between the 12 o'clock (0 degree) and 3 o'clock (90 degree) vectors. In an example, a second segment can span (in an arcuate and/or undulating manner) downward and forward from a person's ear to a location on the side of a person's forehead, then span (in an arcuate and/or undulating manner) upward, and then span (in an arcuate and/or undulating manner) upward and rearward to a location above the ear on the side of the head.

In an example, a third segment can extend across a person's forehead. In an example, a third segment on the right side of a person's head can connect to a third segment on the left side of the person's head. In an example, a third segment can be directly connected to a second segment. In an example, second and third segments can both be part of the same continuous member and/or piece of material. In an alternative example, this device can further comprise another member between the second and third segments which connects them together. In an example, a third segment can be at least four inches long.

Other components (including the at least one electromagnetic energy sensor, data processor, data transmitter, and power source) can have the same features and variations as the corresponding components discussed in other figures of this disclosure. Also, relevant portions of the narratives which accompany other figures in this disclosure can also be applied to this example, but are not repeated here.

FIGS. 35 through 52 show additional examples of how this invention can be embodied in a wearable device for measuring electromagnetic brain activity. Before showing and discussing these specific examples, however, it is useful to provide an introductory section of material which can apply to these figures. This avoids the redundancy of repeating this material in each of the individual narratives which accompany the figures. As part of this introductory section, it is also useful to define radial clock hour (or degree) vectors around a person's outer ear canal opening. This definition is provided by FIG. 34.

FIG. 34 shows radial clock hour (or degree) vectors extending outwards from the center of an ear canal outer opening. The 12 o'clock (or 0 degree) vector is a vertical line extending upwards from the center of the ear canal outer opening when the person is standing upright. The 3 o'clock (or 90 degree) vector is a horizontal line extending forward from the center of the ear canal outer opening when the person is standing upright. The 6 o'clock (or 180 degree) vector is a vertical line extending downwards from the center of the ear canal outer opening when the person is standing upright. The 9 o'clock (or 270 degree) vector is a horizontal line extending backward from the center of the ear canal outer opening when the person is standing upright. FIG. 34 also shows intermediate clock hour (or degree) vectors between these four vectors.

FIG. 34 can also be used to define the terms "rear", "front", "upper", and "lower" with respect to a person's ear. The term "rear" can be defined as spanning (some or all of) the directional quadrants clockwise between the 6 o'clock (180 degree) and 12 o'clock (0 degree) vectors. The term "front" can be defined as spanning (some or all of) the directional quadrants clockwise between the 12 o'clock (0 degree) and 6 o'clock (180 degree) vectors. The term "upper" can be defined as spanning (some or all) of the directional quadrants clockwise between the 9 o'clock (270 degree) and 3 o'clock (90 degree) vectors. The term "lower" can be defined as spanning some or all of the directional quadrants clockwise between the 3 o'clock (90 degree) and 9 o'clock (270 degree) vectors.

As shown in the figures that follow this introductory section, this invention can be embodied in a wearable device for measuring electromagnetic brain activity comprising: a (circumferential or partially-circumferential) halo and/or headband which is worn on the upper portion of a person's head; a plurality of electromagnetic energy sensors which are configured to be held in proximity to the person's head by the halo and/or headband, wherein these electromagnetic energy sensors collect data concerning electromagnetic activity of the person's brain; a wireless data transmitter and/or receiver; a data processor; and a power source.

In an example, this invention can be embodied in a halo and/or headband. In an example, this invention can be embodied in an undulating rear-tilted halo and/or headband. In an example, this invention can be embodied in an undulating hairband-style halo and/or headband. In an example, this invention can be embodied in a partially-circumferential halo and/or headband. In an example, this invention can be embodied in a halo and/or headband with a movable loop or arm.

In an example, a halo and/or headband can have a uniform width. In an example, this uniform width can be within the range of ½" to 3". In an example, a halo and/or headband can have a variable width. In an example, front and read portions of a halo and/or headband can be wider than side portions of the halo and/or headband. In an alternative example, side portions can be wider than front and rear portions. In an example, a halo and/or headband can be flexible, stretchable, and/or elastic. In an example, a halo and/or headband can be flexibly resilient. In an example, a halo and/or headband can have teeth, prongs, combs, or other protrusions which engage with a person's hair to better hold it on a person's head.

In an example, a halo and/or headband can be made from metal. In an example, a halo and/or headband can be made from a polymer. In an example, a halo and/or headband can be stretchable, elastic, and/or expandable. In an example, one or more sections of the perimeter of a halo and/or headband can be stretchable, elastic, and/or expandable. In an example, the perimeter of a halo and/or headband can further comprise one or more sections with a first degree of stretchability, elasticity, and/or expandability and one or more sections with a second degree of stretchability, elasticity, and/or expandability, wherein the second degree is greater than the first degree.

In an example, a halo and/or headband can further comprise a spring or other tensile member which holds the halo and/or headband against the surface of a person's head. In an example, the perimeter of a halo and/or headband can further comprise a spring or other tensile member which causes the halo and/or headband to exert (modest) pressure against the surface of the person's head to better hold the halo and/or headband on the person's head and/or to better hold electromagnetic energy sensors in proximity to the surface of the person's head.

In an example, a halo and/or headband can be one continuous member and/or piece of material. In an example, a halo and/or headband can comprise multiple members and/or components which are movably-connected so that the size and/or shape of the halo and/or headband can be adjusted. In an example, a halo and/or headband can comprise multiple members and/or components which are slideably-connected so that the size and/or shape of the halo can be adjusted. In an example, a halo and/or headband can comprise multiple telescoping (concentric) members which can be (partially) telescoped to adjust the size and/or shape of the halo and/or headband to best fit a specific person's head.

In an example, a halo and/or headband can be configured to receive the side frame of a pair of eyeglasses (or other eyewear) so that this device can be worn in combination with eyeglasses (or other eyewear). In an example, a halo and/or headband can further comprise an opening which is configured to receive the side-piece of an eyeglass (or other eyewear) frame so that this device can be worn in combination with eyeglasses (or other eyewear). In an example, a halo and/or headband can further comprise a clip or other attachment mechanism to which the side-piece of an eyeglass (or other eyewear) frame can be attached so that this device can be worn in combination with eyeglasses (or other eyewear). In an example, a halo and/or headband can further comprise an indentation, groove, or track into (or against) which the side-piece of the side-piece of an eyeglass (or other eyewear) frame can be placed so that this device can be worn in combination with eyeglasses (or other eyewear).

In an example, this device can include a plurality of electromagnetic energy sensors which are held in proximity to a person's head by the halo and/or headband. In an example, electromagnetic energy sensors can be held within 1" of the surface of a person's head by the halo and/or headband. In an example, a halo and/or headband can hold two electromagnetic energy sensors in position, one on each side of a person's head. In an example, a halo and/or headband can hold four electromagnetic energy sensors, two on each side of a person's head. In an example, a halo and/or headband can hold at least four electromagnetic energy sensors, at least one on each side of a person's head, at least one on a person's forehead, and at least one on the rear portion of a person's head. In an example, a halo and/or headband can hold at least eight electromagnetic energy sensors, at least two on each side of a person's head, at least two on a person's forehead, and at least two on the rear portion of a person's head.

In an example, this device can comprise at least two electromagnetic energy sensors forward of the 12 o'clock (0 degree) vector. In an example, this device can comprise at least two electromagnetic energy sensors to the rear of the 12 o'clock (0 degree) vector. In an example, one or more electromagnetic energy sensors which collect data concerning brain activity can be placed at one or more standard EEG placement sites selected from the group consisting of: FP1, FPz, FP2, AF7, AF5, AF3, AFz, AF4, AF6, AF8, F7, F5, F3, F1, Fz, F2, F4, F6, F8, FT7, FC5, FC3, FC1, FCz, FC2, FC4, FC6, FT8, T3/T7, C3, C4, C1, Cz, C2, C5, C6, T4/T8, TP7, CP5, CP3, CP1, CPz, CP2, CP4, CP6, DJC, TP8, T5/P7, P5, P3, P1, Pz, P2, P4, P6, T6/P8, PO7, PO5, PO3, POz, PO4, PO6, PO8, O1, Oz, and O2.

In an example, one or more electromagnetic energy sensors can be held in permanent locations on a halo and/or headband. In an example, one or more electromagnetic energy sensors can be moveably, slideably, and/or removably attached to a halo and/or headband so that their locations can be moved and/or adjusted. In an example, the locations of a plurality of electromagnetic energy sensors can be moved on a halo and/or headband to find the optimal locations on that halo from which to collect data concerning electromagnetic brain activity for a specific person. In an example, one or more electromagnetic energy sensors can be slid along tracks and/or grooves to different locations along a halo and/or headband. In an example, one or more electromagnetic energy sensors can be snapped onto, clipped to, or plugged into different locations on a halo and/or headband.

In an example, the locations of a plurality of electromagnetic energy sensors can be moved manually. In an example, the locations of a plurality of electromagnetic energy sensors can be moved automatically by one or more actuators. In an example, the locations of a plurality of electromagnetic energy sensors can be moved automatically by one or more actuators based on data from the sensors in order to optimize the locations of the sensors for data collection. In an example, the locations of a plurality of electromagnetic energy sensors can be moved automatically and data collected from different locations in order to identify the optimal locations for data collection for a specific person. In an example, the locations of a plurality of electromagnetic energy sensors can be manually or automatically adjusted in order to customize this device for collection of brain activity data for a specific person.

In an example, an electromagnetic energy sensor can be an electromagnetic energy receiver which receives electromagnetic energy which is naturally generated by the electromagnetic activity of the brain. In an example, an electromagnetic energy sensor can comprise an electromagnetic energy emitter at a first location and an electromagnetic energy receiver at a second location, wherein the electromagnetic energy receiver receives energy which has been transmitted from the electromagnetic energy emitter through body tissue. In an example, the electromagnetic energy receiver can collect data concerning (changes in) the conductivity, resistance, and/or impedance of electromagnetic energy transmitted through body tissue from the electromagnetic energy emitter to the electromagnetic energy receiver. In an example, an electromagnetic energy emitter and an electromagnetic energy receiver can together by referred to as an electromagnetic energy sensor.

In an example, an electromagnetic energy sensor of this device can be an electroencephalographic (EEG) sensor. In an example, an electromagnetic energy sensor can be a dry sensor. In an example, an electromagnetic energy sensor can be a wet sensor. In an example, an electromagnetic energy sensor can be an inductive sensor. In an example, an electromagnetic energy sensor can be a capacitive sensor. In an example, an electromagnetic energy sensor can comprise an electromagnetic energy emitter and an electromagnetic energy receiver. In an example, an electromagnetic energy sensor can comprise only an electromagnetic energy receiver. In an example, an electromagnetic energy sensor can be an EEG sensor which collects data concerning the natural emission of electromagnetic energy by a person's brain. In an example, an electromagnetic energy sensor can collect data concerning changes in transmission of electromagnetic energy from an emitter to a receiver due to changes in electromagnetic brain activity. In an example, an electromagnetic brain activity sensor can measure voltage fluctuations resulting from ionic current within the neurons of the brain.

In an example, an electromagnetic energy sensor which collects data concerning brain activity can measure voltage fluctuations between a first electrode (e.g. sensor) and a second (reference) electrode (e.g. sensor) due to electromagnetic brain activity. In an example, voltage differences between a first electrode and a second (reference) electrode can be called a "channel" In an example, a set of channels can be called a "montage."

In an example, a pattern of electromagnetic brain activity can be a change in activity in a specific area of a person's brain. In an example, this pattern can be a transient pattern. In an example, this pattern can be a repeating pattern. In an example, this pattern can be a change in an ongoing repeating pattern. In an example, this pattern can be a change in electromagnetic brain activity measured from one location or channel relative to electromagnetic brain activity measured from one or more different locations or channels.

In an example, a repeating electromagnetic brain activity pattern can be modeled as a composite of multiple sine waves. In an example, a repeating electromagnetic brain activity pattern can be decomposed into sub-patterns in different frequency bands. In an example, these frequency bands can be selected from the group consisting of: Delta, Theta, Alpha, Beta, and Gamma. Ongoing brain waveforms classified as Delta waves can be within a frequency band selected from the group consisting of: 0.5-3.5 Hz, 0.5-4 Hz, 1-3 Hz, 1-4 Hz, and 2-4 Hz. Ongoing brain waveforms classified as Theta waves can be within a frequency band selected from the group consisting of: from the group consisting of: 3.5-7 Hz, 3-7 Hz, 4-7 Hz, 4-7.5 Hz, 4-8 Hz, and 5-7 Hz. Ongoing brain waveforms classified as Alpha waves can be within a frequency band selected from the group consisting of: 7-13 Hz, 7-14 Hz, 8-12 Hz, 8-13 Hz, 7-11 Hz, 8-10 Hz, and 8-10 Hz. Ongoing brain waveforms classified as Beta waves can be within a frequency band selected from the group consisting of: 11-30 Hz, 12-30 Hz, 13-18 Hz, 13-22 Hz, 13-26 Hz, 13-26 Hz, 13-30 Hz, 13-32 Hz, 14-24 Hz, 14-30 Hz, and 14-40 Hz. Ongoing brain waveforms classified as Gamma waves can be within a frequency band selected from the group consisting of: group consisting of: 30-100 Hz, 35-100 Hz, 40-100 Hz, and greater than 30 Hz.

In an example, this device can include a data processor which receives data from at least one electromagnetic energy sensor. In an example, a data processor can be selected from the group consisting of: central processing unit, microchip, and microprocessor. In an example, patterns of electromagnetic brain activity can be analyzed using one or more methods selected from the group consisting of: Analysis of Variance (ANOVA), Artificial Neural Network (ANN), Auto-Regressive (AR) Modeling, Bayesian Analysis, Bonferroni Analysis (BA), Centroid Analysis, Chi-Squared Analysis, Cluster Analysis, Correlation, Covariance, Data Normalization (DN), Decision Tree Analysis (DTA), Discrete Fourier transform (DFT), Discriminant Analysis (DA), Empirical Mode Decomposition (EMD), Factor Analysis (FA), Fast Fourier Transform (FFT), Feature Vector Analysis (FVA), Fisher Linear Discriminant, Fourier Transformation (FT) Method, Fuzzy Logic (FL) Modeling, Gaussian Model (GM), Generalized Auto-Regressive Conditional Heteroscedasticity (GARCH) Modeling, Hidden Markov Model (HMM), Independent Components Analysis (ICA), Inter-Band Power Ratio, Inter-Channel Power Ratio, Inter-Montage Power Mean, Inter-Montage Ratio, Kalman Filter (KF), Kernel Estimation, Laplacian Filter, Laplacian Montage Analysis, Least Squares Estimation, Linear Regression, Linear Transform, Logit Model, Machine Learning (ML), Markov Model, Maximum Entropy Modeling, Maximum Likelihood, Mean Power, Multi-Band Covariance Analysis, Multi-Channel Covariance Analysis, Multivariate Linear Regression, Multivariate Logit, Multivariate Regression, Naive Bayes Classifier, Neural Network, Non-Linear Programming, Non-negative Matrix Factorization (NMF), Power Spectral Density, Power Spectrum Analysis, Principal Components Analysis (PCA), Probit Model, Quadratic Minimum Distance Classifier, Random Forest (RF), Random Forest Analysis (RFA), Regression Model, Signal Amplitude (SA), Signal Averaging, Signal Decomposition, Sine Wave Compositing, Singular Value Decomposition (SVD), Spine Function, Support Vector and/or Machine (SVM), Time Domain Analysis, Time Frequency Analysis, Time Series Model, Trained Bayes Classifier, Variance, Waveform Identification, Wavelet Analysis, and Wavelet Transformation.

In an example, this device can include a wireless data transmitter and/or receiver. In an example, this device can include a data processor. In an example, a first data processor and/or data transmitter which is physically part of a wearable component can be in electronic communication with a second data processor and/or data receiver which is not physically part of a wearable component. In an example, data processing can be distributed between first and second data processors. In an example, a second data processor can be part of a remote computing device. In an example, a second data processor can be part of a wearable data processing hub, mobile computer, electronic tablet, electronic pad, mobile phone, smart phone, implanted medical device, internet-connected remote computer, communication network tower, satellite, or home control system.

In an example, this device can include a power source which powers an electromagnetic energy sensor, a data processor, and/or a data transmitter. In an example, a power source can be a battery. In an example, a power source and/or power transducer can transduce, harvest, and/or generate energy from body motion or kinetic energy. In an example, a power source and/or power transducer can transduce, harvest, and/or generate energy from ambient light energy. In an example, a power source and/or power transducer can transduce, harvest, and/or generate energy from body thermal energy. In an example, a power source and/or power transducer can transduce, harvest, and/or generate energy from ambient electromagnetic energy.

In an example, this device can serve as a human-to-computer-interface (HCI) based on electromagnetic brain activity. In addition, this device can further comprise one or more other human-to-computer-interface (HCI) components. One or more human-computer-interface components can be selected from the group consisting of: touch screen, gesture recognition interface, speech and/or voice recognition interface, button and/or keypad, dial and/or knob, and motion sensor. In an example, this device can further comprise one or more computer-to-human interface (HCI) components. In an example, this device can be customized for Weird Al by including aluminum foil inside the halo. One or more computer-to-human interface components can be selected from the group consisting of: display screen, light emitter and/or light-emitting array, light-emitting fabric, optical emitter, speaker, buzzer, or other sound-emitting member, electromagnetic signal generator, vibrating member, actuator, Micro Electro Mechanical Systems (MEMS), augmented reality eyewear, virtual reality eyewear, and electronically-functional eyewear. Relevant variations and components discussed in the just-concluded introductory section can be applied to the examples which follow.

FIG. 35 shows an example of how this invention can be embodied in a wearable device for measuring electromagnetic brain activity comprising: a saddle-shaped halo 3501 which is configured to be worn around the upper portion of a person's head; a plurality of electromagnetic energy sensors (including 3505, 3506, 3507, and 3508) which are configured to be held in proximity to the person's head by the saddle-shaped halo, wherein these electromagnetic energy sensors collect data concerning electromagnetic activity of the person's brain; a wireless data transmitter and/or receiver 3502; a data processor 3503; and a power source 3504. In an example, this device can have a symmetric configuration on the other side of the person's head, which is not shown here.

In an example, front and rear portions of a saddle-shaped halo which span the front and rear portions of a person's head, respectively, can be configured to be a first average distance from the top of the person's head. Right and left side portions of a saddle-shaped halo which span the right and left sides of the person's head, respectively, can be configured to be a second average distance from the top of the person's head. Further, the second distance can be greater than the first distance. In an example: front and rear portions of a saddle-shaped halo which span the front and rear portions of the person's head, respectively, can be configured to have a first height when the person is standing upright; right and left side portions of a saddle-shaped halo which span the right and left sides of the person's head, respectively, can be configured to have a second height when the person is standing upright; and the second height can be lower than the first height.

In an example, a saddle-shaped halo can be shaped like the perimeter of a hyperbolic paraboloid. In an example, a saddle-shaped halo can be shaped like the perimeter of a Pringles™ brand chip. In an example, the perimeter of a saddle-shaped halo can be shaped like a circle or oval which has been placed on top of a person's head and then virtually melted (inspired perhaps by Salvatore Dali?) so that its sides droop downward.

In an example, a front portion of a saddle-shaped halo can span the front of a person's head between the 1 o'clock (30 degree) vector and the 2 o'clock (60 degree) vector. In an example, a front portion of a saddle-shaped halo can be configured to at least partially span a person's forehead. In an example, a front portion of a saddle-shaped halo can be configured to span the front of a person's head within 2" of the person's hairline and/or the top of the person's forehead.

In an example, a rear portion of a saddle-shaped halo can span the rear of a person's head between the 10 o'clock (300 degree) vector and the 11 o'clock (330 degree) vector. In an example, a side portion of a saddle-shaped halo can span the side of a person's head between the 10 o'clock (300 degree) vector and the 2 o'clock (60 degree) vector. In an example, a side portion of a saddle-shaped halo can be configured to span the side of a person's head within 2" of the top of the person's ear (on that side).

In an example, a saddle-shaped halo can have a uniform width. In an example, this uniform width can be within the range of ½" to 3". In an example, a saddle-shaped halo can have a variable width. In an example, front and read portions of a saddle-shaped halo can be wider than side portions of the saddle-shaped halo. In an alternative example, side portions can be wider than front and rear portions. In an example, a saddle-shaped halo can be flexible, stretchable, and/or elastic. In an example, a saddle-shaped halo can be flexibly resilient. In an example, a saddle-shaped halo can have teeth, prongs, combs, or other protrusions which engage with a person's hair to better hold the halo on the person's head.

In an example, a saddle-shaped halo can be made from metal. In an example, a saddle-shaped halo can be made from a polymer. In an example, a saddle-shaped halo can be stretchable, elastic, and/or expandable. In an example, one or more sections of the perimeter of a saddle-shaped halo can be stretchable, elastic, and/or expandable. In an example, the perimeter of a saddle-shaped halo can further comprise one or more sections with a first degree of stretchability, elasticity, and/or expandability and one or more sections with a second degree of stretchability, elasticity, and/or expandability, wherein the second degree is greater than the first degree.

In an example, the perimeter of a saddle-shaped halo can further comprise a spring or other tensile member which holds the saddle-shaped halo against the surface of the person's head. In an example, the perimeter of a saddle-shaped halo can further comprise a spring or other tensile member which causes the saddle-shaped halo to exert (modest) pressure against the surface of the person's head to better hold the saddle-shaped halo on the person's head and/or to better hold the electromagnetic energy sensors in proximity to the surface of the person's head.

In an example, a saddle-shaped halo can be one continuous member and/or piece of material. In an example, a saddle-shaped halo can comprise multiple members and/or components which are movably-connected so that the size and/or shape of the halo can be adjusted. In an example, a saddle-shaped halo can comprise multiple members and/or components which are slideably-connected so that the size and/or shape of the halo can be adjusted. In an example, a saddle-shaped halo can comprise multiple telescoping (concentric) members which can be (partially) telescoped to adjust the size and/or shape of the halo to best fit a specific person's head.

In an example, a saddle-shaped halo can be configured to receive the side frame of a pair of eyeglasses (or other eyewear) so that this device can be worn in combination with eyeglasses (or other eyewear). In an example, a rear segment of this device can further comprise an opening which is configured to receive the side-piece of an eyeglass (or other eyewear) frame so that this device can be worn in combination with eyeglasses (or other eyewear). In an example, a rear segment of this device can further comprise a clip or other attachment mechanism to which the side-piece of an eyeglass (or other eyewear) frame can be attached so that this device can be worn in combination with eyeglasses (or other eyewear). In an example, a rear segment of this device can further comprise an indentation, groove, or track into (or against) which the side-piece of the side-piece of an eyeglass (or other eyewear) frame can be placed so that this device can be worn in combination with eyeglasses (or other eyewear).

In an example, this device includes a plurality of electromagnetic energy sensors which are held in proximity to a person's head by the saddle-shaped halo. In an example, electromagnetic energy sensors can be held within 1" of the surface of a person's head by the saddle-shaped halo. In an example, a saddle-shaped halo can hold two electromagnetic energy sensors in position, one on each side of a person's head. In an example, a saddle-shaped halo can hold four electromagnetic energy sensors, two on each side of a person's head. In an example, a saddle-shaped halo can hold at least four electromagnetic energy sensors, at least one on each side of a person's head, at least one on a person's forehead, and at least one on the rear portion of a person's head. In an example, a saddle-shaped halo can hold at least eight electromagnetic energy sensors, at least two on each side of a person's head, at least two on a person's forehead, and at least two on the rear portion of a person's head.

In an example, this device can comprise at least two electromagnetic energy sensors forward of the 12 o'clock (0 degree) vector. In an example, this device can comprise at least two electromagnetic energy sensors to the rear of the 12 o'clock (0 degree) vector. In an example, one or more electromagnetic energy sensors which collect data concerning brain activity can be placed at one or more standard EEG placement sites selected from the group consisting of: FP1, FPz, FP2, AF7, AF5, AF3, AFz, AF4, AF6, AF8, F7, F5, F3, F1, Fz, F2, F4, F6, F8, FT7, FC5, FC3, FC1, FCz, FC2, FC4, FC6, FT8, T3/T7, C3, C4, C1, Cz, C2, C5, C6, T4/T8, TP7, CP5, CP3, CP1, CPz, CP2, CP4, CP6, DJC, TP8, T5/P7, P5, P3, P1, Pz, P2, P4, P6, T6/P8, PO7, PO5, PO3, POz, PO4, PO6, PO8, O1, Oz, and O2.

In an example, one or more electromagnetic energy sensors can be held in permanent locations on a saddle-shaped halo. In an example, one or more electromagnetic energy sensors can be moveably, slideably, and/or removably attached to a saddle-shaped halo so that their locations can be moved and/or adjusted. In an example, the locations of a plurality of electromagnetic energy sensors can be moved on a saddle-shaped halo to find the optimal locations on that halo from which to collect data concerning electromagnetic brain activity for a specific person. In an example, one or more electromagnetic energy sensors can be slid along tracks and/or grooves to different locations along a saddle-shaped halo. In an example, one or more electromagnetic energy sensors can be snapped onto, clipped to, or plugged into different locations on a saddle-shaped halo.

In an example, the locations of a plurality of electromagnetic energy sensors can be moved manually. In an example, the locations of a plurality of electromagnetic energy sensors can be moved automatically by one or more actuators. In an example, the locations of a plurality of electromagnetic energy sensors can be moved automatically by one or more actuators based on data from the sensors in order to optimize the locations of the sensors for data collection. In an example, the locations of a plurality of electromagnetic energy sensors can be moved automatically and data collected from different locations in order to identify the optimal locations for data collection for a specific person. In an example, the locations of a plurality of electromagnetic energy sensors can be manually or automatically adjusted in order to customize this device for collection of brain activity data for a specific person.

In an example, an electromagnetic energy sensor can be an electromagnetic energy receiver which receives electromagnetic energy which is naturally generated by the electromagnetic activity of the brain. In an example, an electromagnetic energy sensor can comprise an electromagnetic energy emitter at a first location and an electromagnetic energy receiver at a second location, wherein the electromagnetic energy receiver receives energy which has been transmitted from the electromagnetic energy emitter through body tissue. In an example, the electromagnetic energy receiver can collect data concerning (changes in) the conductivity, resistance, and/or impedance of electromagnetic energy transmitted through body tissue from the electromagnetic energy emitter to the electromagnetic energy receiver. In an example, an electromagnetic energy emitter and an electromagnetic energy receiver can together by referred to as an electromagnetic energy sensor.

In an example, an electromagnetic energy sensor of this device can be an electroencephalographic (EEG) sensor. In an example, an electromagnetic energy sensor can be a dry sensor. In an example, an electromagnetic energy sensor can be a wet sensor. In an example, an electromagnetic energy sensor can be an inductive sensor. In an example, an electromagnetic energy sensor can be a capacitive sensor. In an example, an electromagnetic energy sensor can comprise an electromagnetic energy emitter and an electromagnetic energy receiver. In an example, an electromagnetic energy sensor can comprise only an electromagnetic energy receiver. In an example, an electromagnetic energy sensor can be an EEG sensor which collects data concerning the natural emission of electromagnetic energy by a person's brain. In an example, an electromagnetic energy sensor can collect data concerning changes in transmission of electromagnetic energy from an emitter to a receiver due to changes in electromagnetic brain activity. In an example, an electromagnetic brain activity sensor can measure voltage fluctuations resulting from ionic current within the neurons of the brain.

In an example, an electromagnetic energy sensor which collects data concerning brain activity can measure voltage fluctuations between a first electrode (e.g. sensor) and a second (reference) electrode (e.g. sensor) due to electromagnetic brain activity. In an example, voltage differences between a first electrode and a second (reference) electrode can be called a "channel" In an example, a set of channels can be called a "montage."

In an example, a pattern of electromagnetic brain activity can be a change in activity in a specific area of a person's brain. In an example, this pattern can be a transient pattern. In an example, this pattern can be a repeating pattern. In an example, this pattern can be a change in an ongoing repeating pattern. In an example, this pattern can be a change in electromagnetic brain activity measured from one location or channel relative to electromagnetic brain activity measured from one or more different locations or channels.

In an example, a repeating electromagnetic brain activity pattern can be modeled as a composite of multiple sine waves. In an example, a repeating electromagnetic brain activity pattern can be decomposed into sub-patterns in different frequency bands. In an example, these frequency bands can be selected from the group consisting of: Delta, Theta, Alpha, Beta, and Gamma. Ongoing brain waveforms classified as Delta waves can be within a frequency band selected from the group consisting of: 0.5-3.5 Hz, 0.5-4 Hz, 1-3 Hz, 1-4 Hz, and 2-4 Hz. Ongoing brain waveforms classified as Theta waves can be within a frequency band selected from the group consisting of: from the group consisting of: 3.5-7 Hz, 3-7 Hz, 4-7 Hz, 4-7.5 Hz, 4-8 Hz, and 5-7 Hz. Ongoing brain waveforms classified as Alpha waves can be within a frequency band selected from the group consisting of: 7-13 Hz, 7-14 Hz, 8-12 Hz, 8-13 Hz, 7-11 Hz, 8-10 Hz, and 8-10 Hz. Ongoing brain waveforms classified as Beta waves can be within a frequency band selected from the group consisting of: 11-30 Hz, 12-30 Hz, 13-18 Hz, 13-22 Hz, 13-26 Hz, 13-26 Hz, 13-30 Hz, 13-32 Hz, 14-24 Hz, 14-30 Hz, and 14-40 Hz. Ongoing brain waveforms classified as Gamma waves can be within a frequency band selected from the group consisting of: group consisting of: 30-100 Hz, 35-100 Hz, 40-100 Hz, and greater than 30 Hz.

In an example, this device can include a data processor which receives data from at least one electromagnetic energy sensor. In an example, a data processor can be selected from the group consisting of: central processing unit, microchip, and microprocessor. In an example, patterns of electromagnetic brain activity can be analyzed using one or more methods selected from the group consisting of: Analysis of Variance (ANOVA), Artificial Neural Network (ANN), Auto-Regressive (AR) Modeling, Bayesian Analysis, Bonferroni Analysis (BA), Centroid Analysis, Chi-Squared Analysis, Cluster Analysis, Correlation, Covariance, Data Normalization (DN), Decision Tree Analysis (DTA), Discrete Fourier transform (DFT), Discriminant Analysis (DA), Empirical Mode Decomposition (EMD), Factor Analysis (FA), Fast Fourier Transform (FFT), Feature Vector Analysis (FVA), Fisher Linear Discriminant, Fourier Transformation (FT) Method, Fuzzy Logic (FL) Modeling, Gaussian Model (GM), Generalized Auto-Regressive Conditional Heteroscedasticity (GARCH) Modeling, Hidden Markov Model (HMM), Independent Components Analysis (ICA), Inter-Band Power Ratio, Inter-Channel Power Ratio, Inter-Montage Power Mean, Inter-Montage Ratio, Kalman Filter (KF), Kernel Estimation, Laplacian Filter, Laplacian Montage Analysis, Least Squares Estimation, Linear Regression, Linear Transform, Logit Model, Machine Learning (ML), Markov Model, Maximum Entropy Modeling, Maximum Likelihood, Mean Power, Multi-Band Covariance Analysis, Multi-Channel Covariance Analysis, Multivariate Linear Regression, Multivariate Logit, Multivariate Regression, Naive Bayes Classifier, Neural Network, Non-Linear Programming, Non-negative Matrix Factorization (NMF), Power Spectral Density, Power Spectrum Analysis, Principal Components Analysis (PCA), Probit Model, Quadratic Minimum Distance Classifier, Random Forest (RF), Random Forest Analysis (RFA), Regression Model, Signal Amplitude (SA), Signal Averaging, Signal Decomposition, Sine Wave Compositing, Singular Value Decomposition (SVD), Spine Function, Support Vector and/or Machine (SVM), Time Domain Analysis, Time Frequency Analysis, Time Series Model, Trained Bayes Classifier, Variance, Waveform Identification, Wavelet Analysis, and Wavelet Transformation.

In an example, this device can include a wireless data transmitter and/or receiver. In an example, this device can include a data processor. In an example, a first data processor and/or data transmitter which is physically part of a wearable component can be in electronic communication with a second data processor and/or data receiver which is not physically part of a wearable component. In an example, data processing can be distributed between first and second data processors. In an example, a second data processor can be part of a remote computing device. In an example, a second data processor can be part of a wearable data processing hub, mobile computer, electronic tablet, electronic pad, mobile phone, smart phone, implanted medical device, internet-connected remote computer, communication network tower, satellite, or home control system.

In an example, this device can include a power source which powers an electromagnetic energy sensor, a data processor, and/or a data transmitter. In an example, a power source can be a battery. In an example, a power source and/or power transducer can transduce, harvest, and/or generate energy from body motion or kinetic energy. In an example, a power source and/or power transducer can transduce, harvest, and/or generate energy from ambient light energy. In an example, a power source and/or power transducer can transduce, harvest, and/or generate energy from body thermal energy. In an example, a power source and/or power transducer can transduce, harvest, and/or generate energy from ambient electromagnetic energy.

In an example, this device can serve as a human-to-computer-interface (HCl) based on electromagnetic brain activity. In addition, this device can further comprise one or more other human-to-computer-interface (HCl) components. One or more human-computer-interface components can be selected from the group consisting of: touch screen, gesture recognition interface, speech and/or voice recognition interface, button and/or keypad, dial and/or knob, and motion sensor. In an example, this device can further comprise one or more computer-to-human interface (HCl) components. In an example, this device can be customized for Weird Al by including aluminum foil inside the halo. One or more computer-to-human interface components can be selected from the group consisting of: display screen, light emitter and/or light-emitting array, light-emitting fabric, optical emitter, speaker, buzzer, or other sound-emitting member, electromagnetic signal generator, vibrating member, actuator, Micro Electro Mechanical Systems (MEMS), augmented reality eyewear, virtual reality eyewear, and electronically-functional eyewear. Other relevant variations and components discussed in other portions of this concurrent disclosure or prior disclosures incorporated herein by reference can also be applied to this example.

FIG. 36 shows an example of how this invention can be embodied in a wearable device for measuring electromagnetic brain activity comprising: an undulating rear-tilted headband 3601 which is configured to be worn around a person's head; a plurality of electromagnetic energy sensors (including 3605, 3606, 3607, and 3608) which are configured to be held in proximity to the person's head by the undulating rear-tilted headband, wherein these electromagnetic energy sensors collect data concerning electromagnetic activity of the person's brain; a wireless data transmitter and/or receiver 3602; a data processor 3603; and a power source 3604. In an example, this device can have a symmetric configuration on the other side of the person's head, which is not shown here.

In an example, an undulating rear-tilted headband can be tilted at an angle (relative to a horizontal plane when the person is standing upright) between 10 degree and 70 degrees. In an example, an undulating rear-tilted headband can circle a person's head from the upper-front portion of the person's head (including the person's forehead) to the lower-rear portion of the person's head. In an example, a virtual circle can be drawn which most closely fits the perimeter of the undulating rear-tilted headband. In an example, closest fit can be done by minimizing the average distance between points around the perimeters of the undulating rear-tilted headband and the virtual circle. In an example, the plane formed by this virtual circle can be parallel to a rear-facing vector between the 7 o'clock (210 degree) vector and the 9 o'clock (270 degree) vector and/or a front-facing vector between the 12 o'clock (0 degree) vector and the 2 o'clock (60 degree) vector. In other words, the rear portion of the rear-tilted headband is lower and the front portion of this headband is higher.

In an example: the front portion of the undulating rear-tilted headband can span the front portion of the person's head at an average first distance from the top of the person's head; a side portion of the undulating rear-tilted headband can span the side of the person's head at an average second distance from the top of the person's head; the rear portion of the undulating rear-tilted headband can span the rear of the person's head at an average third distance from the top of the person's head; the second average distance can be greater than the first average distance; and the third average distance can be greater than the second average distance.

In an example, an undulating rear-tilted headband can have a wave shape which is sinusoidal or the composite of multiple sinusoidal waves. In an example, an undulating rear-tilted headband can comprise have four wavelike undulations. In an example, an undulating rear-tilted headband can comprise four sinusoidal undulations. In an example, an undulating rear-tilted headband can comprise four upward-opening concavities and four downward-opening concavities. In an example, the front portion of an undulating rear-tilted headband can cross over a person's hairline. In an example, the front portion of an undulating rear-tilted headband can partially span a person's forehead and partially span a person's hair. In an example, the front portion of an undulating rear-tilted headband can curve upwards from a person's temple to loop over the top of a person's head.

In an example, a side of an undulating rear-tilted headband can comprise a downward-opening concavity which spans at least a portion of the perimeter of the ear on that side. In an example, a side of an undulating rear-tilted headband can comprise a downward-opening concavity which at least partially encircles a person's ear. In an example, the right and left sides of an undulating rear-tilted headband can rest on top of a person's right and left ears, respectively. In an example, the right and left sides of an undulating rear-tilted headband can curve around the upper-rear portions of a person's right and left ears, respectively. In an example, an undulating rear-tilted headband can further comprise a wave and/or curve which is configured to peak above the person's ear. In an example, an undulating rear-tilted headband can further comprise a wave and/or curve which is configured to peak directly above the person's ear.

In an example, an undulating rear-tilted headband can have at least two upward-opening concavities on the right side of a person's head and at least two upward-opening concavities on the left side of the person's head. In an example, and undulating rear-tilted headband can have at least two downward-opening concavities on the right side of a person's head and at least two downward-opening concavities on the left side of the person's head. In an example, an undulating rear-tilted headband can have a downward-opening concavity above a person's ear. In an example, and undulating rear-tilted headband can have a concavity above a person's ear, wherein the central axis of this concavity (from the peak of the concavity extending through the center of the concavity opening) is parallel to a vector between the 3 o'clock (90 degree) and 6 o'clock (180 degree) vectors. In an example, and undulating rear-tilted headband can have a concavity above a person's ear, wherein the central axis of this concavity (from the peak of the concavity extending through the center of the concavity opening) is parallel to a vector between the 4 o'clock (120 degree) and 6 o'clock (180 degree) vectors.

In an example, an undulating rear-tilted headband can have at least two undulations as it spans a side of a person's head. In an example, an undulating rear-tilted headband can have a first upward-opening concavity as it spans between the rear of a person's head and the person's ear and a second upward-opening concavity as it spans between a person's ear and the frontal center of the person's head. In an example, an undulating rear-tilted headband can have: a first concavity with a central axis (from the peak of the concavity through the center of the concavity opening) parallel to a vector between the 10 o'clock (300 degree) and 12 o'clock (0 degree) vectors as it spans between the rear of a person's head and the person's ear; and a second concavity with a central axis (from the peak of the concavity through the center of the concavity opening) parallel to a vector between the 10 o'clock (300 degree) and 12 o'clock (0 degree) vectors as it spans between the rear of a person's head and the person's ear. In an example, the first and second concavities can be configured so that a person's ear is between them. In an example, an undulating rear-tilted headband can rest on the top of a person's ear (and/or the portion of the person's ear which connects it to the head).

In an example, a front portion of an undulating rear-tilted headband can span the front of a person's head between the 1 o'clock (30 degree) vector and the 2 o'clock (60 degree) vector. In an example, a rear portion of an undulating rear-tilted headband can span the rear of a person's head between the 7 o'clock (210 degree) vector and the 9 o'clock (270 degree) vector. In an example, a front portion of an undulating rear-tilted headband can be configured to span the front of a person's head within 2" of the person's hairline and/or the top of the person's forehead. In an example, a side portion of an undulating rear-tilted headband can be configured to span the side of a person's head within a distance of 1" from the top of the person's ear on that side.

In an example, an undulating rear-tilted headband can have a uniform width within the range of ½" to 3". In an example, an undulating rear-tilted headband can have a variable width wherein the front and read portions are wider than the side portions. In an example, an undulating rear-tilted headband can have a variable width wherein the side portions are wider than the front and rear portions. In an example, an undulating rear-tilted headband can be flexible, stretchable, and/or elastic. In an example, an undulating rear-tilted headband can be flexibly resilient. In an example, an undulating rear-tilted headband can have teeth, prongs, combs, or other protrusions which engage the ring with a person's hair to better hold the ring on the person's head. In an example, an undulating rear-tilted headband can be made from metal. In an example, an undulating rear-tilted headband can be made from a polymer.

In an example, an undulating rear-tilted headband can be one continuous member and/or one piece of material. In an example, an undulating rear-tilted headband can comprise multiple members and/or components which are movably-connected so that the size and/or shape of the ring can be adjusted. In an example, an undulating rear-tilted headband can comprise multiple members and/or components which are slideably-connected so that the size and/or shape of the ring can be adjusted. In an example, an undulating rear-tilted headband can comprise multiple members and/or components which are telescoping so that the size and/or shape of the ring can be adjusted to best fit a specific person's head.

In an example, an undulating rear-tilted headband can be configured to receive the side frame of a pair of eyeglasses so that this device can be worn in combination with eyeglasses. In an example, a rear segment of this device can further comprise an opening which is configured to receive the side-piece of the frame of a pair of eyeglasses so that this device can be worn in combination with eyeglasses. In an example, a rear segment of this device can further comprise a clip or other attachment mechanism to which the side-piece of the frame of a pair of eyeglasses can be attached so that this device can be worn in combination with eyeglasses. In an example, a rear segment of this device can further comprise an indentation, groove, or track into (or against) which the side-piece of the frame of a pair of eyeglasses can be placed so that this device can be worn in combination with eyeglasses.

In an example, this device can include a plurality of electromagnetic energy sensors which are held in proximity to a person's head by the undulating rear-tilted headband. In an example, a plurality of electromagnetic energy sensors can be held within 1" of the surface of a person's head by the undulating rear-tilted headband. In an example, there can be at least one electromagnetic energy sensor on the front portion of the undulating rear-tilted headband which spans the front of the person's head. In an example, there can be at least one electromagnetic energy sensor which is held on a person's forehead by the undulating rear-tilted headband. In an example, there can be at least one electromagnetic energy sensor on a side portion of the undulating rear-tilted headband which spans a side of the person's head. In an example, there can be at least one electromagnetic energy sensor on the rear portion of the undulating rear-tilted headband which spans the rear the person's head.

In an example, there can be at least two electromagnetic energy sensors forward of the 12 o'clock (0 degree) vector. In an example, there can be at least two electromagnetic energy sensors to the rear of the 12 o'clock (0 degree) vector. In an example, there can be at least three electromagnetic energy sensors forward of the 12 o'clock (0 degree) vector. In an example, there can be at least three electromagnetic energy sensors to the rear of the 12 o'clock (0 degree) vector.

In an example, one or more electromagnetic energy sensors which collect data concerning brain activity can be placed at one or more standard EEG placement sites selected from the group consisting of: FP1, FPz, FP2, AF7, AF5, AF3, AFz, AF4, AF6, AF8, F7, F5, F3, F1, Fz, F2, F4, F6, F8, FT7, FC5, FC3, FC1, FCz, FC2, FC4, FC6, FT8, T3/T7, C3, C4, C1, Cz, C2, C5, C6, T4/T8, TP7, CP5, CP3, CP1, CPz, CP2, CP4, CP6, DJC, TP8, T5/P7, P5, P3, P1, Pz, P2, P4, P6, T6/P8, PO7, PO5, PO3, POz, PO4, PO6, PO8, O1, Oz, and O2.

In an example, one or more electromagnetic energy sensors can be held in permanent locations on an undulating rear-tilted headband. In an example, one or more electromagnetic energy sensors can be moveably and/or slideably attached to an undulating rear-tilted headband so that their locations can be moved and/or adjusted. In an example, the locations of a plurality of electromagnetic energy sensors can be moved on an undulating rear-tilted headband to find the optimal locations on that ring from which to collect data concerning electromagnetic brain activity for a specific person. In an example, one or more electromagnetic energy sensors can be slid along tracks and/or grooves on an undulating rear-tilted headband in order to adjust their locations. In an example, one or more electromagnetic energy sensors can be snapped or clipped to different locations on an undulating rear-tilted headband in order to adjust their locations. In an example, one or more electromagnetic energy sensors can be plugged into different locations on an undulating rear-tilted headband in order to adjust their locations.

In an example, the locations of a plurality of electromagnetic energy sensors can be moved manually. In an example, the locations of a plurality of electromagnetic energy sensors can be moved automatically by one or more actuators. In an example, the locations of a plurality of electromagnetic energy sensors can be moved automatically by one or more actuators based on data from the sensors in order to optimize the locations of the sensors for data collection. In an example, the locations of a plurality of electromagnetic energy sensors can be moved automatically and data collected from different locations in order to identify the optimal locations for data collection for a specific person. In an example, the locations of a plurality of electromagnetic energy sensors can be manually or automatically adjusted in order to customize this device for collection of brain activity data for a specific person.

In an example, an electromagnetic energy sensor can be an electromagnetic energy receiver which receives electromagnetic energy which is naturally generated by the electromagnetic activity of the brain. In an example, an electromagnetic energy sensor can comprise an electromagnetic energy emitter at a first location and an electromagnetic energy receiver at a second location, wherein the electromagnetic energy receiver receives energy which has been transmitted from the electromagnetic energy emitter through body tissue. In an example, the electromagnetic energy receiver can collect data concerning (changes in) the conductivity, resistance, and/or impedance of electromagnetic energy transmitted through body tissue from the electromagnetic energy emitter to the electromagnetic energy receiver. In an example, an electromagnetic energy emitter and an electromagnetic energy receiver can together by referred to as an electromagnetic energy sensor.

In an example, an electromagnetic energy sensor of this device can be an electroencephalographic (EEG) sensor. In an example, an electromagnetic energy sensor can be a dry sensor. In an example, an electromagnetic energy sensor can be a wet sensor. In an example, the electromagnetic energy sensor can be an inductive sensor. In an example, an electromagnetic energy sensor can be a capacitive sensor. In an example, an electromagnetic energy sensor can comprise an electromagnetic energy emitter and an electromagnetic energy receiver. In an example, an electromagnetic energy sensor can comprise only an electromagnetic energy receiver. In an example, an electromagnetic energy sensor can be an EEG sensor which collects data concerning the natural emission of electromagnetic energy by a person's brain. In an example, an electromagnetic energy sensor can collect data concerning changes in transmission of electromagnetic energy from an emitter to a receiver due to changes in electromagnetic brain activity. In an example, an electromagnetic brain activity sensor can measure voltage fluctuations resulting from ionic current within the neurons of the brain.

In an example, a pattern of electromagnetic brain activity can be a change in activity in a specific area of a person's brain. In an example, this pattern can be a transient pattern. In an example, this pattern can be a repeating pattern. In an example, this pattern can be a change in an ongoing repeating pattern. In an example, this pattern can be a change in electromagnetic brain activity measured from one location or channel relative to electromagnetic brain activity measured from one or more different locations or channels.

In an example, a repeating electromagnetic brain activity pattern can be modeled as a composite of multiple sine waves. In an example, a repeating electromagnetic brain activity pattern can be decomposed into sub-patterns in different frequency bands. In an example, these frequency bands can be selected from the group consisting of: Delta, Theta, Alpha, Beta, and Gamma. Ongoing brain waveforms classified as Delta waves can be within a frequency band selected from the group consisting of: 0.5-3.5 Hz, 0.5-4 Hz, 1-3 Hz, 1-4 Hz, and 2-4 Hz. Ongoing brain waveforms classified as Theta waves can be within a frequency band selected from the group consisting of: from the group consisting of: 3.5-7 Hz, 3-7 Hz, 4-7 Hz, 4-7.5 Hz, 4-8 Hz, and 5-7 Hz. Ongoing brain waveforms classified as Alpha waves can be within a frequency band selected from the group consisting of: 7-13 Hz, 7-14 Hz, 8-12 Hz, 8-13 Hz, 7-11 Hz, 8-10 Hz, and 8-10 Hz. Ongoing brain waveforms classified as Beta waves can be within a frequency band selected from the group consisting of: 11-30 Hz, 12-30 Hz, 13-18 Hz, 13-22 Hz, 13-26 Hz, 13-26 Hz, 13-30 Hz, 13-32 Hz, 14-24 Hz, 14-30 Hz, and 14-40 Hz. Ongoing brain waveforms classified as Gamma waves can be within a frequency band selected from the group consisting of: group consisting of: 30-100 Hz, 35-100 Hz, 40-100 Hz, and greater than 30 Hz.

In an example, this device can include a wireless data transmitter and/or receiver. In an example, this device can include a data processor. In an example, a first data processor and/or data transmitter which is physically part of a wearable component can be in electronic communication with a second data processor and/or data receiver which is not physically part of a wearable component. In an example, data processing can be distributed between first and second data processors. In an example, a second data processor can be part of a remote computing device. In an example, a second data processor can be part of a wearable data processing hub, mobile computer, electronic tablet, electronic pad, mobile phone, smart phone, implanted medical device, internet-connected remote computer, communication network tower, satellite, or home control system.

In an example, this device can include a power source which powers an electromagnetic energy sensor, a data processor, and/or a data transmitter. In an example, a power source can be a battery. In an example, a power source and/or power transducer can transduce, harvest, and/or generate energy from body motion or kinetic energy. In an example, a power source and/or power transducer can transduce, harvest, and/or generate energy from ambient light energy. In an example, a power source and/or power transducer can transduce, harvest, and/or generate energy from body thermal energy. In an example, a power source and/or power transducer can transduce, harvest, and/or generate energy from ambient electromagnetic energy. Other relevant variations and components discussed in other portions of this concurrent disclosure or prior disclosures incorporated herein by reference can also be applied to this example.

FIG. 37 shows an example that is similar to the one shown in FIG. 36 except that an undulating headband is configured to span the front of the person's head over the center of the person's forehead. FIG. 37 shows an example of how this invention can be embodied in a wearable device for measuring electromagnetic brain activity comprising: an undulating headband 3701 which is configured to be worn around a person's head; a plurality of electromagnetic energy sensors (including 3705, 3706, 3707, and 3708) which are configured to be held in proximity to the person's head by the undulating headband, wherein these electromagnetic energy sensors collect data concerning electromagnetic activity of the person's brain; a wireless data transmitter and/or receiver 3702; a data processor 3703; and a power source 3704. In an example, this device can have a symmetric configuration on the other side of the person's head, which is not shown here. Other relevant variations and components discussed in other portions of this concurrent disclosure or prior disclosures incorporated herein by reference can also be applied to this example.

FIG. 38 shows an example of how this invention can be embodied in a wearable device for measuring electromagnetic brain activity comprising: an undulating hairband-style loop 3801 which is configured to span from the right ear to the left ear (or vice versa) over the upper-front portion a person's head; a plurality of electromagnetic energy sensors (including 3805, 3806, and 3807) which are configured to be held in proximity to the person's head by the undulating headband, wherein these electromagnetic energy sensors collect data concerning electromagnetic activity of the person's brain; a wireless data transmitter and/or receiver 3802; a data processor 3803; and a power source 3804. In an example, this device can have a symmetric configuration on the other side of the person's head, which is not shown here.

In an example, an undulating hairband-style loop can span from one ear to the other ear, across the front portion of a person's head. In an example, the left-side end of an undulating hairband-style loop can curve around the rear portion of a person's left ear and the right-side end of the undulating hairband-type loop can curve around the rear portion of the person's right ear. In an example, an undulating hairband-style loop can start behind a person's right ear, loop over the top of the right ear, curve forward toward (but not reach) the person's right eye, curve upward toward the top of the head, span the upper-front of the person's head, curve downward (but not reach) the person's left eye, curve backward toward the left ear, loop over the top of the left ear, and then curve behind the person's left ear. In an example, an arc of a virtual circle can be drawn to closely fit an undulating hairband-style loop by minimizing the average distance from the perimeter of the arc to the perimeter of the loop. In an example, the plane of this arc can be parallel to a forward-facing vector between the 12 o'clock (0 degree) vector and the 2 o'clock (60 degree) vector.

In an example, an undulating hairband-style loop can have an arcuate shape which is a sinusoidal curve or the composite of multiple sinusoidal curves. In an example, an undulating hairband-style loop can further comprise an arcuate wave and/or curve which partially encircles the person's ear. In an example, an undulating hairband-style loop can further comprise a sinusoidal wave and/or curve which partially encircles the person's ear. In an example, an undulating hairband-style loop can further comprise an upward arcuate wave and/or curve which is configured to peak above the person's ear. In an example, an undulating hairband-style loop can further comprise an upward sinusoidal wave and/or curve which is configured to peak above the person's ear.

In an example, an undulating hairband-style loop can have two forward and/or downward opening concavities and three rear and/or upward opening concavities. In an example, an undulating hairband-style loop can have two side forward and/or downward opening concavities which partially encircle the right and left ears, respectively. In an example, the central axis (opening outward from the peak of the concavity) of a concavity which partially encircles an ear can be parallel to a vector between the 3 o'clock (90 degree) vector and the 6 o'clock (180 degree) vector.

In an example, an undulating hairband-style loop can have right and left side forward and/or downward opening concavities, wherein these concavities partially encircle the right and left ears, respectively. In an example, the central axis of a concavity (opening outward from the peak of the concavity) which partially encircles an ear can be parallel to a vector between the 3 o'clock (90 degree) vector and the 6 o'clock (180 degree) vector. In an example, an undulating hairband-style loop can have a central forward and/or downward opening concavity which goes over the front of the head, opening toward the person's forehead. In an example, an undulating hairband-style loop can have right and left side rear and upward opening concavities which connect the right and left side forward and/or downward opening concavities, respectively, with the central forward and/or downward opening concavity. In an example, the most frontal points of an undulating hairband-style loop are on waves or curves between the ears and a central forward and/or downward opening concavity which goes over the front of the head. In an example, the most rearward points of an undulating hairband-style loop are on portions which curve around the rear portions of ears.

In an example, an undulating hairband-style loop can be configured to receive the side frame of a pair of eyeglasses so that this device can be worn in combination with eyeglasses. In an example, a rear segment of this device can further comprise an opening which is configured to receive the side-piece of the frame of a pair of eyeglasses so that this device can be worn in combination with eyeglasses. In an example, a rear segment of this device can further comprise a clip or other attachment mechanism to which the side-piece of the frame of a pair of eyeglasses can be attached so that this device can be worn in combination with eyeglasses. In an example, a rear segment of this device can further comprise an indentation, groove, or track into (or against) which the side-piece of the frame of a pair of eyeglasses can be placed so that this device can be worn in combination with eyeglasses. Other relevant variations and components discussed in other portions of this concurrent disclosure or prior disclosures incorporated herein by reference can also be applied to this example.

FIG. 39 shows an example of how this invention can be embodied in a wearable device for measuring electromagnetic brain activity comprising: an undulating headband (including rear portion 3901 and front portion 3902) which is configured to be worn around a person's head and also ear prong (603) which engages a portion of the perimeter of the person's outer ear; a plurality of electromagnetic energy sensors (including 3907 and 3908) which are configured to be held in proximity to the person's head by the undulating headband, wherein these electromagnetic energy sensors collect data concerning electromagnetic activity of the person's brain; a wireless data transmitter and/or receiver 3904; a data processor 3905; and a power source 3906. In an example, this device can have a symmetric configuration on the other side of the person's head, which is not shown here.

In an example, front and rear portions of an undulating headband can be higher than side portions of the undulating headband. In an example, the front portion of the undulating headband is configured to span across a person's forehead. In an example, the right and left side portions of the undulating headband are configured to dip down to within 1" of the person's right and left ears, respectively. In an example, the right and left side portions of the undulating headband are attached to right and left ear prongs, wherein each ear prong partially encircles the perimeter of the person's outer ear and/or the connection between the main body of the head and the outer ear. In an example, the ear prongs frictionally-engage the person's outer ears and help to hold the undulating headband in place.

In an example, an undulating headband encircles a person's head. In an example, the front portion of this headband spans the person's forehead and the rear portion of this headband spans the rear of the person's head. In an example, the front and rear portions of the headband can be at substantially the same height when the person is standing upright. In an example, the side portions of the headband can dip below the height of the front and rear portions of the headband. In an example, an undulating headband can be sinusoidal, with the lowest points of the sinusoidal waves above the person's ears. In an example, an undulating headband can be sinusoidal, with the lowest points of the sinusoidal waves directly above the person's ears. Other relevant variations and components discussed in other portions of this concurrent disclosure or prior disclosures incorporated herein by reference can also be applied to this example.

FIG. 40 shows an example of how this invention can be embodied in a wearable device for measuring electromagnetic brain activity comprising: a forward-upward sloped headband (including rear portion 4001 and front portion 4002) which is configured to be worn around a person's head and also ear prong (4003) which engages the perimeter of the person's outer ear; a plurality of electromagnetic energy sensors (including 4007 and 4008) which are configured to be held in proximity to the person's head by the undulating headband, wherein these electromagnetic energy sensors collect data concerning electromagnetic activity of the person's brain; a wireless data transmitter and/or receiver 4004; a data processor 4005; and a power source 4006. In an example, this device can have a symmetric configuration on the other side of the person's head, which is not shown here.

In an example, the front portion of an undulating headband can be higher than the rear portion of the undulating headband. In an example, the front third of an undulating headband can have a uniform first height, the rear third of the undulating headband can have a uniform second height, and the middle third of the headband can be an arcuate transition from the first height to the second height. In an example, the first height can be between 1" and 3" higher than the second height. In an example, the front third of an undulating headband can be relatively level and the rear third of the undulating headband can be relatively level.

In an example, the front portion of an undulating headband can be configured to span across a person's forehead. In an example, the right and left side portions of the undulating headband can be configured to dip down to within 1" of the person's right and left ears, respectively. In an example, the rear portion of an undulating headband can span the rear of the head at the level to which the right and left side portions dip down. In an example, the right and left side portions of the undulating headband can be attached to right and left ear prongs, wherein each ear prong partially encircles the perimeter of the person's outer ear and/or the connection between the main body of the head and the outer ear. In an example, the ear prongs frictionally-engage the person's outer ears and help to hold the undulating headband in place. Other relevant variations and components discussed in other portions of this concurrent disclosure or prior disclosures incorporated herein by reference can also be applied to this example.

In an example, this invention can be embodied in a Brain Computer Interface (BCI) device comprising: a forward-upward sloped headband which is configured to encircle a person's head; an ear prong which is configured to engage a portion of the perimeter of an outer ear; at least one electromagnetic energy sensor which is held in proximity to the person's head by the forward-sloped headband or the ear prong, wherein the at least one electromagnetic energy sensor collects data concerning electromagnetic brain activity; a data processor which receives data from the at least one electromagnetic energy sensor; a data transmitter; and a power source which powers the at least one electromagnetic energy sensor, the data processor, and/or the data transmitter.

In an example, a front portion of the headband can be higher than a rear portion of the headband. In an example, the front third of the headband can have a first average height, the rear third of the undulating headband can have a second average height, and the first height can be between 1" and 3" higher than the second height. In an example, a front portion of the headband can be configured to span across the person's forehead. In an example, right and left side portions of the headband can be attached to right and left side ear prongs, and each ear prong can partially encircle the perimeter of an outer ear and/or the connection between the main body of the head and the outer ear. In an example, right and left side portions of the headband can be attached to right and left side ear prongs and each ear prong can engage the rear-facing surface of an outer ear.

FIG. 41 shows an example of how this invention can be embodied in a wearable device for measuring electromagnetic brain activity comprising: a partially-circumferential headband (including rear portion 4101, front portion 4102, and ear-perimeter-engaging member 4103) which spans a portion of the circumference of a person's head, including a portion of the person's forehead; a plurality of electromagnetic energy sensors (including 4107 and 4108) which are configured to be held in proximity to the person's head by the headband, wherein these electromagnetic energy sensors collect data concerning electromagnetic activity of the person's brain; a wireless data transmitter and/or receiver 4104; a data processor 4105; and a power source 4106. In an example, this device can have a symmetric configuration on the other side of the person's head, which is not shown here.

In an example, a rear portion of a partially-circumferential headband can extend rearward from a person's right and left ears, looping completely around the rear of a person's head from the right ear to the left ear. In an example, right and left front portions of a partially-circumferential headband can extend forward from a person's right and left ears, respectively, partially extending onto the right and left sides of a person's forehead, respectively, but not completely spanning from the right ear to the left ear. In an example, the right and left front portions of a partially-circumferential headband can have ends which terminate on the right and left sides of a person's forehead, respectively, leaving a gap between them. In an example, this gap can include the center of the person's forehead.

In an example, a partially-circumferential headband can span between 380% and 415% of the circumference of a person's head. In an example, a partially-circumferential headband can span between 60% and 80% of the circumference of a person's head. In an example, a partially-circumferential headband can have an arcuate axial shape like that of an ancient Roman laurel wreath. In an example, a partially-circumferential headband can be shaped like a horseshoe or like the letter "U", with upturned front ends. In an example, a partially-circumferential headband can loop around the sides and rear of a person's head from the right side of a person's forehead to the left side of the person's forehead, but not fully span across the person's forehead. In an example, a partially-circumferential headband can fully span the rear of a person's head, between their ears, but only partially span the front of the person's head.

In an example, a partially-circumferential headband can rest on top of a person's ears. In an example, a partially-circumferential headband can span the sides of a person's head above the person's ears. In an example, a partially-circumferential headband can loop around the rear of a person's head at a substantially level height, pass over the tops of a person's ears, and then arc upwards and forward to terminal positions on the sides of the person's forehead, stopping short of the center of the person's forehead. In an example, the right and left ends of a partially-circumferential headband can be on a person's forehead above the person's right and left eyes, respectively.

In an example, a side of a partially-circumferential headband can extend forward from a person's ear at an overall vector between the 1 o'clock (30 degree) vector and the 3 o'clock (90 degree) vector. In an example, a front portion of a partially-circumferential headband can initially extend forward from a person's ear along a vector between the 2 o'clock (60 degree) and 3 o'clock (90 degree) vectors, and then curve upward toward the person's forehead along a vector between the 1 o'clock (30 degree) and 2 o'clock (60 degree) vectors. In an example, a front portion of a partially-circumferential headband can be configured to end between 25% and 75% of the way from a person's ear to the center of their forehead. In an example, this end can be within the range of 1" to 4" above the top of the person's ear.

In an example, this headband can further comprise an ear-perimeter-engaging member which curves around the rear of a person's ear to better hold the headband in place. In an example, this ear-perimeter-engaging member can span between the 7 o'clock (210 degree) and 12 o'clock (0 degree) vectors. In an example, this ear-perimeter-engaging member can span between the 9 o'clock (270 degree) and 12 o'clock (0 degree) vectors. In an example, this ear-perimeter-engaging member can also be attached to an earlobe.

Other relevant variations and components discussed in other portions of this concurrent disclosure or prior disclosures incorporated herein by reference can also be applied to this example.

FIG. 42 shows an example of how this invention can be embodied in a wearable device for measuring electromagnetic brain activity comprising: a headband (or halo) 4201; a rearward ear-engaging member 4202; a frontal ear-engaging member 4203; a plurality of electromagnetic energy sensors (including 4207, 4208, 4209, and 4210) which are configured to be held in proximity to the person's head by the headband (or halo), wherein these electromagnetic energy sensors collect data concerning electromagnetic activity of the person's brain; a wireless data transmitter and/or receiver 4204; a data processor 4205; and a power source 4206. In an example, this device can have a symmetric configuration on the other side of the person's head, which is not shown here.

In an example, a headband (or halo) can encircle a person's head, including spanning at least a portion of the person's forehead. In an example, a headband (or halo) can span the center of a person's forehead. In an example, a headband (or halo) can encircle a person's head, from rear to front, at a height above a person's ears when the person is standing upright. In an example, a headband (or halo) can encircle a person's head, from rear to front, at a height (or heights) within 1" to 4" from the height of a person's ears (when the person is standing upright). In an example, a headband (or halo) can encircle a person's head, from rear to front, at a distance (or distances) within 3" to 6" from the top of the person's head. In an example, a headband (or halo) can encircle a person's head at a substantially uniform height when the person is standing upright. In an example, a headband (or halo) can encircle a person's head at a substantially uniform distance from the top of the person's head.

In an example, a headband (or halo) can have a shape which is selected from the group consisting of: circle, oval, ellipse, and egg-shape. In an example, a headband (or halo) can be made from a metal or a polymer. In an example, a headband (or halo) can be gas permeable (e.g. breathable) and/or liquid permeable. In an example, the perimeter of a headband (or halo) can further comprise a spring or other tensile member which holds the headband (or halo) against the surface of the person's head. In an example, the perimeter of a headband (or halo) can further comprise a spring or other tensile member which causes the headband to exert (modest) pressure against the surface of the person's head to better hold the headband on the person's head and/or better hold the electromagnetic energy sensors in proximity to the surface of the person's head.

In an example, a headband (or halo) can be stretchable, elastic, and/or expandable. In an example, one or more sections of the perimeter of a headband (or halo) can be stretchable, elastic, and/or expandable. In an example, the perimeter of a headband (or halo) can comprise one or more sections with a first degree of stretchability, elasticity, and/or expandability and one or more sections with a second degree of stretchability, elasticity, and/or expandability, wherein the second degree is greater than the first degree. In an example, the rear portion of the perimeter of a headband (spanning the rear of the person's head) can have a first degree of stretchability, elasticity, and/or expandability and the front portion of the perimeter of the headband (spanning the person's forehead) can have a second degree of stretchability, elasticity, and/or expandability, wherein the second degree is greater than the first degree. In an example, the rear portion of the perimeter of a headband (spanning the rear of the person's head) can have a first degree of stretchability, elasticity, and/or expandability and the front portion of the perimeter of the headband (spanning the person's forehead) can have a second degree of stretchability, elasticity, and/or expandability, wherein the second degree is less than the first degree.

In an example, a headband (or halo) can rest on the top portions of a person's ears (or the top portions of the tissue which connects the outer ears to the main body of the head). In an example, a rearward ear-engaging member can be configured to curve around (and frictionally engage) a rear portion of the perimeter of a person's outer ear. In an example, a rearward ear-engaging member can curve around (and frictionally engage) a person's outer ear between the 6 o'clock (210 degree) and 12 o'clock (0 degree) vectors. In an example, a rearward ear-engaging member can curve around (and frictionally engage) a person's outer ear between the 8 o'clock (210 degree) and 12 o'clock (0 degree) vectors. In an example, a rearward ear-engaging member can be configured to span between 20% and 50% of the perimeter of a person's ear. In an example, a rearward ear-engaging member can be configured to be attached to a person's earlobe.

In an example, a frontal ear-engaging member can be configured to curve around (and frictionally engage) a front portion of the perimeter of a person's outer ear. In an example, a frontal ear-engaging member can curve around (and frictionally engage) a person's outer ear between the 12 o'clock (0 degree) and 4 o'clock (120 degree) vectors. In an example, a frontal ear-engaging member can curve around (and frictionally engage) a person's outer ear between the 12 o'clock (0 degree) and 2 o'clock (60 degree) vectors. In an example, a rearward ear-engaging member can be configured to span between 10% and 30% of the perimeter of a person's ear.

In an example, a headband (or halo) can be configured to receive the side frame of a pair of eyeglasses so that this headband (or halo) can be worn in combination with eyeglasses. In an example, a headband (or halo) can further comprise an opening which is configured to receive the side-piece of an eyeglass frame so that this headband (or halo) can be worn in combination with eyeglasses. In an example, a headband (or halo) can further comprise a clip or other attachment mechanism to which the side-piece of an eyeglass frame can be attached so that this headband (or halo) can be worn in combination with eyeglasses. In an example, headband (or halo) can further comprise an indentation, groove, or track into (or against) which the side-piece of the side-piece of an eyeglass frame can be placed so that this headband (or halo) can be worn in combination with eyeglasses. Other relevant variations and components discussed in other portions of this concurrent disclosure or prior disclosures incorporated herein by reference can also be applied to this example.

FIGS. 43 and 44 show two sequential views of another example of how this invention can be embodied in a wearable device for measuring electromagnetic brain activity. This example includes a movable loop. FIG. 43 shows a view of this example at a first time wherein a movable loop with one or more electromagnetic energy sensors is configured to loop around the rear and/or upper-rear portion of a person's head. FIG. 44 shows a view of this example at a second time wherein the movable loop has been moved so that it is configured to loop around the person's forehead.

FIGS. 43 and 44 show an example of a wearable device for measuring electromagnetic brain activity comprising: a rear loop 4301 which is configured to loop around the rear portion and/or upper-rear portion of a person's head, from the right ear to the left ear (or vice versa); a frontal ear-engaging member 4302 which is configured to curve around at least a portion of the front of an ear; a rear ear-engaging member 4303 which is configured to curve around at least a portion of the rear of the ear; a movable loop (including joint 4307, stretchable portion 4308, and end portion 4309), wherein this movable loop has a first configuration in which it loops around the rear and/or upper-rear portion of a person's head, wherein this movable loop has a second configuration in which it loops across the person's forehead, and wherein this movable loop can be reversibly moved from the first configuration to the second configuration; at least one electromagnetic energy sensor 4310 which is configured to be held in proximity to the person's forehead by the movable loop in the second configuration, wherein the electromagnetic energy sensor collects data concerning electromagnetic activity of the person's brain; a wireless data transmitter and/or receiver 4304; a data processor 4305; and a power source 4306. In an example, this device can have a symmetric configuration on the other side of the person's head, which is not shown here.

In an example, a rear loop can span the rear portion and/or upper-rear portion a person's head, from one ear to the other, at a substantially uniform height when the person is standing upright. In an example, this uniform height can be within 1" of the height of the top of the person's ear. In an example, this uniform height can be within 1" of the height of the bottom of the person's ear. In an example, a rear loop can span the rear and/or upper-rear portion of a person's head, from one ear to the other, at a substantially uniform distance from the top of the person's head. In an example, a rear loop can be configured to span the rear and/or upper-rear portion of a person's head at a height which is lower than the top of the person's ear, but above the height of the bottom of the person's ear. In an example, a rear loop can be stretchable, elastic, and/or expandable. In an example, selected portions of a rear loop can be stretchable, elastic, or expandable. In an example, a rear loop can further comprise teeth, prongs, combs, or protrusions which engage the person's hair to better hold the rear loop in place.

In an example, a frontal ear-engaging member can be configured to curve around (and frictionally engage) a front portion of the perimeter of a person's outer ear. In an example, a frontal ear-engaging member can curve around (and frictionally engage) a person's outer ear between the 12 o'clock (0 degree) and 4 o'clock (120 degree) vectors. In an example, a frontal ear-engaging member can curve around (and frictionally engage) a person's outer ear between the 12 o'clock (0 degree) and 2 o'clock (60 degree) vectors. In an example, a rearward ear-engaging member can be configured to span between 10% and 30% of the perimeter of a person's ear. In an example, a frontal ear-engaging member can further comprise a speaker located near, or inserted within, the person's ear canal.

In an example, a rear ear-engaging member can be configured to curve around (and frictionally engage) a rear portion of the perimeter of a person's outer ear. In an example, a rear ear-engaging member can curve around (and frictionally engage) a person's outer ear between the 6 o'clock (210 degree) and 12 o'clock (0 degree) vectors. In an example, a rear ear-engaging member can curve around (and frictionally engage) a person's outer ear between the 8 o'clock (210 degree) and 12 o'clock (0 degree) vectors. In an example, a rear ear-engaging member can be configured to span between 20% and 50% of the perimeter of a person's ear. In an example, a rear ear-engaging member can be configured to be attached to a person's earlobe.

In an example, a movable loop can include a joint, hinge, or axle. In an example, a movable loop can pivot or rotate around a joint, hinge, or axle. In an example, the portion of a movable loop which is furthest from a person's ear can pivot or rotate around a joint, hinge, or axle which is within 1" of a person's ear. In an example, the portion of a movable loop which is furthest from a person's ear can pivot or rotate around a joint, hinge, or axle which is within 3" of a person's ear. In an example, a movable loop can be manually and reversibly moved from its first configuration to its second configuration. In an example, a joint, hinge, or axle can be reversibly locked or unlocked, so as to reversibly lock a movable loop in its first configuration or second configuration.

In an example, a movable loop can have a first configuration in which it loops around the rear and/or upper-rear portion of a person's head and a second configuration in which it loops around (across) a person's forehead. In an example, a movable loop can transition from its first configuration to its second configuration by pivoting or rotating around a joint, hinge, or axle. In an example, a movable loop can have a first configuration wherein its longitudinal axis is parallel to a vector between the 9 o'clock (270 degree) and 11 o'clock (330 degree) vectors and can have a second configuration wherein its longitudinal axis is parallel to a vector between the 1 o'clock (30 degree) and 3 o'clock (90 degree) vectors. In an example, a movable loop can have a first configuration wherein its longitudinal axis is parallel to a vector between the 10 o'clock (300 degree) and 12 o'clock (0 degree) vectors and can have a second configuration wherein its longitudinal axis is parallel to a vector between the 1 o'clock (30 degree) and 3 o'clock (90 degree) vectors.

In an example, a movable loop can be stretchable, elastic, and/or expandable. In an example, a movable loop can further comprise a first portion with a first degree of stretchability, elasticity, and/or expandability and a second portion with a second degree of stretchability, elasticity, and/or expandability, wherein the second degree is less than the first degree. In the example shown in FIGS. 43 and 44, the movable loop has a stretchable portion 4308 (with a greater degree of stretchability) and an end portion 4309 (with a lower degree of stretchability). Having at least one stretchable, elastic, and/or expandable portion of a movable loop allows the loop to be more easily moved from its first configuration to its second configuration. Having at least one stretchable, elastic, and/or expandable portion of a movable loop can also enable to loop to hold one or more electromagnetic energy sensors more securely against a person's forehead in the second configuration.

In an example, a stretchable portion of a movable loop can be an elastic band or strap. In an example, a stretchable portion of a movable loop can include a spring mechanism. In an example, a movable loop can include telescoping members. In an example, telescoping members can be held in tension by a spring mechanism so that they are compelled toward a contracted configuration in order to fit snugly against a person's head. In an example, a movable loop can have a first perimeter distance in a first configuration and a second perimeter distance in a second configuration, wherein the first distance is shorter than the second distance.

In an example, this invention can be embodied in a Brain Computer Interface (BCI) device comprising: a rear loop which is configured to loop around the rear portion or upper-rear portion of a person's head, from a first side of the person's head to a second side of the person's head; a rear ear-engaging member which is configured to curve around at least a portion of the rear of an ear; a movable loop, wherein this movable loop has a first configuration in which it loops around the rear or upper-rear portion of a person's head, wherein this movable loop has a second configuration in which it loops across the person's forehead, and wherein this movable loop can be reversibly moved from the first configuration to the second configuration; at least one electromagnetic energy sensor which is held in proximity to the person's head by the movable loop in the second configuration, wherein the at least one electromagnetic energy sensor collects data concerning electromagnetic brain activity; a data processor which receives data from the at least one electromagnetic energy sensor; a data transmitter; and a power source which powers the at least one electromagnetic energy sensor, the data processor, and/or the data transmitter.

In an example, a movable loop can further comprise a stretchable, elastic, and/or expandable portion. In an example, this device can further comprise a frontal ear-engaging member which is configured to curve around at least a portion of the front of an outer ear. In an example, this device can further comprise a joint, hinge, or axle around which the movable loop pivots or rotates. Other relevant variations and components discussed in other portions of this concurrent disclosure or prior disclosures incorporated herein by reference can also be applied to this example.

FIGS. 45 and 46 show two sequential views of another example of how this invention can be embodied in a wearable device for measuring electromagnetic brain activity. This example is similar to the one just shown in FIGS. 43 and 44 except that a movable loop attaches to the frame of eyewear instead of a rear loop. FIG. 45 shows a view of this example at a first time wherein a movable loop with one or more electromagnetic energy sensors is configured to loop around the rear and/or upper-rear portion of a person's head. FIG. 46 shows a view of this example at a second time wherein the movable loop has been moved so that it is configured to loop around the person's forehead.

FIGS. 45 and 46 show an example of a wearable device for measuring electromagnetic brain activity comprising: eyewear 4501; a movable loop (including joint 4505, stretchable portion 4506, and end portion 4507), wherein this movable loop has a first configuration in which it loops around the rear and/or upper-rear portion of a person's head, wherein this movable loop has a second configuration in which is loops across the person's forehead, and wherein this movable loop can be reversibly moved from the first configuration to the second configuration; at least one electromagnetic energy sensor 4508 which is configured to be held in proximity to the person's forehead by the movable loop in the second configuration, wherein the electromagnetic energy sensor collects data concerning electromagnetic activity of the person's brain; a wireless data transmitter and/or receiver 4502; a data processor 4503; and a power source 4504. In an example, this device can have a symmetric configuration on the other side of the person's head, which is not shown here.

In an example, a movable loop can include a joint, hinge, or axle. In an example, a movable loop can pivot or rotate around a joint, hinge, or axle. In an example, the portion of a movable loop which is furthest from a person's ear can pivot or rotate around a joint, hinge, or axle which is within 1" of a person's ear. In an example, the portion of a movable loop which is furthest from a person's ear can pivot or rotate around a joint, hinge, or axle which is within 3" of a person's ear. In an example, a movable loop can be manually and reversibly moved from its first configuration to its second configuration. In an example, a joint, hinge, or axle can be reversibly locked or unlocked, so as to reversibly lock a movable loop in its first configuration or second configuration.

In an example, a movable loop can have a first configuration in which it loops around the rear and/or upper-rear portion of a person's head and a second configuration in which it loops around (across) a person's forehead. In an example, a movable loop can transition from its first configuration to its second configuration by pivoting or rotating around a joint, hinge, or axle. In an example, a movable loop can have a first configuration wherein its longitudinal axis is parallel to a vector between the 9 o'clock (270 degree) and 11 o'clock (330 degree) vectors and can have a second configuration wherein its longitudinal axis is parallel to a vector between the 1 o'clock (30 degree) and 3 o'clock (90 degree) vectors. In an example, a movable loop can have a first configuration wherein its longitudinal axis is parallel to a vector between the 10 o'clock (300 degree) and 12 o'clock (0 degree) vectors and can have a second configuration wherein its longitudinal axis is parallel to a vector between the 1 o'clock (30 degree) and 3 o'clock (90 degree) vectors.

In an example, a movable loop can be stretchable, elastic, and/or expandable. In an example, a movable loop can further comprise a first portion with a first degree of stretchability, elasticity, and/or expandability and a second portion with a second degree of stretchability, elasticity, and/or expandability, wherein the second degree is less than the first degree. In the example shown in FIGS. 45 and 46, the movable loop has a stretchable portion 4506 (with a greater degree of stretchability) and an end portion 4507 (with a lower degree of stretchability). Having at least one stretchable, elastic, and/or expandable portion of a movable loop allows the loop to be more easily moved from its first configuration to its second configuration. Having at least one stretchable, elastic, and/or expandable portion of a movable loop can also enable to loop to hold one or more electromagnetic energy sensors more securely against a person's forehead in the second configuration.

In an example, the stretchable portion of a movable loop can be an elastic band or strap. In an example, the stretchable portion of a movable loop can include a spring mechanism. In an example, a movable loop can include telescoping members. In an example, telescoping members can be held in tension by a spring mechanism so that they are compelled toward a contracted configuration in order to fit snugly against a person's head. In an example, a movable loop can have a first perimeter distance in a first configuration and a second perimeter distance in a second configuration, wherein the first distance is shorter than the second distance.

In an example, a movable loop and eyeglasses (or other eyewear) can be integral components of a single wearable device. In an example, a movable loop can be a separate device which is attached to eyeglasses (or other eyewear). In an example, a movable loop can be configured to receive the side frame of a pair of eyeglasses (or other eyewear). In an example, a movable loop can further comprise an opening which is configured to receive the side-piece of an eyeglass (or other eyewear) frame. In an example, a movable loop can further comprise a clip or other attachment mechanism to which the side-piece of an eyeglass (or other eyewear) frame can be attached. Other relevant variations and components discussed in other portions of this concurrent disclosure or prior disclosures incorporated herein by reference can also be applied to this example.

FIGS. 47 and 48 show two sequential views of another example of how this invention can be embodied in a wearable device for measuring electromagnetic brain activity. This example is similar to the one shown in FIG. 41, except that it includes a movable arm which extends (e.g. telescopes) out onto the side of a person's forehead instead of a movable loop. FIG. 47 shows this example at a first time wherein the movable arm is in a first (withdrawn) configuration. FIG. 48 shows this example at a second time wherein the movable arm has been moved to a second (extended) configuration onto the person's forehead.

FIGS. 47 and 48 show an example of a wearable device for measuring electromagnetic brain activity comprising: a partially-circumferential headband (including rear portion 4701, front portion 4702, and ear-perimeter-engaging member 4703) which spans a portion of the circumference of a person's head; a movable arm 4801, wherein this movable arm has a first configuration in which it extends a first distance from front portion 4702, wherein this movable arm has a second configuration in which it extends a second distance from front portion 4702, and wherein the second distance is greater than the first distance; at least one electromagnetic energy sensor 4802 which is configured to be held in proximity to the person's forehead by the movable arm in the second configuration, wherein this electromagnetic energy sensor collects data concerning electromagnetic activity of the person's brain; a wireless data transmitter and/or receiver 4704; a data processor 4705; and a power source 4706. In an example, this device can have a symmetric configuration on the other side of the person's head, which is not shown here.

In an example, the first distance can be zero. In an example, the second distance can be within the range of 1" to 7". In an example, a movable arm can be concentric with the front portion of a headband. In an example, a movable arm can telescope into (or out of) the front portion of a headband. In an example, a movable arm can slid into (or out of) the front portion of a headband. In an example, a movable arm can be manually moved from a first configuration to a second configuration, or vice versa. In an example, a movable arm can be automatically moved by an actuator from a first configuration to a second configuration, or vice versa. In an example, the end of a movable arm can be between 1" and 3" from a person's ear in a first configuration and between 2" and 6" from a person's ear in a second configuration. Other relevant variations and components discussed in other portions of this concurrent disclosure or prior disclosures incorporated herein by reference can also be applied to this example.

FIGS. 49 and 50 show two sequential views of another example of how this invention can be embodied in a wearable device for measuring electromagnetic brain activity. This example is similar to the one just shown in FIGS. 47 and 48, except that a movable arm pivots out over the forehead instead of telescoping out over the forehead. FIG. 49 shows this example at a first time wherein the movable arm is pivoted into a first configuration near the person's ear. FIG. 50 shows this example at a second time wherein the movable arm has been pivoted into a second (extended) configuration onto the person's forehead.

FIGS. 49 and 50 show an example of a wearable device for measuring electromagnetic brain activity comprising: a partially-circumferential headband (including rear portion 4901, front portion 4902, and ear-perimeter-engaging member 4903) which spans a portion of the circumference of a person's head; a joint 4908; a movable arm 4907, wherein this movable arm pivots and/or rotates around joint 4908, wherein this movable arm has a first configuration in which it is a first distance from the center of the person forehead, wherein this movable arm has a second configuration in which it is a second distance from the center of the person's forehead, wherein the second distance is less than the first distance; at least one electromagnetic energy sensor 4802 which is configured to be held in proximity to the person's forehead by the movable arm in the second configuration, wherein this electromagnetic energy sensor collects data concerning electromagnetic activity of the person's brain; a wireless data transmitter and/or receiver 4904; a data processor 4905; and a power source 4906. In an example, this device can have a symmetric configuration on the other side of the person's head, which is not shown here.

In an example, a movable arm can pivot and/or rotate around a joint, hinge, or axle. In an example, a movable arm can pivot or rotate around a joint, hinge, or axle which is within 1" of a person's ear. In an example, a joint, hinge, or axle can be reversibly locked or unlocked, so as to reversibly lock a movable arm in its first configuration or second configuration. In an example, this device can further comprise a spring or other tensile member which compels movable arm into close contact with the person's forehead in the second configuration. In an example, this device can further comprise a spring or other tensile member which compels an electromagnetic energy sensor on movable arm into close contact with the person's forehead in the second configuration. Other relevant variations and components discussed in other portions of this concurrent disclosure or prior disclosures incorporated herein by reference can also be applied to this example.

FIGS. 51 and 52 show two sequential views of a wearable and mobile Brain Computer Interface (BCI) comprising: eyewear which further comprises—a side frame (5101), a front frame (5102), a joint (5104) on the side frame, a movable loop (5103) which is configured to loop over the top of a person's head or around back of a person's head in a first configuration and which is configured to span across a person's forehead in a second configuration, wherein the movable loop pivots and/or rotates around the joint from the first configuration to the second configuration; one or more electromagnetic energy sensors (5105 and 5106) which are part of, or attached to, the movable loop, wherein these electromagnetic energy sensors collect data concerning electromagnetic brain activity; a power source (5107); a data processor (5108); and a data transmitter and/or receiver (5109). FIG. 51 shows this device when the movable loop is in the first configuration. FIG. 52 shows this device when the movable loop is in the second configuration. In an example, this device can be symmetric, with symmetric components and structure on the other side of the person's head.

In an example, the side frame of eyewear can be configured to span from a person's ear to a front frame. In an example, a rear portion of a side frame can curve around the rear of the person's outer ear. In an example, a side frame can be arcuate. In an example, a portion of a side frame between a person's ear and a front frame can arc, curve, wave, and/or undulate upwards. In an example, a side frame can have a downward-facing concave portion. In an example, a front frame of eyewear can hold one or more lenses. In an example, this eyewear can be a pair of eyeglasses. In an example, the front frame of eyewear can hold one or more image displays. In an example, this eyewear can be virtual reality (VR) and/or augmented reality (AR) eyewear.

In an example, the joint around which a movable loop pivots and/or rotates can be located along the (rear to front) longitudinal mid-section of a side frame. In an example, a joint can be located within 2" of the longitudinal mid-point of a side frame. In an example, a joint around which a movable loop pivots and/or rotates can be located along the rear third of a side frame. In an example, a joint can be located within 2" of the rear end a side frame. In an example, a joint can further comprise a locking mechanism which locks it in place when a movable loop is at a selected angle and/or in a selected position. In an example, a joint can have restricted movement such that it restricts the movement of a movable loop so that the loop does not descend lower than a selected position on a person's forehead.

In an example, a movable loop can be made out of metal or a polymer. In an example, a movable loop can be flexibly resilient. In an example, a movable loop can be made out of fabric. In an example, a movable loop can be elastic, stretchable, and/or expandable. In an example, a movable loop can further comprise an elastic, stretchable, and/or expandable portion. In an example, a movable loop can further comprise a telescoping portion. In an example, a movable loop holds one or more electromagnetic energy sensors on a person's forehead when the loop is in the second configuration. Other relevant variations and components discussed in other portions of this concurrent disclosure or prior disclosures incorporated herein by reference can also be applied to this example.

I claim:

1. A Brain Computer Interface (BCI) device comprising:
   a continuous undulating band which is configured to be worn on a person's head;
   wherein the continuous undulating band further comprises a rear ear-engaging segment, wherein the rear ear-engaging segment is configured to be worn on a first side of the person's head around at least a portion of the rear-facing surface of the person's ear on the first side;
   wherein the continuous undulating band further comprises a side segment, wherein the side segment is configured to span on the first side of the person's head from the rear ear-engaging segment to a side portion of the person's forehead, and wherein the side segment has a rear-facing concavity and a forward-facing peak;
   wherein the continuous undulating band further comprises a top segment, wherein the top segment is configured to span on the first side of the person's head from the side segment to the top of the person's head;
   at least one electromagnetic energy sensor which is held in proximity to the person's head by the rear ear-engaging segment, the side segment, or the top segment, wherein the at least one electromagnetic energy sensor collects data concerning electromagnetic brain activity;
   a data processor which receives data from the at least one electromagnetic energy sensor;
   a data transmitter; and
   a power source which powers the at least one electromagnetic energy sensor, the data processor, and/or the data transmitter.

2. The device in claim 1 wherein this device further comprises rear ear-engaging, side, and top segments on a second side of the person's head opposite to the first side, and wherein first side and second side top segments connect at the top of the person's head.

3. The device in claim 1 wherein the side segment is configured to loop from the person's ear: at least two inches toward the person's eye; at least two inches toward the center of the person's forehead; between one quarter and three-quarters of the way toward the person's eye; or between one quarter and three-quarters of the way toward the center of the person's forehead.

4. The device in claim 1 wherein the side segment has a loop shape.

5. The device in claim 1 wherein the side segment is configured to: (a) span in an undulating manner downward and forward from a person's ear to a location on the side of a person's face, (b) then span in an undulating manner upward, and (c) then span in an undulating manner upward and rearward to a location above the ear on the side of the head.

6. A Brain Computer Interface (BCI) device comprising:
   a rear loop which is configured to loop around the rear portion or upper-rear portion of a person's head, from a first side of the person's head to a second side of the person's head;
   a rear ear-engaging member which is configured to curve around at least a portion of the rear of an ear;
   a movable loop, wherein the movable loop has a first configuration in which the movable loop loops around the rear or upper-rear portion of a person's head, wherein the movable loop has a second configuration in which the movable loop loops across the person's forehead, wherein the movable loop can be reversibly moved from the first configuration to the second configuration; wherein the movable loop further comprises a first portion with a first level of elasticity or expandability and a second portion with a second level of elasticity or expandability; and wherein the second level is less than the first level;
   at least one electromagnetic energy sensor which is held in proximity to the person's head by the movable loop in the second configuration, wherein the at least one electromagnetic energy sensor collects data concerning electromagnetic brain activity;
   a data processor which receives data from the at least one electromagnetic energy sensor;
   a data transmitter; and
   a power source which powers the at least one electromagnetic energy sensor, the data processor, and/or the data transmitter.

7. The device in claim 6 wherein this device further comprises a frontal ear-engaging member which is configured to curve around at least a portion of the front of an outer ear.

8. The device in claim 6 wherein this device further comprises a joint, hinge, or axle around which the movable loop pivots or rotates.

* * * * *